(12) United States Patent
Larrinua et al.

(10) Patent No.: US 9,427,003 B2
(45) Date of Patent: Aug. 30, 2016

(54) SYNTHETIC GENES

(75) Inventors: Ignacio M. Larrinua, Indianapolis, IN (US); Donald J. Merlo, Carmel, IN (US); Avutu S. Reddy, Carmel, IN (US); Arvind Kumar ThirumalaiswamySekhar, Zionsville, IN (US); Aaron T. Woosley, Fishers, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 643 days.

(21) Appl. No.: 13/447,836

(22) Filed: Apr. 16, 2012

(65) Prior Publication Data

US 2012/0266335 A1 Oct. 18, 2012

Related U.S. Application Data

(60) Provisional application No. 61/475,921, filed on Apr. 15, 2011.

(51) Int. Cl.

| | | |
|---|---|---|
| C12N 15/11 | (2006.01) |
| C12N 15/63 | (2006.01) |
| A01H 5/00 | (2006.01) |
| A23L 1/10 | (2006.01) |
| A23D 9/00 | (2006.01) |
| A23L 1/20 | (2006.01) |
| A23L 1/214 | (2006.01) |
| C07K 14/325 | (2006.01) |
| C07K 14/435 | (2006.01) |
| C11B 1/00 | (2006.01) |
| C12N 9/08 | (2006.01) |
| C12N 9/02 | (2006.01) |
| C12N 15/82 | (2006.01) |

(52) U.S. Cl.
CPC .............. *A23L 1/1041* (2013.01); *A23D 9/00* (2013.01); *A23L 1/10* (2013.01); *A23L 1/20* (2013.01); *A23L 1/2005* (2013.01); *A23L 1/214* (2013.01); *C07K 14/325* (2013.01); *C07K 14/43595* (2013.01); *C11B 1/00* (2013.01); *C12N 9/0065* (2013.01); *C12N 9/0083* (2013.01); *C12N 15/8286* (2013.01); *C12Y 111/01015* (2013.01)

(58) Field of Classification Search
CPC .......... A23L 1/1041; A23L 1/10; A23L 1/20; A23L 1/2005; A23L 1/214; C12N 9/0083; C12N 9/0065
USPC ........................................................ 800/302
See application file for complete search history.

(56) References Cited

U.S. PATENT DOCUMENTS

| 5,625,136 | A | 4/1997 | Koziel et al. |
| 6,043,415 | A | 3/2000 | Strizhov et al. |
| 7,741,118 | B1 | 6/2010 | Fischhoff et al. |
| 2004/0168213 | A1 | 8/2004 | Verbsky et al. |
| 2007/0028321 | A1 | 2/2007 | Manjunath et al. |
| 2008/0028482 | A1* | 1/2008 | Beazley et al. ............... 800/265 |
| 2009/0093366 | A1 | 4/2009 | Wright et al. |
| 2009/0260107 | A1 | 10/2009 | English et al. |
| 2009/0270327 | A1 | 10/2009 | Baum et al. |
| 2010/0138953 | A1 | 6/2010 | Flasinski |

FOREIGN PATENT DOCUMENTS

WO    WO 90/10076    9/1990

OTHER PUBLICATIONS

Perlak F. J. et al., Modification of the coding sequence enhances plant expression of insect control protein genes, Proceedings of the National Academy of Sciences, National Academy of Sciences, Apr. 1, 1991, vol. 88, pp. 3324-3328.
Murray E. E. et al., Codon usage in plant genes, Nucleic Acids Research, Oxford University Press, GB, Jan. 25, 1989, vol. 17, No. 2, pp. 477-498.

\* cited by examiner

*Primary Examiner* — Li Zheng
(74) *Attorney, Agent, or Firm* — Ronald S. Maciak; Barnes & Thornburg LLP

(57) ABSTRACT

The invention provides synthetic nucleic acid sequences encoding proteins of interest that are particularly adapted to express well in plants. The claimed synthetic sequences utilize plant-optimized codons roughly in the same frequency at which they are utilized, on average, in genes naturally occurring in the plant species. The invention further includes synthetic DNA sequence for herbicide tolerance, water and/or heat stress tolerance, healthy oil modifications and for transformation marker genes and selectable marker genes are used. DNA construct and transgenic plants containing the synthetic sequences are taught as are methods and compositions for using the plants in agriculture.

9 Claims, No Drawings

SYNTHETIC GENES

CROSS-REFERENCE TO RELATED APPLICATION

This application claims priority to provisional application Ser. No. 61/475,921 filed Apr. 15, 2011, the disclosure of which is incorporated herein by reference in its entirety.

BACKGROUND OF THE INVENTION

To achieve desired expression levels of heterologous proteins in transgenic plants it has been found beneficial to alter the native, sometimes referred to as wild-type or original, DNA coding sequence in various ways, e.g. so that codon usage more closely matches the codon usage of the host plant species, and/or so the G+C content of the coding sequence more closely matches the G+C level typically found in coding sequences of the host plant species, and/or so that certain sequences that destabilize mRNA are removed. Expression in plants of *Bacillus thuringiensis* (B. t.) crystal protein insect toxins, for example, has been improved using one or more of these approaches. See, for example, U.S. Pat. No. 5,380,301, U.S. Pat. No. 5,625,136, U.S. Pat. No. 6,218,188, U.S. Pat. No. 6,340,593, U.S. Pat. No. 6,673,990, U.S. Pat. No. 7,741,118. Codon degeneracy allows one to make synthetic DNA sequences that encode a protein of interest using codons that differ from those used in the original DNA coding sequence.

In regard to removing sequences that may destabilize mRNA, U.S. Pat. No. 7,741,118 discloses a list of 16 polyadenylation signal sequences (column 15, Table II) and calls for reducing the number of such sequences in synthetic coding sequences that are intended for expression in plants. The polyadenylation signal sequences listed in U.S. Pat. No. 7,741,118, Table II are listed below in Table 1:

TABLE 1

Polyadenylation signal sequences listed in U.S. Pat. No. 7,741,118, Table II.

| | |
|---|---|
| 1 | AATAAA |
| 2 | AATAAT |
| 3 | AACCAA |
| 4 | ATATAA |
| 5 | AATCAA |
| 6 | ATACTA |
| 7 | ATAAAA |
| 8 | ATGAAA |
| 9 | AAGCAT |
| 10 | ATTAAT |
| 11 | ATACAT |
| 12 | AAAATA |
| 13 | ATTAAA |
| 14 | AATTAA |
| 15 | AATACA |
| 16 | CATAAA |

U.S. Pat. No. 7,741,118 also calls for preferably removing the sequence ATTTA (known as the Shaw-Kamen sequence), because it has been identified as potentially destabilizing mRNA.

Contrary to the teaching of U.S. Pat. No. 7,741,118, we have found that reduction in the number of the polyadenylation signal sequences identified in Table 1 above is neither necessary nor sufficient to enable enhanced expression of synthetic genes in plants.

SUMMARY OF THE INVENTION

Table 2 below identifies 20 potential polyadenylation signal sequences that occur frequently in maize genes.

TABLE 2

Potential poyadenylation signal sequences found in maize genes

| | |
|---|---|
| 1 | ATATAT |
| 2 | TTGTTT |
| 3 | TTTTGT |
| 4 | TGTTTT |
| 5 | TATATA |
| 6 | TATTTT |
| 7 | TTTTTT |
| 8 | ATTTTT |
| 9 | TTATTT |
| 10 | TTTATT |
| 11 | TAATAA |
| 12 | ATTTAT |
| 13 | TATATT |
| 14 | TTTTAT |
| 15 | ATATTT |
| 16 | TATTAT |
| 17 | TGTTTG |
| 18 | TTATAT |
| 19 | TGTAAT |
| 20 | AAATAA |

Table 3 below identifies 20 potential polyadenylation signal sequences that occur frequently in soybean genes.

TABLE 3

Potential poyadenylation signal sequences found in soybean genes.

| | |
|---|---|
| 1 | ATTTTT |
| 2 | TATTTT |
| 3 | TTATTT |
| 4 | TTTATT |
| 5 | TTTTTT |
| 6 | TTTTAT |
| 7 | AATTTT |
| 8 | TTTTTA |
| 9 | TAATTT |
| 10 | TTAATT |
| 11 | AAATTT |
| 12 | AAATAA |
| 13 | ATATTT |
| 14 | TTTGTT |
| 15 | TTGTTT |
| 16 | ATATAT |
| 17 | ATTATT |
| 18 | ATTTTA |
| 19 | TTTAAT |
| 20 | TTTTAA |

The present invention provides a synthetic DNA sequence for expressing a protein of interest in maize cells which comprises:
  a) a codon-optimized DNA sequence encoding the protein of interest,
  b) at least one polyadenylation signal sequence chosen from the group consisting of Class I and Class II wherein;
    Class I is chosen from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA; and
    Class II is chosen from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, and AAATAA; and
  wherein said codon-optimized DNA sequence contains— at least one polyadenylation signal sequence from Class II and wherein said synthetic DNA sequence contains fewer Class II polyadenylation signal sequences than the protein's native DNA sequence and contains the same number of Class I polyadenylation signal sequences compared to the native DNA sequence.

The present invention also provides a synthetic DNA sequence for expressing a protein of interest in soybean cells which comprises:
  a) a codon-optimized DNA sequence encoding the protein of interest,
  b) at least one polyadenylation signal sequence chosen from the group consisting of Class I and Class III wherein;
    Class I is chosen from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA; and
    Class III is chosen from the group consisting of ATTTTT, TATTTT, TTATTT, TTTATT, TTTTTT, TTTTAT, AATTTT, TTTTTA, ATATAT, TAATTT, TTAATT, AAATTT, AAATAA, ATATTT, TTTGTT, TTGTTT, ATTATT, ATTTTA, TTTAAT, and TTTAA, and
  wherein said codon-optimized DNA sequence contains at least one polyadenylation signal sequence from Class III and wherein said synthetic DNA sequence contains fewer Class III polyadenylation signal sequences than the protein's native DNA sequence and contains the same number of Class I polyadenylation signal sequences compared to the native DNA sequence.

The invention also provides a method of making a synthetic DNA sequence that encodes a protein of interest which comprises (a) starting with an amino acid sequence of a protein of interest derived from naturally occurring polypeptide(s) encoded by native sequence(s) that comprise at least one polyadenylation signal sequence listed in Table 2, and (b) making a synthetic DNA sequence that encodes said amino acid sequence and contains fewer polyadenylation signal sequences listed in Table 2 compared to the corresponding coding sequence of the native sequence(s) and contains the same number of polyadenylation signal sequences listed in Table 1.

In another embodiment the invention provides a method of making a synthetic DNA sequence that encodes a protein of interest which comprises (a) starting with an amino acid sequence of a protein of interest derived from naturally occurring polypeptide(s) encoded by native sequence(s) that comprise at least one polyadenylation signal sequence-listed in Table 3, and (b) making a synthetic DNA sequence that encodes said amino acid sequence and contains fewer polyadenylation signal sequences listed in Table 3 compared to the corresponding coding sequence of the native sequence(s) and contains the same number of polyadenylation signal sequences listed in Table 1.

In some embodiments the synthetic DNA sequences provided by the invention are devoid of the polyadenylation signal sequences listed in Table 2 and/or Table 3, or the number of polyadenylation signal sequences identified in Table 2 and/or Table 3 is reduced as much as possible consistent with maintaining the same number of polyadenylation signal sequences identified in Table 1 and maintaining the Table 1 sequences in their original positions in the sequence.

In some embodiments the synthetic DNA sequences provided by the invention encode an insecticidal protein, optionally derived from *Bacillus thuringiensis*, as well as DNA sequences useful for herbicide tolerance, water and/or heat stress tolerance, healthy oil modifications and for transformation marker genes and selectable marker genes.

The synthetic DNA sequences of the invention may be used in a DNA construct for expression of a protein of interest, where the construct comprises a 5' non-translated sequence, a synthetic DNA sequence of the invention, and a 3' non-translated region, and said 5' non-translated sequence contains a promoter that functions in plants, and said 3' non-translated sequence comprises a transcription termination and polyadenylation signal.

The invention also provides a transgenic plant containing the synthetic DNA sequences of the invention.

Also provided is a method of controlling pests in a plant which comprises expressing a synthetic DNA sequence of the invention in the plant where the synthetic DNA sequence encodes an insect toxin, for example a *Bacillus thuringiensis* Cry protein.

Also provided is a method for herbicide tolerance in a plant which comprises expressing a synthetic DNA sequence of the invention in the plant where the synthetic DNA sequence encodes a known herbicide tolerance enzyme, for example the aryloxyalkanoate dioxygenase (AAD1) see WO/2005/107437, or phosphinothricin acetylransferase, or 5-enolpyruvylshikimate-3-phosphate synthase enzymes.

Also provided is a method for modifying oil profiles in a plant which comprises expressing one or more synthetic DNA sequences of the invention in the plant where the synthetic DNA sequence encodes one or more known enzymes for modifying oil profiles in plants, for example fatty acid desaturase.

Also provided is a method for stress tolerance in a plant which comprises expressing a synthetic DNA sequence of the invention in the plant where the synthetic DNA sequence encodes known stress tolerance genes for water and/or heat stress, for example the stress associated protein (SAP1); US Patent Publication No: 2010/0275327, and 1-Cys peroxiredoxin (Per1) proteins (Mowla, et al., 2002, Planta 215:716-726).

Also provided is a method adding reporter genes in a plant which comprises expressing a synthetic DNA sequence of the invention in the plant where the synthetic DNA sequence encodes a known transformation marker protein functional in plants, for example green fluorescence protein (GFP) or beta glucuronidase enzyme.

Also provided is a method of controlling pests in grain or seed which comprises obtaining said grain or seed from plants containing a synthetic gene of the invention that expresses an insect toxin, and a method of controlling pests in meal or flour which comprises obtaining said meal or flour from grain containing a synthetic gene of the invention that expresses an insect toxin.

Also provided is a composition derived from transgenic plants containing synthetic DNA of the invention wherein said composition is a commodity product selected from the group consisting of meal, flour, protein concentrate, or oil.

In some cases the number of polyadenylation signals listed in Table 1 can be maintained in synthetic DNA sequences of the invention by deleting occurrences of AATAAA and substituting another polyadenylation signal sequence listed in Table 1. This is exemplified in Example 1, SEQ ID NO:5.

DESCRIPTION OF THE SEQUENCES

SEQ ID NO:1 is the native DNA sequence encoding *Bacillus thuringiensis* Cry1Fa core toxin.

SEQ ID NO:2 is *Bacillus thuringiensis* Cry1Fa core toxin sequence.

SEQ ID NO:3 is a synthetic DNA sequence encoding *Bacillus thuringiensis* Cry1Fa core toxin using codons optimized for maize and Table 1 sequences are maintained.

SEQ ID NO:4 is *Bacillus thuringiensis* Cry1Fa core toxin sequence.

SEQ ID NO:5 is a synthetic DNA sequence in accordance with the invention encoding-*Bacillus thuringiensis* Cry1Fa core toxin using codons optimized for maize and with sequences identified in Table 2 removed and Table 1 sequences are maintained.

SEQ ID NO 6 is *Bacillus thuringiensis* Cry1Fa core toxin sequence.

SEQ ID NO:7 is the native DNA sequence encoding *Bacillus thuringiensis* Cry34Ab1 toxin.

SEQ ID NO:8 is *Bacillus thuringiensis* Cry34Ab1 toxin sequence.

SEQ ID NO:9 is a synthetic DNA sequence encoding *Bacillus thuringiensis* Cry34Ab1 toxin using codons optimized for maize and Table 1 sequences are maintained.

SEQ ID NO:10 is *Bacillus thuringiensis* Cry34Ab1 toxin sequence.

SEQ ID NO:11 is a synthetic DNA sequence in accordance with the invention encoding *Bacillus thuringiensis* Cry34Ab1 toxin using codons optimized for maize and with sequences identified in Table 2 removed and Table 1 sequences are maintained.

SEQ ID NO:12 is *Bacillus thuringiensis* Cry34Ab1 toxin sequence.

SEQ ID NO:13 is the native DNA sequence encoding *Bacillus thuringiensis* Cry35Ab1 toxin.

SEQ ID NO:14 is *Bacillus thuringiensis* Cry35Ab1 toxin sequence.

SEQ ID NO:15 is a synthetic DNA sequence encoding *Bacillus thuringiensis* Cry35Ab1 toxin using codons optimized for maize and Table 1 sequences are maintained SEQ ID NO:16 is *Bacillus thuringiensis* Cry35Ab1 toxin sequence.

SEQ ID NO:17 is a synthetic DNA sequence in accordance with the invention encoding *Bacillus thuringiensis* Cry35Ab1 toxin using codons optimized for maize and with sequences identified in Table 2 removed and Table 1 sequences are maintained.

SEQ ID NO:18 is *Bacillus thuringiensis* Cry35Ab1 toxin sequence.

SEQ ID NO:19 is the native DNA sequence encoding *Bacillus thuringiensis* Cry1Ab1 core toxin.

SEQ ID NO:20 is *Bacillus thuringiensis* Cry1Ab1 core toxin sequence.

SEQ ID NO:21 is a synthetic DNA sequence encoding *Bacillus thuringiensis* Cry1Ab1 core toxin using codons optimized for maize and Table 1 sequences are maintained.

SEQ ID NO:22 is *Bacillus thuringiensis* Cry1Ab1 core toxin sequence.

SEQ ID NO:23 is a synthetic DNA sequence in accordance with the invention encoding-*Bacillus thuringiensis* Cry1Ab1 core toxin using codons optimized for maize and with sequences identified in Table 2 removed and Table 1 sequences are maintained.

SEQ ID NO:24 is *Bacillus thuringiensis* Cry1Ab1 core toxin sequence.

SEQ ID NO:25 is the native DNA sequence encoding *Bacillus thuringiensis* Cry1Ca core toxin.

SEQ ID NO:26 is encoding *Bacillus thuringiensis* Cry1Ca core toxin sequence.

SEQ ID NO:27 is a synthetic DNA sequence encoding *Bacillus thuringiensis* Cry1Ca core toxin using codons optimized for maize and Table 1 sequences are maintained.

SEQ ID NO:28 is encoding *Bacillus thuringiensis* Cry1Ca core toxin sequence.

SEQ ID NO:29 is a synthetic DNA sequence in accordance with the invention encoding *Bacillus thuringiensis* Cry1Ca core toxin using codons optimized for maize and with sequences identified in Table 2 removed and Table 1 sequences are maintained.

SEQ ID NO:30 is encoding *Bacillus thuringiensis* Cry1Ca core toxin sequence.

SEQ ID NO:31 is the native DNA sequence encoding *Bacillus thuringiensis* Cry6Aa toxin.

SEQ ID NO:32 is *Bacillus thuringiensis* Cry6Aa toxin sequence.

SEQ ID NO:33 is a synthetic DNA sequence encoding *Bacillus thuringiensis* Cry6Aa toxin using codons optimized for maize and Table 1 sequences are maintained.

SEQ ID NO:34 is *Bacillus thuringiensis* Cry6Aa toxin sequence.

SEQ ID NO:35 is a synthetic DNA sequence in accordance with the invention encoding *Bacillus thuringiensis* Cry6Aa toxin using codons optimized for maize and with sequences identified in Table 2 removed and Table 1 sequences are maintained.

SEQ ID NO:36 is *Bacillus thuringiensis* Cry6Aa toxin sequence.

SEQ ID NO:37 is the native DNA sequence encoding *Sphingobiurn herbicidovorans* AAD1 protein.

SEQ ID NO:38 is *Sphingobiurn herbicidovorans* AAD1 protein sequence.

SEQ ID NO:39 is a synthetic DNA sequence encoding *Sphingobiurn herbicidovorans* AAD1 protein using codons optimized for maize and Table 1 & Table 2 sequences are maintained.

SEQ ID NO:40 is *Sphingobiurn herbicidovorans* AAD1 protein sequence.

SEQ ID NO:41 is a synthetic DNA sequence in accordance with the invention encoding *Sphingobiurn herbicidovorans* AAD1 protein using codons optimized for maize and with sequences identified in Table 2 removed and Table 1 sequences are maintained.

SEQ ID NO:42 is *Sphingobiurn herbicidovorans* AAD1 protein sequence.

SEQ ID NO:43 is the native DNA sequence encoding *Aspergillus nidulans* delta-9 fatty acid desaturase protein.

SEQ ID NO:44 is *Aspergillus nidulans* delta-9 fatty acid desaturase protein sequence.

SEQ ID NO:45 is a synthetic DNA sequence encoding *Aspergillus nidulans* delta-9 fatty acid desaturase protein using codons optimized for maize and Table 1 & Table 2 sequences are maintained.

SEQ ID NO:46 is *Aspergillus nidulans* delta-9 fatty acid desaturase protein sequence.

SEQ ID NO:47 is a synthetic DNA sequence in accordance with the invention encoding *Aspergillus nidulans* delta-9 fatty acid desaturase protein using codons optimized for maize and with sequences identified in Table 2 removed and Table 1 sequences are maintained.

SEQ ID NO:48 is *Aspergillus nidulans* delta-9 fatty acid desaturase protein.

SEQ ID NO:49 is the native DNA sequence encoding *Xerophyta viscosa* SAP1 protein.

SEQ ID NO:50 is *Xerophyta viscosa* SAP1 protein sequence.

SEQ ID NO:51 is a synthetic DNA sequence encoding *Xerophyta viscosa* SAP1 protein using codons optimized for maize and Table 1 & Table 2 sequences are maintained SEQ ID NO:52 is *Xerophyta viscosa* SAP1 protein sequence.

SEQ ID NO:53 is a synthetic DNA sequence in accordance with the invention encoding *Xerophyta viscosa* SAP1 protein using codons optimized for maize and with sequences identified in Table 2 removed and Table 1 sequences are maintained SEQ ID NO:54 is *Xerophyta viscosa* SAP1 protein sequence.

SEQ ID NO:55 is the native DNA sequence encoding *Aequorea victoria* GFP1 protein.

SEQ ID NO:56 is *Aequorea victoria* GFP1 protein sequence.

SEQ ID NO:57 is a synthetic DNA sequence encoding *Aequorea victoria* GFP1 protein using codons optimized for maize and Table 1 & Table 2 sequences are maintained.

SEQ ID NO:58 is *Aequorea victoria* GFP1 protein sequence.

SEQ ID NO:59 is a synthetic DNA sequence in accordance with the invention encoding *Aequorea victoria* GFP1 protein using codons optimized for maize and with sequences identified in Table 2 removed and Table 1 sequences are maintained.

SEQ ID NO:60 is *Aequorea victoria* GFP1 protein sequence.

SEQ ID NO:61 is the native DNA sequence encoding *Leptosphaeria nodorum* delta-9 fatty acid desaturase protein.

SEQ ID NO:62 is *Leptosphaeria nodorum* delta-9 fatty acid desaturase protein sequence.

SEQ ID NO:63 is a synthetic DNA sequence encoding *Leptosphaeria nodorum* delta-9 fatty acid desaturase protein using codons optimized for maize and Table 1 & Table 2 sequences are maintained SEQ ID NO:64 is *Leptosphaeria nodorum* delta-9 fatty acid desaturase protein sequence.

SEQ ID NO:65 is a synthetic DNA sequence in accordance with the invention encoding *Leptosphaeria nodorum* delta-9 fatty acid desaturase protein using codons optimized for maize and with sequences identified in Table 2 removed and Table 1 sequences are maintained SEQ ID NO:66 is *Leptosphaeria nodorum* delta-9 fatty acid desaturase protein sequence.

SEQ ID NO:67 is the native DNA sequence encoding *Xerophyta viscosa* PER1 protein.

SEQ ID NO:68 is *Xerophyta viscosa* PER1 protein sequence.

SEQ ID NO:69 is a synthetic DNA sequence encoding *Xerophyta viscosa* PER1 protein using codons optimized for maize and Table 1 & Table 2 sequences are maintained.

SEQ ID NO:70 is *Xerophyta viscosa* PER1 protein sequence.

SEQ ID NO:71 is a synthetic DNA sequence in accordance with the invention encoding-*Xerophyta viscosa* PER1 protein using codons optimized for maize and with sequences identified in Table 2 removed and Table 1 sequences are maintained.

SEQ ID NO:72 is *Xerophyta viscosa* PER1 protein sequence.

DETAILED DESCRIPTION OF THE INVENTION

The invention provides synthetic nucleic acid sequences encoding proteins of interest. The synthetic coding sequences are particularly adapted for use in expressing the proteins of interest in transgenic plants.

A protein of interest is any protein or polypeptide that occurs in nature, or any naturally occurring variant including but not limited to processed forms of such proteins. The protein of interest also may be a protein formed by combining portions or fragments of more than one naturally occurring protein such as by mixing and matching functional protein domains.

A preferred group of proteins of interest is one in which the resulting phenotype is an agronomic trait or reporter protein useful for creating agronomic traits. These include but are not limited to resistance to insects, tolerance to herbicides, tolerance to water and/or heat stress, and oil profile modification.

A more preferred group of proteins of interest is one in which the resulting phenotype is an agronomic trait. Another preferred group is one in which the resulting phenotype provides herbicide tolerance. Another preferred group is one in which the resulting phenotype provides stress tolerance. Another preferred group is one in which the resulting phenotype provides a modified oil profile for healthier food. A more highly preferred group is one in which the protein of interest is a Cry protein that provides insect resistance.

The native/wild-type DNA sequences encoding the protein of interest must be identified and analyzed to determine whether polyadenylation signal sequences listed in Tables 1 and 2 and/or 3 are present. In accordance with the invention, for coding sequences intended for use in maize, the number of polyadenylation signal sequences listed in Table 2 is reduced compared to the number present in the native sequence. For coding sequences intended for use in soybean, the number of polyadenylation signal sequences listed in Table 3 is reduced. It is very important to remove the polyadenylation signal sequences listed in Tables 2 and 3, particularly where they occur in nested multimeric form.

In addition to removing polyadenylation signal sequences listed in Tables 2 and 3, it may be desirable to remove occurrences of the Shaw-Kamen sequence, ATTTA.

In addition to removing polyadenylation signal sequences and Shaw-Kamen sequences, we prefer to build synthetic DNA coding sequences that utilize codons roughly in the same frequency at which they are utilized, on average, in genes naturally occurring in the plant species in which the synthetic DNA sequence will be used. Table 4 gives suitable target percentages for codon usage in synthetic genes intended for use in various specific crops as well as for use in dicots generally or plants generally.

TABLE 4

Target rescaled codon compositions of synthetic plant genes.

| Amino Acid | Codon | Maize % | Soybean % |
|---|---|---|---|
| ALA (A) | GCA | 18.0 | 33.1 |
| | GCC | 34.0 | 24.5 |
| | GCG | 24.0 | 0 |
| | GCT | 24.0 | 42.3 |
| ARG (R) | AGA | 18.8 | 36.0 |
| | AGG | 32.5 | 32.2 |
| | CGA | 0 | 0 |
| | CGC | 30.0 | 15 |
| | CGG | 18.8 | 0 |
| | CGT | 0 | 16.9 |
| ASN (N) | AAC | 68.0 | 50.0 |
| | AAT | 32.0 | 50.0 |
| ASP (D) | GAC | 63.0 | 38.1 |
| | GAT | 37.0 | 61.9 |
| CYS (C) | TGC | 68.0 | 50.0 |
| | TGT | 32.0 | 50.0 |
| END | TAA | 0 | 0 |
| | TAG | 0 | 0 |
| | TGA | 100 | 100 |
| GLN (Q) | CAA | 38.0 | 55.5 |
| | CAG | 62.0 | 44.5 |

TABLE 4-continued

Target rescaled codon compositions of synthetic plant genes.

| Amino Acid | Codon | Maize % | Soybean % |
|---|---|---|---|
| GLU (E) | GAA | 29.0 | 50.5 |
| | GAG | 71.0 | 49.5 |
| GLY (G) | GGA | 19.0 | 31.9 |
| | GGC | 42.0 | 19.3 |
| | GGG | 19.0 | 18.4 |
| | GGT | 20.0 | 30.4 |
| HIS (H) | CAC | 62.0 | 44.8 |
| | CAT | 38.0 | 55.2 |
| ILE (I) | ATA | 14.0 | 23.4 |
| | ATC | 58.0 | 29.9 |
| | ATT | 28.0 | 46.7 |
| LEU (L) | CTA | 0 | 0 |
| | CTC | 29.9 | 22.4 |
| | CTG | 33.3 | 16.3 |
| | CTT | 19.5 | 31.5 |
| | TTA | 0 | 0 |
| | TTG | 17.2 | 29.9 |
| LYS (K) | AAA | 22.0 | 42.5 |
| | AAG | 78.0 | 57.5 |
| MET (M) | ATG | 100 | 100 |
| PHE (F) | TTC | 71.0 | 49.2 |
| | TTT | 29.0 | 50.8 |
| PRO (P) | CCA | 26.0 | 39.8 |
| | CCC | 24.0 | 20.9 |
| | CCG | 28.0 | 0.0 |
| | CCT | 22.0 | 39.3 |
| SER (S) | AGC | 25.3 | 16.0 |
| | AGT | 0.0 | 18.2 |
| | TCA | 17.6 | 21.9 |
| | TCC | 25.3 | 18.0 |
| | TCG | 15.4 | 0 |
| | TCT | 16.5 | 25.8 |
| THR (T) | ACA | 21.0 | 32.4 |
| | ACC | 37.0 | 30.2 |
| | ACG | 22.0 | 0.0 |
| | ACT | 20.0 | 37.4 |
| TRP (W) | TGG | 100 | 100 |
| TYR (Y) | TAC | 73.0 | 48.2 |
| | TAT | 27.0 | 51.8 |
| VAL (V) | GTA | 0 | 11.5 |
| | GTC | 34.8 | 17.8 |
| | GTG | 42.4 | 32.0 |
| | GTT | 22.8 | 38.7 |

Transgenic Plants

A preferred embodiment of the subject invention is the transformation of plants with genes encoding insect toxins. The transformed plants that express insect toxin genes are resistant to attack by an insect target pest by virtue of the presence of controlling amounts of the subject insecticidal protein or its variants in the cells of the transformed plant. By incorporating genetic material that encodes the insecticidal properties of the B. t. insecticidal toxins into the genome of a plant eaten by a particular insect pest, the adult or larvae die after consuming the food plant. Numerous members of the monocotyledonous and dicotyledonous classifications have been transformed. Transgenic agronomic crops as well as fruits and vegetables are of commercial interest. Such crops include but are not limited to maize, rice, soybeans, canola, sunflower, alfalfa, sorghum, wheat, cotton, peanuts, tomatoes, potatoes, and the like. Several techniques exist for introducing foreign genetic material into plant cells, and for obtaining plants that stably maintain and express the introduced gene. Such techniques include acceleration of genetic material coated onto microparticles directly into cells (U.S. Pat. No. 4,945,050 and U.S. Pat. No. 5,141,131). Plants may be transformed using *Agrobacterium* technology, see U.S. Pat. No. 5,177,010, European Patent No. EP131624B1, European Patent No. EP159418B1, European Patent No. EP176112B1, U.S. Pat. No. 5,149,645, EP120516B1, U.S. Pat. No. 5,464,763, U.S. Pat. No. 4,693, 976, European Patent No. EP116718B1, European Patent No. EP290799B1, European Patent No. EP320500B1, European Patent No. EP604662B1, U.S. Pat. No. 7,060,876, U.S. Pat. No. 6,037,526, U.S. Pat. No. 6,376,234, European Patent No. EP292435B1, U.S. Pat. No. 5,231,019, U.S. Pat. No. 5,463,174, U.S. Pat. No. 4,762,785, U.S. Pat. No. 5,608,142, and U.S. Pat. No. 5,159,135. Other transformation technology includes WHISKERS™ technology, see U.S. Pat. No. 5,302,523 and U.S. Pat. No. 5,464,765. Electroporation technology has also been used to transform plants, see WO1987006614, U.S. Pat. No. 5,472,869, U.S. Pat. No. 5,384,253, WO199209696, U.S. Pat. No. 6,074, 877, WO1993021335, and U.S. Pat. No. 5,679,558. In addition to numerous technologies for transforming plants, the type of tissue which is contacted with the foreign genes may vary as well. Such tissue would include but would not be limited to embryogenic tissue, callus tissue type I and type II, hypocotyl, meristem, and the like. Almost all plant tissues may be transformed during dedifferentiation using appropriate techniques within the skill of an artisan.

Known techniques of inserting DNA into plants include transformation with T-DNA delivered by *Agrobacterium tumefaciens* or *Agrobacterium rhizogenes* as the transformation agent. The use of T-DNA-containing vectors for the transformation of plant cells has been intensively researched and sufficiently described in European Patent No. EP120516B1; Lee and Gelvin (2008) Plant Physiol. 146: 325-332; Fraley et al. (1986) Crit. Rev. Plant Sci. 4:1-46; and An et al. (1985) EMBO J. 4:277-284; and is well established in the field. Additionally, fusion of plant protoplasts with liposomes containing the DNA to be delivered, direct injection of the DNA, biolistics transformation (microparticle bombardment), or electroporation, as well as other possible methods, may be employed.

Once the inserted DNA has been integrated into the plant genome, it is relatively stable throughout subsequent generations. The vector used to transform the plant cell normally contains a selectable marker gene encoding a protein that confers on the transformed plant cells resistance to a herbicide or an antibiotic, such as Bialaphos, Kanamycin, G418, Bleomycin, or Hygromycin, inter alia. The individually employed selectable marker gene should accordingly permit the selection of transformed cells while the growth of cells that do not contain the inserted DNA is suppressed by the selective compound.

In a preferred embodiment of the subject invention, plants are transformed with genes wherein the codon usage of the protein coding region has been optimized for plants. See, for example, U.S. Pat. No. 5,380,831. Also, advantageously, plants encoding a truncated toxin, e.g. a functional protein domain, maybe used. The truncated toxin typically encodes about 55% to about 80% of the native full length toxin. Methods for creating synthetic B. t. genes for use in plants are known in the art (Stewart 2007, Frontiers in Drug Design and Discovery 1:297-341).

Regardless of transformation technique, the gene is preferably incorporated into a gene transfer vector adapted to express the protein of interest in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g. actin, ubiquitin, CaMV 35S). Tissue specific promoters are responsible for gene expression in specific cell or tissue types, such as the leaves or seeds (e.g. zein, oleosin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen-specific, embryo specific, corn silk specific, cotton fiber specific, seed endosperm specific, phloem specific, and the like.

Under certain circumstances it may be desirable to use an inducible promoter. An inducible promoter is responsible for expression of genes in response to a specific signal, such as: physical stimulus (e.g. heat shock genes); light (e.g. RUBP carboxylase); hormone (e.g. glucocorticoid); antibiotic (e.g. tetracycline); metabolites; and stress (e.g. drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

Transgenic crops containing insect resistance (IR) traits are prevalent in corn and cotton plants throughout North America, and usage of these traits is expanding globally. Commercial transgenic crops combining IR and herbicide tolerance (HT) traits have been developed by numerous seed companies. These include combinations of IR traits conferred by B. t. insecticidal proteins and HT traits such as tolerance to Acetolactate Synthase (ALS) inhibitors such as sulfonylureas, imidazolinones, triazolopyrimidine, sulfonanilides, and the like, Glutamine Synthetase (GS) inhibitors such as Bialaphos, glufosinate, and the like, 4-HydroxyPhenylPyruvate Dioxygenase (HPPD) inhibitors such as mesotrione, isoxaflutole, and the like, 5-EnolPyruvylShikimate-3-Phosphate Synthase (EPSPS) inhibitors such as glyphosate and the like, and Acetyl-Coenzyme A Carboxylase (ACCase) inhibitors such as haloxyfop, quizalofop, diclofop, and the like. Other examples are known in which transgenically provided proteins provide plant tolerance to herbicide chemical classes such as phenoxy acids herbicides and pyridyloxyacetates auxin herbicides (see WO2007053482), or phenoxy acids herbicides and aryloxyphenoxypropionates herbicides (see US Patent Application No. 20090093366). The ability to control multiple pest problems through IR traits is a valuable commercial product concept, and the convenience of this product concept is enhanced if insect control traits and weed control traits are combined in the same plant. Further, improved value may be obtained via single plant combinations of IR traits conferred by a B. t. insecticidal protein such as that of the subject invention with one or more additional HT traits such as those mentioned above, plus one or more additional input traits (e.g. other insect resistance conferred by B. t.-derived or other insecticidal proteins, insect resistance conferred by mechanisms such as RNAi and the like, nematode resistance, disease resistance, stress tolerance, improved nitrogen utilization, and the like), or output traits (e.g high oils content, healthy oil composition, nutritional improvement, and the like). Such combinations may be obtained either through conventional breeding (breeding stack) or jointly as a novel transformation event involving the simultaneous introduction of multiple genes (molecular stack or co-transformation). Benefits include the ability to manage insect pests and improved weed control in a crop plant that provides secondary benefits to the producer and/or the consumer. Thus, the subject invention can be used in connection with a variety of traits to provide a complete agronomic package of improved crop quality with the ability to flexibly and cost effectively control any number of agronomic issues.

All patents, patent applications, provisional applications, and publications referred to or cited herein are incorporated by reference in their entirety to the extent they are not inconsistent with the explicit teachings of this specification. Unless specifically indicated or implied, the terms "a", "an", and "the" signify "at least one" as used herein. By "isolated" applicants mean that the nucleotide or polypeptide molecules have been removed from their native environment and have been placed in a different environment by the hand of man.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

All percentages are by weight and all solvent mixture proportions are by volume unless otherwise noted. All temperatures are in degrees Celsius.

Example 1

Synthetic Coding Region Encoding Bacillus thuringiensis Cry1Fa Core Toxin

Comparative Sequence. The native DNA sequence encoding the Cry1Fa core toxin is given in SEQ ID NO:1. This sequence was analyzed to determine which sequences identified in Table 1 are present in SEQ ID NO:1 and their locations. The amino acid sequence encoded by SEQ ID NO:1 was then reverse translated using the target codon frequencies given in the column of Table 4 for synthetic genes to be used in maize. The resulting DNA sequence was analyzed and codons were changed where necessary to remove unwanted open reading frames and remove unwanted restriction sites, and restore sequences identified in Table 1. The amino acid sequence encoded by SEQ ID NO:1 was preserved. The resulting DNA sequence is given in SEQ ID NO:3.

SEQ ID NO:3 was analyzed and codons were changed to remove potential polyadenylation signal sequences identified in Table 2, while maintaining the same number of sequences identified in Table 1. The resulting sequence, which embodies the present invention, is given in SEQ ID NO:5. Table 5 shows that the number and locations of polyadenylation signal sequences identified in Table 1 are maintained in SEQ ID NO:5, with the exception that the two occurrences of AATAAA, one at nt 426 and one at nt 582, in SEQ ID NO:1 were replaced with AATCAA, which maintains the number and location of polyadenylation signal sequences identified in Table 1, but substitutes a less problematic sequence for each of the two AATAAA sequences. Table 6 shows that the number of polyadenylation signal sequences identified in Table 2 are reduced in SEQ ID NO:5. Because there is overlap in the sequences identified in Tables 2 and 3 (sequences 1, 2, 6, 7, 8, 9, 10, 14, 13, and 20 in Table 2 correspond to sequences 16, 15, 2, 5, 1, 3, 4, 6, 13, and 12, respectively, in Table 3) it is also true that the number of polyadenylation signal sequences identified in Table 3 are reduced in SEQ ID NO:5.

The synthetic coding region of SEQ ID NO:5 was optimized for expression in maize.

A construct for use in expressing the synthetic coding region of SEQ ID NO:5 is made by combining the synthetic coding region of SEQ ID NO:5 with a 5' non-translated region comprising a promoter that functions in plant cells and a 3' non-translated region comprising a transcription termination and polyadenylation sequence.

In one embodiment of such a construct, production of the primary mRNA transcript comprising SEQ ID NO:5 was driven by a copy of a maize ubiquitin) promoter with its native intron) (U.S. Pat. No. 5,510,474). A fragment comprising a 3' untranslated region from a maize peroxidase 5 gene (ZmPer5 3'UTR v2; U.S. Pat. No. 6,699,984) was used to terminate transcription. A binary plant transformation plasmid, pDAB111440, containing the aforementioned gene expression cassette, was constructed and utilized in the production of transgenic maize plants. Plasmid pDAB111440 further comprises a herbicide resistance gene comprising a coding region for aryloxyalknoate dioxygenase (AAD-1 v3; U.S. Pat. No. 7,838,733(B2), and Wright et al. (2010) Proc. Natl. Acad. Sci. U.S.A. 107: 20240-5) under the transcriptional control of a sugarcane bacilliform badnavirus (ScBV) promoter (Schenk et al. (1999) Plant Molec. Biol. 39:1221-30). A fragment comprising a 3' untranslated region from a maize lipase gene (ZmLip 3'UTR; U.S. Pat. No. 7,179,902) was used to terminate transcription.

TABLE 5

Table 1 sequences found in the native Cry1Fa core toxin coding region (SEQ ID NO: 1) and in the redesigned version (SEQ ID NO: 5)

| Table 1 Sequence | | No. Sites in Native Cry1Fa core sequence (SEQ ID NO: 1) | nt Location in Native Cry1Fa core sequence (SEQ ID NO: 1) | No. Sites in redesigned Cry1Fa core sequence (SEQ ID NO: 5) | nt Location in redesigned Cry1Fa core sequence (SEQ ID NO: 5) |
|---|---|---|---|---|---|
| 1 | AATAAA | 2 | 426; 582 | 0 | NA* |
| 2 | AATAAT | 5 | 7; 46; 358; 430; 562 | 5 | 7; 46; 358; 430; 562 |
| 3 | AACCAA | 0 | NA | 0 | NA |

TABLE 5-continued

Table 1 sequences found in the native Cry1Fa core toxin coding region (SEQ ID NO: 1) and in the redesigned version (SEQ ID NO: 5)

| Table 1 Sequence | No. Sites in Native Cry1Fa core sequence (SEQ ID NO: 1) | nt Location in Native Cry1Fa core sequence (SEQ ID NO: 1) | No. Sites in redesigned Cry1Fa core sequence (SEQ ID NO: 5) | nt Location in redesigned Cry1Fa core sequence (SEQ ID NO: 5) |
|---|---|---|---|---|
| 4 ATATAA | 1 | 1520 | 1 | 1520 |
| 5 AATCAA | 2 | 19; 628 | 4 | 19; 426; 582; 628 |
| 6 ATACTA | 1 | 1508 | 1 | 1508 |
| 7 ATAAAA | 0 | NA | 0 | NA |
| 8 ATGAAA | 2 | 314; 1211 | 2 | 314; 1211 |
| 9 AAGCAT | 0 | NA | 0 | NA |
| 10 ATTAAT | 2 | 579; 1690 | 2 | 579; 1690 |
| 11 ATACAT | 0 | NA | 0 | NA |
| 12 AAAATA | 0 | NA | 0 | NA |
| 13 ATTAAA | 2 | 66; 1266 | 2 | 66; 1266 |
| 14 AATTAA | 2 | 368; 779 | 2 | 368; 779 |
| 15 AATACA | 3 | 400; 1369; 1693 | 3 | 400; 1369; 1693 |
| 16 CATAAA | 0 | NA | 0 | NA |
| Total | 22 | | 22 | |

*NA = Not Applicable

TABLE 6

Table 2 sequences found in the native Cry1Fa core toxin coding region (SEQ ID NO: 1) and in the redesigned version (SEQ ID NO: 5)

| Table 2 Sequence | No. Sites in Native Cry1Fa core sequence (SEQ ID NO: 1) | nt Location in Native Cry1Fa core sequence (SEQ ID NO: 1) | No. Sites in redesigned Cry1Fa core Sequence (SEQ ID NO: 5) | nt Location in redesigned Cry1Fa core Sequence (SEQ ID NO: 5) |
|---|---|---|---|---|
| 1 ATATAT | 1 | 104 | 0 | NA* |
| 2 TTGTTT | 3 | 39; 612; 907 | 0 | NA |
| 3 TTTTGT | 1 | 1089 | 0 | NA |
| 4 TGTTTT | 2 | 1086; 13340 | 0 | NA |
| 5 TATATA | 1 | 1771 | 0 | NA |
| 6 TATTTT | 0 | NA | 0 | NA |
| 7 TTTTTT | 0 | NA | 0 | NA |
| 8 ATTTTT | 1 | 1615 | 0 | NA |
| 9 TTATTT | 2 | 172; 217 | 0 | NA |
| 10 TTTATT | 0 | NA | 0 | NA |
| 11 TAATAA | 4 | 357; 416; 561; 581 | 0 | NA |
| 12 ATTTAT | 3 | 319; 497; 793 | 0 | NA |
| 13 TATATT | 1 | 322 | 0 | NA |
| 14 TTTTAT | 3 | 192; 464; 1063 | 0 | NA |
| 15 ATATTT | 0 | NA | 0 | NA |
| 16 TATTAT | 0 | NA | 0 | NA |
| 17 TGTTTG | 2 | 613; 908 | 0 | NA |
| 18 TTATAT | 2 | 321; 17700 | 0 | NA |
| 19 TGTAAT | 0 | NA | 0 | NA |
| 20 AAATAA | 2 | 45; 429 | 0 | NA |
| Total | 28 | | 0 | NA |

*NA = Not Applicable

Example 2

Synthetic Coding Region Encoding *Bacillus thuringiensis* Cry34A Toxin

Comparative Sequences. The native DNA sequence encoding the Cry34A toxin is given in SEQ ID NO:7. This sequence was analyzed to determine which sequences identified in Table 1 are present in SEQ ID NO:7 and their locations. The native DNA sequence was translated into the corresponding amino acid sequence using the standard genetic code. The amino acid sequence encoded by SEQ ID NO:7 was then reverse translated using the target codon frequencies given in the column of Table 7 for synthetic genes to be used in maize. The resulting DNA sequence was analyzed and codons were changed where necessary to remove unwanted open reading frames and remove unwanted restriction sites, and restore all sequences identified in Table 1. The amino acid sequence encoded by SEQ ID NO:7 was preserved. The resulting DNA sequence is given in SEQ ID NO:9. DNA having the sequence of SEQ ID NO:9 is synthesized.

SEQ ID NO:9 was analyzed and codons were changed to remove potential polyadenylation signal sequences identified in Table 2, while maintaining the same number of sequences identified in Table 1. The resulting sequence, which embodies the present invention, is given in SEQ ID NO:11. Table 7 shows that the number and locations of polyadenylation signals sequences identified in Table 1 are maintained in SEQ ID NO:11. Table 8 shows that the number of polyadenylation signal sequences identified in Tables 2 and 3 are reduced in SEQ ID NO:5.

DNA of SEQ ID NO:5 is synthesized, and expression levels observed in plant cells transformed to express this sequence are compared with expression levels observed in plant cells transformed to express SEQ ID NO:1 and SEQ ID NO:3.

The synthetic coding region of SEQ ID NO:5 was optimized for expression in maize.

A construct for use in expressing the synthetic coding region of SEQ ID NO:5 is made by combining the synthetic coding region of SEQ ID NO:5 with a 5' non-translated region comprising a promoter that functions in plant cells and a 3' non-translated region comprising a transcription termination and polyadenylation sequence.

TABLE 7

Table 1 sequences found in the native Cry34Ab1 coding region (SEQ ID NO: 7) and the redesigned version (SEQ ID NO: 11)

| Table 1 Sequence | No. Sites in native Cry34Ab1 sequence (SEQ ID NO: 7) | nt Location in native Cry34Ab1 sequence (SEQ ID NO: 7) | No. Sites in redesigned Cry34Ab1 sequence (SEQ ID NO: 11) | nt Location in redesigned Cry34Ab1 sequence (SEQ ID NO: 11) |
|---|---|---|---|---|
| 1 AATAAA | 2 | 247; 268 | 2 | 247; 268 |
| 2 AATAAT | 1 | 31 | 1 | 31 |
| 3 AACCAA | 0 | NA* | 0 | NA |
| 4 ATATAA | 0 | NA | 0 | NA |
| 5 AATCAA | 2 | 146; 310 | 2 | 146; 310 |
| 6 ATACTA | 1 | 329 | 1 | 329 |
| 7 ATAAAA | 1 | 65 | 1 | 65 |
| 8 ATGAAA | 1 | 281 | 1 | 281 |
| 9 AAGCAT | 0 | NA | 0 | NA |
| 10 ATTAAT | 0 | NA | 0 | NA |
| 11 ATACAT | 1 | 47 | 1 | 47 |
| 12 AAAATA | 0 | NA | 0 | NA |
| 13 ATTAAA | 1 | 127 | 1 | 127 |
| 14 AATTAA | 1 | 126 | 1 | 126 |
| 15 AATACA | 0 | NA | 0 | NA |
| 16 CATAAA | 1 | 361 | 1 | 361 |
| Total | 12 | | 12 | |

*NA = Not Applicable

TABLE 8

Table 2 sequences found in the native Cry34Ab1 coding region (SEQ ID NO: 7) and in the redesigned version (SEQ ID NO: 11)

| Table 2 Sequence | No. Sites in native Cry34Ab1 sequence (SEQ ID NO: 7) | nt Location in native Cry34Ab1 sequence (SEQ ID NO: 7) | No. Sites in redesigned Cry34Ab1 sequence (SEQ ID NO: 11) | nt Location in redesigned Cry34Ab1 sequence (SEQ ID NO: 11) |
|---|---|---|---|---|
| 1 ATATAT | 1 | 181 | 0 | NA* |
| 2 TTGTTT | 0 | NA | 0 | NA |
| 3 TTTTGT | 0 | NA | 0 | NA |
| 4 TGTTTT | 0 | NA | 0 | NA |
| 5 TATATA | 1 | 180 | 0 | NA |
| 6 TATTTT | 1 | 220 | 0 | NA |
| 7 TTTTTT | 0 | NA | 0 | NA |
| 8 ATTTTT | 0 | NA | 0 | NA |
| 9 TTATTT | 0 | NA | 0 | NA |
| 10 TTTATT | 0 | NA | 0 | NA |
| 11 TAATAA | 2 | 33; 246 | 2 | 33; 246 |
| 12 ATTTAT | 0 | NA | 0 | NA |
| 13 TATATT | 2 | 182; 218 | 0 | NA |
| 14 TTTTAT | 1 | 156 | 0 | NA |
| 15 ATATTT | 1 | 219 | 0 | NA |
| 16 TATTAT | 1 | 184 | 0 | NA |
| 17 TGTTTG | 0 | NA | 0 | NA |
| 18 TTATAT | 1 | 217 | 0 | NA |
| 19 TGTAAT | 0 | NA | 0 | NA |
| 20 AAATAA | 1 | 30 | 1 | 30 |
| Total | 12 | | 3 | |

*NA = Not Applicable

Example 3

Synthetic Coding Region Encoding *Bacillus thuringiensis* Cry35Ab1 Toxin

Comparative Sequences. The native DNA sequence encoding the Cry35Ab1 toxin is given in SEQ ID NO:13. This sequence was analyzed to determine which sequences identified in Table 1 are present in SEQ ID NO:13 and their locations. The amino acid sequence encoded by SEQ ID NO:13 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:13 was preserved. The resulting DNA sequence is given in SEQ ID NO:15. This sequence will be synthesized and used for comparison with a synthetic coding region designed in accordance with the invention.

SEQ ID NO:15 was analyzed and codons were changed to remove potential polyadenylation signal sequences identified in Table 2, while maintaining the same number of sequences identified in Table 1, except that two of the occurrences of AATAAA, one at nt 228 and one at nt 276 of SEQ ID NO:8 were changed to AATCAA. The resulting sequence, which embodies the present invention, is given in SEQ ID NO:17. Table 9 shows that the number and location of polyadenylation signal sequences identified in Table 1 are maintained in SEQ ID NO:17. Table 10 shows that the number of polyadenylation signal sequences identified in Tables 2 and 3 are reduced in SEQ ID NO:17 compared to SEQ ID NO:13.

DNA of SEQ ID NO:17 is synthesized, and expression levels observed in plant cells transformed to express this sequence are compared with expression levels observed in plant cells transformed to express SEQ ID NO:13 and SEQ ID NO:15.

The synthetic coding region of SEQ ID NO:17 was optimized for expression in maize.

A construct for use in expressing the synthetic coding region of SEQ ID NO:17 is made by combining the synthetic coding region of SEQ ID NO:17 with a 5' non-translated region comprising a promoter that functions in plant cells and a 3' non-translated region comprising a transcription termination and polyadenylation sequence.

TABLE 9

Table 1 sequences found in the native Cry35Ab1 coding region (SEQ ID NO: 13) and in the redesigned version (SEQ ID NO: 17)

| Table 1 Sequence | Table 1 Sequence | No. Sites in native Cry35Ab1 sequence (SEQ ID NO: 13) | nt Location in native Cry35Ab1 sequence (SEQ ID NO: 13) | No. Sites in redesigned Cry35Ab1 sequence (SEQ ID NO: 17) | nt Location in redesigned Cry35Ab1 sequence (SEQ ID NO: 17) |
|---|---|---|---|---|---|
| 1 | AATAAA | 5 | 13; 100; 228; 276; 810 | 3 | 13; 100; 810 |
| 2 | AATAAT | 4 | 193; 217; 385; 864 | 4 | 193; 217; 385; 864 |
| 3 | AATCAA | 0 | NA* | 0 | NA |
| 4 | ATATAA | 1 | 966 | 1 | 966 |
| 5 | AATCAA | 3 | 394; 750; 914 | 5 | 228; 276; 394; 750; 914 |
| 6 | ATACTA | 1 | 8 | 1 | 8 |
| 7 | ATAAAA | 5 | 101; 224; 277; 575; 811 | 5 | 101; 224; 277; 575; 811 |
| 8 | ATGAAA | 5 | 23; 671; 769; 806; 854 | 5 | 23; 671; 769; 806; 854 |
| 9 | AAGCAT | 0 | NA | 0 | NA |
| 10 | ATTAAT | 1 | 522 | 1 | 522 |
| 11 | ATACAT | 1 | 734 | 1 | 734 |
| 12 | AAAATA | 7 | 226; 578; 618; 838; 862; 873; 1137 | 7 | 226; 578; 618; 838; 862; 873; 1137 |
| 13 | ATTAAA | 4 | 462; 589; 834; 1131 | 4 | 462; 589; 834; 1131 |
| 14 | AATTAA | 5 | 461; 521; 588; 833; 1130 | 5 | 461; 521; 588; 833; 1130 |
| 15 | AATACA | 3 | 261; 303; 733 | 3 | 261; 303; 733 |
| 16 | CATAAA | 0 | NA | 0 | NA |
| Total | | 45 | | 45 | |

*NA = Not Applicable

TABLE 10

Table 2 sequences found in the native Cry35Ab1 coding region (SEQ ID NO: 13) and in the redesigned version (SEQ ID NO: 17)

| Table 2 Sequence | Table 2 Sequence | No. Sites in native Cry35Ab1 sequence (SEQ ID NO: 13) | nt Location in native Cry35Ab1 sequence (SEQ ID NO: 13) | No. Sites in redesigned Cry35Ab1 sequence (SEQ ID NO: 17) | nt Location in redesigned Cry35Ab1 sequence (SEQ ID NO: 17) |
|---|---|---|---|---|---|
| 1 | ATATAT | 1 | 168 | 0 | NA* |
| 2 | TTGTTT | 0 | NA | 0 | NA |
| 3 | TTTTGT | 0 | NA | 0 | NA |
| 4 | TGTTTT | 0 | NA | 0 | NA |
| 5 | TATATA | 1 | 959 | 0 | NA |
| 6 | TATTTT | 2 | 609; 1144 | 0 | NA |
| 7 | TTTTTT | 0 | NA | 0 | NA |
| 8 | ATTTTT | 1 | 1145 | 0 | NA |
| 9 | TTATTT | 3 | 63; 145; 1143 | 1 | 1143 |
| 10 | TTTATT | 2 | 144; 1056 | 0 | NA |
| 11 | TAATAA | 2 | 12; 216 | 1 | 12 |
| 12 | ATTTAT | 0 | NA | 0 | NA |
| 13 | TATATT | 2 | 169; 607 | 0 | NA |

TABLE 10-continued

Table 2 sequences found in the native Cry35Ab1 coding region (SEQ ID NO: 13) and in the redesigned version (SEQ ID NO: 17)

| Table 2 Sequence | No. Sites in native Cry35Ab1 sequence (SEQ ID NO: 13) | nt Location in native Cry35Ab1 sequence (SEQ ID NO: 13) | No. Sites in redesigned Cry35Ab1 sequence (SEQ ID NO: 17) | nt Location in redesigned Cry35Ab1 sequence (SEQ ID NO: 17) |
|---|---|---|---|---|
| 14 TTTTAT | 1 | 143 | 0 | NA |
| 15 ATATTT | 1 | 608 | 0 | NA |
| 16 TATTAT | 4 | 171; 549; 604; 1141 | 1 | 1141 |
| 17 TGTTTG | 0 | NA | 0 | NA |
| 18 TTATAT | 2 | 606; 958 | 0 | NA |
| 19 TGTAAT | 1 | 300 | 0 | NA |
| 20 AAATAA | 8 | 26; 192; 227; 275; 384; 809; 863; 1097 | 2 | 809; 863 |
| Total | 31 | | 5 | |

*NA = Not Applicable

Example 4

Synthetic Coding Region Encoding Bacillus thuringiensis Cry1Ab Core Toxin

Comparative Sequences. The native DNA sequence encoding Cry1Ab core toxin is given in SEQ ID NO:19. This sequence was analyzed to determine which sequences identified in Table 1 are present in SEQ ID NO:19 and their locations. The amino acid sequence encoded by SEQ ID NO:19 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:19 was preserved. The resulting DNA sequence is given in SEQ ID NO:21.

SEQ ID NO:21 was analyzed and codons were changed to remove potential polyadenylation signal sequences identified in Table 2, while maintaining the same number of sequences identified in Table 1. The resulting sequence, which embodies the present invention, is given in SEQ ID NO:23. Table 11 shows that the number and location of polyadenylation signal sequences identified in Table 1 are maintained in SEQ ID NO:23. Table 12 shows that the number of polyadenylation signal sequences identified in Tables 2 and 3 are reduced in SEQ ID NO:23 compared to SEQ ID NO:19.

The synthetic coding region of SEQ ID NO:23 was optimized for expression in maize.

A construct for use in expressing the synthetic coding region of SEQ ID NO:23 was made by combining the synthetic coding region of SEQ ID NO:23 with a 5' non-translated region comprising a promoter that functions in plant cells and a 3' non-translated region comprising a transcription termination and polyadenylation sequence.

In one embodiment of such a construct, production of the primary mRNA transcript comprising SEQ ID NO:23 was driven by a copy of a maize ubiquitin1 promoter with its native intron1 (U.S. Pat. No. 5,510,474). A fragment comprising a 3' untranslated region from a maize peroxidase 5 gene (ZmPer5 3'UTR v2; U.S. Pat. No. 6,699,984) was used to terminate transcription. A binary plant transformation plasmid, pDAB111449, containing the aforementioned gene expression cassette, was constructed and utilized in the production of transgenic maize plants. Plasmid pDAB111449 further comprises a herbicide resistance gene comprising a coding region for aryloxyalknoate dioxygenase (AAD-1 v3; U.S. Pat. No. 7,838,733(B2), and Wright et al. (2010) Proc. Natl. Acad. Sci. U.S.A. 107: 20240-5) under the transcriptional control of a sugarcane bacilliform badnavirus (ScBV) promoter (Schenk et al. (1999) Plant Molec. Biol. 39:1221-30). A fragment comprising a 3' untranslated region from a maize lipase gene (ZmLip 3'UTR; U.S. Pat. No. 7,179,902) was used to terminate transcription.

TABLE 11

Table 1 sequences found in the native Cry1Ab core toxin coding region (SEQ ID NO: 19) and in the redesigned version (SEQ ID NO: 23)

| Table 1 Sequence | No. Sites in Native Cry1Ab core sequence (SEQ ID NO: 19) | nt Location in Native Cry1Ab core sequence (SEQ ID NO: 19) | No. Sites in redesigned Cry1Ab core sequence (SEQ ID NO: 23) | nt Location in redesigned Cry1Ab core sequence (SEQ ID NO: 23) |
|---|---|---|---|---|
| 1 AATAAA | 0 | NA* | 0 | NA |
| 2 AATAAT | 3 | 960, 1126, 1387 | 3 | 960, 1126, 1387 |
| 3 AACCAA | 2 | 253, 280 | 2 | 253, 280 |
| 4 ATATAA | 2 | 185, 1391 | 2 | 185, 1391 |
| 5 AATCAA | 2 | 688, 1129 | 3 | 688, 1129, 1639 |
| 6 ATACTA | 0 | NA | 0 | NA |
| 7 ATAAAA | 0 | NA | 0 | NA |
| 8 ATGAAA | 1 | 1232 | 1 | 1232 |
| 9 AAGCAT | 0 | NA | 0 | NA |
| 10 ATTAAT | 1 | 1636 | 1 | 1636 |
| 11 ATACAT | 2 | 1366, 1613 | 2 | 1366, 1613 |
| 12 AAAATA | 0 | NA | 0 | NA |
| 13 ATTAAA | 3 | 249, 704, 785 | 3 | 249, 704, 785 |

TABLE 11-continued

Table 1 sequences found in the native Cry1Ab core toxin coding region (SEQ ID NO: 19) and in the redesigned version (SEQ ID NO: 23)

| Table 1 Sequence | No. Sites in Native Cry1Ab core sequence (SEQ ID NO: 19) | nt Location in Native Cry1Ab core sequence (SEQ ID NO: 19) | No. Sites in redesigned Cry1Ab core sequence (SEQ ID NO: 23) | nt Location in redesigned Cry1Ab core sequence (SEQ ID NO: 23) |
|---|---|---|---|---|
| 13 AATTAA | 0 | NA | 0 | NA |
| 15 AATACA | 0 | NA | 0 | NA |
| 16 CATAAA | 0 | NA | 0 | NA |
| Total | 16 | NA | 17 | NA |

*NA = Not Applicable

TABLE 12

Table 2 sequences found in the native Cry1Ab coding region (SEQ ID NO: 19) and in the redesigned version (SEQ ID NO: 23)

| Table 2 Sequence | No. Sites in Native Cry1Ab core sequence (SEQ ID NO: 19) | nt Location in Native Cry1Ab core sequence (SEQ ID NO: 19) | No. Sites in redesigned Cry1Ab core sequence (SEQ ID NO: 23) | nt Location in redesigned Cry1Ab core sequence (SEQ ID NO: 23) |
|---|---|---|---|---|
| 1 ATATAT | 0 | NA* | 0 | NA |
| 2 TTGTTT | 1 | 42 | 0 | NA |
| 3 TTTTGT | 0 | NA | 0 | NA |
| 4 TGTTTT | 0 | NA | 0 | NA |
| 5 TATATA | 2 | 1097, 1792 | 0 | NA |
| 6 TATTTT | 0 | NA | 0 | NA |
| 7 TTTTTT | 0 | NA | 0 | NA |
| 8 ATTTTT | 2 | 199, 1649 | 0 | NA |
| 9 TTATTT | 0 | NA | 0 | NA |
| 10 TTTATT | 1 | 470 | 0 | NA |
| 11 TAATAA | 2 | 1340, 1386 | 0 | NA |
| 12 ATTTAT | 2 | 503, 799 | 0 | NA |
| 13 TATATT | 0 | NA | 0 | NA |
| 14 TTTTAT | 0 | NA | 0 | NA |
| 15 ATATTT | 1 | 110 | 0 | NA |
| 16 TATTAT | 2 | 937, 940 | 0 | NA |
| 17 TGTTTG | 1 | 530 | 0 | NA |
| 18 TTATAT | 2 | 1096, 1791 | 0 | NA |
| 19 TGTAAT | 0 | NA | 0 | NA |
| 20 AAATAA | 2 | 959, 1125 | 1 | 959 |
| Total | 18 | | 1 | |

*NA = Not Applicable

Example 5

Synthetic Coding Region Encoding *Bacillus thuringiensis* Cry1Ca Core Toxin

Comparative Sequences. The native DNA sequence encoding the Cry35A core toxin is given in SEQ ID NO:25. This sequence was analyzed to determine which sequences identified in Table 1 are present in SEQ ID NO:25 and their locations. The amino acid sequence encoded by SEQ ID NO:25 was then reverse translated using the target codon frequencies given in the column of Table 4 for synthetic genes to be used in maize. The resulting DNA sequence was analyzed and codons were changed where necessary to remove unwanted open reading frames, and remove unwanted restriction enzyme recognition sites, while maintaining all sequences identified in Table 1. The amino acid sequence encoded by SEQ ID NO:25 was preserved. The resulting DNA sequence is given in SEQ ID NO:27. This sequence will be synthesized and used for comparison with a synthetic gene designed in accordance with the invention.

SEQ ID NO:27 was analyzed and codons were changed to remove potential polyadenylation signal sequences identified in Table 2, while maintaining the same number of sequences identified in Table 1. The resulting sequence, which embodies the present invention, is given in SEQ ID NO:29. Table 13 shows that the number and location of polyadenylation signal sequences identified in Table 1 are maintained in SEQ ID NO:29. Table 14 shows that the number of polyadenylation signal sequences identified in Tables 2 and 3 are reduced in SEQ ID NO:29 compared to SEQ ID NO:25.

DNA of SEQ ID NO:29 is synthesized, and expression levels observed in plant cells transformed to express this sequence are compared with expression levels observed in plant cells transformed to express SEQ ID NO:25 and SEQ ID NO:27.

The synthetic gene of SEQ ID NO:29 was optimized for expression in maize.

A construct for use in expressing the synthetic gene of SEQ ID NO:29 is made by combining the synthetic gene of SEQ ID NO:29 with a 5' non-translated region comprising a promoter that functions in plant cells and a 3' non-translated region comprising a transcription terminator and polyadenylation sequence.

TABLE 13

Table 1 sequences found in the native Cry1Ca core toxin coding region (SEQ ID NO: 25) and in the redesigned version (SEQ ID NO: 29)

| Table 1 Sequence | | No. Sites in Native Cry1Ca core sequence (SEQ ID NO: 25) | nt Location in Native Cry1Ca core sequence (SEQ ID NO: 25) | No. Sites in redesigned Cry1Ca core sequence (SEQ ID NO: 29) | nt Location in redesigned Cry1Ca core sequence (SEQ ID NO: 29) |
|---|---|---|---|---|---|
| 1 | AATAAA | 0 | NA* | 0 | NA |
| 2 | AATAAT | 2 | 646, 916 | 2 | 646, 916 |
| 3 | AACCAA | 0 | NA | 1 | 1042 |
| 4 | ATATAA | 2 | 684, 1757 | 2 | 684, 1757 |
| 5 | AATCAA | 1 | 1405 | 1 | 1405 |
| 6 | ATACTA | 0 | NA | 0 | NA |
| 7 | ATAAAA | 1 | 1826 | 1 | 1826 |
| 8 | ATGAAA | 2 | 254, 569 | 2 | 254, 569 |
| 9 | AAGCAT | 1 | 335 | 1 | 335 |
| 10 | ATTAAT | 7 | 177, 246, 250, 813, 817, 1402, 1534 | 7 | 177, 246, 250, 813, 817, 1402, 1534 |
| 11 | ATACAT | 0 | NA | 0 | NA |
| 12 | AAAATA | 0 | NA | 0 | NA |
| 13 | ATTAAA | 4 | 245, 249, 816, 1401 | 4 | 245, 249, 816, 1401 |
| 13 | AATTAA | 1 | 642 | 1 | 642 |
| 15 | AATACA | 1 | 1381 | 1 | 1381 |
| 16 | CATAAA | 0 | NA | 0 | NA |
| Total | | 22 | | 23 | |

*NA = Not Applicable

TABLE 14

Table 2 sequences found in the native Cry1Ca core toxin coding region (SEQ ID NO: 25) and in the redesigned version (SEQ ID NO: 29)

| Table 2 Sequence | | No. Sites in Native Cry1Ca core sequence (SEQ ID NO: 25) | nt Location in Native Cry1Ca core sequence (SEQ ID NO: 25) | No. Sites in redesigned Cry1Ca core sequence (SEQ ID NO: 29) | nt Location in redesigned Cry1Ca core sequence (SEQ ID NO: 29) |
|---|---|---|---|---|---|
| 1 | ATATAT | 4 | 323, 325, 908, 1024 | 0 | NA* |
| 2 | TTGTTT | | NA | 0 | NA |
| 3 | TTTTGT | 3 | 186, 1302, 1512 | 0 | NA |
| 4 | TGTTTT | 0 | NA | 0 | NA |
| 5 | TATATA | 3 | 324, 1023, 1819 | 0 | NA |
| 6 | TATTTT | 1 | 1346 | 0 | NA |
| 7 | TTTTTT | 1 | 1326 | 0 | NA |
| 8 | ATTTTT | 2 | 529, 959 | 0 | NA |
| 9 | TTATTT | 1 | 901 | 0 | NA |
| 10 | TTTATT | 2 | 900, 962 | 0 | NA |
| 11 | TAATAA | 0 | NA | 0 | NA |
| 12 | ATTTAT | 1 | 899 | 0 | NA |
| 13 | TATATT | 2 | 510, 909 | 0 | NA |
| 14 | TTTTAT | 2 | 470, 961 | 0 | NA |
| 15 | ATATTT | 1 | 110 | 0 | NA |
| 16 | TATTAT | 0 | NA | 0 | NA |
| 17 | TGTTTG | 0 | NA | 0 | NA |
| 18 | TTATAT | 1 | 1818 | 0 | NA |
| 19 | TGTAAT | 1 | 525 | 0 | NA |
| 20 | AAATAA | 1 | 645 | 1 | 645 |
| Total | | 26 | | 1 | |

*NA = Not Applicable

Example 6

Synthetic Coding Region Encoding *Bacillus thuringiensis* Cry6Aa Toxin

Comparative Sequences. The native DNA sequence encoding the Cry6Aa toxin is given in SEQ ID NO:31. This sequence was analyzed to determine which sequences identified in Table 1 are present in SEQ ID NO:31 and their locations. The amino acid sequence encoded by SEQ ID NO:31 was then reverse translated using the target codon frequencies given in the column of Table 4 for synthetic genes to be used in maize. The resulting DNA sequence was analyzed and codons were changed where necessary to remove unwanted open reading frames, and remove unwanted restriction enzyme recognition sites, while maintaining all sequences identified in Table 1. The amino acid sequence encoded by SEQ ID NO:31 was preserved. The resulting DNA sequence is given in SEQ ID NO:33. This sequence will be synthesized and used for comparison with a synthetic gene designed in accordance with the invention.

SEQ ID NO:33 was analyzed and codons were changed to remove potential polyadenylation signal sequences identified in Table 2, while maintaining the number of sequences identified in Table 1. The resulting sequence, which embodies the present invention, is given in SEQ ID NO:35. Table 15 shows that the number and location of polyadenylation signal sequences identified in Table 1 are maintained in SEQ ID NO:35. Table 16 shows that the number of polyadenylation signal sequences identified in Tables 2 and 3 are reduced in SEQ ID NO:35 compared to SEQ ID NO:31.

DNA of SEQ ID NO:35 is synthesized, and expression levels observed in plant cells transformed to express this sequence are compared with expression levels observed in plant cells transformed to express SEQ ID NO:31 and SEQ ID NO:33.

The synthetic coding region of SEQ ID NO:35 was optimized for expression in maize.

A construct for use in expressing the synthetic coding region of SEQ ID NO:35 is made by combining the synthetic coding region of SEQ ID NO:35 with a 5' non-translated region comprising a promoter that functions in plant cells and a 3' non-translated region comprising a transcription terminator and polyadenylation sequence.

TABLE 15

Table 1 sequences found in the native Cry6Aa coding region (SEQ ID NO: 31) and in the redesigned version (SEQ ID NO: 35)

| Table 1

TABLE 16-continued

Table 2 sequences found in the native Cry6Aa coding region (SEQ ID NO: 31) and in the redesigned version (SEQ ID NO: 35)

| Table 2 Sequence | No. Sites in Native Cry6Aa sequence (SEQ ID NO: 31) | nt Location in Native Cry6Aa sequence (SEQ ID NO: 31) | No. Sites in redesigned Cry6Aa sequence (SEQ ID NO: 35) | nt Location in redesigned Cry6Aa sequence (SEQ ID NO: 35) |
|---|---|---|---|---|
| 18 TTATAT | 4 | 247, 301, 940, 1190 | 0 | NA |
| 19 TGTAAT | 1 | 1204 | 0 | NA |
| 20 AAATAA | 2 | 1308, 1359 | 1 | 1359 |
| Total | 33 | | 1 | |

*NA = Not Applicable

Example 7

Synthetic Coding Region Encoding *Sphingobium herbicidovorans* AAD1

Comparative Sequences. The native DNA sequence encoding the AAD1 protein is given in SEQ ID NO:37. This sequence was analyzed to determine which sequences identified in Table 1 are present in SEQ ID NO:37 and their locations. The amino acid sequence encoded by SEQ ID NO:37 was then reverse translated using the target codon frequencies given in the column of Table 4 for synthetic genes to be used in maize. The resulting DNA sequence was analyzed and codons were changed where necessary to remove unwanted open reading frames, and remove unwanted restriction enzyme recognition sites, while maintaining all sequences identified in Table 1. The amino acid sequence encoded by SEQ ID NO:37 was preserved. The resulting DNA sequence is given in SEQ ID NO:39. This sequence will be synthesized and used for comparison with a synthetic gene designed in accordance with the invention.

SEQ ID NO:39 was analyzed and codons were changed to remove potential polyadenylation signal sequences identified in Table 2, while maintaining the number of sequences identified in Table 1. The resulting sequence, which embodies the present invention, is given in SEQ ID NO:41. Table 17 shows that the number and location of polyadenylation signal sequences identified in Table 1 are maintained in SEQ ID NO:41. Table 18 shows that the number of polyadenylation signal sequences identified in Tables 2 and 3 are reduced in SEQ ID NO:41 compared to SEQ ID NO:37.

DNA of SEQ ID NO:41 is synthesized, and expression levels observed in plant cells transformed to express this sequence are compared with expression levels observed in plant cells transformed to express SEQ ID NO:37 and SEQ ID NO:39.

The synthetic coding region of SEQ ID NO:41 was optimized for expression in maize.

A construct for use in expressing the synthetic coding region of SEQ ID NO:41 is made by combining the synthetic coding region of SEQ ID NO:41 with a 5' non-translated region comprising a promoter that functions in plant cells and a 3' non-translated region comprising a transcription terminator and polyadenylation sequence.

TABLE 17

Table 1 sequences found in the native AAD1 coding region (SEQ ID NO: 37) and in the redesigned version (SEQ ID NO: 41)

| Table 1 Sequence | No. Sites in Native AAD1 sequence (SEQ ID NO: 37) | nt Location in Native AAD1 sequence (SEQ ID NO: 37) | No. Sites in redesigned AAD1 sequence (SEQ ID NO: 41) | nt Location in redesigned AAD1 sequence (SEQ ID NO: 41) |
|---|---|---|---|---|
| 1 AATAAA | 0 | NA* | 0 | NA |
| 2 AATAAT | 0 | NA | 0 | NA |
| 3 AACCAA | 0 | NA | 1 | 652 |
| 4 ATATAA | 0 | NA | 0 | NA |
| 5 AATCAA | 0 | NA | 0 | NA |
| 6 ATACTA | 0 | NA | 0 | NA |
| 7 ATAAAA | 0 | NA | 0 | NA |
| 8 ATGAAA | 0 | NA | 0 | NA |
| 9 AAGCAT | 0 | NA | 0 | NA |
| 10 ATTAAT | 0 | NA | 0 | NA |
| 11 ATACAT | 0 | NA | 0 | NA |
| 12 AAAATA | 0 | NA | 0 | NA |
| 13 ATTAAA | 0 | NA | 0 | NA |
| 14 AATTAA | 0 | NA | 0 | NA |
| 15 AATACA | 0 | NA | 0 | NA |
| 16 CATAAA | 0 | NA | 0 | NA |
| Total | 0 | | 1 | |

*NA = Not Applicable

TABLE 18

Table 2 sequences found in the native AAD1 coding region (SEQ ID NO: 37) and in the redesigned version (SEQ ID NO: 41)

| Table 2 Sequence | No. Sites in Native AAD1 sequence (SEQ ID NO: 37) | nt Location in Native AAD1 sequence (SEQ ID NO: 37) | No. Sites in redesigned AAD1 sequence (SEQ ID NO: 41) | nt Location in redesigned AAD1 sequence (SEQ ID NO: 41) |
|---|---|---|---|---|
| 1 ATATAT | 0 | NA* | 0 | NA |
| 2 TTGTTT | 0 | NA | 0 | NA |
| 3 TTTTGT | 0 | NA | 0 | NA |
| 4 TGTTTT | 0 | NA | 0 | NA |
| 5 TATATA | 0 | NA | 0 | NA |
| 6 TATTTT | 1 | 166 | 0 | NA |
| 7 TTTTTT | 0 | NA | 0 | NA |
| 8 ATTTTT | 0 | NA | 0 | NA |

TABLE 18-continued

Table 2 sequences found in the native AAD1 coding region (SEQ ID NO: 37) and in the redesigned version (SEQ ID NO: 41)

| Table 2 Sequence | No. Sites in Native AAD1 sequence (SEQ ID NO: 37) | nt Location in Native AAD1 sequence (SEQ ID NO: 37) | No. Sites in redesigned AAD1 sequence (SEQ ID NO: 41) | nt Location in redesigned AAD1 sequence (SEQ ID NO: 41) |
|---|---|---|---|---|
| 9 TTATTT | 0 | NA | 0 | NA |
| 10 TTTATT | 0 | NA | 0 | NA |
| 11 TAATAA | 0 | NA | 0 | NA |
| 12 ATTTAT | 0 | NA | 0 | NA |
| 13 TATATT | 0 | NA | 0 | NA |
| 14 TTTTAT | 0 | NA | 0 | NA |
| 15 ATATTT | 0 | NA | 0 | NA |
| 16 TATTAT | 0 | NA | 0 | NA |
| 17 TGTTTG | 0 | NA | 0 | NA |
| 18 TTATAT | 0 | NA | 0 | NA |
| 19 TGTAAT | 0 | NA | 0 | NA |
| 20 AAATAA | 0 | NA | 0 | NA |
| Total | 1 | | 0 | |

*NA = Not Applicable

Example 8

Synthetic Coding Region Encoding *Aspergillus nidulans* Delta-9 Desaturase

Comparative Sequences. The native DNA sequence encoding the *Aspergillus nidulans* Delta-9 Desaturase protein is given in SEQ ID NO:43. This sequence was analyzed to determine which sequences identified in Table 1 are present in SEQ ID NO:43 and their locations. The amino acid sequence encoded by SEQ ID NO:43 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:43 was preserved. The resulting DNA sequence is given in SEQ ID NO:45. This sequence will be synthesized and used for comparison with a synthetic gene designed in accordance with the invention.

SEQ ID NO:45 was analyzed and codons were changed to remove potential polyadenylation signal sequences identified in Table 2, while maintaining the number of sequences identified in Table 1. The resulting sequence, which embodies the present invention, is given in SEQ ID NO:47. Table 1 shows that the number and location of polyadenylation signal sequences identified in Table 1 are maintained in SEQ ID NO:47. Table 20 shows that the number of polyadenylation signal sequences identified in Tables 2 and 3 are reduced in SEQ ID NO:47 compared to SEQ ID NO:43.

DNA of SEQ ID NO:47 is synthesized, and expression levels observed in plant cells transformed to express this sequence are compared with expression levels observed in plant cells transformed to express SEQ ID NO:43 and SEQ ID NO:45.

The synthetic coding region of SEQ ID NO:47 was optimized for expression in maize.

A construct for use in expressing the synthetic coding region of SEQ ID NO:47 is made by combining the synthetic coding region of SEQ ID NO:47 with a 5' non-translated region comprising a promoter that functions in plant cells and a 3' non-translated region comprising a transcription termination and polyadenylation sequence.

TABLE 19

Table 1 sequences found in the native *Aspergillus nidulans* Delta-9 Desaturase coding region (SEQ ID NO: 43) and in the redesigned version (SEQ ID NO: 47)

| Table 1 Sequence | No. Sites in Native Asp-Δ9 sequence (SEQ ID NO: 43) | nt Location in Native Asp-Δ9 sequence (SEQ ID NO: 43) | No. Sites in redesigned Asp-Δ9 sequence (SEQ ID NO: 47) | nt Location in redesigned Asp-Δ9 Sequence (SEQ ID NO: 47) |
|---|---|---|---|---|
| 1 AATAAA | 0 | NA* | 0 | NA |
| 2 AATAAT | 0 | NA | 0 | NA |
| 3 AACCAA | 1 | 1326 | 1 | 1326 |
| 4 ATATAA | 0 | NA | 0 | NA |
| 5 AATCAA | 0 | NA | 0 | NA |
| 6 ATACTA | 0 | NA | 0 | NA |
| 7 ATAAAA | 0 | NA | 0 | NA |
| 8 ATGAAA | 0 | NA | 0 | NA |
| 9 AAGCAT | 1 | 94 | 1 | 94 |
| 10 ATTAAT | 0 | NA | 0 | NA |
| 11 ATACAT | 0 | NA | 0 | NA |
| 12 AAAATA | 0 | NA | 0 | NA |
| 13 ATTAAA | 0 | NA | 0 | NA |
| 14 AATTAA | 0 | NA | 0 | NA |
| 15 AATACA | 0 | NA | 0 | NA |
| 16 CATAAA | 0 | NA | 0 | NA |
| Total | 2 | | 2 | |

*NA = Not Applicable

TABLE 20

Table 2 sequences found in the native *Aspergillus nidulans* Delta-9 Desaturase coding region (SEQ ID NO: 43) and in the redesigned version (SEQ ID NO: 47)

| Table 2 Sequence | | No. Sites in Native Asp-Δ9 sequence (SEQ ID NO: 43) | nt Location in Native Asp-Δ9 Sequence (SEQ ID NO: 43) | No. Sites in redesigned Asp-Δ9 Sequence (SEQ ID NO: 47) | nt Location in redesigned Asp-Δ9 Sequence (SEQ ID NO: 47) |
|---|---|---|---|---|---|
| 1 | ATATAT | 0 | NA* | 0 | NA |
| 2 | TTGTTT | 0 | NA | 0 | NA |
| 3 | TTTTGT | 0 | NA | 0 | NA |
| 4 | TGTTTT | 0 | NA | 0 | NA |
| 5 | TATATA | 0 | NA | 0 | NA |
| 6 | TATTTT | 1 | 166 | 0 | NA |
| 7 | TTTTTT | 0 | NA | 0 | NA |
| 8 | ATTTTT | 0 | NA | 0 | NA |
| 9 | TTATTT | 0 | NA | 0 | NA |
| 10 | TTTATT | 0 | NA | 0 | NA |
| 11 | TAATAA | 0 | NA | 0 | NA |
| 12 | ATTTAT | 0 | NA | 0 | NA |
| 13 | TATATT | 0 | NA | 0 | NA |
| 14 | TTTTAT | 0 | NA | 0 | NA |
| 15 | ATATTT | 1 | 479 | 0 | NA |
| 16 | TATTAT | 0 | NA | 0 | NA |
| 17 | TGTTTG | 0 | NA | 0 | NA |
| 18 | TTATAT | 0 | NA | 0 | NA |
| 19 | TGTAAT | 0 | NA | 0 | NA |
| 20 | AAATAA | 0 | NA | 0 | NA |
| | Total | 1 | | 0 | |

*NA = Not Applicable

Example 9

Synthetic Coding Region Encoding *Xerophyta viscosa* SAP1

Comparative Sequences. The native DNA sequence encoding the *Xerophyta viscosa* SAP1 protein is given in SEQ ID NO:49. This sequence was analyzed to determine which sequences identified in Table 1 are present in SEQ ID NO:49 and their locations. The amino acid sequence encoded by SEQ ID NO:49 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:49 was preserved. The resulting DNA sequence is given in SEQ ID NO:51. This sequence will be synthesized and used for comparison with a synthetic gene designed in accordance with the invention.

SEQ ID NO:52 was analyzed and codons were changed to remove potential polyadenylation signal sequences identified in Table 2, while maintaining the number of sequences identified in Table 1. The resulting sequence, which embodies the present invention, is given in SEQ ID NO:53. Table 1 shows that the number and location of polyadenylation signal sequences identified in Table 1 are maintained in SEQ ID NO:53. Table 21 shows that the number of polyadenylation signal sequences identified in Tables 2 and 3 are reduced in SEQ ID NO:53 compared to SEQ ID NO:49.

DNA of SEQ ID NO:53 is synthesized, and expression levels observed in plant cells transformed to express this sequence are compared with expression levels observed in plant cells transformed to express SEQ ID NO:49 and SEQ ID NO:51.

The synthetic coding region of SEQ ID NO:53 was optimized for expression in maize.

A construct for use in expressing the synthetic coding region of SEQ ID NO:53 is made by combining the synthetic coding region of SEQ ID NO:53 with a 5' non-translated region comprising a promoter that functions in plant cells and a 3' non-translated region comprising a transcription terminator and polyadenylation sequence.

TABLE 21

Table 1 sequences found in the native *Xerophyta viscosa* SAP1 coding region (SEQ ID NO: 49) and in the redesigned version (SEQ ID NO: 53)

| Table 1 Sequence | | No. Sites in Native XvSAP1 sequence (SEQ ID NO: 49) | nt Location in Native XvSAP1 sequence (SEQ ID NO: 49) | No. Sites in redesigned XvSAP1 sequence (SEQ ID NO: 53) | nt Location in redesigned XvSAP1 sequence (SEQ ID NO: 53) |
|---|---|---|---|---|---|
| 1 | AATAAA | 0 | NA* | 0 | NA |
| 2 | AATAAT | 0 | NA | 0 | NA |
| 3 | AACCAA | 0 | NA | 0 | NA |
| 4 | ATATAA | 0 | NA | 0 | NA |
| 5 | AATCAA | 0 | NA | 0 | NA |
| 6 | ATACTA | 0 | NA | 0 | NA |
| 7 | ATAAAA | 0 | NA | 0 | NA |
| 8 | ATGAAA | 0 | NA | 1 | 25 |
| 9 | AAGCAT | 0 | NA | 0 | NA |
| 10 | ATTAAT | 0 | NA | 0 | NA |
| 11 | ATACAT | 0 | NA | 0 | NA |
| 12 | AAAATA | 0 | NA | 0 | NA |
| 13 | ATTAAA | 0 | NA | 0 | NA |

TABLE 21-continued

Table 1 sequences found in the native Xerophyta viscosa SAP1 coding region (SEQ ID NO: 49) and in the redesigned version (SEQ ID NO: 53)

| Table 1 Sequence | No. Sites in Native XvSAP1 sequence (SEQ ID NO: 49) | nt Location in Native XvSAP1 sequence (SEQ ID NO: 49) | No. Sites in redesigned XvSAP1 sequence (SEQ ID NO: 53) | nt Location in redesigned XvSAP1 sequence (SEQ ID NO: 53) |
|---|---|---|---|---|
| 14 AATTAA | 0 | NA | 0 | NA |
| 15 AATACA | 0 | NA | 0 | NA |
| 16 CATAAA | 0 | NA | 0 | NA |
| Total | 0 | | 1 | |

*NA = Not Applicable

TABLE 22

Table 2 sequences found in native the Native Xerophyta viscosa SAP1 coding region (SEQ ID NO: 49) and in the redesigned version (SEQ ID NO: 53)

| Table 2 Sequence | No. Sites in Native XvSAP1 sequence (SEQ ID NO: 49) | nt Location in Native XvSAP1 sequence (SEQ ID NO: 49) | No. Sites in redesigned XvSAP1 sequence (SEQ ID NO: 53) | nt Location in redesigned XvSAP1 sequence (SEQ ID NO: 53) |
|---|---|---|---|---|
| 1 ATATAT | 0 | NA* | 0 | NA |
| 2 TTGTTT | 0 | NA | 0 | NA |
| 3 TTTTGT | 0 | NA | 0 | NA |
| 4 TGTTTT | 0 | NA | 0 | NA |
| 5 TATATA | 0 | NA | 0 | NA |
| 6 TATTTT | 1 | 755 | 0 | NA |
| 7 TTTTTT | 0 | NA | 0 | NA |
| 8 ATTTTT | 1 | 756 | 0 | NA |
| 9 TTATTT | 0 | NA | 0 | NA |
| 10 TTTATT | 0 | NA | 0 | NA |
| 11 TAATAA | 0 | NA | 0 | NA |
| 12 ATTTAT | 0 | NA | 0 | NA |
| 13 TATATT | 0 | NA | 0 | NA |
| 14 TTTTAT | 0 | NA | 0 | NA |
| 15 ATATTT | 1 | 754 | 0 | NA |
| 16 TATTAT | 1 | 665 | 0 | NA |
| 17 TGTTTG | 1 | 696 | 0 | NA |
| 18 TTATAT | 0 | NA | 0 | NA |
| 19 TGTAAT | 0 | NA | 0 | NA |
| 20 AAATAA | 0 | NA | 0 | NA |
| Total | 5 | | 0 | |

*NA = Not Applicable

Example 10

Synthetic Coding Region Encoding *Aequorea victoria* GFP1

Comparative Sequences. The native DNA sequence encoding the *Aequorea victoria* GFP1 is given in SEQ ID NO:55. This sequence was analyzed to determine which sequences identified in Table 1 are present in SEQ ID NO:55 and their locations. The amino acid sequence encoded by SEQ ID NO:55 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:55 was preserved. The resulting DNA sequence is given in SEQ ID NO:57. This sequence will be synthesized and used for comparison with a synthetic gene designed in accordance with the invention.

SEQ ID NO:57 was analyzed and codons were changed to remove potential polyadenylation signal sequences identified in Table 2, while maintaining the number of sequences identified in Table 1. The resulting sequence, which embodies the present invention, is given in SEQ ID NO:59. Table 1 shows that the number and location of polyadenylation signal sequences identified in Table 1 are maintained in SEQ ID NO:59. Table 23 shows that the number of polyadenylation signal sequences identified in Tables 2 and 3 are reduced in SEQ ID NO:59 compared to SEQ ID NO:55.

DNA of SEQ ID NO:59 is synthesized, and expression levels observed in plant cells transformed to express this sequence are compared with expression levels observed in plant cells transformed to express SEQ ID NO:55 and SEQ ID NO:57.

The synthetic coding region of SEQ ID NO:59 was optimized for expression in maize.

A construct for use in expressing the synthetic coding region of SEQ ID NO:59 is made by combining the synthetic coding region of SEQ ID NO:59 with a 5' non-translated region comprising a promoter that functions in plant cells and a 3' non-translated region comprising a transcription terminator and polyadenylation sequence.

TABLE 23

Table 1 sequences found in the native
*Aequorea victoria* GFP1 coding region
(SEQ ID NO: 55) and in the redesigned
version (SEQ ID NO: 59)

| Table 1 Sequence | No. Sites in Native GFP1 sequence (SEQ ID NO: 55) | nt Location in Native GFP1 sequence (SEQ ID NO: 55) | No. Sites in redesigned GFP1 sequence (SEQ ID NO: 59) | nt Location in redesigned GFP1 sequence (SEQ ID NO: 59) |
|---|---|---|---|---|
| 1 AATAAA | 0 | NA* | 0 | NA |
| 2 AATAAT | 0 | NA | 0 | NA |
| 3 AACCAA | 1 | 467 | 1 | 467 |
| 4 ATATAA | 0 | NA | 0 | NA |
| 5 AATCAA | 0 | NA | 0 | NA |
| 6 ATACTA | 0 | NA | 0 | NA |
| 7 ATAAAA | 0 | NA | 0 | NA |
| 8 ATGAAA | 1 | 237 | 1 | 237 |
| 9 AAGCAT | 0 | NA | 0 | NA |
| 10 ATTAAT | 0 | NA | 0 | NA |
| 11 ATACAT | 1 | 450 | 1 | 450 |
| 12 AAAATA | 1 | 551 | 1 | 551 |
| 13 ATTAAA | 1 | 511 | 1 | 511 |
| 14 AATTAA | 0 | NA | 0 | NA |
| 15 AATACA | 1 | 425 | 1 | 425 |
| 16 CATAAA | 0 | NA | 1 | 480 |
| Total | 6 | | 7 | |

*NA = Not Applicable

TABLE 24

Table 2 sequences found in the native the
*Aequorea victoria* GFP1 coding region
(SEQ ID NO: 55) and in the redesigned
version (SEQ ID NO: 59)

| Table 2 Sequence | No. Sites in Native GFP1 sequence (SEQ ID NO: 55) | nt Location in Native GFP1 sequence (SEQ ID NO: 55) | No. Sites in redesigned GFP1 sequence (SEQ ID NO: 59) | nt Location in redesigned GFP1 sequence (SEQ ID NO: 59) |
|---|---|---|---|---|
| 1 ATATAT | 0 | NA* | 0 | NA |
| 2 TTGTTT | 0 | NA | 0 | NA |
| 3 TTTTGT | 0 | NA | 0 | NA |
| 4 TGTTTT | 0 | NA | 0 | NA |
| 5 TATATA | 0 | NA | 0 | NA |
| 6 TATTTT | 1 | 293 | 0 | NA |
| 7 TTTTTT | 0 | NA | 0 | NA |
| 8 ATTTTT | 0 | NA | 0 | NA |
| 9 TTATTT | 1 | 137 | 0 | NA |
| 10 TTTATT | 1 | 136 | 0 | NA |
| 11 TAATAA | 0 | NA | 0 | NA |
| 12 ATTTAT | 0 | NA | 0 | NA |
| 13 TATATT | 1 | 291 | 0 | NA |
| 14 TTTTAT | 1 | 135 | 0 | NA |
| 15 ATATTT | 1 | 292 | 0 | NA |
| 16 TATTAT | 0 | NA | 0 | NA |
| 17 TGTTTG | 0 | NA | 0 | NA |
| 18 TTATAT | 0 | NA | 0 | NA |
| 19 TGTAAT | 0 | NA | 0 | NA |
| 20 AAATAA | 0 | NA | 0 | NA |
| Total | 6 | | 0 | |

*NA = Not Applicable

Example 11

Synthetic Coding Region Encoding *Leptosphaeria nodorum* FAD9

Comparative Sequences. The native DNA sequence encoding the *Leptosphaeria nodorum* FAD9 protein is given in SEQ ID NO:61. This sequence was analyzed to determine which sequences identified in Table 1 are present in SEQ ID NO:61 and their locations. The amino acid sequence encoded by SEQ ID NO:61 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:61 was preserved. The resulting DNA sequence is given in SEQ ID NO:63. This sequence will be synthesized and used for comparison with a synthetic gene designed in accordance with the invention.

SEQ ID NO:63 was analyzed and codons were changed to remove potential polyadenylation signal sequences identified in Table 2, while maintaining the number of sequences identified in Table 1. The resulting sequence, which embodies the present invention, is given in SEQ ID NO:65. Table 1 shows that the number and location of polyadenylation signal sequences identified in Table 1 are maintained in SEQ ID NO:65. Table 25 shows that the number of polyadenylation signal sequences identified in Tables 2 and 3 are reduced in SEQ ID NO:65 compared to SEQ ID NO:61.

DNA of SEQ ID NO:65 is synthesized, and expression levels observed in plant cells transformed to express this sequence are compared with expression levels observed in plant cells transformed to express SEQ ID NO:61 and SEQ ID NO:63.

The synthetic coding region of SEQ ID NO:65 was optimized for expression in maize.

A construct for use in expressing the synthetic coding region of SEQ ID NO:65 is made by combining the synthetic coding region of SEQ ID NO:65 with a 5' non-translated region comprising a promoter that functions in plant cells and a 3' non-translated region comprising a transcription terminator and polyadenylation sequence.

TABLE 25

Table 1 sequences found in the native *Leptosphaeria nodorum* FAD9 coding region (SEQ ID NO: 61) and in the redesigned version (SEQ ID NO: 65)

| | Table 1 Sequence | No. Sites in Native Ln FAD9 sequence (SEQ ID NO: 61) | nt Location in Native Ln FAD9 sequence (SEQ ID NO: 61) | No. Sites in redesigned Ln FAD9 sequence (SEQ ID NO: 65) | nt Location in redesigned Ln FAD9 sequence (SEQ ID NO: 65) |
|---|---|---|---|---|---|
| 1 | AATAAA | 0 | NA* | 0 | NA |
| 2 | AATAAT | 0 | NA | 0 | NA |
| 3 | AACCAA | 0 | NA | 0 | NA |
| 4 | ATATAA | 0 | NA | 0 | NA |
| 5 | AATCAA | 0 | NA | 0 | NA |
| 6 | ATACTA | 0 | NA | 0 | NA |
| 7 | ATAAAA | 0 | NA | 0 | NA |
| 8 | ATGAAA | 0 | NA | 0 | NA |
| 9 | AAGCAT | 0 | NA | 0 | NA |
| 10 | ATTAAT | 0 | NA | 0 | NA |
| 11 | ATACAT | 0 | NA | 0 | NA |
| 12 | AAAATA | 0 | NA | 0 | NA |
| 13 | ATTAAA | 0 | NA | 0 | NA |
| 14 | AATTAA | 0 | NA | 0 | NA |
| 15 | AATACA | 0 | NA | 0 | NA |
| 16 | CATAAA | 0 | NA | 0 | NA |
| | Total | 0 | | 0 | |

*NA = Not Applicable

TABLE 26

Table 2 sequences found in the native *Leptosphaeria nodorum* FAD9 coding region (SEQ ID NO: 61) and redesigned version (SEQ ID NO: 65)

| | Table 2 Sequence | No. Sites in Native Ln FAD9 sequence (SEQ ID NO: 61) | nt Location in Native Ln FAD9 sequence (SEQ ID NO: 61) | No. Sites in redesigned Ln FAD9 sequence (SEQ ID NO: 65) | nt Location in redesigned Ln FAD9 sequence (SEQ ID NO: 65) |
|---|---|---|---|---|---|
| 1 | ATATAT | 0 | NA* | 0 | NA |
| 2 | TTGTTT | 0 | NA | 0 | NA |
| 3 | TTTTGT | 0 | NA | 0 | NA |
| 4 | TGTTTT | 1 | 1275 | 0 | NA |
| 5 | TATATA | 0 | NA | 0 | NA |
| 6 | TATTTT | 0 | NA | 0 | NA |
| 7 | TTTTTT | 0 | NA | 0 | NA |
| 8 | ATTTTT | 0 | NA | 0 | NA |
| 9 | TTATTT | 0 | NA | 0 | NA |
| 10 | TTTATT | 1 | 1090 | 0 | NA |
| 11 | TAATAA | 0 | NA | 0 | NA |
| 12 | ATTTAT | 0 | NA | 0 | NA |
| 13 | TATATT | 0 | NA | 0 | NA |
| 14 | TTTTAT | 0 | NA | 0 | NA |
| 15 | ATATTT | 0 | NA | 0 | NA |
| 16 | TATTAT | 1 | 416 | 0 | NA |
| 17 | TGTTTG | 0 | NA | 0 | NA |
| 18 | TTATAT | 0 | NA | 0 | NA |
| 19 | TGTAAT | 0 | NA | 0 | NA |
| 20 | AAATAA | 0 | NA | 0 | NA |
| | Total | 3 | | 0 | |

*NA = Not Applicable

Example 12

Synthetic Coding Region Encoding *Xerophyta viscosa* PER1

Comparative Sequences. The native DNA sequence encoding the *Xerophyta viscosa* PER1 protein is given in SEQ ID NO:67. This sequence was analyzed to determine which sequences identified in Table 1 are present in SEQ ID NO:67 and their locations. The amino acid sequence encoded by SEQ ID NO:67 was then reverse translated using the target codon frequencies given in the column of Table 4 for synthetic genes to be used in maize. The resulting DNA sequence was analyzed and codons were changed where necessary to remove unwanted open reading frames and remove unwanted restriction enzyme recognition sites, while maintaining all sequences identified in Table 1. The amino acid sequence encoded by SEQ ID NO:67 was preserved. The resulting DNA sequence is given in SEQ ID NO:69. This sequence will be synthesized and used for comparison with a synthetic gene designed in accordance with the invention.

SEQ ID NO:69 was analyzed and codons were changed to remove potential polyadenylation signal sequences identified in Table 2, while maintaining the number of sequences identified in Table 1. The resulting sequence, which embodies the present invention, is given in SEQ ID NO:71. Table 1 shows that the number and location of polyadenylation signal sequences identified in Table 1 are maintained in SEQ ID NO:71. Table 27 shows that the number of polyadenylation signal sequences identified in Tables 2 and 3 are reduced in SEQ ID NO:71 compared to SEQ ID NO:67.

DNA of SEQ ID NO:71 is synthesized, and expression levels observed in plant cells transformed to express this sequence are compared with expression levels observed in plant cells transformed to express SEQ ID NO:67 and SEQ ID NO:69.

The synthetic coding region of SEQ ID NO:71 was optimized for expression in maize.

A construct for use in expressing the synthetic coding region of SEQ ID NO:71 is made by combining the synthetic coding region of SEQ ID NO:71 with a 5' non-translated region comprising a promoter that functions in plant cells and a 3' non-translated region comprising a transcription terminator and polyadenylation sequence.

TABLE 27

Table 1 sequences found in the native Xerophyta viscosa PER1 coding region (SEQ ID NO: 67) and in the redesigned version (SEQ ID NO: 71)

| Table 1 Sequence | No. Sites in Native XvPER1 sequence (SEQ ID NO: 67) | nt Location in Native XvPER1 sequence (SEQ ID NO: 67) | No. Sites in redesigned XvPER1 sequence (SEQ ID NO: 71) | nt Location in redesigned XvPER1 sequence (SEQ ID NO: 71) |
|---|---|---|---|---|
| 1 AATAAA | 0 | NA* | 0 | NA |
| 2 AATAAT | 0 | NA | 0 | NA |
| 3 AACCAA | 0 | NA | 0 | NA |
| 4 ATATAA | 0 | NA | 0 | NA |
| 5 AATCAA | 0 | NA | 0 | NA |
| 6 ATACTA | 0 | NA | 0 | NA |
| 7 ATAAAA | 1 | 605 | 1 | 605 |
| 8 ATGAAA | 0 | NA | 0 | NA |
| 9 AAGCAT | 0 | NA | 0 | NA |
| 10 ATTAAT | 0 | NA | 0 | NA |
| 11 ATACAT | 0 | NA | 0 | NA |
| 12 AAAATA | 1 | 282 | 1 | 282 |
| 13 ATTAAA | 0 | NA | 0 | NA |
| 14 AATTAA | 0 | NA | 0 | NA |
| 15 AATACA | 0 | NA | 0 | NA |
| 16 CATAAA | 0 | NA | 0 | NA |
| Total | 2 | | 2 | |

*NA = Not Applicable

TABLE 28

Table 2 sequences found in the native the Xerophyta viscosa PER1 coding region (SEQ ID NO: 67 and in the redesigned version (SEQ ID NO: 71)

| Table 2 Sequence | No. Sites in Native XvPER1 sequence (SEQ ID NO: 67) | nt Location in Native XvPER1 sequence (SEQ ID NO: 67) | No. Sites in redesigned XvPER1 sequence (SEQ ID NO: 71) | nt Location in redesigned XvPER1 sequence (SEQ ID NO: 71) |
|---|---|---|---|---|
| 1 ATATAT | 0 | NA* | 0 | NA |
| 2 TTGTTT | 0 | NA | 0 | NA |
| 3 TTTTGT | 0 | NA | 0 | NA |
| 4 TGTTTT | 0 | NA | 0 | NA |
| 5 TATATA | 0 | NA | 0 | NA |
| 6 TATTTT | 0 | NA | 0 | NA |
| 7 TTTTTT | 0 | NA | 0 | NA |
| 8 ATTTTT | 0 | NA | 0 | NA |
| 9 TTATTT | 0 | NA | 0 | NA |
| 10 TTTATT | 0 | NA | 0 | NA |
| 11 TAATAA | 0 | NA | 0 | NA |
| 12 ATTTAT | 0 | NA | 0 | NA |
| 13 TATATT | 0 | NA | 0 | NA |
| 14 TTTTAT | 0 | NA | 0 | NA |
| 15 ATATTT | 0 | NA | 0 | NA |
| 16 TATTAT | 0 | NA | 0 | NA |
| 17 TGTTTG | 0 | NA | 0 | NA |

TABLE 28-continued

Table 2 sequences found in the native the
Xerophyta viscosa PER1 coding region (SEQ
ID NO: 67 and in the redesigned version
(SEQ ID NO: 71)

| Table 2 Sequence | No. Sites in Native XvPER1 sequence (SEQ ID NO: 67) | nt Location in Native XvPER1 sequence (SEQ ID NO: 67) | No. Sites in redesigned XvPER1 sequence (SEQ ID NO: 71) | nt Location in redesigned XvPER1 sequence (SEQ ID NO: 71) |
|---|---|---|---|---|
| 18 TTATAT | 0 | NA | 0 | NA |
| 19 TGTAAT | 0 | NA | 0 | NA |
| 20 AAATAA | 0 | NA | 0 | NA |
| Total | 0 | | 0 | |

*NA = Not Applicable

Example 13

WHISKERS® Transformation of Maize with Xv SAP1

A standard WHISKERS transformation vector was constructed in which the *Arabidopsis thaliana* promoter, Rd29A, was placed 5' to the XvSAP1 redesigned coding region sequence of the invention (SEQ ID NO:53). These sequences were flanked by *Zea maize* PER5, 3' and 5' untranslated regions to stabilize expression of the redesigned coding region. A pat selection cassette (See, for example, U.S. Pat. No. 5,648,477) driven by the rice actin1 promoter was placed 3' to the XvSAP1 expression cassette.

Vector DNA was digested with appropriate restriction enzymes to release a fragment containing the bacterial ampicillin resistance gene present in the vector backbone, and to produce a linear DNA fragment suitable for WHISKERS™-mediated transformation. Purification of the linear fragment containing the XvSAP1 and pat expression cassettes was accomplished on a preparative scale by high pressure liquid chromatography (HPLC). This plant transformation DNA was delivered into maize Hi-II suspension cell cultures via WHISKERS™-mediated transformation (essentially as described in U.S. Pat. Nos. 5,302,523 and 5,464,765; US Patent Publication No. 2008/0182332; and Petolino and Arnold (2009) (Methods Molec. Biol. 526:59-67).

Transformants were placed in selective medium after which transformed isolates were obtained over the course of approximately 8 weeks. The selection medium was an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L AgNO$_3$, 250 mg/L cefotaxime, 2.5 gm/L Gellan gum, pH 5.7) containing Bialaphos (Gold BioTechnology). The embryos were transferred to selection media containing 3 mg/L Bialaphos until embryogenic isolates were obtained. Recovered isolates were bulked up by transferring to fresh selection medium at 2-week intervals for regeneration and further analysis.

For regeneration, the cultures were transferred to "28" induction medium (MS salts and vitamins, 30 gm/L sucrose, 5 mg/L Benzylaminopurine, 0.25 mg/L 2,4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues were subsequently transferred to "36" regeneration medium (same as induction medium except lacking plant growth regulators). When plantlets reached 3-5 cm in length, they were transferred to glass culture tubes containing SHGA medium (Schenk and Hildebrandt salts and vitamins (1972); PhytoTechnologies Labr.), 1.0 gm/L myo-inositol, 10 gm/L sucrose and 2.0 gm/L Gellan gum, pH 5.8) to allow for further growth and development of the shoot and roots. Plants were transplanted to the same soil mixture as described earlier herein and grown to flowering in the greenhouse. Controlled pollinations for seed production were conducted.

Example 14

*Agrobacterium* Transformation

Standard cloning methods are used in the construction of binary plant transformation and expression plasmids. Restriction endonucleases and T4 DNA Ligase are obtained from NEB. Plasmid preparations are performed using the NucleoSpin® Plasmid Preparation kit or the NucleoBond® AX Xtra Midi kit (both from Macherey-Nagel), following the instructions of the manufacturers. DNA fragments are purified using the QIAquick® PCR Purification Kit or the QIAEX II® Gel Extraction Kit (both from Qiagen) after gel isolation.

Synthetic genes in accordance with the invention may be synthesized by a commercial vendor (e.g. DNA2.0, Menlo Park, Calif.) and supplied as cloned fragments in standard plasmid vectors, or may be obtained by standard molecular biology manipulation of other constructs containing appropriate nucleotide sequences.

In a non-limiting example, a basic cloning strategy may be to subclone full length coding sequences (CDS) into a plant expression plasmid at NcoI and SacI restriction sites. The resulting plant expression cassettes containing the appropriate coding region under the control of plant expression elements, (e.g., plant expressible promoters, 3' terminal transcription termination and polyadenylate addition determinants, and the like) are subcloned into a binary vector plasmid, utilizing, for example, Gateway® technology or standard restriction enzyme fragment cloning procedures. LR Clonase™ (Invitrogen) for example, may be used to recombine the full length and modified gene plant expression cassettes into a binary plant transformation plasmid if the Gateway® technology is utilized. It is convenient to employ a binary plant transformation vector that harbors a bacterial gene that confers resistance to the antibiotic spectinomycin when the plasmid is present in *E. coli* and *Agrobacterium* cells. It is also convenient to employ a binary vector plasmid that contains a plant-expressible selectable marker gene that is functional in the desired host plants. Examples of plant-expressible selectable marker genes include but are not limited those that encode the aminoglycoside phosphotransferase gene (aphII) of transposon Tn5, which confers resistance to the antibiotics kanamycin, neomycin and G418, as well as those genes which code for resistance or tolerance to glyphosate; hygromycin; methotrexate; phosphinothricin (bialaphos), imidazolinones, sulfonylureas and triazolopyrimidine herbicides, such as chlorosulfuron, bromoxynil, dalapon and the like.

Electro-competent cells of *Agrobacterium tumefaciens* strain Z7075 (a streptomycin-resistant derivative of Z707; Hepburn et al., 1985, J. Gen. Microbiol. 131:2961-2969.) are prepared and transformed using electroporation (Weigel and Glazebrook, 2002, *Arabidopsis*: A Laboratory Manual). After electroporation, 1 mL of YEP broth (gm/L: yeast extract, 10; peptone, 10; NaCl, 5) are added to the cuvette and the cell-YEP suspension is transferred to a 15 mL culture tube for incubation at 28° in a water bath with constant agitation for 4 hours. The cells are plated on YEP plus agar (25 gm/L) with spectinomycin (200 µg/mL) and streptomycin (250 µg/mL) and the plates are incubated for 2-4 days at 28°. Well separated single colonies are selected and streaked onto fresh YEP+agar plates with spectinomycin and streptomycin as before, and incubated at 28° for 1-3 days.

The presence of the synthetic gene insert in the binary plant transformation vector is performed by PCR analysis using vector-specific primers with template plasmid DNA prepared from selected *Agrobacterium* colonies. The cell pellet from a 4 mL aliquot of a 15 mL overnight culture grown in YEP with spectinomycin and streptomycin as before is extracted using Qiagen Spin® Mini Preps, performed per manufacturer's instructions. Plasmid DNA from the binary vector used in the *Agrobacterium* electroporation transformation is included as a control. The PCR reaction is completed using Taq DNA polymerase from Invitrogen per manufacture's instructions at 0.5× concentrations. PCR reactions are carried out in a MJ Research Peltier Thermal Cycler programmed with the following conditions: Step 1) 94° for 3 minutes; Step 2) 94° for 45 seconds; Step 3) 55° for 30 seconds; Step 4) 72° for 1 minute per kb of expected product length; Step 5) 29 times to Step 2; Step 6) 72° for 10 minutes. The reaction is maintained at 4° after cycling. The amplification products are analyzed by agarose gel electrophoresis (e.g. 0.7% to 1% agarose, w/v) and visualized by ethidium bromide staining A colony is selected whose PCR product is identical to the plasmid control.

Alternatively, the plasmid structure of the binary plant transformation vector containing the synthetic gene insert is performed by restriction digest fingerprint mapping of plasmid DNA prepared from candidate *Agrobacterium* isolates by standard molecular biology methods well known to those skilled in the art of *Agrobacterium* manipulation.

Those skilled in the art of obtaining transformed plants via *Agrobacterium*-mediated transformation methods will understand that other *Agrobacterium* strains besides Z7075 may be used to advantage, and the choice of strain may depend upon the identity of the host plant species to be transformed.

Example 15

Production of Insecticidal Proteins in Dicot Plants

*Arabidopsis* Transformation.

*Arabidopsis thaliana* Col-01 is transformed using the floral dip method (Weigel and Glazebrook, supra). The selected *Agrobacterium* colony is used to inoculate 1 mL to 15 mL cultures of YEP broth containing appropriate antibiotics for selection. The culture is incubated overnight at 28° with constant agitation at 220 rpm. Each culture is used to inoculate two 500 mL cultures of YEP broth containing appropriate antibiotics for selection and the new cultures are incubated overnight at 28° with constant agitation. The cells are pelleted at approximately 8700×g for 10 minutes at room temperature, and the resulting supernatant is discarded. The cell pellet is gently resuspended in 500 mL of infiltration media containing: 1/2× Murashige and Skoog salts (Sigma-Aldrich)/Gamborg's B5 vitamins (Gold BioTechnology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22°, with a 16-hour light/8-hour dark photoperiod. Approximately 4 weeks after dipping, the seeds are harvested.

*Arabidopsis* Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron (Models CMP4030 or CMP3244; Controlled Environments Limited, Winnipeg, Manitoba, Canada) under long day conditions (16 hours light/8 hours dark) at a light intensity of 120-150 µmol/m$^2$ sec under constant temperature (22°) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996, Nat. Biotech. 14:1274-1278), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron under the above-mentioned growth conditions.

Those skilled in the art of dicot plant transformation will understand that other methods of selection of transformed plants are available when other plant expressible selectable marker genes (e.g. herbicide tolerance genes) are used.

Insect Bioassays of Transgenic *Arabidopsis*.

Transgenic *Arabidopsis* lines expressing Cry proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

Example 16

*Agrobacterium* Transformation for Generation of Superbinary Vectors

The *Agrobacterium* superbinary system is conveniently used for transformation of monocot plant hosts. Methodologies for constructing and validating superbinary vectors are well disclosed and incorporated herein by reference (Operating Manual for Plasmid pSB1, Version 3.1, available from Japan Tobacco, Inc., Tokyo, Japan). Standard molecular biological and microbiological methods are used to generate superbinary plasmids. Verification/validation of the structure of the superbinary plasmid is done using methodologies as described above for binary vectors, and may be modified as suggested in the Operating Manual for Plasmid pSB1.

Example 17

Production of Insecticidal Proteins in Monocot Plants

*Agrobacterium*-Mediated Transformation of Maize.

Seeds from a High II $F_1$ cross (Armstrong et al., 1991, Maize Genet. Coop. Newsletter 65:92-93) are planted into 5-gallon-pots containing a mixture of 95% Metro-Mix 360 soilless growing medium (Sun Gro Horticulture, Bellevue, Wash.) and 5% clay/loam soil. The plants are grown in a greenhouse using a combination of high pressure sodium and metal halide lamps with a 16:8 hour Light:Dark photoperiod. For obtaining immature $F_2$ embryos for transformation, controlled sib-pollinations are performed. Immature embryos are isolated at 8-10 days post-pollination when embryos are approximately 1.0 to 2.0 mm in size.

Infection and Co-Cultivation.

Maize ears are surface sterilized by scrubbing with liquid soap, immersing in 70% ethanol for 2 minutes, and then immersing in 20% commercial bleach (0.1% sodium hypochlorite) for 30 minutes before being rinsed with sterile water. A suspension of *Agrobacterium* cells containing a superbinary vector is prepared by transferring 1-2 loops of bacteria grown on YEP solid medium containing 100 mg/L spectinomycin, 10 mg/L tetracycline, and 250 mg/L streptomycin at 28° for 2-3 days into 5 mL of liquid infection medium (LS Basal Medium (Linsmaier and Skoog, 1965, Physiol. Plant. 18:100-127), N6 vitamins (Chu et al., 1975, Scientia Sinica 18:659-668), 1.5 mg/L 2,4-Dichlorophenoxyacetic acid (2,4-D), 68.5 gm/L sucrose, 36.0 gm/L glucose, 6 mM L-proline, pH 5.2) containing 100 µM acetosyringone. The solution was vortexed until a uniform suspension was achieved, and the concentration is adjusted to a final density of about 200 Klett units, using a Klett-Summerson colorimeter with a purple filter, or an optical density of approximately 0.4 at 550 nm. Immature embryos are isolated directly into a micro centrifuge tube containing 2 mL of the infection medium. The medium is removed and replaced with 1 mL of the *Agrobacterium* solution with a density of 200 Klett units, and the *Agrobacterium* and embryo solution is incubated for 5 minutes at room temperature and then transferred to co-cultivation medium (LS Basal Medium, N6 vitamins, 1.5 mg/L 2,4-D, 30.0 gm/L sucrose, 6 mM L-proline, 0.85 mg/L $AgNO_3$, 100 µM acetosyringone, 3.0 gm/L Gellan gum (PhytoTechnology Laboratories, Lenexa, Kans.), pH 5.8) for 5 days at 25° under dark conditions.

After co-cultivation, the embryos are transferred to selective medium after which transformed isolates are obtained over the course of approximately 8 weeks. For selection of maize tissues transformed with a superbinary plasmid containing a plant expressible pat or bar selectable marker gene, an LS based medium (LS Basal medium, N6 vitamins, 1.5 mg/L 2,4-D, 0.5 gm/L MES (2-(N-morpholino)ethanesulfonic acid monohydrate; PhytoTechnologies Labr.), 30.0 gm/L sucrose, 6 mM L-proline, 1.0 mg/L $AgNO_3$, 250 mg/L cefotaxime, 2.5 gm/L Gellan gum, pH 5.7) is used with Bialaphos (Gold BioTechnology). The embryos are transferred to selection media containing 3 mg/L Bialaphos until embryogenic isolates were obtained. Recovered isolates are bulked up by transferring to fresh selection medium at 2-week intervals for regeneration and further analysis.

Those skilled in the art of maize transformation will understand that other methods of selection of transformed plants are available when other plant expressible selectable marker genes (e.g. herbicide tolerance genes) are used.

Regeneration and Seed Production.

For regeneration, the cultures are transferred to "28" induction medium (MS salts and vitamins, 30 gm/L sucrose, 5 mg/L Benzylaminopurine, 0.25 mg/L 2,4-D, 3 mg/L Bialaphos, 250 mg/L cefotaxime, 2.5 gm/L Gellan gum, pH 5.7) for 1 week under low-light conditions (14 $\mu Em^{-2}s^{-1}$) then 1 week under high-light conditions (approximately 89 $\mu Em^{-2}s^{-1}$). Tissues are subsequently transferred to "36" regeneration medium (same as induction medium except lacking plant growth regulators). When plantlets grow to 3-5 cm in length, they were transferred to glass culture tubes containing SHGA medium (Schenk and Hildebrandt salts and vitamins (1972); PhytoTechnologies Labr.), 1.0 gm/L myo-inositol, 10 gm/L sucrose and 2.0 gm/L Gellan gum, pH 5.8) to allow for further growth and development of the shoot and roots. Plants are transplanted to the same soil mixture as described earlier herein and grown to flowering in the greenhouse. Controlled pollinations for seed production are conducted.

Alternatively, binary vectors may be used to produce transgenic maize plants that contain one or more chimeric genes stably-integrated into the plant genome and comprising a coding region disclosed herein. For example, plants comprising at least one coding region of SEQ ID NOs:5, 11, 17, 23, 29, 35, 41, 47, 53, 59, 65, or 71 are produced following *Agrobacterium*-mediated transformation. Maize transformation methods employing binary transformation vectors are known in the art. In one embodiment, transformed tissues are selected by their ability to grow on haloxyfop-containing medium and are screened for protein production, as appropriate.

Ear Sterilization and Embryo Isolation.

Maize immature embryos were obtained from plants of *Zea mays* inbred line B104 grown in the greenhouse and self- or sib-pollinated to produce ears. The ears were harvested approximately 9 to 12 days post-pollination. On the experimental day, de-husked ears were surface-sterilized by immersion in a 20% solution of sodium hypochlorite (6.15%) and shaken for 20 to 30 min, followed by three rinses in sterile water. After sterilization, immature zygotic embryos (1.5 to 2.4 mm) were aseptically dissected from each ear and randomly distributed into microcentrifuge tubes containing liquid Inoculation Medium. Inoculation Medium contains: 2.2 gm/L MS salts (Frame et al., 2011, *Genetic Transformation Using Maize Immature Zygotic Embryos*. IN Plant Embryo Culture Methods and Protocols: Methods in Molecular Biology. T. A. Thorpe and E. C. Yeung, (Eds), SPRINGER SCIENCE AND BUSINESS MEDIA, LLC. pp 327-341); 1×ISU Modified MS Vitamins (Frame et al., 2011 supra); 68.4 gm/L sucrose; 36 gm/L glucose; 115 mg/L L-proline; 100 mg/L myo-inositol; and 200 µM acetosyringone (prepared in DMSO); at pH 5.4. For a given set of experiments, embryos from pooled ears were used for each transformation.

*Agrobacterium* Culture Initiation.

Glycerol stocks of *Agrobacterium* strain DAt13192 (International PCT Publication No. WO2012016222(A2)) containing the binary transformation vector pDAB111440 (Example 1) were streaked on AB minimal medium plates (Watson, et al., (1975) J. Bacteriol. 123:255-264) containing appropriate antibiotics and were grown at 20° C. for 3 to 4 days. A single colony was picked and streaked onto YEP plates (gm/L: yeast extract, 10; Peptone, 10; NaCl 5) containing the same antibiotics and was incubated at 20° C. for 1-2 days.

Agrobacterium Culture and Co-Cultivation.

Agrobacterium colonies were taken from a YEP plate, suspended in 10 mL of Inoculation Medium in a 50 mL disposable tube, and the cell density was adjusted to an $OD_{550}$ of 0.2 to 0.4 (Optical Density measured at 550 nm; a measure of cell growth) using a spectrophotometer. The Agrobacterium cultures were incubated on a rotary shaker at 125 rpm (room temperature) while embryo dissection was performed. Immature zygotic embryos (previously isolated from the sterilized maize kernels and placed in 1 mL of Inoculation Medium) were washed once in the same medium. Two ml of the Agrobacterium suspension was added to each tube of embryos and the tubes were placed on a shaker platform for 10 to 15 minutes. The embryos were transferred onto Co-cultivation Medium, oriented with the scutellum facing up, and incubated at 25° C., under 24-hour light at 50 $\mu Em^{-2}$ $sec^{-1}$ light intensity for 3 days. Co-cultivation Medium, contains 4.33 gm/L MS salts; 1×ISU Modified MS Vitamins; 30 gm/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L $AgNO_3$; 100 µM acetosyringone in DMSO; and 3 gm/L GELZAN™ (SIGMA-ALDRICH); at pH 5.8.

Callus Selection and Regeneration of Putative Events.

Following the co-cultivation period, embryos were transferred to Resting Medium and incubated under 24-hour light at 50 $\mu Em^{-2}$ $sec^{-1}$ light intensity and at 25° C. for 3 days. Resting Medium contains 4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L $AgNO_3$; 0.5 gm/L MES (2-(N-morpholino)ethanesulfonic acid monohydrate; PHYTOTECHNOLOGIES LABR.; Lenexa, Kans.); 250 mg/L Carbenicillin; and 2.3 gm/L GELZAN™; at pH 5.8. Embryos were transferred onto Selection Medium 1 (which consists of the Resting Medium (above) with 100 nM R-Haloxyfop acid (0.0362 mg/L)), and incubated in either dark and/or under 24-hour light at 50 $\mu Em^{-2}$ $sec^{-1}$ light intensity for 7 to 14 days at 28° C. Proliferating embryogenic calli were transferred onto Selection Medium 2 (which consists of Resting Medium (above), with 500 nM R-Haloxyfop acid (0.1810 mg/L)), and were incubated in 24-hour light at 50 $\mu Em^{-2}$ $sec^{-1}$ light intensity for 14 to 21 days at 28° C. This selection step allowed transgenic callus to further proliferate and differentiate.

Proliferating, embryogenic calli were transferred onto PreRegeneration Medium and cultured under 24-hour light at 50 $\mu m^{-2}$ $sec^{-1}$ light intensity for 7 days at 28° C. PreRegeneration Medium contains 4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L $AgNO_3$; 0.25 mg/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 500 nM R-Haloxyfop acid; at pH 5.8. Embryogenic calli with shoot-like buds were transferred onto Regeneration Medium and cultured under 24-hour light at 50 $\mu Em^{-2}$ $sec^{-1}$ light intensity for 7 days. Regeneration Medium I contains 4.33 gm/L MS salts; 1×ISU Modified MS Vitamins; 60 gm/L sucrose; 100 mg/L myo-inositol; 125 mg/L Carbenicillin; 3.0 gm/L GELZAN™; and 500 nM R-Haloxyfop acid; at pH 5.8. Small shoots with primary roots were transferred to Shoot/Root medium in PHYTATRAYS (PHYTOTECHNOLOGIES LABR.; Lenexa, Kans.) and were incubated under 16:8 hr. light:dark at 140 to 190 $\mu Em^{-2}$ $sec^{-1}$ light intensity for 7 days at 27° C. Shoot/Root Medium contains 4.33 gm/L MS salts; 1×ISU Modified MS Vitamins; 30 gm/L sucrose; 100 mg/L myo-inositol; 3.5 gm/L GELZAN™; at pH 5.8. Putative transgenic plantlets were analyzed for transgene copy number by quantitative real-time PCR or other standard molecular analysis techniques, and were transferred to soil.

Transfer and establishment of $T_o$ plants in the greenhouse for seed production. Transformed plant tissues selected by their ability to grow on medium containing 500 nM R-Haloxyfop acid were transplanted into METRO-MIX 360 soilless growing medium (SUN GRO HORTICULTURE) and hardened-off in a growth room. Plants were then transplanted into SUNSHINE CUSTOM BLEND 160 soil mixture and grown to flowering in the greenhouse. Controlled pollinations for seed production are conducted.

Leaf tissues of selected $T_0$ plants were sampled at the V-3 to V-5 stage. Two 6 mm diameter leaf samples were stored in a 96 well cluster tube rack at −80° C. until the day of analysis. Two DAISY™ steel BB's and 200 µL of extraction buffer (PBS solution containing 0.05% of Tween 20 and 5 µL/ml of SIGMA protease inhibitor cocktail (catalog number 9599)) were added to each tube. The samples were milled in a KLECO bead mill (Visalia, Calif.) for 3 minutes, on maximum setting. Samples were centrifuged at 3,000×g for 5 minutes, then 100 µL of the supernatant were transferred to an empty sample tube. Another 100 µL of extraction buffer was added to the plant sample and bead-milled an 3 additional minutes. After centrifuging again, 100 µL of this extract was combined with the first 100 pt. The combined supernatants were mixed and analyzed on the same day as the extraction.

Proteins extracted from measured areas of leaf tissue were analyzed for expression of Cry1Fa protein and AAD-1 protein by standard ELISA (Enzyme-Linked Immunosorbant Assay) or protein immunoblots (western blots). For Cry1Fa ELISA detection, reagents from an ENVIROLOGIX ELISA kit (Cat. No. AP 016 NW V10; Portland, Me.) were used according to the manufacturer's instructions. AAD-1 detection was performed by standard ELISA methodologies (for example, as taught in Ausubel et al. (1995 and updates) Current Protocols in Molecular Biology, John Wiley and Sons, New York) using rabbit antibodies prepared against purified AAD-1 protein.

The ELISA results obtained from extracts of pDAB111440-transformed plants are disclosed in Table 29. Protein levels are expressed as ng of the subject protein detected per square centimeter of leaf area harvested.

TABLE 29

Expression levels of Cry1Fa and AAD-1 proteins extracted from maize plants transformed with plasmid pDAB111440, as detected by ELISA methods.

| Sample ID | Cry1Fa ng/cm$^2$ | AAD-1 ng/cm$^2$ |
|---|---|---|
| 111440[3]-001.001 | 2.30 | 14.0 |
| 111440[3]-015.001 | 3.80 | 0.0 |

TABLE 29-continued

Expression levels of Cry1Fa and AAD-1 proteins
extracted from maize plants transformed with plasmid
pDAB111440, as detected by ELISA methods.

| Sample ID | Cry1Fa ng/cm$^2$ | AAD-1 ng/cm$^2$ |
|---|---|---|
| 111440[3]-023.001 | 3.80 | 320.0 |
| 111440[3]-020.001 | 5.40 | 190.0 |
| 111440[3]-011.001 | 17.00 | 0.0 |

Protein extracts of the five pDAB111440-transformed plants listed in Table 29 (as well as extract from a non-transformed negative control plant) were prepared as above and probed with Cry1Fa antibody on immunoblots (western blots). Immunoblot procedures were essentially as described by Gallagher et al. (2008; Immunoblotting and Immunodetection. Current Protocols in Immunology 8.10.1-8.10.28). Protein samples (80 µL) were mixed with 20 µL of INVITROGEN NuPAGE LDS Sample Buffer, heated at >90° C. for five min, loaded on an INVITROGEN NuPAGE 4-12% Bis-Tris gel, and run in MOPS SDS Running Buffer (200 Volts for 45 minutes). BIORAD PRECISION PLUS Dual Color Standards were loaded in a separate lane. Proteins were transferred to 0.2 µM nitrocellulose membrane by means of an INVITROGEN iBLOT Gel Transfer system according to the manufacturer's instructions. The membrane was blocked with INVITROGEN WESTERN BREEZE BLOCKING MIX, then reacted with Primary antibody (anti-Cry1F Purified Rabbit Antibody No. D0609RA07-A0; Strategic Diagnostics Inc., Newark, Del.), followed by Secondary antibody (INVITROGEN Biotinylated goat anti-rabbit antibody.) This was followed by INVITROGEN HRP-Streptavidin conjugate and reacted bands were detected by PIERCE SUPERSIGNAL WEST PICO LUMINOL ENHANCER AND STABLE PEROXIDE (No. 34080).

Positive control lanes contained 0.5 ng or 1.0 ng of purified Cry1Fa core toxin protein produced by expression of a full length Cry1Fa coding region in a *Pseudomonas fluorescens* expression system (See, for example, US Patent Application No. 20100269223A1). The full-length Cry1Fa protein was trypsin treated to release the Cry1Fa core toxin segment of calculated molecular size 68 kDa, which was used as the positive control standard on the immunoblot. No antibody-reacting bands were detected in the extract from the negative control plant, while all five transgenic plant extracts contained a single predominant band (roughly equal in intensity to the control Cry1Fa proteins) of estimated size somewhat larger than 75 kDa.

Methods of Controlling Insect Pests.

When an insect comes into contact with an effective amount of toxin delivered via transgenic plant expression the results are typically death of the insect, or the insects do not feed upon the source which makes the toxins available to the insects.

The invention claimed is:

1. A synthetic DNA sequence for expressing a protein of interest in maize cells which comprises:
   a) a codon-optimized DNA sequence encoding the protein of interest, and
   b) at least one polyadenylation signal sequence chosen from the group consisting of Class I and Class II; wherein
   Class I is chosen from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA; and
   Class II is chosen from the group consisting of ATATAT, TTGTTT, TTTTGT, TGTTTT, TATATA, TATTTT, TATTTT, TTTTTT, ATTTT, TTATTT, TTTATT, TAATAA, ATTTAT, TATATT, TITTAT, ATATTT, TATTAT, TGTTTG, TTATAT, TGTAAT, and AAATAA; and
   wherein said codon-optimized DNA sequence contains at least one polyadenylation signal sequence from Class II and wherein said synthetic DNA sequence contains fewer Class II polyadenylation signal sequences than the protein's native DNA sequence and contains the same number of class I polyadenylation signal sequences compared to said native DNA sequence and wherein the synthetic DNA sequence comprises a sequence selected from the group consisting of SEQ ID NO:5, SEQ ID NO: 11, SEQ ID NO: 17, SEQ ID NO:23, SEQ ID NO:29, SEQ ID NO:35, SEQ ID NO:41, SEQ ID NO:47, SEQ ID NO:53, SEQ ID NO:59, SEQ ID NO:65, and SEQ ID NO:71.

2. The synthetic DNA sequence of claim 1 wherein said synthetic DNA sequence encodes a native protein selected from the group consisting of insecticidal proteins, herbicide tolerance proteins, stress tolerance-related proteins, and oil profile modification proteins.

3. The synthetic DNA sequence of claim 2 wherein said synthetic DNA sequence encodes an insecticidal protein.

4. The synthetic DNA sequence of claim 2 wherein said synthetic DNA sequence encodes aryloxyalkanoate dioxygenase 1 protein.

5. A DNA construct for expression of a protein of interest comprising a 5' non-translated sequence, a coding sequence for a protein of interest, and a 3' non-translated region, wherein said 5' nontranslated sequence contains a promoter functional in a plant cell, said coding sequence is the synthetic DNA coding sequence of claim 1, and wherein said 3' nontranslated sequence comprises a transcription termination sequence and a polyadenylation signal.

6. A transgenic plant containing the synthetic DNA sequence of claim 1.

7. A method of controlling pests in grain or seed which comprises obtaining said grain or seed from plants containing the synthetic DNA of claim 3.

8. A method of controlling pests in meal or flour which comprises obtaining said grain or seed from plants containing the synthetic DNA of claim 3.

9. A method of controlling pests in meal or flour which comprises obtaining said meal or flour from the grain containing the synthetic DNA of claim 4.

* * * * *

SEQUENCE LISTING

```
<160> NUMBER OF SEQ ID NOS: 72

<210> SEQ ID NO 1
<211> LENGTH: 1818
<212> TYPE: DNA
<213> ORGANISM: Bacillus thuringiensis
<220> FEATURE:
<221> NAME/KEY: CDS
<222> LOCATION: (1)..(1818)
<223> OTHER INFORMATION: Native DNA sequence encoding Bacillus
      thuringiensis Cry1Fa core toxin

<400> SEQUENCE: 1 atg gag aat aat att caa aat caa tgc gta cct tac aat tgt tta aat        48
Met Glu Asn Asn Ile Gln Asn Gln Cys Val Pro Tyr Asn Cys Leu Asn
1               5                   10                  15 aat cct gaa gta gaa ata tta aat gaa gaa aga agt act ggc aga tta        96
Asn Pro Glu Val Glu Ile Leu Asn Glu Glu Arg Ser Thr Gly Arg Leu
            20                  25                  30 ccg tta gat ata tcc tta tcg ctt aca cgt ttc ctt ttg agt gaa ttt       144
Pro Leu Asp Ile Ser Leu Ser Leu Thr Arg Phe Leu Leu Ser Glu Phe
        35                  40                  45 gtt cca ggt gtg gga gtt gcg ttt gga tta ttt gat tta ata tgg ggt       192
Val Pro Gly Val Gly Val Ala Phe Gly Leu Phe Asp Leu Ile Trp Gly
    50                  55                  60 ttt ata act cct tct gat tgg agc tta ttt ctt tta cag att gaa caa       240
Phe Ile Thr Pro Ser Asp Trp Ser Leu Phe Leu Leu Gln Ile Glu Gln
65                  70                  75                  80 ttg att gag caa aga ata gaa aca ttg gaa agg aac cgg gca att act       288
Leu Ile Glu Gln Arg Ile Glu Thr Leu Glu Arg Asn Arg Ala Ile Thr
                85                  90                  95 aca tta cga ggg tta gca gat agc tat gaa att tat att gaa gca cta       336
Thr Leu Arg Gly Leu Ala Asp Ser Tyr Glu Ile Tyr Ile Glu Ala Leu
            100                 105                 110
```

-continued

| | | |
|---|---|---|
| aga gag tgg gaa gca aat cct aat aat gca caa tta agg gaa gat gtg<br>Arg Glu Trp Glu Ala Asn Pro Asn Asn Ala Gln Leu Arg Glu Asp Val<br>115                     120                     125 | 384 |
| cgt att cga ttt gct aat aca gac gac gct tta ata aca gca ata aat<br>Arg Ile Arg Phe Ala Asn Thr Asp Asp Ala Leu Ile Thr Ala Ile Asn<br>130                     135                     140 | 432 |
| aat ttt aca ctt aca agt ttt gaa atc cct ctt tta tcg gtc tat gtt<br>Asn Phe Thr Leu Thr Ser Phe Glu Ile Pro Leu Leu Ser Val Tyr Val<br>145                     150                     155                     160 | 480 |
| caa gcg gcg aat tta cat tta tca cta tta aga gac gct gta tcg ttt<br>Gln Ala Ala Asn Leu His Leu Ser Leu Leu Arg Asp Ala Val Ser Phe<br>                     165                     170                     175 | 528 |
| ggg cag ggt tgg gga ctg gat ata gct act gtt aat aat cat tat aat<br>Gly Gln Gly Trp Gly Leu Asp Ile Ala Thr Val Asn Asn His Tyr Asn<br>                     180                     185                     190 | 576 |
| aga tta ata aat ctt att cat aga tat acg aaa cat tgt ttg gac aca<br>Arg Leu Ile Asn Leu Ile His Arg Tyr Thr Lys His Cys Leu Asp Thr<br>                 195                     200                     205 | 624 |
| tac aat caa gga tta gaa aac tta aga ggt act aat act cga caa tgg<br>Tyr Asn Gln Gly Leu Glu Asn Leu Arg Gly Thr Asn Thr Arg Gln Trp<br>210                     215                     220 | 672 |
| gca aga ttc aat cag ttt agg aga gat tta aca ctt act gta tta gat<br>Ala Arg Phe Asn Gln Phe Arg Arg Asp Leu Thr Leu Thr Val Leu Asp<br>225                     230                     235                     240 | 720 |
| atc gtt gct ctt ttt ccg aac tac gat gtt aga aca tat cca att caa<br>Ile Val Ala Leu Phe Pro Asn Tyr Asp Val Arg Thr Tyr Pro Ile Gln<br>                     245                     250                     255 | 768 |
| acg tca tcc caa tta aca agg gaa att tat aca agt tca gta att gag<br>Thr Ser Ser Gln Leu Thr Arg Glu Ile Tyr Thr Ser Ser Val Ile Glu<br>                     260                     265                     270 | 816 |
| gat tct cca gtt tct gct aat ata cct aat ggt ttt aat agg gcg gaa<br>Asp Ser Pro Val Ser Ala Asn Ile Pro Asn Gly Phe Asn Arg Ala Glu<br>                     275                     280                     285 | 864 |
| ttt gga gtt aga ccg ccc cat ctt atg gac ttt atg aat tct ttg ttt<br>Phe Gly Val Arg Pro Pro His Leu Met Asp Phe Met Asn Ser Leu Phe<br>290                     295                     300 | 912 |
| gta act gca gag act gtt aga agt caa act gtg tgg gga gga cac tta<br>Val Thr Ala Glu Thr Val Arg Ser Gln Thr Val Trp Gly Gly His Leu<br>305                     310                     315                     320 | 960 |
| gtt agt tca cga aat acg gct ggt aac cgt ata aat ttc cct agt tac<br>Val Ser Ser Arg Asn Thr Ala Gly Asn Arg Ile Asn Phe Pro Ser Tyr<br>                     325                     330                     335 | 1008 |
| ggg gtc ttc aat cct ggt ggc gcc att tgg att gca gat gag gat cca<br>Gly Val Phe Asn Pro Gly Gly Ala Ile Trp Ile Ala Asp Glu Asp Pro<br>                     340                     345                     350 | 1056 |
| cgt cct ttt tat cgg aca tta tca gat cct gtt ttt gtc cga gga gga<br>Arg Pro Phe Tyr Arg Thr Leu Ser Asp Pro Val Phe Val Arg Gly Gly<br>                     355                     360                     365 | 1104 |
| ttt ggg aat cct cat tat gta ctg ggg ctt agg gga gta gca ttt caa<br>Phe Gly Asn Pro His Tyr Val Leu Gly Leu Arg Gly Val Ala Phe Gln<br>370                     375                     380 | 1152 |
| caa act ggt acg aac cac acc cga aca ttt aga aat agt ggg acc ata<br>Gln Thr Gly Thr Asn His Thr Arg Thr Phe Arg Asn Ser Gly Thr Ile<br>385                     390                     395                     400 | 1200 |
| gat tct cta gat gaa atc cca cct cag gat aat agt ggg gca cct tgg<br>Asp Ser Leu Asp Glu Ile Pro Pro Gln Asp Asn Ser Gly Ala Pro Trp<br>                     405                     410                     415 | 1248 |
| aat gat tat agt cat gta tta aat cat gtt aca ttt gta cga tgg cca<br>Asn Asp Tyr Ser His Val Leu Asn His Val Thr Phe Val Arg Trp Pro<br>420                     425                     430 | 1296 |

```
ggt gag att tca gga agt gat tca tgg aga gct cca atg ttt tct tgg      1344
Gly Glu Ile Ser Gly Ser Asp Ser Trp Arg Ala Pro Met Phe Ser Trp
        435                 440                 445 acg cac cgt agt gca acc cct aca aat aca att gat ccg gag agg att      1392
Thr His Arg Ser Ala Thr Pro Thr Asn Thr Ile Asp Pro Glu Arg Ile
    450                 455                 460 act caa ata cca ttg gta aaa gca cat aca ctt cag tca ggt act act      1440
Thr Gln Ile Pro Leu Val Lys Ala His Thr Leu Gln Ser Gly Thr Thr
465                 470                 475                 480 gtt gta aga ggg ccc ggg ttt acg gga gga gat att ctt cga cga aca      1488
Val Val Arg Gly Pro Gly Phe Thr Gly Gly Asp Ile Leu Arg Arg Thr
                485                 490                 495 agt gga gga cca ttt gct tat act att gtt aat ata aat ggg caa tta      1536
Ser Gly Gly Pro Phe Ala Tyr Thr Ile Val Asn Ile Asn Gly Gln Leu
            500                 505                 510 ccc caa agg tat cgt gca aga ata cgc tat gcc tct act aca aat cta      1584
Pro Gln Arg Tyr Arg Ala Arg Ile Arg Tyr Ala Ser Thr Thr Asn Leu
        515                 520                 525 aga att tac gta acg gtt gca ggt gaa cgg att ttt gct ggt caa ttt      1632
Arg Ile Tyr Val Thr Val Ala Gly Glu Arg Ile Phe Ala Gly Gln Phe
    530                 535                 540 aac aaa aca atg gat acc ggt gac cca tta aca ttc caa tct ttt agt      1680
Asn Lys Thr Met Asp Thr Gly Asp Pro Leu Thr Phe Gln Ser Phe Ser
545                 550                 555                 560 tac gca act att aat aca gct ttt aca ttc cca atg agc cag agt agt      1728
Tyr Ala Thr Ile Asn Thr Ala Phe Thr Phe Pro Met Ser Gln Ser Ser
                565                 570                 575 ttc aca gta ggt gct gat act ttt agt tca ggg aat gaa gtt tat ata      1776
Phe Thr Val Gly Ala Asp Thr Phe Ser Ser Gly Asn Glu Val Tyr Ile
            580                 585                 590 gac aga ttt gaa ttg att cca gtt act gca aca ttt gaa tag             1818
Asp Arg Phe Glu Leu Ile Pro Val Thr Ala Thr Phe Glu
        595                 600                 605

<210> SEQ ID NO 2
<211> LENGTH: 605
<212> TYPE: PRT
<213> ORGANISM: Bacillus thuringiensis

<400> SEQUENCE: 2

Met Glu Asn Asn Ile Gln

```
Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
            165                 170                 175

Gly Gln Gly Trp Gly Leu Asp Ile Ala Thr Val Asn Asn His Tyr Asn
        180                 185                 190

Arg Leu Ile Asn Leu Ile His Arg Tyr Thr Lys His Cys Leu Asp Thr
    195                 200                 205

Tyr Asn Gln Gly Leu Glu Asn Leu Arg Gly Thr Asn Thr Arg Gln Trp
210                 215                 220

Ala Arg Phe Asn Gln Phe Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560
```

```
Tyr Ala Thr Ile Asn Thr Ala Phe Thr Phe Pro Met Ser Gln Ser Ser
            565                 570                 575

Phe Thr Val Gly Ala Asp Thr Phe Ser Ser Gly Asn Glu Val Tyr Ile
        580                 585                 590

Asp Arg Phe Glu Leu Ile Pro Val Thr Ala Thr Phe Glu
        595                 600                 605

<210> SEQ ID NO 3
<211> LENGTH: 1818
<212> TYPE: DNA
<213> ORGANISM: Artificial Sequence
<220> FEATURE:
<223> OTHER INFORMATION: Synthetic DNA sequence encoding Bacillus
      thuringiensis Cry1Fa core toxin using codons optimized for maize
      and Table 1 sequences are maintained
<220> FEATURE:
<221> NAME/KEY: CDS
<222> LOCATION: (1)..(1818)

<400> SEQUENCE: 3 atg gag aat aat atc cag aat caa tgc gtg cct tac aat tgt tta aat         48
Met Glu Asn Asn Ile Gln Asn Gln Cys Val Pro Tyr Asn Cys Leu Asn
1               5                   10                  15 aat ccc gag gtg gag ata tta aac gag gag aga tcc act ggc aga ctg         96
Asn Pro Glu Val Glu Ile Leu Asn Glu Glu Arg Ser Thr Gly Arg Leu
            20                  25                  30 cca ctc gat ata tcc ttg tcc ctt acc cgt ttc ctt ttg agc gaa ttt        144
Pro Leu Asp Ile Ser Leu Ser Leu Thr Arg Phe Leu Leu Ser Glu Phe
        35                  40                  45 gtt cct ggt gtg gga gtg gct ttc gga tta ttt gat ctg ata tgg ggt        192
Val Pro Gly Val Gly Val Ala Phe Gly Leu Phe Asp Leu Ile Trp Gly
    50                  55                  60 ttt atc act cct tct gat tgg agc tta ttt ctt ctc cag att gag caa        240
Phe Ile Thr Pro Ser Asp Trp Ser Leu Phe Leu Leu Gln Ile Glu Gln
65                  70                  75                  80 ttg att gag cag aga ata gaa acc ttg gaa agg aac cgt gca atc acg        288
Leu Ile Glu Gln Arg Ile Glu Thr Leu Glu Arg Asn Arg Ala Ile Thr
                85                  90                  95 acc ttg cgc ggt ctc gcc gat agc tat gaa att tat att gaa gca ctg        336
Thr Leu Arg Gly Leu Ala Asp Ser Tyr Glu Ile Tyr Ile Glu Ala Leu
            100                 105                 110 agg gag tgg gag gcc aac cct aat aat gct caa tta agg gaa gat gtg        384
Arg Glu Trp Glu Ala Asn Pro Asn Asn Ala Gln Leu Arg Glu Asp Val
        115                 120                 125 cgt att cgt ttt gct aat aca gac gac gct tta ata aca gca ata aat        432
Arg Ile Arg Phe Ala Asn Thr Asp Asp Ala Leu Ile Thr Ala Ile Asn
    130                 135                 140 aat ttc aca ctt aca tcc ttt gaa atc ccg ctt tta tca gtg tac gtt        480
Asn Phe Thr Leu Thr Ser Phe Glu Ile Pro Leu Leu Ser Val Tyr Val
145                 150                 155                 160 caa gcc gcc aat ctc cat tta tca ctt ctg agg gac gct gtc tcc ttt        528
Gln Ala Ala Asn Leu His Leu Ser Leu Leu Arg Asp Ala Val Ser Phe
                165                 170                 175 ggg caa ggt tgg gga ctg gat atc gct act gtt aat aat cac tac aat        576
Gly Gln Gly Trp Gly Leu Asp Ile Ala Thr Val Asn Asn His Tyr Asn
            180                 185                 190 aga tta ata aac ctg att cat aga tat acg aag cat tgt ttg gac aca        624
Arg Leu Ile Asn Leu Ile His Arg Tyr Thr Lys His Cys Leu Asp Thr
        195                 200                 205 tac aat caa gga ctg gag aac ctt agg gga act aac act agg cag tgg        672
Tyr Asn Gln Gly Leu Glu Asn Leu Arg Gly Thr Asn Thr Arg Gln Trp
    210                 215                 220
```

| | | | | | | | | | | | | | | | | |
|---|---|---|---|---|---|---|---|---|---|---|---|---|---|---|---|---|
| gca | agg | ttc | aac | cag | ttc | aga | cgt | gat | ctc | aca | ctt | act | gtg | ctg | gat | 720 |
| Ala | Arg | Phe | Asn | Gln | Phe | Arg | Arg | Asp | Leu | Thr | Leu | Thr | Val | Leu | Asp | |
| 225 | | | | 230 | | | | | 235 | | | | | 240 | | |
| atc | gtt | gct | ctc | ttt | ccg | aac | tac | gat | gtt | cgc | acc | tac | cca | atc | cag | 768 |
| Ile | Val | Ala | Leu | Phe | Pro | Asn | Tyr | Asp | Val | Arg | Thr | Tyr | Pro | Ile | Gln | |
| | | | | 245 | | | | | 250 | | | | | 255 | | |
| acg | tca | tcc | caa | tta | aca | agg | gaa | att | tat | acc | tcc | tca | gtg | att | gag | 816 |
| Thr | Ser | Ser | Gln | Leu | Thr | Arg | Glu | Ile | Tyr | Thr | Ser | Ser | Val | Ile | Glu | |
| | | | 260 | | | | | 265 | | | | | 270 | | | |
| gac | tct | ccc | gtt | tct | gct | aac | ata | cct | aac | ggc | ttc | aac | cgc | gcc | gag | 864 |
| Asp | Ser | Pro | Val | Ser | Ala | Asn | Ile | Pro | Asn | Gly | Phe | Asn | Arg | Ala | Glu | |
| | | 275 | | | | | 280 | | | | | 285 | | | | |
| ttc | gga | gtt | aga | ccg | ccc | cac | ctt | atg | gac | ttt | atg | aat | agc | ttg | ttt | 912 |
| Phe | Gly | Val | Arg | Pro | Pro | His | Leu | Met | Asp | Phe | Met | Asn | Ser | Leu | Phe | |
| 290 | | | | | 295 | | | | | 300 | | | | | | |
| gtg | act | gct | gag | act | gtt | aga | agc | caa | act | gtg | tgg | ggc | ggc | cac | ttg | 960 |
| Val | Thr | Ala | Glu | Thr | Val | Arg | Ser | Gln | Thr | Val | Trp | Gly | Gly | His | Leu | |
| 305 | | | | 310 | | | | | 315 | | | | | 320 | | |
| gtc | agc | tca | cgc | aac | acg | gct | ggc | aac | cgt | atc | aac | ttc | ccg | tct | tac | 1008 |
| Val | Ser | Ser | Arg | Asn | Thr | Ala | Gly | Asn | Arg | Ile | Asn | Phe | Pro | Ser | Tyr | |
| | | | | 325 | | | | | 330 | | | | | 335 | | |
| ggg | gtc | ttt | aac | cct | ggt | ggc | gcc | att | tgg | att | gca | gac | gag | gac | cca | 1056 |
| Gly | Val | Phe | Asn | Pro | Gly | Gly | Ala | Ile | Trp | Ile | Ala | Asp | Glu | Asp | Pro | |
| | | | 340 | | | | | 345 | | | | | 350 | | | |
| cgt | cct | ttt | tat | cgc | acc | ctg | tca | gat | cct | gtt | ttt | gtc | aga | ggc | gga | 1104 |
| Arg | Pro | Phe | Tyr | Arg | Thr | Leu | Ser | Asp | Pro | Val | Phe | Val | Arg | Gly | Gly | |
| | | 355 | | | | | 360 | | | | | 365 | | | | |
| ttt | ggg | aat | cct | cat | tat | gtc | ctg | ggc | ctt | agg | gga | gtg | gct | ttc | caa | 1152 |
| Phe | Gly | Asn | Pro | His | Tyr | Val | Leu | Gly | Leu | Arg | Gly | Val | Ala | Phe | Gln | |
| 370 | | | | | 375 | | | | | 380 | | | | | | |
| cag | act | ggc | acc | aac | cac | acc | cgt | acg | ttt | cgc | aat | agc | ggg | acc | ata | 1200 |
| Gln | Thr | Gly | Thr | Asn | His | Thr | Arg | Thr | Phe | Arg | Asn | Ser | Gly | Thr | Ile | |
| 385 | | | | 390 | | | | | 395 | | | | | 400 | | |
| gat | tct | ctt | gat | gaa | atc | cca | cct | caa | gat | aac | agc | ggc | gca | cct | tgg | 1248 |
| Asp | Ser | Leu | Asp | Glu | Ile | Pro | Pro | Gln | Asp | Asn | Ser | Gly | Ala | Pro | Trp | |
| | | | | 405 | | | | | 410 | | | | | 415 | | |
| aac | gat | tat | tcc | cac | gta | tta | aat | cac | gtt | acg | ttc | gtc | cgc | tgg | ccg | 1296 |
| Asn | Asp | Tyr | Ser | His | Val | Leu | Asn | His | Val | Thr | Phe | Val | Arg | Trp | Pro | |
| | | | 420 | | | | | 425 | | | | | 430 | | | |
| ggt | gag | atc | agc | ggc | agc | gat | tca | tgg | aga | gca | cca | atg | ttt | tct | tgg | 1344 |
| Gly | Glu | Ile | Ser | Gly | Ser | Asp | Ser | Trp | Arg | Ala | Pro | Met | Phe | Ser | Trp | |
| | | 435 | | | | | 440 | | | | | 445 | | | | |
| acg | cac | cgt | tca | gcc | acc | cct | aca | aat | aca | att | gac | ccg | gag | agg | att | 1392 |
| Thr | His | Arg | Ser | Ala | Thr | Pro | Thr | Asn | Thr | Ile | Asp | Pro | Glu | Arg | Ile | |
| 450 | | | | | 455 | | | | | 460 | | | | | | |
| act | caa | atc | cca | ttg | gtc | aaa | gca | cat | aca | ctt | cag | tct | ggg | acc | acc | 1440 |
| Thr | Gln | Ile | Pro | Leu | Val | Lys | Ala | His | Thr | Leu | Gln | Ser | Gly | Thr | Thr | |
| 465 | | | | 470 | | | | | 475 | | | | | 480 | | |
| gtg | gtc | aga | ggg | cct | ggg | ttc | acg | gga | gga | gac | att | ctt | agg | cgc | aca | 1488 |
| Val | Val | Arg | Gly | Pro | Gly | Phe | Thr | Gly | Gly | Asp | Ile | Leu | Arg | Arg | Thr | |
| | | | | 485 | | | | | 490 | | | | | 495 | | |
| tcc | gga | gga | ccc | ttc | gct | tat | act | atc | gtt | aat | ata | aat | ggg | cag | ctc | 1536 |
| Ser | Gly | Gly | Pro | Phe | Ala | Tyr | Thr | Ile | Val | Asn | Ile | Asn | Gly | Gln | Leu | |
| | | | 500 | | | | | 505 | | | | | 510 | | | |
| ccc | cag | cgc | tat | cgt | gcc | aga | atc | cgt | tac | gcc | tct | act | aca | aat | ctc | 1584 |
| Pro | Gln | Arg | Tyr | Arg | Ala | Arg | Ile | Arg | Tyr | Ala | Ser | Thr | Thr | Asn | Leu | |
| | | 515 | | | | | 520 | | | | | 525 | | | | |
| aga | atc | tac | gtg | acg | gtt | gcc | ggt | gag | cgc | att | ttt | gct | ggt | cag | ttt | 1632 |
| Arg | Ile | Tyr | Val | Thr | Val | Ala | Gly | Glu | Arg | Ile | Phe | Ala | Gly | Gln | Phe | |

```
                 530                 535                 540
aac aag acg atg gat act ggc gac cca ctg aca ttc caa tct ttc tca    1680
Asn Lys Thr Met Asp Thr Gly Asp Pro Leu Thr Phe Gln Ser Phe Ser
545                 550                 555                 560 tac gca act att aat aca gct ttc aca ttc cca atg agc cag tca tct    1728
Tyr Ala Thr Ile Asn Thr Ala Phe Thr Phe Pro Met Ser Gln Ser Ser
                565                 570                 575 ttc acc gtc ggt gct gat acc ttc agc tct ggc aac gaa gtt tat ata    1776
Phe Thr Val Gly Ala Asp Thr Phe Ser Ser Gly Asn Glu Val Tyr Ile
            580                 585                 590 gac aga ttt gag ttg att cca gtt act gca acg ttt gag tga             1818
Asp Arg Phe Glu Leu Ile Pro Val Thr Ala Thr Phe Glu
        595                 600                 605

<210> SEQ ID NO 4
<211> LENGTH: 605
<212> TYPE: PRT
<213> ORGANISM: Artificial Sequence
<220> FEATURE:
<223> OTHER INFORMATION: Synthetic Construct

<400> SEQUENCE: 4

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270
```

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu
        595                 600                 605

<210> SEQ ID NO 5
<211> LENGTH: 1818
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry1Fa core toxin using
      codons optimized for maize and with sequences identified in
      Table 2 removed and Table 1 sequences are maintained
<220> FEATURE:
<221> NAME/KEY: CDS
<222> LOCATION: (1)..(1818)

<400> SEQUENCE: 5

```
atg gag aat aat atc cag aat caa tgc gtg cct tac aat tgt ctc aat     48
Met Glu Asn Asn Ile Gln Asn Gln Cys Val Pro Tyr Asn Cys Leu Asn
1               5                   10                  15 aat ccc gag gtg gag ata tta aac gag gag aga tcc act ggc aga ctg     96
Asn Pro Glu Val Glu Ile Leu Asn Glu Glu Arg Ser Thr Gly Arg Leu
            20                  25                  30 cca ctc gac ata tcc ttg tcc ctt acc cgt ttc ctt ttg agc gaa ttt    144
Pro Leu Asp Ile Ser Leu Ser Leu Thr Arg Phe Leu Leu Ser Glu Phe
        35                  40                  45 gtt cct ggt gtg gga gtg gct ttc gga ctg ttc gat ctg ata tgg ggc    192
Val Pro Gly Val Gly Val Ala Phe Gly Leu Phe Asp Leu Ile Trp Gly
50                  55                  60 ttt atc act cct tct gat tgg agc ctc ttc ctc cag att gag caa       240
Phe Ile Thr Pro Ser Asp Trp Ser Leu Phe Leu Gln Ile Glu Gln
65                  70                  75                  80 ttg att gag cag aga ata gaa acc ttg gaa agg aac cgt gca atc acg    288
Leu Ile Glu Gln Arg Ile Glu Thr Leu Glu Arg Asn Arg Ala Ile Thr
                85                  90                  95 acc ttg cgc ggt ctc gcc gat agc tat gaa atc tac att gaa gca ctg    336
Thr Leu Arg Gly Leu Ala Asp Ser Tyr Glu Ile Tyr Ile Glu Ala Leu
            100                 105                 110 agg gag tgg gag gcc aac ccc aat aat gct caa tta agg gaa gat gtg    384
Arg Glu Trp Glu Ala Asn Pro Asn Asn Ala Gln Leu Arg Glu Asp Val
        115                 120                 125 cgt att cgt ttt gct aat aca gac gac gct ctc atc aca gca atc aat    432
Arg Ile Arg Phe Ala Asn Thr Asp Asp Ala Leu Ile Thr Ala Ile Asn
130                 135                 140 aat ttc aca ctt aca tcc ttt gaa atc ccg ctt ttg agc gtg tac gtt    480
Asn Phe Thr Leu Thr Ser Phe Glu Ile Pro Leu Leu Ser Val Tyr Val
145                 150                 155                 160 caa gcc gcc aat ctc cac ctc tca ctt ctg agg gac gct gtc tcc ttt    528
Gln Ala Ala Asn Leu His Leu Ser Leu Leu Arg Asp Ala Val Ser Phe
                165                 170                 175 ggg caa ggt tgg gga ctg gat atc gct act gtg aat aat cac tac aat    576
Gly Gln Gly Trp Gly Leu Asp Ile Ala Thr Val Asn Asn His Tyr Asn
            180                 185                 190 aga tta atc aac ctg att cat aga tat acg aag cac tgc ttg gac aca    624
Arg Leu Ile Asn Leu Ile His Arg Tyr Thr Lys His Cys Leu Asp Thr
        195                 200                 205 tac aat caa gga ctg gag aac ctt agg gga act aac act agg cag tgg    672
Tyr Asn Gln Gly Leu Glu Asn Leu Arg Gly Thr Asn Thr Arg Gln Trp
210                 215                 220 gca agg ttc aac cag ttc aga cgt gat ctc aca ctt act gtg ctg gat    720
Ala Arg Phe Asn Gln Phe Arg Arg Asp Leu Thr Leu Thr Val Leu Asp
225                 230                 235                 240 atc gtt gct ctc ttt ccg aac tac gat gtt cgc acc tac cca atc cag    768
Ile Val Ala Leu Phe Pro Asn Tyr Asp Val Arg Thr Tyr Pro Ile Gln
                245                 250                 255 acg tca tcc caa tta aca agg gaa atc tac acc tcc tca gtg att gag    816
Thr Ser Ser Gln Leu Thr Arg Glu Ile Tyr Thr Ser Ser Val Ile Glu
            260                 265                 270 gac tct ccc gtt tct gct aac ata cct aac ggc ttc aac cgc gcc gag    864
Asp Ser Pro Val Ser Ala Asn Ile Pro Asn Gly Phe Asn Arg Ala Glu
        275                 280                 285 ttc gga gtt aga ccg ccc cac ctt atg gac ttt atg aat agc ttg ttc    912
Phe Gly Val Arg Pro Pro His Leu Met Asp Phe Met Asn Ser Leu Phe
290                 295                 300 gtg act gct gag act gtt aga agc caa act gtg tgg ggc ggc cac ttg    960
Val Thr Ala Glu Thr Val Arg Ser Gln Thr Val Trp Gly Gly His Leu
305                 310                 315                 320
```

```
gtc agc tca cgc aac acg gct ggc aac cgt atc aac ttc ccg tct tac      1008
Val Ser Ser Arg Asn Thr Ala Gly Asn Arg Ile Asn Phe Pro Ser Tyr
            325                 330                 335 ggg gtc ttt aac cct ggt ggc gcc att tgg att gca gac gag gac cca      1056
Gly Val Phe Asn Pro Gly Gly Ala Ile Trp Ile Ala Asp Glu Asp Pro
        340                 345                 350 cgt cct ttt tac cgc acc ctg tca gat ccg gtt ttc gtc aga ggc gga      1104
Arg Pro Phe Tyr Arg Thr Leu Ser Asp Pro Val Phe Val Arg Gly Gly
    355                 360                 365 ttt ggg aat cct cat tat gtc ctg ggc ctt agg gga gtg gct ttc caa      1152
Phe Gly Asn Pro His Tyr Val Leu Gly Leu Arg Gly Val Ala Phe Gln
370                 375                 380 cag act ggc acc aac cac acc cgt acg ttt cgc aat agc ggg acc ata      1200
Gln Thr Gly Thr Asn His Thr Arg Thr Phe Arg Asn Ser Gly Thr Ile
385                 390                 395                 400 gat tct ctt gat gaa atc cca cct caa gat aac agc ggc gca cct tgg      1248
Asp Ser Leu Asp Glu Ile Pro Pro Gln Asp Asn Ser Gly Ala Pro Trp
                405                 410                 415 aac gat tat tcc cac gta tta aat cac gtt acg ttc gtc cgc tgg ccg      1296
Asn Asp Tyr Ser His Val Leu Asn His Val Thr Phe Val Arg Trp Pro
            420                 425                 430 ggt gag atc agc ggc agc gat tca tgg aga gca cca atg ttc tct tgg      1344
Gly Glu Ile Ser Gly Ser Asp Ser Trp Arg Ala Pro Met Phe Ser Trp
        435                 440                 445 acg cac cgt tca gcc acc cct aca aat aca att gac ccg gag agg att      1392
Thr His Arg Ser Ala Thr Pro Thr Asn Thr Ile Asp Pro Glu Arg Ile
    450                 455                 460 act caa atc cca ttg gtc aaa gca cat aca ctt cag tct ggg acc acc      1440
Thr Gln Ile Pro Leu Val Lys Ala His Thr Leu Gln Ser Gly Thr Thr
465                 470                 475                 480 gtg gtc aga ggg cct ggg ttc acg gga gga gac att ctt agg cgc aca      1488
Val Val Arg Gly Pro Gly Phe Thr Gly Gly Asp Ile Leu Arg Arg Thr
                485                 490                 495 tcc gga gga ccc ttc gct tat act atc gtt aat ata aat ggg cag ctc      1536
Ser Gly Gly Pro Phe Ala Tyr Thr Ile Val Asn Ile Asn Gly Gln Leu
            500                 505                 510 ccc cag cgc tat cgt gcc aga atc cgt tac gcc tct act aca aat ctc      1584
Pro Gln Arg Tyr Arg Ala Arg Ile Arg Tyr Ala Ser Thr Thr Asn Leu
        515                 520                 525 aga atc tac gtg acg gtt gcc ggt gag cgc atc ttt gct ggt cag ttt      1632
Arg Ile Tyr Val Thr Val Ala Gly Glu Arg Ile Phe Ala Gly Gln Phe
    530                 535                 540 aac aag acg atg gat act ggc gac cca ctg aca ttc caa tct ttc tca      1680
Asn Lys Thr Met Asp Thr Gly Asp Pro Leu Thr Phe Gln Ser Phe Ser
545                 550                 555                 560 tac gca act att aat aca gct ttc aca ttc cca atg agc cag tca tct      1728
Tyr Ala Thr Ile Asn Thr Ala Phe Thr Phe Pro Met Ser Gln Ser Ser
                565                 570                 575 ttc acc gtc ggt gct gat acc ttc agc tct ggc aac gaa gtc tat atc      1776
Phe Thr Val Gly Ala Asp Thr Phe Ser Ser Gly Asn Glu Val Tyr Ile
            580                 585                 590 gac aga ttt gag ttg att cca gtt act gca acg ttt gag tga              1818
Asp Arg Phe Glu Leu Ile Pro Val Thr Ala Thr Phe Glu
        595                 600                 605

<210> SEQ ID NO 6
<211> LENGTH: 605
<212> TYPE: PRT
<213> ORGANISM: Artificial Sequence
<220> FEATURE:
```

<223> OTHER INFORMATION: Synthetic Construct

<400> SEQUENCE: 6

```
Met Glu Asn Asn Ile Gln Asn Gln Cys Val Pro Tyr Asn Cys Leu Asn
 1               5                  10                  15
Asn Pro Glu Val Glu Ile Leu Asn Glu Glu Arg Ser Thr Gly Arg Leu
            20                  25                  30
Pro Leu Asp Ile Ser Leu Ser Leu Thr Arg Phe Leu Leu Ser Glu Phe
        35                  40                  45
Val Pro Gly Val Gly Val Ala Phe Gly Leu Phe Asp Leu Ile Trp Gly
    50                  55                  60
Phe Ile Thr Pro Ser Asp Trp Ser Leu Phe Leu Gln Ile Glu Gln
65                  70                  75                  80
Leu Ile Glu Gln Arg Ile Glu Thr Leu Glu Arg Asn Arg Ala Ile Thr
                85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
        115                 120                 125
Arg Ile Arg Phe Ala Asn Thr Asp Asp Ala Leu Ile Thr Ala Ile Asn
    130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
            180                 185                 190
Arg Leu Ile Asn Leu Ile His Arg Tyr Thr Lys His Cys Leu Asp Thr
        195                 200                 205
Tyr Asn Gln Gly Leu Glu Asn Leu Arg Gly Thr Asn Thr Arg Gln Trp
    210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
            260                 265                 270
Asp Ser Pro Val Ser Ala Asn Ile Pro Asn Gly Phe Asn Arg Ala Glu
        275                 280                 285
Phe Gly Val Arg Pro Pro His Leu Met Asp Phe Met Asn Ser Leu Phe
    290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
        355                 360                 365
Phe Gly Asn Pro His Tyr Val Leu Gly Leu Arg Gly Val Ala Phe Gln
    370                 375                 380
Gln Thr Gly Thr Asn His Thr Arg Thr Phe Arg Asn Ser Gly Thr Ile
385                 390                 395                 400
```

```
Asp Ser Leu Asp Glu Ile Pro Pro Gln Asp Asn Ser Gly Ala Pro Trp
            405                 410                 415
Asn Asp Tyr Ser His Val Leu Asn His Val Thr Phe Val Arg Trp Pro
        420                 425                 430
Gly Glu Ile Ser Gly Ser Asp Ser Trp Arg Ala Pro Met Phe Ser Trp
        435                 440                 445
Thr His Arg Ser Ala Thr Pro Thr Asn Thr Ile Asp Pro Glu Arg Ile
    450                 455                 460
Thr Gln Ile Pro Leu Val Lys Ala His Thr Leu Gln Ser Gly Thr Thr
465                 470                 475                 480
Val Val Arg Gly Pro Gly Phe Thr Gly Gly Asp Ile Leu Arg Arg Thr
                485                 490                 495
Ser Gly Gly Pro Phe Ala Tyr Thr Ile Val Asn Ile Asn Gly Gln Leu
            500                 505                 510
Pro Gln Arg Tyr Arg Ala Arg Ile Arg Tyr Ala Ser Thr Thr Asn Leu
        515                 520                 525
Arg Ile Tyr Val Thr Val Ala Gly Glu Arg Ile Phe Ala Gly Gln Phe
    530                 535                 540
Asn Lys Thr Met Asp Thr Gly Asp Pro Leu Thr Phe Gln Ser Phe Ser
545                 550                 555                 560
Tyr Ala Thr Ile Asn Thr Ala Phe Thr Phe Pro Met Ser Gln Ser Ser
                565                 570                 575
Phe Thr Val Gly Ala Asp Thr Phe Ser Ser Gly Asn Glu Val Tyr Ile
            580                 585                 590
Asp Arg Phe Glu Leu Ile Pro Val Thr Ala Thr Phe Glu
        595                 600                 605

<210> SEQ ID NO 7
<211> LENGTH: 372
<212> TYPE: DNA
<213> ORGANISM: Bacillus thuringiensis
<220> FEATURE:
<221> NAME/KEY: CDS
<222> LOCATION: (1)..(372)
<223> OTHER INFORMATION: Native DNA sequence encoding Bacillus
      thuringiensis Cry34Ab1 toxin

<400> SEQUENCE: 7 atg tca gca cgt gaa gta cac att gat gta aat aat aag aca ggt cat      48
Met Ser Ala Arg Glu Val His Ile Asp Val Asn Asn Lys Thr Gly His
1               5                   10                  15 aca tta caa tta gaa gat aaa aca aaa ctt gat ggt ggt aga tgg cga      96
Thr Leu Gln Leu Glu Asp Lys Thr Lys Leu Asp Gly Gly Arg Trp Arg
            20                  25                  30 aca tca cct aca aat gtt gct aat gat caa att aaa aca ttt gta gca     144
Thr Ser Pro Thr Asn Val Ala Asn Asp Gln Ile Lys Thr Phe Val Ala
        35                  40                  45 gaa tca aat ggt ttt atg aca ggt aca gaa ggt act ata tat tat agt     192
Glu Ser Asn Gly Phe Met Thr Gly Thr Glu Gly Thr Ile Tyr Tyr Ser
    50                  55                  60 ata aat gga gaa gca gaa att agt tta tat ttt gac aat cct ttt gca     240
Ile Asn Gly Glu Ala Glu Ile Ser Leu Tyr Phe Asp Asn Pro Phe Ala
65                  70                  75                  80 ggt tct aat aaa tat gat gga cat tcc aat aaa tct caa tat gaa att     288
Gly Ser Asn Lys Tyr Asp Gly His Ser Asn Lys Ser Gln Tyr Glu Ile
                85                  90                  95 att acc caa gga gga tca gga aat caa tct cat gtt acg tat act att     336
Ile Thr Gln Gly Gly Ser Gly Asn Gln Ser His Val Thr Tyr Thr Ile
            100                 105                 110
```

```
caa acc aca tcc tca cga tat ggg cat aaa tca taa              372
Gln Thr Thr Ser Ser Arg Tyr Gly His Lys Ser
        115                 120

<210> SEQ ID NO 8
<211> LENGTH: 123
<212> TYPE: PRT
<213> ORGANISM: Bacillus thuringiensis

<400> SEQUENCE: 8

Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120

<210> SEQ ID NO 9
<211> LENGTH: 372
<212> TYPE: DNA
<213> ORGANISM: Artificial Sequence
<220> FEATURE:
<223> OTHER INFORMATION: Synthetic DNA sequence encoding Bacillus
      thuringiensis Cry34Ab1 toxin using codons optimized for maize and
      Table 1 sequences are maintained
<220> FEATURE:
<221> NAME/KEY: CDS
<222> LOCATION: (1)..(372)

<400> SEQUENCE: 9 atg tca gca cgg gag gtc cac atc gat gta aat aat aag acg ggt cat   48
Met Ser Ala Arg Glu Val His Ile Asp Val Asn Asn Lys Thr Gly His
1               5                   10                  15 aca tta cag ttg gag gat aaa aca aag cta gac ggt ggc aga tgg aga   96
Thr Leu Gln Leu Glu Asp Lys Thr Lys Leu Asp Gly Gly Arg Trp Arg
            20                  25                  30 acc agt ccg acc aac gtt gct aac gat caa att aaa aca ttt gta gcc  144
Thr Ser Pro Thr Asn Val Ala Asn Asp Gln Ile Lys Thr Phe Val Ala
        35                  40                  45 gaa tca aac ggt ttt atg act ggc acg gag ggg act ata tat tcc      192
Glu Ser Asn Gly Phe Met Thr Gly Thr Glu Gly Thr Ile Tyr Tyr Ser
    50                  55                  60 atc aac gga gaa gcc gag att tcg tta tat ttt gac aat cca ttc gcg  240
Ile Asn Gly Glu Ala Glu Ile Ser Leu Tyr Phe Asp Asn Pro Phe Ala
65                  70                  75                  80 ggg tct aat aaa tac gac gga cac tcc aat aaa tct caa tat gaa atc  288
Gly Ser Asn Lys Tyr Asp Gly His Ser Asn Lys Ser Gln Tyr Glu Ile
                85                  90                  95 att aca caa ggc ggc agc gga aat caa agc cac gtc acg tat act atc  336
Ile Thr Gln Gly Gly Ser Gly Asn Gln Ser His Val Thr Tyr Thr Ile
            100                 105                 110
```

```
cag acc act tca tcg cgc tac ggg cat aaa tca tag              372
Gln Thr Thr Ser Ser Arg Tyr Gly His Lys Ser
        115                 120

<210> SEQ ID NO 10
<211> LENGTH: 123
<212> TYPE: PRT
<213> ORGANISM: Artificial Sequence
<220> FEATURE:
<223> OTHER INFORMATION: Synthetic Construct

<400> SEQUENCE: 10

Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120

<210> SEQ ID NO 11
<211> LENGTH: 372
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry34Ab1 toxin using
      codons optimized for maize and with sequences identified in
      Table 2 removed and Table 1 sequences are maintained
<220> FEATURE:
<221> NAME/KEY: CDS
<222> LOCATION: (1)..(372)

<400> SEQUENCE: 11 atg tca gca cgg gag gtc cac atc gat gta aat aat aag acg ggt cat    48
Met Ser Ala Arg Glu Val His Ile Asp Val Asn Asn Lys Thr Gly His
1               5                   10                  15 aca tta cag ttg gag gat aaa aca aag cta gac ggt ggc aga tgg aga    96
Thr Leu Gln Leu Glu Asp Lys Thr Lys Leu Asp Gly Gly Arg Trp Arg
            20                  25                  30 acc agt ccg acc aac gtt gct aac gat caa att aaa aca ttt gta gcc   144
Thr Ser Pro Thr Asn Val Ala Asn Asp Gln Ile Lys Thr Phe Val Ala
        35                  40                  45 gaa tca aac ggt ttc atg act ggc acg gag ggg act atc tac tac tcc   192
Glu Ser Asn Gly Phe Met Thr Gly Thr Glu Gly Thr Ile Tyr Tyr Ser
    50                  55                  60 atc aac gga gaa gcc gag att tcg ctg tac ttc gac aat cca ttc gcg   240
Ile Asn Gly Glu Ala Glu Ile Ser Leu Tyr Phe Asp Asn Pro Phe Ala
65                  70                  75                  80 ggg tct aat aaa tac gac gga cac tcc aat aaa tct caa tat gaa atc   288
Gly Ser Asn Lys Tyr Asp Gly His Ser Asn Lys Ser Gln Tyr Glu Ile
                85                  90                  95
```

| att aca caa ggc ggc agc gga aat caa agc cac gtc acg tat act atc | 336 |
| Ile Thr Gln Gly Gly Ser Gly Asn Gln Ser His Val Thr Tyr Thr Ile | |
| 100 105 110 | |

| cag acc act tca tcg cgc tac ggg cat aaa tca tag | 372 |
| Gln Thr Thr Ser Ser Arg Tyr Gly His Lys Ser | |
| 115 120 | |

```
<210> SEQ ID NO 12
<211> LENGTH: 123
<212> TYPE: PRT
<213> ORGANISM: Artificial Sequence
<220> FEATURE:
<223> OTHER INFORMATION: Synthetic Construct

<400> SEQUENCE: 12
```

Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120

```
<210> SEQ ID NO 13
<211> LENGTH: 1152
<212> TYPE: DNA
<213> ORGANISM: Bacillus thuringiensis
<220> FEATURE:
<221> NAME/KEY: CDS
<222> LOCATION: (1)..(1152)
<223> OTHER INFORMATION: Native DNA sequence encoding Bacillus
      thuringiensis Cry35Ab1 toxin

<400> SEQUENCE: 13
```

| atg tta gat act aat aaa gtt tat gaa ata agc aat cat gct aat gga | 48 |
| Met Leu Asp Thr Asn Lys Val Tyr Glu Ile Ser Asn His Ala Asn Gly | |
| 1 5 10 15 | |

| cta tat gca gca act tat tta agt tta gat gat tca ggt gtt agt tta | 96 |
| Leu Tyr Ala Ala Thr Tyr Leu Ser Leu Asp Asp Ser Gly Val Ser Leu | |
| 20 25 30 | |

| atg aat aaa aat gat gat gat att gat gat tat aac tta aaa tgg ttt | 144 |
| Met Asn Lys Asn Asp Asp Asp Ile Asp Asp Tyr Asn Leu Lys Trp Phe | |
| 35 40 45 | |

| tta ttt cct att gat gat gat caa tat att att aca agc tat gca gca | 192 |
| Leu Phe Pro Ile Asp Asp Asp Gln Tyr Ile Ile Thr Ser Tyr Ala Ala | |
| 50 55 60 | |

| aat aat tgt aaa gtt tgg aat gtt aat aat gat aaa ata aat gtt tcg | 240 |
| Asn Asn Cys Lys Val Trp Asn Val Asn Asn Asp Lys Ile Asn Val Ser | |
| 65 70 75 80 | |

| act tat tct tca aca aat tca ata caa aaa tgg caa ata aaa gct aat | 288 |
| Thr Tyr Ser Ser Thr Asn Ser Ile Gln Lys Trp Gln Ile Lys Ala Asn | |
| 85 90 95 | |

```
ggt tct tca tat gta ata caa agt gat aat gga aaa gtc tta aca gca      336
Gly Ser Ser Tyr Val Ile Gln Ser Asp Asn Gly Lys Val Leu Thr Ala
                100                 105                 110 gga acc ggt caa gct ctt gga ttg ata cgt tta act gat gaa tcc tca      384
Gly Thr Gly Gln Ala Leu Gly Leu Ile Arg Leu Thr Asp Glu Ser Ser
            115                 120                 125 aat aat ccc aat caa caa tgg aat tta act tct gta caa aca att caa      432
Asn Asn Pro Asn Gln Gln Trp Asn Leu Thr Ser Val Gln Thr Ile Gln
        130                 135                 140 ctt cca caa aaa cct ata ata gat aca aaa tta aaa gat tat ccc aaa      480
Leu Pro Gln Lys Pro Ile Ile Asp Thr Lys Leu Lys Asp Tyr Pro Lys
145                 150                 155                 160 tat tca cca act gga aat ata gat aat gga aca tct cct caa tta atg      528
Tyr Ser Pro Thr Gly Asn Ile Asp Asn Gly Thr Ser Pro Gln Leu Met
                165                 170                 175 gga tgg aca tta gta cct tgt att atg gta aat gat cca aat ata gat      576
Gly Trp Thr Leu Val Pro Cys Ile Met Val Asn Asp Pro Asn Ile Asp
            180                 185                 190 aaa aat act caa att aaa act act cca tat tat att tta aaa aaa tat      624
Lys Asn Thr Gln Ile Lys Thr Thr Pro Tyr Tyr Ile Leu Lys Lys Tyr
        195                 200                 205 caa tat tgg caa cga gca gta gga agt aat gta gct tta cgt cca cat      672
Gln Tyr Trp Gln Arg Ala Val Gly Ser Asn Val Ala Leu Arg Pro His
210                 215                 220 gaa aaa aaa tca tat act tat gaa tgg ggc aca gaa ata gat caa aaa      720
Glu Lys Lys Ser Tyr Thr Tyr Glu Trp Gly Thr Glu Ile Asp Gln Lys
225                 230                 235                 240 aca aca att ata aat aca tta gga ttt caa atc aat ata gat tca gga      768
Thr Thr Ile Ile Asn Thr Leu Gly Phe Gln Ile Asn Ile Asp Ser Gly
                245                 250                 255 atg aaa ttt gat ata cca gaa gta ggt gga ggt aca gat gaa ata aaa      816
Met Lys Phe Asp Ile Pro Glu Val Gly Gly Gly Thr Asp Glu Ile Lys
            260                 265                 270 aca caa cta aat gaa gaa tta aaa ata gaa tat agt cat gaa act aaa      864
Thr Gln Leu Asn Glu Glu Leu Lys Ile Glu Tyr Ser His Glu Thr Lys
        275                 280                 285 ata atg gaa aaa tat caa gaa caa tct gaa ata gat aat cca act gat      912
Ile Met Glu Lys Tyr Gln Glu Gln Ser Glu Ile Asp Asn Pro Thr Asp
290                 295                 300 caa tca atg aat tct ata gga ttt ctt act att act tcc tta gaa tta      960
Gln Ser Met Asn Ser Ile Gly Phe Leu Thr Ile Thr Ser Leu Glu Leu
305                 310                 315                 320 tat aga tat aat ggc tca gaa att cgt ata atg caa att caa acc tca     1008
Tyr Arg Tyr Asn Gly Ser Glu Ile Arg Ile Met Gln Ile Gln Thr Ser
                325                 330                 335 gat aat gat act tat aat gtt act tct tat cca aat cat caa caa gct     1056
Asp Asn Asp Thr Tyr Asn Val Thr Ser Tyr Pro Asn His Gln Gln Ala
            340                 345                 350 tta tta ctt ctt aca aat cat tca tat gaa gaa gta gaa gaa ata aca     1104
Leu Leu Leu Leu Thr Asn His Ser Tyr Glu Glu Val Glu Glu Ile Thr
        355                 360                 365 aat att cct aaa agt aca cta aaa aaa tta aaa aaa tat tat ttt taa     1152
Asn Ile Pro Lys Ser Thr Leu Lys Lys Leu Lys Lys Tyr Tyr Phe
370                 375                 380

<210> SEQ ID NO 14
<211> LENGTH: 383
<212> TYPE: PRT
<213> ORGANISM: Bacillus thuringiensis

<400> SEQUENCE: 14
```

Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Ile Asp Asp Tyr Asn Leu Lys Trp Phe
        35                  40                  45

Leu Phe Pro Ile Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Thr Asp Glu Ile Lys
            260                 265                 270

Thr Gln Leu Asn Glu Glu Leu Lys Ile Glu Tyr Ser His Glu Thr Lys
        275                 280                 285

Ile Met Glu Lys Tyr Gln Glu Gln Ser Glu Ile Asp Asn Pro Thr Asp
290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
            340                 345                 350

Leu Leu Leu Leu Thr Asn His Ser Tyr Glu Glu Val Glu Glu Ile Thr
        355                 360                 365

Asn Ile Pro Lys Ser Thr Leu Lys Lys Leu Lys Lys Tyr Tyr Phe
370                 375                 380

<210> SEQ ID NO 15
<211> LENGTH: 1152
<212> TYPE: DNA
<213> ORGANISM: Artificial Sequence
<220> FEATURE:

<223> OTHER INFORMATION: Synthetic DNA sequence encoding Bacillus
      thuringiensis Cry35Ab1 toxin using codons optimized for maize and
      Table 1 sequences are maintained
<220> FEATURE:
<221> NAME/KEY: CDS
<222> LOCATION: (1)..(1152)

<400> SEQUENCE: 15

```
atg ctc gat act aat aaa gtg tat gaa ata agc aac cat gcc aac ggg      48
Met Leu Asp Thr Asn Lys Val Tyr Glu Ile Ser Asn His Ala Asn Gly
1               5                   10                  15 cta tat gcc gca act tat ttg agt ctg gac gac agc ggt gtg agc tta      96
Leu Tyr Ala Ala Thr Tyr Leu Ser Leu Asp Asp Ser Gly Val Ser Leu
            20                  25                  30 atg aat aaa aac gac gac gac att gac gac tac aac ctc aag tgg ttt     144
Met Asn Lys Asn Asp Asp Asp Ile Asp Asp Tyr Asn Leu Lys Trp Phe
        35                  40                  45 tta ttt cct att gac gac gat caa tat att att aca agc tac gca gca     192
Leu Phe Pro Ile Asp Asp Asp Gln Tyr Ile Ile Thr Ser Tyr Ala Ala
50                  55                  60 aat aat tgc aaa gtc tgg aac gtt aat aat gat aaa ata aat gtt tcg     240
Asn Asn Cys Lys Val Trp Asn Val Asn Asn Asp Lys Ile Asn Val Ser
65                  70                  75                  80 acc tac agc tcc acc aac tca ata caa aag tgg caa ata aaa gct aat     288
Thr Tyr Ser Ser Thr Asn Ser Ile Gln Lys Trp Gln Ile Lys Ala Asn
                85                  90                  95 gga tcg tcg tat gta ata cag agt gac aat ggg aag gtc ttg aca gcg     336
Gly Ser Ser Tyr Val Ile Gln Ser Asp Asn Gly Lys Val Leu Thr Ala
            100                 105                 110 ggc act ggt caa gct ctt gga ctc ata agg ctc act gac gag tcc tca     384
Gly Thr Gly Gln Ala Leu Gly Leu Ile Arg Leu Thr Asp Glu Ser Ser
        115                 120                 125 aat aat ccc aat caa cag tgg aac ttg act tcc gtg cag acg atc caa     432
Asn Asn Pro Asn Gln Gln Trp Asn Leu Thr Ser Val Gln Thr Ile Gln
130                 135                 140 ctt cca cag aaa cct atc atc gat aca aaa tta aaa gat tac ccc aag     480
Leu Pro Gln Lys Pro Ile Ile Asp Thr Lys Leu Lys Asp Tyr Pro Lys
145                 150                 155                 160 tac tcg cca acc ggc aac atc gat aat gga acg tct cct caa tta atg     528
Tyr Ser Pro Thr Gly Asn Ile Asp Asn Gly Thr Ser Pro Gln Leu Met
                165                 170                 175 ggc tgg acc ctc gta ccc tgt att atg gtg aac gac ccg aat atc gat     576
Gly Trp Thr Leu Val Pro Cys Ile Met Val Asn Asp Pro Asn Ile Asp
            180                 185                 190 aaa aat act caa att aaa acc acg ccg tat tat ata ttg aaa aaa tac     624
Lys Asn Thr Gln Ile Lys Thr Thr Pro Tyr Tyr Ile Leu Lys Lys Tyr
        195                 200                 205 caa tac tgg cag cgc gcg gtt ggc tca aac gtc gct ctg cgg cca cat     672
Gln Tyr Trp Gln Arg Ala Val Gly Ser Asn Val Ala Leu Arg Pro His
    210                 215                 220 gaa aag aag tcc tac act tac gaa tgg ggc aca gag atc gat cag aaa     720
Glu Lys Lys Ser Tyr Thr Tyr Glu Trp Gly Thr Glu Ile Asp Gln Lys
225                 230                 235                 240 acg acc att ata aat aca tta gga ttc caa atc aat atc gac agc gga     768
Thr Thr Ile Ile Asn Thr Leu Gly Phe Gln Ile Asn Ile Asp Ser Gly
                245                 250                 255 atg aaa ttt gac atc ccg gaa gtg ggg ggc ggg acc gat gaa ata aaa     816
Met Lys Phe Asp Ile Pro Glu Val Gly Gly Gly Thr Asp Glu Ile Lys
            260                 265                 270 acg cag ctc aac gaa gaa tta aaa ata gag tac agt cat gaa act aaa     864
Thr Gln Leu Asn Glu Glu Leu Lys Ile Glu Tyr Ser His Glu Thr Lys
```

```
                       275                 280                 285
ata atg gaa aaa tat caa gag caa tct gaa atc gat aac ccg acc gac    912
Ile Met Glu Lys Tyr Gln Glu Gln Ser Glu Ile Asp Asn Pro Thr Asp
    290                 295                 300 caa tca atg aac tct atc ggt ttc ctt act att acc tcc ctg gag tta    960
Gln Ser Met Asn Ser Ile Gly Phe Leu Thr Ile Thr Ser Leu Glu Leu
305                 310                 315                 320 tat aga tat aac ggc tct gag atc cgt ata atg cag att caa acc tca   1008
Tyr Arg Tyr Asn Gly Ser Glu Ile Arg Ile Met Gln Ile Gln Thr Ser
                325                 330                 335 gac aat gac act tat aac gtc acc tct tac ccg aat cat caa caa gct   1056
Asp Asn Asp Thr Tyr Asn Val Thr Ser Tyr Pro Asn His Gln Gln Ala
            340                 345                 350 tta ttg ctt ctt aca aac cac agt tat gaa gag gtg gaa gaa ata acg   1104
Leu Leu Leu Leu Thr Asn His Ser Tyr Glu Glu Val Glu Glu Ile Thr
        355                 360                 365 aac att cct aaa tcc aca cta aag aaa tta aaa aaa tat tat ttt tga   1152
Asn Ile Pro Lys Ser Thr Leu Lys Lys Leu Lys Lys Tyr Tyr Phe
    370                 375                 380
```

<210> SEQ ID NO 16
<211> LENGTH: 383
<212> TYPE: PRT
<213> ORGANISM: Artificial Sequence
<220> FEATURE:
<223> OTHER INFORMATION: Synthetic Construct

<400> SEQUENCE: 16

```
Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Ile Asp Asp Tyr Asn Leu Lys Trp Phe
        35                  40                  45

Leu Phe Pro Ile Asp Asp Gln Tyr Ile Ile Thr Ser Tyr Ala Ala
    50                  55                  60

Asn Asn Cys Lys Val Trp Asn Val Asn Asn Asp Lys Ile Asn Val Ser
65                  70                  75                  80

Thr Tyr Ser Ser Thr Asn Ser Ile Gln Lys Trp Gln Ile Lys Ala Asn
                85                  90                  95

Gly Ser Ser Tyr Val Ile Gln Ser Asp Asn Gly Lys Val Leu Thr Ala
            100                 105                 110

Gly Thr Gly Gln Ala Leu Gly Leu Ile Arg Leu Thr Asp Glu Ser Ser
        115                 120                 125

Asn Asn Pro Asn Gln Gln Trp Asn Leu Thr Ser Val Gln Thr Ile Gln
    130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
            180                 185                 190

Lys Asn Thr Gln Ile Lys Thr Thr Pro Tyr Tyr Ile Leu Lys Lys Tyr
        195                 200                 205

Gln Tyr Trp Gln Arg Ala Val Gly Ser Asn Val Ala Leu Arg Pro His
    210                 215                 220

Glu Lys Lys Ser Tyr Thr Tyr Glu Trp Gly Thr Glu Ile Asp Gln Lys
```

```
                    225                 230                 235                 240
Thr Thr Ile Ile Asn Thr Leu Gly Phe Gln Ile Asn Ile Asp Ser Gly
                        245                 250                 255

Met Lys Phe Asp Ile Pro Glu Val Gly Gly Thr Asp Glu Ile Lys
            260                 265                 270

Thr Gln Leu Asn Glu Glu Leu Lys Ile Glu Tyr Ser His Glu Thr Lys
                275                 280                 285

Ile Met Glu Lys Tyr Gln Glu Gln Ser Glu Ile Asp Asn Pro Thr Asp
            290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                        325                 330                 335

Asp Asn Asp Thr Tyr Asn Val Thr Ser Tyr Pro Asn His Gln Gln Ala
                340                 345                 350

Leu Leu Leu Leu Thr Asn His Ser Tyr Glu Glu Val Glu Glu Ile Thr
                355                 360                 365

Asn Ile Pro Lys Ser Thr Leu Lys Lys Leu Lys Lys Tyr Tyr Phe
        370                 375                 380

<210> SEQ ID NO 17
<211> LENGTH: 1152
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry35Ab1 toxin using
      codons optimized for maize and with sequences identified in
      Table 2 removed and Table 1 sequences are maintained
<220> FEATURE:
<221> NAME/KEY: CDS
<222> LOCATION: (1)..(1152)

<400> SEQUENCE: 17 atg ctc gat act aat aaa gtg tat gaa ata tcg aac cat gcc aac ggg      48
Met Leu Asp Thr Asn Lys Val Tyr Glu Ile Ser Asn His Ala Asn Gly
1               5                   10                  15 cta tat gcc gca act tac ctg agt ctg gac gat agt ggt gtg agc tta     96
Leu Tyr Ala Ala Thr Tyr Leu Ser Leu Asp Asp Ser Gly Val Ser Leu
                20                  25                  30 atg aat aaa aac gac gac gac att gac gac tac aac ctc aag tgg ttc    144
Met Asn Lys Asn Asp Asp Asp Ile Asp Asp Tyr Asn Leu Lys Trp Phe
            35                  40                  45 ctg ttt cct att gac gac gat cag tat atc att aca agc tac gca gcg    192
Leu Phe Pro Ile Asp Asp Asp Gln Tyr Ile Ile Thr Ser Tyr Ala Ala
        50                  55                  60 aat aat tgc aaa gtc tgg aac gtc aat aat gat aaa atc aat gtt tcg    240
Asn Asn Cys Lys Val Trp Asn Val Asn Asn Asp Lys Ile Asn Val Ser
65                  70                  75                  80 acc tac agc tcc acc aac tca ata caa aag tgg caa atc aaa gct aat    288
Thr Tyr Ser Ser Thr Asn Ser Ile Gln Lys Trp Gln Ile Lys Ala Asn
                85                  90                  95 ggc agc tcg tac gta ata cag agt gac aat ggg aag gtc ttg aca gcg    336
Gly Ser Ser Tyr Val Ile Gln Ser Asp Asn Gly Lys Val Leu Thr Ala
            100                 105                 110 ggc act ggt caa gct ctt gga ctc ata agg ctc act gac gag tcc tcg    384
Gly Thr Gly Gln Ala Leu Gly Leu Ile Arg Leu Thr Asp Glu Ser Ser
        115                 120                 125 aat aat ccc aat caa cag tgg aac ttg act tcc gtg cag acg atc caa    432
Asn Asn Pro Asn Gln Gln Trp Asn Leu Thr Ser Val Gln Thr Ile Gln
```

```
                  130                 135                 140
ctt cca cag aaa cct atc atc gat aca aaa tta aaa gat tac ccc aag      480
Leu Pro Gln Lys Pro Ile Ile Asp Thr Lys Leu Lys Asp Tyr Pro Lys
145                 150                 155                 160 tac tcg cca acc ggc aac atc gat aat gga acg tct cct caa tta atg      528
Tyr Ser Pro Thr Gly Asn Ile Asp Asn Gly Thr Ser Pro Gln Leu Met
                165                 170                 175 ggc tgg acc ctc gta ccc tgt ata atg gtg aac gac ccg aat atc gat      576
Gly Trp Thr Leu Val Pro Cys Ile Met Val Asn Asp Pro Asn Ile Asp
            180                 185                 190 aaa aat act caa att aaa acc acg ccg tac tac ata ctc aaa aaa tac      624
Lys Asn Thr Gln Ile Lys Thr Thr Pro Tyr Tyr Ile Leu Lys Lys Tyr
        195                 200                 205 caa tac tgg cag cgc gcg gtt ggc tca aac gtc gct ctg cgg cca cat      672
Gln Tyr Trp Gln Arg Ala Val Gly Ser Asn Val Ala Leu Arg Pro His
    210                 215                 220 gaa aag aag tcc tac act tac gaa tgg ggc aca gag atc gat cag aaa      720
Glu Lys Lys Ser Tyr Thr Tyr Glu Trp Gly Thr Glu Ile Asp Gln Lys
225                 230                 235                 240 acg acc att ata aat aca tta gga ttc caa atc aat atc gac agc gga      768
Thr Thr Ile Ile Asn Thr Leu Gly Phe Gln Ile Asn Ile Asp Ser Gly
                245                 250                 255 atg aaa ttt gac atc ccg gaa gtg ggg ggc ggg acc gat gaa ata aaa      816
Met Lys Phe Asp Ile Pro Glu Val Gly Gly Gly Thr Asp Glu Ile Lys
            260                 265                 270 acg cag ctc aac gaa gaa tta aaa ata gag tac agt cat gaa act aaa      864
Thr Gln Leu Asn Glu Glu Leu Lys Ile Glu Tyr Ser His Glu Thr Lys
        275                 280                 285 ata atg gaa aaa tat caa gag caa tct gaa atc gat aac ccg acc gac      912
Ile Met Glu Lys Tyr Gln Glu Gln Ser Glu Ile Asp Asn Pro Thr Asp
    290                 295                 300 caa tca atg aac tct atc ggt ttc ctt act att acc tcc ctg gag ttg      960
Gln Ser Met Asn Ser Ile Gly Phe Leu Thr Ile Thr Ser Leu Glu Leu
305                 310                 315                 320 tac aga tat aac ggc tct gag atc cgt ata atg cag att caa acc tca     1008
Tyr Arg Tyr Asn Gly Ser Glu Ile Arg Ile Met Gln Ile Gln Thr Ser
                325                 330                 335 gac aat gac act tat aac gtc acc tct tac ccg aat cat cag caa gcc     1056
Asp Asn Asp Thr Tyr Asn Val Thr Ser Tyr Pro Asn His Gln Gln Ala
            340                 345                 350 ctg ctg ctt ctt aca aac cac agt tat gaa gag gtg gaa gag ata acg     1104
Leu Leu Leu Leu Thr Asn His Ser Tyr Glu Glu Val Glu Glu Ile Thr
        355                 360                 365 aac att cct aaa tcc aca cta aag aaa tta aaa aaa tat tat ttc tga     1152
Asn Ile Pro Lys Ser Thr Leu Lys Lys Leu Lys Lys Tyr Tyr Phe
    370                 375                 380

<210> SEQ ID NO 18
<211> LENGTH: 383
<212> TYPE: PRT
<213> ORGANISM: Artificial Sequence
<220> FEATURE:
<223> OTHER INFORMATION: Synthetic Construct

<400> SEQUENCE: 18

Met Leu Asp Thr Asn Lys Val Tyr Glu Ile Ser Asn His Ala Asn Gly
1               5                   10                  15

Leu Tyr Ala Ala Thr Tyr Leu Ser Leu Asp Asp Ser Gly Val Ser Leu
            20                  25                  30

Met Asn Lys Asn Asp Asp Asp Ile Asp Asp Tyr Asn Leu Lys Trp Phe
```

```
              35                  40                  45
Leu Phe Pro Ile Asp Asp Gln Tyr Ile Ile Thr Ser Tyr Ala Ala
 50                  55                  60

Asn Asn Cys Lys Val Trp Asn Val Asn Asp Lys Ile Asn Val Ser
 65                  70                  75                  80

Thr Tyr Ser Ser Thr Asn Ser Ile Gln Lys Trp Gln Ile Lys Ala Asn
                     85                  90                  95

Gly Ser Ser Tyr Val Ile Gln Ser Asp Asn Gly Lys Val Leu Thr Ala
                100                 105                 110

Gly Thr Gly Gln Ala Leu Gly Leu Ile Arg Leu Thr Asp Glu Ser Ser
                115                 120                 125

Asn Asn Pro Asn Gln Gln Trp Asn Leu Thr Ser Val Gln Thr Ile Gln
130                 135                 140

Leu Pro Gln Lys Pro Ile Ile Asp Thr Lys Leu Lys Asp Tyr Pro Lys
145                 150                 155                 160

Tyr Ser Pro Thr Gly Asn Ile Asp Asn Gly Thr Ser Pro Gln Leu Met
                165                 170                 175

Gly Trp Thr Leu Val Pro Cys Ile Met Val Asn Asp Pro Asn Ile Asp
                180                 185                 190

Lys Asn Thr Gln Ile Lys Thr Thr Pro Tyr Tyr Ile Leu Lys Lys Tyr
                195                 200                 205

Gln Tyr Trp Gln Arg Ala Val Gly Ser Asn Val Ala Leu Arg Pro His
210                 215                 220

Glu Lys Lys Ser Tyr Thr Tyr Glu Trp Gly Thr Glu Ile Asp Gln Lys
225                 230                 235                 240

Thr Thr Ile Ile Asn Thr Leu Gly Phe Gln Ile Asn Ile Asp Ser Gly
                245                 250                 255

Met Lys Phe Asp Ile Pro Glu Val Gly Gly Thr Asp Glu Ile Lys
                260                 265                 270

Thr Gln Leu Asn Glu Glu Leu Lys Ile Glu Tyr Ser His Glu Thr Lys
                275                 280                 285

Ile Met Glu Lys Tyr Gln Glu Gln Ser Glu Ile Asp Asn Pro Thr Asp
290                 295                 300

Gln Ser Met Asn Ser Ile Gly Phe Leu Thr Ile Thr Ser Leu Glu Leu
305                 310                 315                 320

Tyr Arg Tyr Asn Gly Ser Glu Ile Arg Ile Met Gln Ile Gln Thr Ser
                325                 330                 335

Asp Asn Asp Thr Tyr Asn Val Thr Ser Tyr Pro Asn His Gln Gln Ala
                340                 345                 350

Leu Leu Leu Leu Thr Asn His Ser Tyr Glu Glu Val Glu Glu Ile Thr
                355                 360                 365

Asn Ile Pro Lys Ser Thr Leu Lys Lys Leu Lys Lys Tyr Tyr Phe
                370                 375                 380

<210> SEQ ID NO 19
<211> LENGTH: 1830
<212> TYPE: DNA
<213> ORGANISM: Bacillus thuringiensis
<220> FEATURE:
<221> NAME/KEY: CDS
<222> LOCATION: (1)..(1830)
<223> OTHER INFORMATION: Native DNA sequence encoding Bacillus
      thuringiensis Cry1Ab1 core toxin

<400> SEQUENCE: 19 atg gat aac aat ccg aac atc aat gaa tgc att cct tat aat tgt tta        48
```

-continued

```
Met Asp Asn Asn Pro Asn Ile Asn Glu Cys Ile Pro Tyr Asn Cys Leu
1               5               10              15 agt aac cct gaa gta gaa gta tta ggt gga gaa aga ata gaa act ggt        96
Ser Asn Pro Glu Val Glu Val Leu Gly Gly Glu Arg Ile Glu Thr Gly
            20              25              30 tac acc cca atc gat att tcc ttg tcg cta acg caa ttt ctt ttg agt       144
Tyr Thr Pro Ile Asp Ile Ser Leu Ser Leu Thr Gln Phe Leu Leu Ser
                35              40              45 gaa ttt gtt ccc ggt gct gga ttt gtg tta gga cta gtt gat ata ata       192
Glu Phe Val Pro Gly Ala Gly Phe Val Leu Gly Leu Val Asp Ile Ile
        50              55              60 tgg gga att ttt ggt ccc tct caa tgg gac gca ttt ctt gta caa att       240
Trp Gly Ile Phe Gly Pro Ser Gln Trp Asp Ala Phe Leu Val Gln Ile
65              70              75              80 gaa cag tta att aac caa aga ata gaa gaa ttc gct agg aac caa gcc       288
Glu Gln Leu Ile Asn Gln Arg Ile Glu Glu Phe Ala Arg Asn Gln Ala
                85              90              95 att tct aga tta gaa gga cta agc aat ctt tat caa att tac gca gaa       336
Ile Ser Arg Leu Glu Gly Leu Ser Asn Leu Tyr Gln Ile Tyr Ala Glu
            100             105             110 tct ttt aga gag tgg gaa gca gat cct act aat cca gca tta aga gaa       384
Ser Phe Arg Glu Trp Glu Ala Asp Pro Thr Asn Pro Ala Leu Arg Glu
        115             120             125 gag atg cgt att caa ttc aat gac atg aac agt gcc ctt aca acc gct       432
Glu Met Arg Ile Gln Phe Asn Asp Met Asn Ser Ala Leu Thr Thr Ala
130             135             140 att cct ctt ttt gca gtt caa aat tat caa gtt cct ctt tta tca gta       480
Ile Pro Leu Phe Ala Val Gln Asn Tyr Gln Val Pro Leu Leu Ser Val
145             150             155             160 tat gtt caa gct gca aat tta cat tta tca gtt ttg aga gat gtt tca       528
Tyr Val Gln Ala Ala Asn Leu His Leu Ser Val Leu Arg Asp Val Ser
                165             170             175 gtg ttt gga caa agg tgg gga ttt gat gcc gcg act atc aat agt cgt       576
Val Phe Gly Gln Arg Trp Gly Phe Asp Ala Ala Thr Ile Asn Ser Arg
            180             185             190 tat aat gat tta act agg ctt att ggc aac tat aca gat tat gct gta       624
Tyr Asn Asp Leu Thr Arg Leu Ile Gly Asn Tyr Thr Asp Tyr Ala Val
        195             200             205 cgc tgg tac aat acg gga tta gaa cgt gta tgg gga ccg gat tct aga       672
Arg Trp Tyr Asn Thr Gly Leu Glu Arg Val Trp Gly Pro Asp Ser Arg
210             215             220 gat tgg gta agg tat aat caa ttt aga aga gaa tta aca cta act gta       720
Asp Trp Val Arg Tyr Asn Gln Phe Arg Arg Glu Leu Thr Leu Thr Val
225             230             235             240 tta gat atc gtt gct ctg ttc ccg aat tat gat agt aga aga tat cca       768
Leu Asp Ile Val Ala Leu Phe Pro Asn Tyr Asp Ser Arg Arg Tyr Pro
                245             250             255 att cga aca gtt tcc caa tta aca aga gaa att tat aca aac cca gta       816
Ile Arg Thr Val Ser Gln Leu Thr Arg Glu Ile Tyr Thr Asn Pro Val
            260             265             270 tta gaa aat ttt gat ggt agt ttt cga ggc tcg gct cag ggc ata gaa       864
Leu Glu Asn Phe Asp Gly Ser Phe Arg Gly Ser Ala Gln Gly Ile Glu
        275             280             285 aga agt att agg agt cca cat ttg atg gat ata ctt aac agt ata acc       912
Arg Ser Ile Arg Ser Pro His Leu Met Asp Ile Leu Asn Ser Ile Thr
290             295             300 atc tat acg gat gct cat agg ggt tat tat tat tgg tca ggg cat caa       960
Ile Tyr Thr Asp Ala His Arg Gly Tyr Tyr Tyr Trp Ser Gly His Gln
305             310             315             320
```

```
ata atg gct tct cct gta ggg ttt tcg ggg cca gaa ttc act ttt ccg         1008
Ile Met Ala Ser Pro Val Gly Phe Ser Gly Pro Glu Phe Thr Phe Pro
            325                 330                 335 cta tat gga act atg gga aat gca gct cca caa caa cgt att gtt gct         1056
Leu Tyr Gly Thr Met Gly Asn Ala Ala Pro Gln Gln Arg Ile Val Ala
                340                 345                 350 caa cta ggt cag ggc gtg tat aga aca tta tcg tcc act tta tat aga         1104
Gln Leu Gly Gln Gly Val Tyr Arg Thr Leu Ser Ser Thr Leu Tyr Arg
            355                 360                 365 aga cct ttt aat ata ggg ata aat aat caa caa cta tct gtt ctt gac         1152
Arg Pro Phe Asn Ile Gly Ile Asn Asn Gln Gln Leu Ser Val Leu Asp
        370                 375                 380 ggg aca gaa ttt gct tat gga acc tcc tca aat ttg cca tcc gct gta         1200
Gly Thr Glu Phe Ala Tyr Gly Thr Ser Ser Asn Leu Pro Ser Ala Val
385                 390                 395                 400 tac aga aaa agc gga acg gta gat tcg ctg gat gaa ata ccg cca cag         1248
Tyr Arg Lys Ser Gly Thr Val Asp Ser Leu Asp Glu Ile Pro Pro Gln
                405                 410                 415 aat aac aac gtg cca cct agg caa gga ttt agt cat cga tta agc cat         1296
Asn Asn Asn Val Pro Pro Arg Gln Gly Phe Ser His Arg Leu Ser His
            420                 425                 430 gtt tca atg ttt cgt tca ggc ttt agt aat agt agt gta agt ata ata         1344
Val Ser Met Phe Arg Ser Gly Phe Ser Asn Ser Ser Val Ser Ile Ile
        435                 440                 445 aga gct cct atg ttc tct tgg ata cat cgt agt gct gaa ttt aat aat         1392
Arg Ala Pro Met Phe Ser Trp Ile His Arg Ser Ala Glu Phe Asn Asn
    450                 455                 460 ata att cct tca tca caa att aca caa ata cct tta aca aaa tct act         1440
Ile Ile Pro Ser Ser Gln Ile Thr Gln Ile Pro Leu Thr Lys Ser Thr
465                 470                 475                 480 aat ctt ggc tct gga act tct gtc gtt aaa gga cca gga ttt aca gga         1488
Asn Leu Gly Ser Gly Thr Ser Val Val Lys Gly Pro Gly Phe Thr Gly
                485                 490                 495 gga gat att ctt cga aga act tca cct ggc cag att tca acc tta aga         1536
Gly Asp Ile Leu Arg Arg Thr Ser Pro Gly Gln Ile Ser Thr Leu Arg
            500                 505                 510 gta aat att act gca cca tta tca caa aga tat cgg gta aga att cgc         1584
Val Asn Ile Thr Ala Pro Leu Ser Gln Arg Tyr Arg Val Arg Ile Arg
        515                 520                 525 tac gct tct acc aca aat tta caa ttc cat aca tca att gac gga aga         1632
Tyr Ala Ser Thr Thr Asn Leu Gln Phe His Thr Ser Ile Asp Gly Arg
    530                 535                 540 cct att aat cag ggg aat ttt tca gca act atg agt agt ggg agt aat         1680
Pro Ile Asn Gln Gly Asn Phe Ser Ala Thr Met Ser Ser Gly Ser Asn
545                 550                 555                 560 tta cag tcc gga agc ttt agg act gta ggt ttt act act ccg ttt aac         1728
Leu Gln Ser Gly Ser Phe Arg Thr Val Gly Phe Thr Thr Pro Phe Asn
                565                 570                 575 ttt tca aat gga tca agt gta ttt acg tta agt gct cat gtc ttc aat         1776
Phe Ser Asn Gly Ser Ser Val Phe Thr Leu Ser Ala His Val Phe Asn
            580                 585                 590 tca ggc aat gaa gtt tat ata gat cga att gaa ttt gtt ccg gca gaa         1824
Ser Gly Asn Glu Val Tyr Ile Asp Arg Ile Glu Phe Val Pro Ala Glu
        595                 600                 605 gta acc                                                                 1830
Val Thr
    610

<210> SEQ ID NO 20
<211> LENGTH: 610
```

<212> TYPE: PRT
<213> ORGANISM: Bacillus thuringiensis

<400> SEQUENCE: 20

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                    85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
        290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Ser Ser Asn Leu Pro Ser Ala Val
385                 390                 395                 400
```

```
Tyr Arg Lys Ser Gly Thr Val Asp Ser Leu Asp Glu Ile Pro Pro Gln
            405                 410                 415

Asn Asn Asn Val Pro Pro Arg Gln Gly Phe Ser His Arg Leu Ser His
        420                 425                 430

Val Ser Met Phe Arg Ser Gly Phe Ser Asn Ser Val Ser Ile Ile
    435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr
    610

<210> SEQ ID NO 21
<211> LENGTH: 1830
<212> TYPE: DNA
<213> ORGANISM: Artificial Sequence
<220> FEATURE:
<223> OTHER INFORMATION: Synthetic DNA sequence encoding Bacillus
      thuringiensis Cry1Ab1 core toxin using codons optimized for maize
      and Table 1 sequences are maintained
<220> FEATURE:
<221> NAME/KEY: CDS
<222> LOCATION: (1)..(1830)

<400> SEQUENCE: 21 atg gat aac aac ccg aac atc aat gag tgc atc ccg tat aac tgt ctc      48
Met Asp Asn Asn Pro Asn Ile Asn Glu Cys Ile Pro Tyr Asn Cys Leu
1               5                   10                  15 agt aac cct gaa gtg gag gtc tta ggt ggc gaa cgc atc gaa act ggt      96
Ser Asn Pro Glu Val Glu Val Leu Gly Gly Glu Arg Ile Glu Thr Gly
            20                  25                  30 tac acc cca atc gac att agc ttg tcg ttg acg cag ttc ctt ttg tcc     144
Tyr Thr Pro Ile Asp Ile Ser Leu Ser Leu Thr Gln Phe Leu Leu Ser
        35                  40                  45 gag ttc gtg ccc ggt gcg ggt ttc gtg ctg ggg cta gtt gat ata atc     192
Glu Phe Val Pro Gly Ala Gly Phe Val Leu Gly Leu Val Asp Ile Ile
    50                  55                  60 tgg gga atc ttt ggt ccc tct cag tgg gac gcc ttt ctt gtg caa att     240
Trp Gly Ile Phe Gly Pro Ser Gln Trp Asp Ala Phe Leu Val Gln Ile
65                  70                  75                  80 gag cag cta att aac caa aga ata gaa gag ttc gcg agg aac caa gcc     288
```

```
                Glu Gln Leu Ile Asn Gln Arg Ile Glu Glu Phe Ala Arg Asn Gln Ala
                                 85                  90                  95 att tcc aga ctg gag gga cta agc aac ctt tat caa atc tac gcg gag              336
Ile Ser Arg Leu Glu Gly Leu Ser Asn Leu Tyr Gln Ile Tyr Ala Glu
            100                 105                 110 tct ttt agg gag tgg gag gca gat cct acg aac ccg gca ctg cgc gaa              384
Ser Phe Arg Glu Trp Glu Ala Asp Pro Thr Asn Pro Ala Leu Arg Glu
        115                 120                 125 gag atg cgt att cag ttc aac gac atg aac agt gcc ctt aca acc gct              432
Glu Met Arg Ile Gln Phe Asn Asp Met Asn Ser Ala Leu Thr Thr Ala
    130                 135                 140 att ccc ctt ttc gca gtt caa aat tac caa gtt ccc ctt ctc tca gtg              480
Ile Pro Leu Phe Ala Val Gln Asn Tyr Gln Val Pro Leu Leu Ser Val
145                 150                 155                 160 tac gtt caa gcc gca aat tta cac cta agc gtt ctc cgc gat gtg tca              528
Tyr Val Gln Ala Ala Asn Leu His Leu Ser Val Leu Arg Asp Val Ser
                165                 170                 175 gtg ttt ggc cag agg tgg gga ttt gat gcc gcc act atc aat agt cgt              576
Val Phe Gly Gln Arg Trp Gly Phe Asp Ala Ala Thr Ile Asn Ser Arg
            180                 185                 190 tat aat gat ctg acg agg ctt atc ggc aac tat acc gac tat gct gtc              624
Tyr Asn Asp Leu Thr Arg Leu Ile Gly Asn Tyr Thr Asp Tyr Ala Val
        195                 200                 205 cgc tgg tac aat acg gga tta gag cgg gtc tgg ggt ccg gat tcc cga              672
Arg Trp Tyr Asn Thr Gly Leu Glu Arg Val Trp Gly Pro Asp Ser Arg
    210                 215                 220 gac tgg gtg cgc tac aat caa ttc cgc cgc gaa tta acc ctc act gtc              720
Asp Trp Val Arg Tyr Asn Gln Phe Arg Arg Glu Leu Thr Leu Thr Val
225                 230                 235                 240 ctc gac atc gtg gcg ctg ttc ccg aac tac gac agt agg aga tac cca              768
Leu Asp Ile Val Ala Leu Phe Pro Asn Tyr Asp Ser Arg Arg Tyr Pro
                245                 250                 255 atc cgc aca gtt tcc caa tta acg cgg gaa att tac acc aac cca gtc              816
Ile Arg Thr Val Ser Gln Leu Thr Arg Glu Ile Tyr Thr Asn Pro Val
            260                 265                 270 ctg gag aat ttt gac ggg agc ttc cga ggc tcg gct caa ggc ata gaa              864
Leu Glu Asn Phe Asp Gly Ser Phe Arg Gly Ser Ala Gln Gly Ile Glu
        275                 280                 285 cgc agc att agg tcg cca cac ttg atg gat atc ctt aac agc atc acc              912
Arg Ser Ile Arg Ser Pro His Leu Met Asp Ile Leu Asn Ser Ile Thr
    290                 295                 300 atc tac acg gat gcc cat agg ggt tac tac tac tgg tcg ggg cat caa              960
Ile Tyr Thr Asp Ala His Arg Gly Tyr Tyr Tyr Trp Ser Gly His Gln
305                 310                 315                 320 ata atg gct tct cct gtc ggg ttt tcg ggg cca gag ttc acc ttc ccg             1008
Ile Met Ala Ser Pro Val Gly Phe Ser Gly Pro Glu Phe Thr Phe Pro
                325                 330                 335 ctc tac ggc act atg gga aat gcc gcg cca caa caa cgt atc gtc gct             1056
Leu Tyr Gly Thr Met Gly Asn Ala Ala Pro Gln Gln Arg Ile Val Ala
            340                 345                 350 caa cta ggt caa ggc gtg tac cgg aca ctg tcg tcc act ctc tat cgg             1104
Gln Leu Gly Gln Gly Val Tyr Arg Thr Leu Ser Ser Thr Leu Tyr Arg
        355                 360                 365 cgg cct ttc aat ata ggg ata aat aat caa cag ttg tct gtg ctg gac             1152
Arg Pro Phe Asn Ile Gly Ile Asn Asn Gln Gln Leu Ser Val Leu Asp
    370                 375                 380 ggg aca gag ttt gct tac gga acc tca agc aac ttg cca tcc gct gta             1200
Gly Thr Glu Phe Ala Tyr Gly Thr Ser Ser Asn Leu Pro Ser Ala Val
385                 390                 395                 400
```

```
tac aga aaa agc ggc acg gtg gac tcg ctg gat gaa atc ccg ccc cag    1248
Tyr Arg Lys Ser Gly Thr Val Asp Ser Leu Asp Glu Ile Pro Pro Gln
            405                 410                 415 aat aac aac gtg ccc cct cgg caa ggc ttc agt cat cga ctg agc cac    1296
Asn Asn Asn Val Pro Pro Arg Gln Gly Phe Ser His Arg Leu Ser His
        420                 425                 430 gtt agc atg ttc cgt tcg ggc ttc agc aac tcc tcc gta agt ata ata    1344
Val Ser Met Phe Arg Ser Gly Phe Ser Asn Ser Ser Val Ser Ile Ile
    435                 440                 445 aga gca cct atg ttc agc tgg ata cat cgt tcc gcc gag ttt aat aat    1392
Arg Ala Pro Met Phe Ser Trp Ile His Arg Ser Ala Glu Phe Asn Asn
450                 455                 460 ata att ccc tcc tct caa atc aca cag atc cct ctg aca aag tct act    1440
Ile Ile Pro Ser Ser Gln Ile Thr Gln Ile Pro Leu Thr Lys Ser Thr
465                 470                 475                 480 aat ctt ggc tct ggg act tct gtc gtt aag ggg cct ggc ttt acg ggc    1488
Asn Leu Gly Ser Gly Thr Ser Val Val Lys Gly Pro Gly Phe Thr Gly
            485                 490                 495 ggc gat att ctg cgg aga act tca cct ggc cag att tcc acc ctg cgc    1536
Gly Asp Ile Leu Arg Arg Thr Ser Pro Gly Gln Ile Ser Thr Leu Arg
        500                 505                 510 gtg aat atc acc gcg cca ttg tca caa cgt tac cgc gtg cgg att cgc    1584
Val Asn Ile Thr Ala Pro Leu Ser Gln Arg Tyr Arg Val Arg Ile Arg
    515                 520                 525 tac gct tct acc aca aac ctc cag ttc cat aca tct att gac ggc aga    1632
Tyr Ala Ser Thr Thr Asn Leu Gln Phe His Thr Ser Ile Asp Gly Arg
530                 535                 540 ccc att aat caa ggg aat ttc tcc gcc acg atg tcg tcc ggc tcc aat    1680
Pro Ile Asn Gln Gly Asn Phe Ser Ala Thr Met Ser Ser Gly Ser Asn
545                 550                 555                 560 ctc cag tcc gga agt ttc cgc acc gta ggt ttt act acc ccg ttc aac    1728
Leu Gln Ser Gly Ser Phe Arg Thr Val Gly Phe Thr Thr Pro Phe Asn
            565                 570                 575 ttt tca aac ggc tca agt gtg ttt acg ctg tcc gct cat gtg ttc aac    1776
Phe Ser Asn Gly Ser Ser Val Phe Thr Leu Ser Ala His Val Phe Asn
        580                 585                 590 tct ggc aat gag gtt tat atc gac cgg att gag ttc gtc ccg gca gaa    1824
Ser Gly Asn Glu Val Tyr Ile Asp Arg Ile Glu Phe Val Pro Ala Glu
    595                 600                 605 gtc acc                                                            1830
Val Thr
    610

<210> SEQ ID NO 22
<211> LENGTH: 610
<212> TYPE: PRT
<213> ORGANISM: Artificial Sequence
<220> FEATURE:
<223> OTHER INFORMATION: Synthetic Construct

<400> SEQUENCE: 22

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
```

```
                65                  70                  75                  80
        Glu Gln Leu Ile Asn Gln Arg Ile Glu Glu Phe Ala Arg Asn Gln Ala
                        85                  90                  95

Ile Ser Arg Leu Glu Gly Leu Ser Asn Leu Tyr Gln Ile Tyr Ala Glu
                        100                 105                 110

Ser Phe Arg Glu Trp Glu Ala Asp Pro Thr Asn Pro Ala Leu Arg Glu
                        115                 120                 125

Glu Met Arg Ile Gln Phe Asn Asp Met Asn Ser Ala Leu Thr Thr Ala
                        130                 135                 140

Ile Pro Leu Phe Ala Val Gln Asn Tyr Gln Val Pro Leu Leu Ser Val
        145                 150                 155                 160

Tyr Val Gln Ala Ala Asn Leu His Leu Ser Val Leu Arg Asp Val Ser
                        165                 170                 175

Val Phe Gly Gln Arg Trp Gly Phe Asp Ala Ala Thr Ile Asn Ser Arg
                        180                 185                 190

Tyr Asn Asp Leu Thr Arg Leu Ile Gly Asn Tyr Thr Asp Tyr Ala Val
                        195                 200                 205

Arg Trp Tyr Asn Thr Gly Leu Glu Arg Val Trp Gly Pro Asp Ser Arg
                        210                 215                 220

Asp Trp Val Arg Tyr Asn Gln Phe Arg Arg Glu Leu Thr Leu Thr Val
        225                 230                 235                 240

Leu Asp Ile Val Ala Leu Phe Pro Asn Tyr Asp Ser Arg Arg Tyr Pro
                        245                 250                 255

Ile Arg Thr Val Ser Gln Leu Thr Arg Glu Ile Tyr Thr Asn Pro Val
                        260                 265                 270

Leu Glu Asn Phe Asp Gly Ser Phe Arg Gly Ser Ala Gln Gly Ile Glu
                        275                 280                 285

Arg Ser Ile Arg Ser Pro His Leu Met Asp Ile Leu Asn Ser Ile Thr
                        290                 295                 300

Ile Tyr Thr Asp Ala His Arg Gly Tyr Tyr Tyr Trp Ser Gly His Gln
        305                 310                 315                 320

Ile Met Ala Ser Pro Val Gly Phe Ser Gly Pro Glu Phe Thr Phe Pro
                        325                 330                 335

Leu Tyr Gly Thr Met Gly Asn Ala Ala Pro Gln Gln Arg Ile Val Ala
                        340                 345                 350

Gln Leu Gly Gln Gly Val Tyr Arg Thr Leu Ser Ser Thr Leu Tyr Arg
                        355                 360                 365

Arg Pro Phe Asn Ile Gly Ile Asn Asn Gln Gln Leu Ser Val Leu Asp
                        370                 375                 380

Gly Thr Glu Phe Ala Tyr Gly Thr Ser Ser Asn Leu Pro Ser Ala Val
        385                 390                 395                 400

Tyr Arg Lys Ser Gly Thr Val Asp Ser Leu Asp Glu Ile Pro Pro Gln
                        405                 410                 415

Asn Asn Asn Val Pro Pro Arg Gln Gly Phe Ser His Arg Leu Ser His
                        420                 425                 430

Val Ser Met Phe Arg Ser Gly Phe Ser Asn Ser Ser Val Ser Ile Ile
                        435                 440                 445

Arg Ala Pro Met Phe Ser Trp Ile His Arg Ser Ala Glu Phe Asn Asn
                        450                 455                 460

Ile Ile Pro Ser Ser Gln Ile Thr Gln Ile Pro Leu Thr Lys Ser Thr
        465                 470                 475                 480

Asn Leu Gly Ser Gly Thr Ser Val Val Lys Gly Pro Gly Phe Thr Gly
                        485                 490                 495
```

```
Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr
    610

<210> SEQ ID NO 23
<211> LENGTH: 1830
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry1Ab1 core toxin
      using codons optimized for maize and with sequences identified
      in Table 2 removed and Table 1 sequences are maintained
<220> FEATURE:
<221> NAME/KEY: CDS
<222> LOCATION: (1)..(1830)

<400> SEQUENCE: 23 atg gat aac aac ccg aac atc aat gag tgc atc ccg tat aac tgt ctc       48
Met Asp Asn Asn Pro Asn Ile Asn Glu Cys Ile Pro Tyr Asn Cys Leu
1               5                   10                  15 agt aac cct gaa gtg gag gtc tta ggt ggc gaa cgc atc gaa act ggt       96
Ser Asn Pro Glu Val Glu Val Leu Gly Gly Glu Arg Ile Glu Thr Gly
            20                  25                  30 tac acc cca atc gac att agc ttg tcg ttg acg cag ttc ctc ttg tcc      144
Tyr Thr Pro Ile Asp Ile Ser Leu Ser Leu Thr Gln Phe Leu Leu Ser
        35                  40                  45 gag ttc gtg ccc ggt gcg ggt ttc gtg ctg ggg cta gtt gat ata atc      192
Glu Phe Val Pro Gly Ala Gly Phe Val Leu Gly Leu Val Asp Ile Ile
    50                  55                  60 tgg gga atc ttt ggt ccc tct cag tgg gac gcc ttt ctt gtg caa att      240
Trp Gly Ile Phe Gly Pro Ser Gln Trp Asp Ala Phe Leu Val Gln Ile
65                  70                  75                  80 gag cag cta att aac caa aga ata gaa gag ttc gcg agg aac caa gcc      288
Glu Gln Leu Ile Asn Gln Arg Ile Glu Glu Phe Ala Arg Asn Gln Ala
                85                  90                  95 att tcc aga ctg gag gga cta agc aac ctt tat caa atc tac gcg gag      336
Ile Ser Arg Leu Glu Gly Leu Ser Asn Leu Tyr Gln Ile Tyr Ala Glu
            100                 105                 110 tct ttt agg gag tgg gag gca gat cct acg aac ccg gca ctg cgc gaa      384
Ser Phe Arg Glu Trp Glu Ala Asp Pro Thr Asn Pro Ala Leu Arg Glu
        115                 120                 125 gag atg cgt att cag ttc aac gac atg aac agt gcc ctt aca acc gct      432
Glu Met Arg Ile Gln Phe Asn Asp Met Asn Ser Ala Leu Thr Thr Ala
    130                 135                 140 att ccc ctt ttc gca gtt caa aat tac caa gtt ccc ctt ctc tca gtg      480
Ile Pro Leu Phe Ala Val Gln Asn Tyr Gln Val Pro Leu Leu Ser Val
```

```
                                        -continued
145              150              155              160
tac gtt caa gcc gca aat tta cac cta agc gtt ctc cgc gat gtg tca    528
Tyr Val Gln Ala Ala Asn Leu His Leu Ser Val Leu Arg Asp Val Ser
                165              170              175 gtg ttc ggc cag agg tgg gga ttt gat gcc gcc act atc aat agt cgt    576
Val Phe Gly Gln Arg Trp Gly Phe Asp Ala Ala Thr Ile Asn Ser Arg
            180              185              190 tat aat gat ctg acg agg ctt atc ggc aac tat acc gac tat gct gtc    624
Tyr Asn Asp Leu Thr Arg Leu Ile Gly Asn Tyr Thr Asp Tyr Ala Val
        195              200              205 cgc tgg tac aat acg gga tta gag cgg gtc tgg ggt ccg gat tcc cga    672
Arg Trp Tyr Asn Thr Gly Leu Glu Arg Val Trp Gly Pro Asp Ser Arg
    210              215              220 gac tgg gtg cgc tac aat caa ttc cgc cgc gaa tta acc ctc act gtc    720
Asp Trp Val Arg Tyr Asn Gln Phe Arg Arg Glu Leu Thr Leu Thr Val
225              230              235              240 ctc gac atc gtg gcg ctg ttc ccg aac tac gac agt agg aga tac cca    768
Leu Asp Ile Val Ala Leu Phe Pro Asn Tyr Asp Ser Arg Arg Tyr Pro
                245              250              255 atc cgc aca gtt tcc caa tta acg cgg gaa att tac acc aac cca gtc    816
Ile Arg Thr Val Ser Gln Leu Thr Arg Glu Ile Tyr Thr Asn Pro Val
            260              265              270 ctg gag aat ttt gac ggg agc ttc cga ggc tcg gct caa ggc ata gaa    864
Leu Glu Asn Phe Asp Gly Ser Phe Arg Gly Ser Ala Gln Gly Ile Glu
        275              280              285 cgc agc att agg tcg cca cac ttg atg gat atc ctt aac agc atc acc    912
Arg Ser Ile Arg Ser Pro His Leu Met Asp Ile Leu Asn Ser Ile Thr
    290              295              300 atc tac acg gat gcc cat agg ggt tac tac tac tgg tcg ggg cat caa    960
Ile Tyr Thr Asp Ala His Arg Gly Tyr Tyr Tyr Trp Ser Gly His Gln
305              310              315              320 ata atg gct tct cct gtc ggg ttt tcg ggg cca gag ttc acc ttc ccg   1008
Ile Met Ala Ser Pro Val Gly Phe Ser Gly Pro Glu Phe Thr Phe Pro
                325              330              335 ctc tac ggc act atg gga aat gcc gcg cca caa caa cgt atc gtc gct   1056
Leu Tyr Gly Thr Met Gly Asn Ala Ala Pro Gln Gln Arg Ile Val Ala
            340              345              350 caa cta ggt caa ggc gtg tac cgg aca ctg tcg tcc act ctc tat cgg   1104
Gln Leu Gly Gln Gly Val Tyr Arg Thr Leu Ser Ser Thr Leu Tyr Arg
        355              360              365 cgg cct ttc aat ata ggg atc aat aat caa cag ttg tct gtg ctg gac   1152
Arg Pro Phe Asn Ile Gly Ile Asn Asn Gln Gln Leu Ser Val Leu Asp
    370              375              380 ggg aca gag ttt gct tac gga acc tca agc aac ttg cca tcc gct gta   1200
Gly Thr Glu Phe Ala Tyr Gly Thr Ser Ser Asn Leu Pro Ser Ala Val
385              390              395              400 tac aga aaa agc ggc acg gtg gac tcg ctg gat gaa atc ccg ccc cag   1248
Tyr Arg Lys Ser Gly Thr Val Asp Ser Leu Asp Glu Ile Pro Pro Gln
                405              410              415 aat aac aac gtg ccc cct cgg caa ggc ttc agt cat cga ctg agc cac   1296
Asn Asn Asn Val Pro Pro Arg Gln Gly Phe Ser His Arg Leu Ser His
            420              425              430 gtt agc atg ttc cgt tcg ggc ttc agc aac tcc tcc gta agt atc ata   1344
Val Ser Met Phe Arg Ser Gly Phe Ser Asn Ser Ser Val Ser Ile Ile
        435              440              445 aga gca cct atg ttc agc tgg ata cat cgt tcc gcc gag ttc aat aat   1392
Arg Ala Pro Met Phe Ser Trp Ile His Arg Ser Ala Glu Phe Asn Asn
    450              455              460 ata att ccc tcc tct caa atc aca cag atc cct ctg aca aag tct act   1440
```

```
Ile Ile Pro Ser Ser Gln Ile Thr Gln Ile Pro Leu Thr Lys Ser Thr
465                 470                 475                 480 aat ctt ggc tct ggg act tct gtc gtt aag ggg cct ggc ttt acg ggc    1488
Asn Leu Gly Ser Gly Thr Ser Val Val Lys Gly Pro Gly Phe Thr Gly
                485                 490                 495 ggc gat att ctg cgg aga act tca cct ggc cag att tcc acc ctg cgc    1536
Gly Asp Ile Leu Arg Arg Thr Ser Pro Gly Gln Ile Ser Thr Leu Arg
            500                 505                 510 gtg aat atc acc gcg cca ttg tca caa cgt tac cgc gtg cgg att cgc    1584
Val Asn Ile Thr Ala Pro Leu Ser Gln Arg Tyr Arg Val Arg Ile Arg
        515                 520                 525 tac gct tct acc aca aac ctc cag ttc cat aca tct att gac ggc aga    1632
Tyr Ala Ser Thr Thr Asn Leu Gln Phe His Thr Ser Ile Asp Gly Arg
    530                 535                 540 ccc att aat caa ggg aat ttc tcc gcc acg atg tcg tcc ggc tcc aat    1680
Pro Ile Asn Gln Gly Asn Phe Ser Ala Thr Met Ser Ser Gly Ser Asn
545                 550                 555                 560 ctc cag tcc gga agt ttc cgc acc gta ggt ttt act acc ccg ttc aac    1728
Leu Gln Ser Gly Ser Phe Arg Thr Val Gly Phe Thr Thr Pro Phe Asn
                565                 570                 575 ttt tca aac ggc tca agt gtg ttt acg ctg tcc gct cat gtg ttc aac    1776
Phe Ser Asn Gly Ser Ser Val Phe Thr Leu Ser Ala His Val Phe Asn
            580                 585                 590 tct ggc aat gag gtt tac atc gac cgg att gag ttc gtc ccg gca gaa    1824
Ser Gly Asn Glu Val Tyr Ile Asp Arg Ile Glu Phe Val Pro Ala Glu
        595                 600                 605 gtc acc                                                            1830
Val Thr
    610

<210> SEQ ID NO 24
<211> LENGTH: 610
<212> TYPE: PRT
<213> ORGANISM: Artificial Sequence
<220> FEATURE:
<223> OTHER INFORMATION: Synthetic Construct

<400> SEQUENCE: 24

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160
```

```
Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
        210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
```

```
                580                 585                 590
Ser Gly Asn Glu Val Tyr Ile Asp Arg Ile Glu Phe Val Pro Ala Glu
        595                 600                 605

Val Thr
    610

<210> SEQ ID NO 25
<211> LENGTH: 1866
<212> TYPE: DNA
<213> ORGANISM: Bacillus thuringiensis
<220> FEATURE:
<221> NAME/KEY: CDS
<222> LOCATION: (1)..(1866)
<223> OTHER INFORMATION: Native DNA sequence encoding Bacillus
      thuringiensis Cry1Ca core toxin

<400> SEQUENCE: 25 atg aat aac cca aac atc aat gaa tgc atc ccg tac aac tgc ctg          48
Met Asn Asn Pro Asn Ile Asn Glu Cys Ile Pro Tyr Asn Cys Leu
1               5                   10                  15 agc aac ccg gaa gaa gtg ctg ttg gat gga gaa cgg ata tca act ggt      96
Ser Asn Pro Glu Glu Val Leu Leu Asp Gly Glu Arg Ile Ser Thr Gly
            20                  25                  30 aat tca tca att gat att tct ctg tca ctt gtt cag ttt ctg gta tct     144
Asn Ser Ser Ile Asp Ile Ser Leu Ser Leu Val Gln Phe Leu Val Ser
        35                  40                  45 aac ttc gtc cca ggc gga gga ttc ctg gtt gga tta ata gat ttt gta     192
Asn Phe Val Pro Gly Gly Gly Phe Leu Val Gly Leu Ile Asp Phe Val
    50                  55                  60 tgg gga ata gtt ggc cct tct caa tgg gat gca ttt cta gta caa att     240
Trp Gly Ile Val Gly Pro Ser Gln Trp Asp Ala Phe Leu Val Gln Ile
65                  70                  75                  80 gaa caa tta att aat gaa aga ata gct gaa ttt gct agg aat gct gca     288
Glu Gln Leu Ile Asn Glu Arg Ile Ala Glu Phe Ala Arg Asn Ala Ala
                85                  90                  95 att gct aat tta gaa gga tta gga aac aat ttc aat ata tat gtg gaa     336
Ile Ala Asn Leu Glu Gly Leu Gly Asn Asn Phe Asn Ile Tyr Val Glu
            100                 105                 110 gca ttt aaa gaa tgg gaa gaa gat cct aag aat cca gca acc agg acc     384
Ala Phe Lys Glu Trp Glu Glu Asp Pro Lys Asn Pro Ala Thr Arg Thr
        115                 120                 125 aga gta att gat cgc ttt cgt ata ctt gat ggg cta ctt gaa agg gac     432
Arg Val Ile Asp Arg Phe Arg Ile Leu Asp Gly Leu Leu Glu Arg Asp
    130                 135                 140 att cct tcg ttt cga att tct gga ttt gaa gta ccc ctt tta tcc gtt     480
Ile Pro Ser Phe Arg Ile Ser Gly Phe Glu Val Pro Leu Leu Ser Val
145                 150                 155                 160 tat gct caa gcg gcc aat ctg cat cta gct ata tta aga gat tct gta     528
Tyr Ala Gln Ala Ala Asn Leu His Leu Ala Ile Leu Arg Asp Ser Val
                165                 170                 175 att ttt gga gaa aga tgg gga ttg aca acg ata aat gtc aat gaa aac     576
Ile Phe Gly Glu Arg Trp Gly Leu Thr Thr Ile Asn Val Asn Glu Asn
            180                 185                 190 tat aat aga cta att agg cat att gat gaa tat gct gat cac tgt gca     624
Tyr Asn Arg Leu Ile Arg His Ile Asp Glu Tyr Ala Asp His Cys Ala
        195                 200                 205 aat acg tat aat cgg gga tta aat aat tta ccg aaa tct acg tat caa     672
Asn Thr Tyr Asn Arg Gly Leu Asn Asn Leu Pro Lys Ser Thr Tyr Gln
    210                 215                 220 gat tgg ata aca tat aat cga ttg cgg aga gac tta acg ttg act gta     720
Asp Trp Ile Thr Tyr Asn Arg Leu Arg Arg Asp Leu Thr Leu Thr Val
```

-continued

```
          225                 230                 235                 240
    tta gat atc gcc gct ttc ttt cca aac tat gac aat agg aga tat cca         768
    Leu Asp Ile Ala Ala Phe Phe Pro Asn Tyr Asp Asn Arg Arg Tyr Pro
                        245                 250                 255 att cag cca gtt ggt caa cta aca agg gaa gtt tat acg gac cca tta         816
    Ile Gln Pro Val Gly Gln Leu Thr Arg Glu Val Tyr Thr Asp Pro Leu
                    260                 265                 270 att aat ttt aat cca cag tta cag tct gta gct caa tta cct act ttt         864
    Ile Asn Phe Asn Pro Gln Leu Gln Ser Val Ala Gln Leu Pro Thr Phe
                275                 280                 285 aac gtt atg gag aac agc gca att aga aat cct cat tta ttt gat ata         912
    Asn Val Met Glu Asn Ser Ala Ile Arg Asn Pro His Leu Phe Asp Ile
            290                 295                 300 ttg aat aat ctt aca atc ttt acg gat tgg ttt agt gtt gga cgc aat         960
    Leu Asn Asn Leu Thr Ile Phe Thr Asp Trp Phe Ser Val Gly Arg Asn
    305                 310                 315                 320 ttt tat tgg gga gga cat cga gta ata tct agc ctt ata gga ggt ggt        1008
    Phe Tyr Trp Gly Gly His Arg Val Ile Ser Ser Leu Ile Gly Gly Gly
                        325                 330                 335 aac ata aca tct cct ata tat gga aga gag gcg aac cag gag cct cca        1056
    Asn Ile Thr Ser Pro Ile Tyr Gly Arg Glu Ala Asn Gln Glu Pro Pro
                    340                 345                 350 aga tcc ttt act ttt aat gga ccg gta ttt agg act tta tca aat cct        1104
    Arg Ser Phe Thr Phe Asn Gly Pro Val Phe Arg Thr Leu Ser Asn Pro
                355                 360                 365 act tta cga tta tta cag caa cct tgg cca gcg cca cca ttt aat tta        1152
    Thr Leu Arg Leu Leu Gln Gln Pro Trp Pro Ala Pro Pro Phe Asn Leu
            370                 375                 380 cgt ggt gtt gaa gga gta gaa ttt tct aca cct aca aat agc ttt acg        1200
    Arg Gly Val Glu Gly Val Glu Phe Ser Thr Pro Thr Asn Ser Phe Thr
    385                 390                 395                 400 tat cga gga aga ggt acg gtt gat tct tta act gaa ttg ccg cct gag        1248
    Tyr Arg Gly Arg Gly Thr Val Asp Ser Leu Thr Glu Leu Pro Pro Glu
                        405                 410                 415 gat aat agt gtg cca cct cgc gaa gga tat agt cat cgt tta tgt cat        1296
    Asp Asn Ser Val Pro Pro Arg Glu Gly Tyr Ser His Arg Leu Cys His
                    420                 425                 430 gca act ttt gtt caa aga tct gga aca cct ttt tta aca act ggt gta        1344
    Ala Thr Phe Val Gln Arg Ser Gly Thr Pro Phe Leu Thr Thr Gly Val
                435                 440                 445 gta ttt tct tgg acg cat cgt agt gca act ctt aca aat aca att gat        1392
    Val Phe Ser Trp Thr His Arg Ser Ala Thr Leu Thr Asn Thr Ile Asp
    450                 455                 460 cca gag aga att aat caa ata cct tta gtg aaa gga ttt aga gtt tgg        1440
    Pro Glu Arg Ile Asn Gln Ile Pro Leu Val Lys Gly Phe Arg Val Trp
    465                 470                 475                 480 ggg ggc acc tct gtc att aca gga cca gga ttt aca gga ggg gat atc        1488
    Gly Gly Thr Ser Val Ile Thr Gly Pro Gly Phe Thr Gly Gly Asp Ile
                        485                 490                 495 ctt cga aga aat acc ttt ggt gat ttt gta tct cta caa gtc aat att        1536
    Leu Arg Arg Asn Thr Phe Gly Asp Phe Val Ser Leu Gln Val Asn Ile
                    500                 505                 510 aat tca cca att acc caa aga tac cgt tta aga ttt cgt tac gct tcc        1584
    Asn Ser Pro Ile Thr Gln Arg Tyr Arg Leu Arg Phe Arg Tyr Ala Ser
                515                 520                 525 agt agg gat gca cga gtt ata gta tta aca gga gcg gca tcc aca gga        1632
    Ser Arg Asp Ala Arg Val Ile Val Leu Thr Gly Ala Ala Ser Thr Gly
            530                 535                 540 gtg gga ggc caa gtt agt gta aat atg cct ctt cag aaa act atg gaa        1680
```

-continued

```
                                    Val Gly Gly Gln Val Ser Val Asn Met Pro Leu Gln Lys Thr Met Glu
                                    545                 550                 555                 560 ata ggg gag aac tta aca tct aga aca ttt aga tat acc gat ttt agt          1728
Ile Gly Glu Asn Leu Thr Ser Arg Thr Phe Arg Tyr Thr Asp Phe Ser
                565                 570                 575 aat cct ttt tca ttt aga gct aat cca gat ata att ggg ata agt gaa          1776
Asn Pro Phe Ser Phe Arg Ala Asn Pro Asp Ile Ile Gly Ile Ser Glu
                580                 585                 590 caa cct cta ttt ggt gca ggt tct att agt agc ggt gaa ctt tat ata          1824
Gln Pro Leu Phe Gly Ala Gly Ser Ile Ser Ser Gly Glu Leu Tyr Ile
                595                 600                 605 gat aaa att gaa att att cta gca gat gca aca ttt gaa taa                  1866
Asp Lys Ile Glu Ile Ile Leu Ala Asp Ala Thr Phe Glu
                610                 615                 620
```

<210> SEQ ID NO 26
<211> LENGTH: 621
<212> TYPE: PRT
<213> ORGANISM: Bacillus thuringiensis

<400> SEQUENCE: 26

```
Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
                20                  25                  30

Asn Ser Ser Ile Asp Ile Ser Leu Ser Leu Val Gln Phe Leu Val Ser
            35                  40                  45

Asn Phe Val Pro Gly Gly Gly Phe Leu Val Gly Leu Ile Asp Phe Val
        50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
                100                 105                 110

Ala Phe Lys Glu Trp Glu Glu Asp Pro Lys Asn Pro Ala Thr Arg Thr
            115                 120                 125

Arg Val Ile Asp Arg Phe Arg Ile Leu Asp Gly Leu Leu Glu Arg Asp
        130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
                180                 185                 190

Tyr Asn Arg Leu Ile Arg His Ile Asp Glu Tyr Ala Asp His Cys Ala
            195                 200                 205

Asn Thr Tyr Asn Arg Gly Leu Asn Asn Leu Pro Lys Ser Thr Tyr Gln
        210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
                260                 265                 270

Ile Asn Phe Asn Pro Gln Leu Gln Ser Val Ala Gln Leu Pro Thr Phe
```

```
              275                 280                 285
Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                485                 490                 495

Leu Arg Arg Asn Thr Phe Gly Asp Phe Val Ser Leu Gln Val Asn Ile
            500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Phe Glu
    610                 615                 620

<210> SEQ ID NO 27
<211> LENGTH: 1866
<212> TYPE: DNA
<213> ORGANISM: Artificial Sequence
<220> FEATURE:
<223> OTHER INFORMATION: Synthetic DNA sequence encoding Bacillus
      thuringiensis Cry1Ca core toxin using codons optimized for maize
      and Table 1 sequences are maintained
<220> FEATURE:
<221> NAME/KEY: CDS
<222> LOCATION: (1)..(1866)

<400> SEQUENCE: 27
```

```
atg gat aac aat ccg aac atc aat gag tgc atc ccg tac aac tgc ctg      48
Met Asp Asn Asn Pro Asn Ile Asn Glu Cys Ile Pro Tyr Asn Cys Leu
1               5                   10                  15 agc aac ccg gaa gaa gtg ctg ttg gat gga gaa cgg ata tca act ggc      96
Ser Asn Pro Glu Glu Val Leu Leu Asp Gly Glu Arg Ile Ser Thr Gly
            20                  25                  30 aat tca tcc att gat att tct ctg tca ctt gtt cag ttt ctg gtg tct     144
Asn Ser Ser Ile Asp Ile Ser Leu Ser Leu Val Gln Phe Leu Val Ser
        35                  40                  45 aac ttc gtc ccc gga gga ttc ctg gtt gga tta ata gat ttt gta         192
Asn Phe Val Pro Gly Gly Phe Leu Val Gly Leu Ile Asp Phe Val
    50                  55                  60 tgg gga ata gtt ggc cct tct caa tgg gac gca ttt cta gta caa att     240
Trp Gly Ile Val Gly Pro Ser Gln Trp Asp Ala Phe Leu Val Gln Ile
65                  70                  75                  80 gaa caa tta att aat gaa aga ata gct gaa ttt gct agg aac gct gct     288
Glu Gln Leu Ile Asn Glu Arg Ile Ala Glu Phe Ala Arg Asn Ala Ala
                85                  90                  95 att gct aat tta gaa gga tta gga aac aat ttc aat ata tat gtg gaa     336
Ile Ala Asn Leu Glu Gly Leu Gly Asn Asn Phe Asn Ile Tyr Val Glu
            100                 105                 110 gca ttt aag gaa tgg gaa gaa gat cct aag aat cca gca acg agg acc     384
Ala Phe Lys Glu Trp Glu Glu Asp Pro Lys Asn Pro Ala Thr Arg Thr
        115                 120                 125 aga gta att gat cgc ttt cgt ata ctt gat ggg cta ctt gaa agg gac     432
Arg Val Ile Asp Arg Phe Arg Ile Leu Asp Gly Leu Leu Glu Arg Asp
    130                 135                 140 att cct tcg ttt cga att tct gga ttt gaa gta ccc ctt tta tcc gtt     480
Ile Pro Ser Phe Arg Ile Ser Gly Phe Glu Val Pro Leu Leu Ser Val
145                 150                 155                 160 tat gct caa gcg gcc aat ctg cat cta gct ata tta aga gat tct gta     528
Tyr Ala Gln Ala Ala Asn Leu His Leu Ala Ile Leu Arg Asp Ser Val
                165                 170                 175 att ttt gga gaa aga tgg gga ttg aca acg ata aat gtc aat gaa aac     576
Ile Phe Gly Glu Arg Trp Gly Leu Thr Thr Ile Asn Val Asn Glu Asn
            180                 185                 190 tat aat aga cta att agg cat att gat gaa tat gct gat cac tgt gca     624
Tyr Asn Arg Leu Ile Arg His Ile Asp Glu Tyr Ala Asp His Cys Ala
        195                 200                 205 aat acg tat aat cgg gga tta aat aat tta ccg aaa tct acg tat caa     672
Asn Thr Tyr Asn Arg Gly Leu Asn Asn Leu Pro Lys Ser Thr Tyr Gln
    210                 215                 220 gat tgg ata aca tat aat cga ttg cgg aga gac tta aca ttg act gta     720
Asp Trp Ile Thr Tyr Asn Arg Leu Arg Arg Asp Leu Thr Leu Thr Val
225                 230                 235                 240 tta gat atc gcc gct ttc ttt cca aac tat gac aat agg aga tat cca     768
Leu Asp Ile Ala Ala Phe Phe Pro Asn Tyr Asp Asn Arg Arg Tyr Pro
                245                 250                 255 att cag cca gtt ggt caa cta aca agg gaa gtt tat acg gac cca tta     816
Ile Gln Pro Val Gly Gln Leu Thr Arg Glu Val Tyr Thr Asp Pro Leu
            260                 265                 270 att aat ttt aat cca cag tta cag tct gta gct caa tta cct act ttt     864
Ile Asn Phe Asn Pro Gln Leu Gln Ser Val Ala Gln Leu Pro Thr Phe
        275                 280                 285 aac gtt atg gag aac agc gca att aga aat cct cat tta ttt gat ata     912
Asn Val Met Glu Asn Ser Ala Ile Arg Asn Pro His Leu Phe Asp Ile
    290                 295                 300 ttg aat aat ctt aca atc ttt acg gat tgg ttt agt gtt gga cgc aat     960
Leu Asn Asn Leu Thr Ile Phe Thr Asp Trp Phe Ser Val Gly Arg Asn
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 305 |     |     |     | 310 |     |     |     | 315 |     |     |     | 320 |     |     |      |
| ttt | tat | tgg | gga | gga | cat | cga | gta | ata | tct | agc | ctt | ata | gga | ggt | ggg | 1008 |
| Phe | Tyr | Trp | Gly | Gly | His | Arg | Val | Ile | Ser | Ser | Leu | Ile | Gly | Gly | Gly |      |
|     |     |     |     | 325 |     |     |     |     | 330 |     |     |     |     | 335 |     |      |
| aac | atc | aca | tcg | cct | ata | tat | gga | aga | gag | gcg | aac | caa | gag | cct | cca | 1056 |
| Asn | Ile | Thr | Ser | Pro | Ile | Tyr | Gly | Arg | Glu | Ala | Asn | Gln | Glu | Pro | Pro |      |
|     |     |     | 340 |     |     |     |     | 345 |     |     |     |     | 350 |     |     |      |
| aga | tcc | ttt | act | ttt | aat | gga | ccc | gtg | ttt | agg | act | tta | tca | aat | cct | 1104 |
| Arg | Ser | Phe | Thr | Phe | Asn | Gly | Pro | Val | Phe | Arg | Thr | Leu | Ser | Asn | Pro |      |
|     |     | 355 |     |     |     |     | 360 |     |     |     |     | 365 |     |     |     |      |
| act | tta | cga | tta | tta | cag | caa | cct | tgg | cca | gcg | cca | cca | ttt | aat | tta | 1152 |
| Thr | Leu | Arg | Leu | Leu | Gln | Gln | Pro | Trp | Pro | Ala | Pro | Pro | Phe | Asn | Leu |      |
|     | 370 |     |     |     |     | 375 |     |     |     |     | 380 |     |     |     |     |      |
| cgt | ggt | gtt | gaa | gga | gta | gaa | ttt | tct | aca | cct | aca | aat | agc | ttt | acg | 1200 |
| Arg | Gly | Val | Glu | Gly | Val | Glu | Phe | Ser | Thr | Pro | Thr | Asn | Ser | Phe | Thr |      |
| 385 |     |     |     |     | 390 |     |     |     |     | 395 |     |     |     |     | 400 |      |
| tat | cga | gga | aga | ggg | acg | gtt | gat | tct | tta | act | gaa | ttg | ccg | cct | gag | 1248 |
| Tyr | Arg | Gly | Arg | Gly | Thr | Val | Asp | Ser | Leu | Thr | Glu | Leu | Pro | Pro | Glu |      |
|     |     |     |     | 405 |     |     |     |     | 410 |     |     |     |     | 415 |     |      |
| gat | aat | agt | gtg | cca | cct | cgc | gaa | gga | tat | agt | cat | cgt | tta | tgt | cat | 1296 |
| Asp | Asn | Ser | Val | Pro | Pro | Arg | Glu | Gly | Tyr | Ser | His | Arg | Leu | Cys | His |      |
|     |     |     | 420 |     |     |     |     | 425 |     |     |     |     | 430 |     |     |      |
| gca | act | ttt | gtt | caa | aga | tcg | gga | aca | cct | ttt | tta | aca | act | ggt | gta | 1344 |
| Ala | Thr | Phe | Val | Gln | Arg | Ser | Gly | Thr | Pro | Phe | Leu | Thr | Thr | Gly | Val |      |
|     |     | 435 |     |     |     |     | 440 |     |     |     |     | 445 |     |     |     |      |
| gta | ttt | tct | tgg | acg | cat | cgt | agt | gca | act | ctt | aca | aat | aca | atc | gac | 1392 |
| Val | Phe | Ser | Trp | Thr | His | Arg | Ser | Ala | Thr | Leu | Thr | Asn | Thr | Ile | Asp |      |
|     | 450 |     |     |     |     | 455 |     |     |     |     | 460 |     |     |     |     |      |
| cca | gag | aga | att | aat | caa | ata | cct | tta | gtg | aag | gga | ttt | aga | gtt | tgg | 1440 |
| Pro | Glu | Arg | Ile | Asn | Gln | Ile | Pro | Leu | Val | Lys | Gly | Phe | Arg | Val | Trp |      |
| 465 |     |     |     |     | 470 |     |     |     |     | 475 |     |     |     |     | 480 |      |
| ggg | ggc | acc | tct | gtc | att | acc | gga | ccc | gga | ttt | acc | gga | ggg | gat | atc | 1488 |
| Gly | Gly | Thr | Ser | Val | Ile | Thr | Gly | Pro | Gly | Phe | Thr | Gly | Gly | Asp | Ile |      |
|     |     |     |     | 485 |     |     |     |     | 490 |     |     |     |     | 495 |     |      |
| ctt | cga | aga | aat | acc | ttt | ggt | gat | ttt | gta | tct | cta | caa | gtc | aac | att | 1536 |
| Leu | Arg | Arg | Asn | Thr | Phe | Gly | Asp | Phe | Val | Ser | Leu | Gln | Val | Asn | Ile |      |
|     |     |     | 500 |     |     |     |     | 505 |     |     |     |     | 510 |     |     |      |
| aat | tca | cca | att | acc | caa | aga | tac | cgt | tta | aga | ttt | cgt | tac | gct | tcc | 1584 |
| Asn | Ser | Pro | Ile | Thr | Gln | Arg | Tyr | Arg | Leu | Arg | Phe | Arg | Tyr | Ala | Ser |      |
|     |     | 515 |     |     |     |     | 520 |     |     |     |     | 525 |     |     |     |      |
| agt | agg | gat | gca | cga | gtt | ata | gta | tta | acg | gga | gcg | gca | tcc | acc | gga | 1632 |
| Ser | Arg | Asp | Ala | Arg | Val | Ile | Val | Leu | Thr | Gly | Ala | Ala | Ser | Thr | Gly |      |
|     | 530 |     |     |     |     | 535 |     |     |     |     | 540 |     |     |     |     |      |
| gtg | gga | ggc | caa | gtt | agt | gta | aat | atg | cct | ctt | cag | aaa | act | atg | gaa | 1680 |
| Val | Gly | Gly | Gln | Val | Ser | Val | Asn | Met | Pro | Leu | Gln | Lys | Thr | Met | Glu |      |
| 545 |     |     |     |     | 550 |     |     |     |     | 555 |     |     |     |     | 560 |      |
| ata | ggg | gag | aac | tta | aca | tcc | aga | aca | ttt | aga | tat | acc | gat | ttt | agt | 1728 |
| Ile | Gly | Glu | Asn | Leu | Thr | Ser | Arg | Thr | Phe | Arg | Tyr | Thr | Asp | Phe | Ser |      |
|     |     |     |     | 565 |     |     |     |     | 570 |     |     |     |     | 575 |     |      |
| aat | cct | ttt | tca | ttt | aga | gct | aat | cca | gat | ata | att | ggg | ata | agt | gaa | 1776 |
| Asn | Pro | Phe | Ser | Phe | Arg | Ala | Asn | Pro | Asp | Ile | Ile | Gly | Ile | Ser | Glu |      |
|     |     |     | 580 |     |     |     |     | 585 |     |     |     |     | 590 |     |     |      |
| caa | cct | cta | ttt | ggg | gcg | ggt | tct | att | agt | agc | ggt | gaa | ctt | tat | ata | 1824 |
| Gln | Pro | Leu | Phe | Gly | Ala | Gly | Ser | Ile | Ser | Ser | Gly | Glu | Leu | Tyr | Ile |      |
|     |     | 595 |     |     |     |     | 600 |     |     |     |     | 605 |     |     |     |      |
| gat | aaa | att | gaa | att | att | cta | gca | gat | gca | aca | ttt | gaa | tga |     |     | 1866 |
| Asp | Lys | Ile | Glu | Ile | Ile | Leu | Ala | Asp | Ala | Thr | Phe | Glu |     |     |     |      |
|     | 610 |     |     |     | 615 |     |     |     | 620 |     |     |     |     |     |     |      |

```
<210> SEQ ID NO 28
<211> LENGTH: 621
<212> TYPE: PRT
<213> ORGANISM: Artificial Sequence
<220> FEATURE:
<223> OTHER INFORMATION: Synthetic Construct

<400> SEQUENCE: 28

Met Asp Asn Asn Pro Asn Ile Asn Glu Cys Ile Pro Tyr Asn Cys Leu
1               5                   10                  15

Ser Asn Pro Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45

Asn Phe Val Pro Gly Gly Gly Phe Leu Val Gly Leu Ile Asp Phe Val
    50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Lys Asn Pro Ala Thr Arg Thr
        115                 120                 125

Arg Val Ile Asp Arg Phe Arg Ile Leu Asp Gly Leu Leu Glu Arg Asp
    130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
```

```
                    370                 375                 380
Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                    405                 410                 415

Asp Asn Ser Val Pro Pro Arg Glu Gly Tyr Ser His Arg Leu Cys His
                    420                 425                 430

Ala Thr Phe Val Gln Arg Ser Gly Thr Pro Phe Leu Thr Thr Gly Val
                435                 440                 445

Val Phe Ser Trp Thr His Arg Ser Ala Thr Leu Thr Asn Thr Ile Asp
            450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
                    485                 490                 495

Leu Arg Arg Asn Thr Phe Gly Asp Phe Val Ser Leu Gln Val Asn Ile
                500                 505                 510

Asn Ser Pro Ile Thr Gln Arg Tyr Arg Leu Arg Phe Arg Tyr Ala Ser
            515                 520                 525

Ser Arg Asp Ala Arg Val Ile Val Leu Thr Gly Ala Ala Ser Thr Gly
530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
                565                 570                 575

Asn Pro Phe Ser Phe Arg Ala Asn Pro Asp Ile Ile Gly Ile Ser Glu
            580                 585                 590

Gln Pro Leu Phe Gly Ala Gly Ser Ile Ser Ser Gly Leu Tyr Ile
            595                 600                 605

Asp Lys Ile Glu Ile Ile Leu Ala Asp Ala Thr Phe Glu
        610                 615                 620

<210> SEQ ID NO 29
<211> LENGTH: 1866
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry1Ca core toxin using
      codons optimized for maize and with sequences identified in
      Table 2 removed and Table 1 sequences are maintained
<220> FEATURE:
<221> NAME/KEY: CDS
<222> LOCATION: (1)..(1866)

<400> SEQUENCE: 29 atg gat aac aat ccg aac atc aat gag tgc atc ccg tac aac tgc ctg      48
Met Asp Asn Asn Pro Asn Ile Asn Glu Cys Ile Pro Tyr Asn Cys Leu
1               5                   10                  15 agc aac ccg gaa gaa gtg ctg ttg gat gga gaa cgg ata tca act ggc      96
Ser Asn Pro Glu Glu Val Leu Leu Asp Gly Glu Arg Ile Ser Thr Gly
            20                  25                  30 aat tca tcc att gac att tct ctg tca ctt gtt cag ttt ctg gtg tct     144
Asn Ser Ser Ile Asp Ile Ser Leu Ser Leu Val Gln Phe Leu Val Ser
        35                  40                  45 aac ttc gtc ccc ggc gga gga ttc ctg gtt gga tta ata gat ttc gta     192
Asn Phe Val Pro Gly Gly Gly Phe Leu Val Gly Leu Ile Asp Phe Val
    50                  55                  60
```

```
tgg gga ata gtt ggc cct tct caa tgg gac gca ttt cta gta caa att      240
Trp Gly Ile Val Gly Pro Ser Gln Trp Asp Ala Phe Leu Val Gln Ile
 65                  70                  75                  80 gaa caa tta att aat gaa aga ata gct gaa ttt gct agg aac gct gct      288
Glu Gln Leu Ile Asn Glu Arg Ile Ala Glu Phe Ala Arg Asn Ala Ala
                 85                  90                  95 att gct aat tta gaa gga tta gga aac aat ttc aac atc tat gtg gaa      336
Ile Ala Asn Leu Glu Gly Leu Gly Asn Asn Phe Asn Ile Tyr Val Glu
                100                 105                 110 gca ttt aag gaa tgg gaa gaa gat cct aag aat cca gca acg agg acc      384
Ala Phe Lys Glu Trp Glu Glu Asp Pro Lys Asn Pro Ala Thr Arg Thr
            115                 120                 125 aga gta att gat cgc ttt cgt ata ctt gat ggg cta ctt gaa agg gac      432
Arg Val Ile Asp Arg Phe Arg Ile Leu Asp Gly Leu Leu Glu Arg Asp
        130                 135                 140 att cct tcg ttt cga att tct gga ttt gaa gta ccc ctt ctc tcc gtt      480
Ile Pro Ser Phe Arg Ile Ser Gly Phe Glu Val Pro Leu Leu Ser Val
145                 150                 155                 160 tat gct caa gcg gcc aat ctg cat cta gct atc tta aga gat tct gtc      528
Tyr Ala Gln Ala Ala Asn Leu His Leu Ala Ile Leu Arg Asp Ser Val
                165                 170                 175 atc ttt gga gaa aga tgg gga ttg aca acg ata aat gtc aat gaa aac      576
Ile Phe Gly Glu Arg Trp Gly Leu Thr Thr Ile Asn Val Asn Glu Asn
            180                 185                 190 tat aat aga cta att agg cat att gat gaa tat gct gat cac tgt gca      624
Tyr Asn Arg Leu Ile Arg His Ile Asp Glu Tyr Ala Asp His Cys Ala
        195                 200                 205 aat acg tat aat cgg gga tta aat aat tta ccg aaa tct acg tat caa      672
Asn Thr Tyr Asn Arg Gly Leu Asn Asn Leu Pro Lys Ser Thr Tyr Gln
    210                 215                 220 gat tgg ata aca tat aat cga ttg cgg aga gac tta aca ttg act gta      720
Asp Trp Ile Thr Tyr Asn Arg Leu Arg Arg Asp Leu Thr Leu Thr Val
225                 230                 235                 240 tta gat atc gcc gct ttc ttt cca aac tat gac aat agg aga tat cca      768
Leu Asp Ile Ala Ala Phe Phe Pro Asn Tyr Asp Asn Arg Arg Tyr Pro
                245                 250                 255 att cag cca gtt ggt caa cta aca agg gaa gtt tat acg gac cca tta      816
Ile Gln Pro Val Gly Gln Leu Thr Arg Glu Val Tyr Thr Asp Pro Leu
            260                 265                 270 att aat ttt aat cca cag tta cag tct gta gct caa tta cct act ttt      864
Ile Asn Phe Asn Pro Gln Leu Gln Ser Val Ala Gln Leu Pro Thr Phe
        275                 280                 285 aac gtt atg gag aac agc gca att aga aat cct cat ttg ttc gac ata      912
Asn Val Met Glu Asn Ser Ala Ile Arg Asn Pro His Leu Phe Asp Ile
    290                 295                 300 ttg aat aat ctt aca atc ttt acg gat tgg ttt agt gtt gga cgc aac      960
Leu Asn Asn Leu Thr Ile Phe Thr Asp Trp Phe Ser Val Gly Arg Asn
305                 310                 315                 320 ttc tat tgg gga gga cat cga gta ata tct agc ctt ata gga ggt ggg     1008
Phe Tyr Trp Gly Gly His Arg Val Ile Ser Ser Leu Ile Gly Gly Gly
                325                 330                 335 aac atc aca tcg cct atc tat gga aga gag gcg aac caa gag cct cca     1056
Asn Ile Thr Ser Pro Ile Tyr Gly Arg Glu Ala Asn Gln Glu Pro Pro
            340                 345                 350 aga tcc ttt act ttt aat gga ccc gtg ttt agg act tta tca aat cct     1104
Arg Ser Phe Thr Phe Asn Gly Pro Val Phe Arg Thr Leu Ser Asn Pro
        355                 360                 365 act tta cga tta tta cag caa cct tgg cca gcg cca cca ttt aat tta     1152
Thr Leu Arg Leu Leu Gln Gln Pro Trp Pro Ala Pro Pro Phe Asn Leu
    370                 375                 380
```

```
cgt ggt gtt gaa gga gta gaa ttt tct aca cct aca aat agc ttt acg   1200
Arg Gly Val Glu Gly Val Glu Phe Ser Thr Pro Thr Asn Ser Phe Thr
385                 390                 395                 400 tat cga gga aga ggg acg gtt gat tct tta act gaa ttg ccg cct gag   1248
Tyr Arg Gly Arg Gly Thr Val Asp Ser Leu Thr Glu Leu Pro Pro Glu
            405                 410                 415 gat aat agt gtg cca cct cgc gaa gga tat agt cat cgt tta tgt cat   1296
Asp Asn Ser Val Pro Pro Arg Glu Gly Tyr Ser His Arg Leu Cys His
        420                 425                 430 gca acc ttt gtt caa aga tcg gga aca cct ttc tta aca act ggt gta   1344
Ala Thr Phe Val Gln Arg Ser Gly Thr Pro Phe Leu Thr Thr Gly Val
    435                 440                 445 gta ttc tct tgg acg cat cgt agt gca act ctt aca aat aca atc gac   1392
Val Phe Ser Trp Thr His Arg Ser Ala Thr Leu Thr Asn Thr Ile Asp
450                 455                 460 cca gag aga att aat caa ata cct tta gtg aag gga ttt aga gtt tgg   1440
Pro Glu Arg Ile Asn Gln Ile Pro Leu Val Lys Gly Phe Arg Val Trp
465                 470                 475                 480 ggg ggc acc tct gtc att acc gga ccc gga ttt acc gga ggg gat atc   1488
Gly Gly Thr Ser Val Ile Thr Gly Pro Gly Phe Thr Gly Gly Asp Ile
            485                 490                 495 ctt cga aga aat acc ttt ggt gat ttc gta tct cta caa gtc aac att   1536
Leu Arg Arg Asn Thr Phe Gly Asp Phe Val Ser Leu Gln Val Asn Ile
        500                 505                 510 aat tca cca att acc caa aga tac cgt tta aga ttt cgt tac gct tcc   1584
Asn Ser Pro Ile Thr Gln Arg Tyr Arg Leu Arg Phe Arg Tyr Ala Ser
    515                 520                 525 agt agg gat gca cga gtt ata gta tta acg gga gcg gca tcc acc gga   1632
Ser Arg Asp Ala Arg Val Ile Val Leu Thr Gly Ala Ala Ser Thr Gly
530                 535                 540 gtg gga ggc caa gtt agt gta aat atg cct ctt cag aaa act atg gaa   1680
Val Gly Gly Gln Val Ser Val Asn Met Pro Leu Gln Lys Thr Met Glu
545                 550                 555                 560 ata ggg gag aac tta aca tcc aga aca ttt aga tat acc gat ttt agt   1728
Ile Gly Glu Asn Leu Thr Ser Arg Thr Phe Arg Tyr Thr Asp Phe Ser
            565                 570                 575 aat cct ttt tca ttt aga gct aat cca gat ata att ggg ata agt gaa   1776
Asn Pro Phe Ser Phe Arg Ala Asn Pro Asp Ile Ile Gly Ile Ser Glu
        580                 585                 590 caa cct cta ttt ggg gcg ggt tct att agt agc ggt gaa ctt tac ata   1824
Gln Pro Leu Phe Gly Ala Gly Ser Ile Ser Ser Gly Glu Leu Tyr Ile
    595                 600                 605 gat aaa att gaa att att cta gca gat gca aca ttt gaa tga           1866
Asp Lys Ile Glu Ile Ile Leu Ala Asp Ala Thr Phe Glu
610                 615                 620

<210> SEQ ID NO 30
<211> LENGTH: 621
<212> TYPE: PRT
<213> ORGANISM: Artificial Sequence
<220> FEATURE:
<223> OTHER INFORMATION: Synthetic Construct

<400> SEQUENCE: 30

Met Asp Asn Asn Pro Asn Ile Asn Glu Cys Ile Pro Tyr Asn Cys Leu
1               5                   10                  15

Ser Asn Pro Glu Glu Val Leu Leu Asp Gly Glu Arg Ile Ser Thr Gly
            20                  25                  30

Asn Ser Ser Ile Asp Ile Ser Leu Ser Leu Val Gln Phe Leu Val Ser
        35                  40                  45
```

```
Asn Phe Val Pro Gly Gly Phe Leu Val Gly Leu Ile Asp Phe Val
         50                  55                  60

Trp Gly Ile Val Gly Pro Ser Gln Trp Asp Ala Phe Leu Val Gln Ile
 65                  70                  75                  80

Glu Gln Leu Ile Asn Glu Arg Ile Ala Glu Phe Ala Arg Asn Ala Ala
                     85                  90                  95

Ile Ala Asn Leu Glu Gly Leu Gly Asn Asn Phe Asn Ile Tyr Val Glu
                100                 105                 110

Ala Phe Lys Glu Trp Glu Glu Asp Pro Lys Asn Pro Ala Thr Arg Thr
            115                 120                 125

Arg Val Ile Asp Arg Phe Arg Ile Leu Asp Gly Leu Leu Glu Arg Asp
130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Asn Ser Ala Ile Arg Asn Pro His Leu Phe Asp Ile
    290                 295                 300

Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly
                325                 330                 335

Asn Ile Thr Ser Pro Ile Tyr Gly Arg Glu Ala Asn Gln Glu Pro Pro
            340                 345                 350

Arg Ser Phe Thr Phe Asn Gly Pro Val Phe Arg Thr Leu Ser Asn Pro
        355                 360                 365

Thr Leu Arg Leu Leu Gln Gln Pro Trp Pro Ala Pro Pro Phe Asn Leu
    370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
                405                 410                 415

Asp Asn Ser Val Pro Pro Arg Glu Gly Tyr Ser His Arg Leu Cys His
            420                 425                 430

Ala Thr Phe Val Gln Arg Ser Gly Thr Pro Phe Leu Thr Thr Gly Val
        435                 440                 445

Val Phe Ser Trp Thr His Arg Ser Ala Thr Leu Thr Asn Thr Ile Asp
    450                 455                 460
```

```
Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
            485                 490                 495

Leu Arg Arg Asn Thr Phe Gly Asp Phe Val Ser Leu Gln Val Asn Ile
        500                 505                 510

Asn Ser Pro Ile Thr Gln Arg Tyr Arg Leu Arg Phe Arg Tyr Ala Ser
        515                 520                 525

Ser Arg Asp Ala Arg Val Ile Val Leu Thr Gly Ala Ala Ser Thr Gly
    530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
            565                 570                 575

Asn Pro Phe Ser Phe Arg Ala Asn Pro Asp Ile Ile Gly Ile Ser Glu
        580                 585                 590

Gln Pro Leu Phe Gly Ala Gly Ser Ile Ser Ser Gly Glu Leu Tyr Ile
        595                 600                 605

Asp Lys Ile Glu Ile Ile Leu Ala Asp Ala Thr Phe Glu
    610                 615                 620

<210> SEQ ID NO 31
<211> LENGTH: 1428
<212> TYPE: DNA
<213> ORGANISM: Bacillus thuringiensis
<220> FEATURE:
<221> NAME/KEY: CDS
<222> LOCATION: (1)..(1428)
<223> OTHER INFORMATION: Native DNA sequence encoding Bacillus
      thuringiensis Cry6Aa toxin

<400> SEQUENCE: 31 atg att att gat agt aaa acg act tta cct aga cat tca ctt att cat      48
Met Ile Ile Asp Ser Lys Thr Thr Leu Pro Arg His Ser Leu Ile His
1               5                   10                  15 aca att aaa tta aat tct aat aag aaa tat ggt cct ggt gat atg act     96
Thr Ile Lys Leu Asn Ser Asn Lys Lys Tyr Gly Pro Gly Asp Met Thr
            20                  25                  30 aat gga aat caa ttt att att tca aaa caa gaa tgg gct acg att gga    144
Asn Gly Asn Gln Phe Ile Ile Ser Lys Gln Glu Trp Ala Thr Ile Gly
        35                  40                  45 gca tat att cag act gga tta ggt tta cca gta aat gaa caa caa tta    192
Ala Tyr Ile Gln Thr Gly Leu Gly Leu Pro Val Asn Glu Gln Gln Leu
    50                  55                  60 aga aca cat gtt aat tta agt cag gat ata tca ata cct agt gat ttt    240
Arg Thr His Val Asn Leu Ser Gln Asp Ile Ser Ile Pro Ser Asp Phe
65                  70                  75                  80 tct caa tta tat gat gtt tat tgt tct gat aaa act tca gca gaa tgg    288
Ser Gln Leu Tyr Asp Val Tyr Cys Ser Asp Lys Thr Ser Ala Glu Trp
                85                  90                  95 tgg aat aaa aat tta tat cct tta att att aaa tct gct aat gat att    336
Trp Asn Lys Asn Leu Tyr Pro Leu Ile Ile Lys Ser Ala Asn Asp Ile
            100                 105                 110 gct tca tat ggt ttt aaa gtt gct ggt gat cct tct att aag aaa gat    384
Ala Ser Tyr Gly Phe Lys Val Ala Gly Asp Pro Ser Ile Lys Lys Asp
        115                 120                 125 gga tat ttt aaa aaa ttg caa gat gaa tta gat aat att gtt gat aat    432
Gly Tyr Phe Lys Lys Leu Gln Asp Glu Leu Asp Asn Ile Val Asp Asn
    130                 135                 140
```

| | | |
|---|---|---|
| aat tcc gat gat gat gca ata gct aaa gct att aaa gat ttt aaa gcg<br>Asn Ser Asp Asp Asp Ala Ile Ala Lys Ala Ile Lys Asp Phe Lys Ala<br>145                        150                     155                     160 | 480 |
| cga tgt ggt att tta att aaa gaa gct aaa caa tat gaa gaa gct gca<br>Arg Cys Gly Ile Leu Ile Lys Glu Ala Lys Gln Tyr Glu Glu Ala Ala<br>                      165                     170                     175 | 528 |
| aaa aat att gta aca tct tta gat caa ttt tta cat ggt gat cag aaa<br>Lys Asn Ile Val Thr Ser Leu Asp Gln Phe Leu His Gly Asp Gln Lys<br>180                             185                     190 | 576 |
| aaa tta gaa ggt gtt atc aat att caa aaa cgt tta aaa gaa gtt caa<br>Lys Leu Glu Gly Val Ile Asn Ile Gln Lys Arg Leu Lys Glu Val Gln<br>         195                     200                     205 | 624 |
| aca gct ctt aat caa gcc cat ggg gaa agt agt cca gct cat aaa gag<br>Thr Ala Leu Asn Gln Ala His Gly Glu Ser Ser Pro Ala His Lys Glu<br>210                        215                     220 | 672 |
| tta tta gaa aaa gta aaa aat tta aaa aca aca tta gaa agg act att<br>Leu Leu Glu Lys Val Lys Asn Leu Lys Thr Thr Leu Glu Arg Thr Ile<br>225                        230                     235                     240 | 720 |
| aaa gct gaa caa gat tta gag aaa aaa gta gaa tat agt ttt cta tta<br>Lys Ala Glu Gln Asp Leu Glu Lys Lys Val Glu Tyr Ser Phe Leu Leu<br>                               245                     250                     255 | 768 |
| gga cca ttg tta gga ttt gtt gtt tat gaa att ctt gaa aat act gct<br>Gly Pro Leu Leu Gly Phe Val Val Tyr Glu Ile Leu Glu Asn Thr Ala<br>         260                     265                     270 | 816 |
| gtt cag cat ata aaa aat caa att gat gag ata aag aaa caa tta gat<br>Val Gln His Ile Lys Asn Gln Ile Asp Glu Ile Lys Lys Gln Leu Asp<br>275                        280                     285 | 864 |
| tct gct cag cat gat ttg gat aga gat gtt aaa att ata gga atg tta<br>Ser Ala Gln His Asp Leu Asp Arg Asp Val Lys Ile Ile Gly Met Leu<br>290                             295                     300 | 912 |
| aat agt att aat aca gat att gat aat tta tat agt caa gga caa gaa<br>Asn Ser Ile Asn Thr Asp Ile Asp Asn Leu Tyr Ser Gln Gly Gln Glu<br>305                        310                     315                     320 | 960 |
| gca att aaa gtt ttc caa aag tta caa ggt att tgg gct act att gga<br>Ala Ile Lys Val Phe Gln Lys Leu Gln Gly Ile Trp Ala Thr Ile Gly<br>                      325                     330                     335 | 1008 |
| gct caa ata gaa aat ctt aga aca acg tcg tta caa gaa gtt caa gat<br>Ala Gln Ile Glu Asn Leu Arg Thr Thr Ser Leu Gln Glu Val Gln Asp<br>         340                     345                     350 | 1056 |
| tct gat gat gct gat gag ata caa att gaa ctt gag gac gct tct gat<br>Ser Asp Asp Ala Asp Glu Ile Gln Ile Glu Leu Glu Asp Ala Ser Asp<br>                      355                     360                     365 | 1104 |
| gct tgg tta gtt gtg gct caa gaa gct cgt gat ttt aca cta aat gct<br>Ala Trp Leu Val Val Ala Gln Glu Ala Arg Asp Phe Thr Leu Asn Ala<br>370                        375                     380 | 1152 |
| tat tca act aat agt aga caa aat tta ccg att aat gtt ata tca gat<br>Tyr Ser Thr Asn Ser Arg Gln Asn Leu Pro Ile Asn Val Ile Ser Asp<br>385                        390                     395                     400 | 1200 |
| tca tgt aat tgt tca aca aca aat atg aca tca aat caa tac agt aat<br>Ser Cys Asn Cys Ser Thr Thr Asn Met Thr Ser Asn Gln Tyr Ser Asn<br>                      405                     410                     415 | 1248 |
| cca aca aca aat atg aca tca aat caa tat atg att tca cat gaa tat<br>Pro Thr Thr Asn Met Thr Ser Asn Gln Tyr Met Ile Ser His Glu Tyr<br>420                        425                     430 | 1296 |
| aca agt tta cca aat aat ttt atg tta tca aga aat agt aat tta gaa<br>Thr Ser Leu Pro Asn Asn Phe Met Leu Ser Arg Asn Ser Asn Leu Glu<br>                      435                     440                     445 | 1344 |
| tat aaa tgt cct gaa aat aat ttt atg ata tat tgg tat aat aat tcg<br>Tyr Lys Cys Pro Glu Asn Asn Phe Met Ile Tyr Trp Tyr Asn Asn Ser<br>450                        455                     460 | 1392 |

```
gat tgg tat aat aat tcg gat tgg tat aat aat tga                          1428
Asp Trp Tyr Asn Asn Ser Asp Trp Tyr Asn Asn
465             470                 475

<210> SEQ ID NO 32
<211> LENGTH: 475
<212> TYPE: PRT
<213> ORGANISM: Bacillus thuringiensis

<400> SEQUENCE: 32

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gly Ile Trp Ala Thr Ile Gly
                325                 330                 335

Ala Gln Ile Glu Asn Leu Arg Thr Thr Ser Leu Gln Glu Val Gln Asp
            340                 345                 350
```

```
Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn
465                 470                 475

<210> SEQ ID NO 33
<211> LENGTH: 1428
<212> TYPE: DNA
<213> ORGANISM: Artificial Sequence
<220> FEATURE:
<223> OTHER INFORMATION: Synthetic DNA sequence encoding Bacillus
      thuringiensis Cry6Aa toxin using codons optimized for maize and
      Table 1 sequences are maintained
<220> FEATURE:
<221> NAME/KEY: CDS
<222> LOCATION: (1)..(1428)

<400> SEQUENCE: 33 atg atc atc gac tcc aag acg acc ctg cca cgg cac tcc ctt atc cac       48
Met Ile Ile Asp Ser Lys Thr Thr Leu Pro Arg His Ser Leu Ile His
1               5                   10                  15 aca att aaa tta aat agc aat aag aag tac ggt ccc ggt gat atg act       96
Thr Ile Lys Leu Asn Ser Asn Lys Lys Tyr Gly Pro Gly Asp Met Thr
            20                  25                  30 aac gga aat caa ttc att att tca aag caa gag tgg gct acc atc gga      144
Asn Gly Asn Gln Phe Ile Ile Ser Lys Gln Glu Trp Ala Thr Ile Gly
        35                  40                  45 gcg tac atc cag act ggg ctg ggc cta cca gta aat gaa caa caa tta      192
Ala Tyr Ile Gln Thr Gly Leu Gly Leu Pro Val Asn Glu Gln Gln Leu
    50                  55                  60 agg acc cat gtc aac ctc agc caa gat atc agc atc cct agc gac ttt      240
Arg Thr His Val Asn Leu Ser Gln Asp Ile Ser Ile Pro Ser Asp Phe
65                  70                  75                  80 tct cag ctc tac gac gtc tat tgc agc gat aaa act tcc gca gaa tgg      288
Ser Gln Leu Tyr Asp Val Tyr Cys Ser Asp Lys Thr Ser Ala Glu Trp
                85                  90                  95 tgg aat aaa aac ctg tac ccc ctc atc att aaa tct gcc aac gat att      336
Trp Asn Lys Asn Leu Tyr Pro Leu Ile Ile Lys Ser Ala Asn Asp Ile
            100                 105                 110 gcc agc tac ggc ttc aag gtc gcg ggt gat cct tct att aag aag gac      384
Ala Ser Tyr Gly Phe Lys Val Ala Gly Asp Pro Ser Ile Lys Lys Asp
        115                 120                 125 ggc tac ttc aag aag ctg caa gat gag ctg gac aac att gtt gac aat      432
Gly Tyr Phe Lys Lys Leu Gln Asp Glu Leu Asp Asn Ile Val Asp Asn
    130                 135                 140 aat tcc gat gat gat gca ata gcg aaa gcc att aaa gac ttc aag gcg      480
Asn Ser Asp Asp Asp Ala Ile Ala Lys Ala Ile Lys Asp Phe Lys Ala
145                 150                 155                 160
```

```
cga tgc ggc atc cta att aaa gaa gca aag cag tat gaa gag gca gcg      528
Arg Cys Gly Ile Leu Ile Lys Glu Ala Lys Gln Tyr Glu Glu Ala Ala
                165                 170                 175 aaa aat atc gta aca tcc ctc gac caa ttt ctg cat ggc gat cag aag      576
Lys Asn Ile Val Thr Ser Leu Asp Gln Phe Leu His Gly Asp Gln Lys
            180                 185                 190 aaa ttg gag ggt gtg atc aac atc caa aaa cgt ctg aag gag gtg cag      624
Lys Leu Glu Gly Val Ile Asn Ile Gln Lys Arg Leu Lys Glu Val Gln
        195                 200                 205 acg gct ctt aat caa gcc cac ggg gaa agt tca cca gct cat aaa gag      672
Thr Ala Leu Asn Gln Ala His Gly Glu Ser Ser Pro Ala His Lys Glu
    210                 215                 220 ctg tta gag aaa gtc aag aat ctc aag acc aca ctt gag agg acc att      720
Leu Leu Glu Lys Val Lys Asn Leu Lys Thr Thr Leu Glu Arg Thr Ile
225                 230                 235                 240 aaa gct gag caa gac ctg gag aag aaa gtg gag tac agt ttc ctt ctc      768
Lys Ala Glu Gln Asp Leu Glu Lys Lys Val Glu Tyr Ser Phe Leu Leu
                245                 250                 255 ggc ccc ttg ctg ggc ttc gtc gtt tat gaa atc ctt gaa aat act gcc      816
Gly Pro Leu Leu Gly Phe Val Val Tyr Glu Ile Leu Glu Asn Thr Ala
            260                 265                 270 gtc cag cat ata aaa aac caa att gac gag ata aag aag caa ctg gac      864
Val Gln His Ile Lys Asn Gln Ile Asp Glu Ile Lys Lys Gln Leu Asp
        275                 280                 285 tct gcc cag cac gac ttg gac aga gac gtt aag atc ata ggg atg ctg      912
Ser Ala Gln His Asp Leu Asp Arg Asp Val Lys Ile Ile Gly Met Leu
    290                 295                 300 aac agt att aat aca gac att gat aac ttg tat agc caa gga caa gag      960
Asn Ser Ile Asn Thr Asp Ile Asp Asn Leu Tyr Ser Gln Gly Gln Glu
305                 310                 315                 320 gca att aaa gtg ttc caa aag ctc caa ggc atc tgg gca act atc gga     1008
Ala Ile Lys Val Phe Gln Lys Leu Gln Gly Ile Trp Ala Thr Ile Gly
                325                 330                 335 gcg cag ata gag aac ctt agg aca acg tcg ctc caa gaa gtg caa gac     1056
Ala Gln Ile Glu Asn Leu Arg Thr Thr Ser Leu Gln Glu Val Gln Asp
            340                 345                 350 tct gac gac gcc gat gag atc caa att gaa ctt gag gac gcg tct gat     1104
Ser Asp Asp Ala Asp Glu Ile Gln Ile Glu Leu Glu Asp Ala Ser Asp
        355                 360                 365 gct tgg tta gtg gtg gcc caa gaa gct cgc gac ttc aca cta aat gcc     1152
Ala Trp Leu Val Val Ala Gln Glu Ala Arg Asp Phe Thr Leu Asn Ala
    370                 375                 380 tac tca act aac tcg cgt cag aat cta ccg att aat gtt ata tcc gat     1200
Tyr Ser Thr Asn Ser Arg Gln Asn Leu Pro Ile Asn Val Ile Ser Asp
385                 390                 395                 400 tcc tgc aac tgt tcc aca acg aac atg acc tca aat caa tac agt aat     1248
Ser Cys Asn Cys Ser Thr Thr Asn Met Thr Ser Asn Gln Tyr Ser Asn
                405                 410                 415 cca acc aca aat atg acc tca aat caa tat atg atc tca cac gag tat     1296
Pro Thr Thr Asn Met Thr Ser Asn Gln Tyr Met Ile Ser His Glu Tyr
            420                 425                 430 acc tcg ttg ccg aat aat ttc atg ctc tca aga aat agc aat ctg gaa     1344
Thr Ser Leu Pro Asn Asn Phe Met Leu Ser Arg Asn Ser Asn Leu Glu
        435                 440                 445 tat aag tgt cct gaa aat aat ttc atg ata tac tgg tac aat aat tcg     1392
Tyr Lys Cys Pro Glu Asn Asn Phe Met Ile Tyr Trp Tyr Asn Asn Ser
    450                 455                 460 gac tgg tac aat aat tcg gat tgg tac aat aat tga                     1428
Asp Trp Tyr Asn Asn Ser Asp Trp Tyr Asn Asn
465                 470                 475
```

<210> SEQ ID NO 34
<211> LENGTH: 475
<212> TYPE: PRT
<213> ORGANISM: Artificial Sequence
<220> FEATURE:
<223> OTHER INFORMATION: Synthetic Construct

<400> SEQUENCE: 34

```
Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365
```

```
Ala Trp Leu Val Val Ala Gln Glu Ala Arg Asp Phe Thr Leu Asn Ala
    370             375                 380

Tyr Ser Thr Asn Ser Arg Gln Asn Leu Pro Ile Asn Val Ile Ser Asp
385             390                 395                 400

Ser Cys Asn Cys Ser Thr Thr Asn Met Thr Ser Asn Gln Tyr Ser Asn
            405                 410                 415

Pro Thr Thr Asn Met Thr Ser Asn Gln Tyr Met Ile Ser His Glu Tyr
        420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460

Asp Trp Tyr Asn Asn Ser Asp Trp Tyr Asn Asn
465                 470                 475

<210> SEQ ID NO 35
<211> LENGTH: 1428
<212> TYPE: DNA
<213> ORGANISM: Artificial Sequence
<220> FEATURE:
<223> OTHER INFORMATION: Synthetic DNA sequence in accordance with the
      invention encoding Bacillus thuringiensis Cry6Aa toxin using
      codons optimized for maize and with sequences identified in
      Table 2 removed and Table 1 sequences are maintained
<220> FEATURE:
<221> NAME/KEY: CDS
<222> LOCATION: (1)..(1428)

<400> SEQUENCE: 35 atg atc atc gac tcc aag acg acc ctg cca cgg cac tcc ctt atc cac      48
Met Ile Ile Asp Ser Lys Thr Thr Leu Pro Arg His Ser Leu Ile His
1               5                   10                  15 aca att aaa tta aat agc aat aag aag tac ggt ccc ggt gat atg act      96
Thr Ile Lys Leu Asn Ser Asn Lys Lys Tyr Gly Pro Gly Asp Met Thr
                20                  25                  30 aac gga aat caa ttc att atc tca aag caa gag tgg gct acc atc gga     144
Asn Gly Asn Gln Phe Ile Ile Ser Lys Gln Glu Trp Ala Thr Ile Gly
            35                  40                  45 gcg tac atc cag act ggg ctg ggc cta cca gta aat gaa caa caa tta     192
Ala Tyr Ile Gln Thr Gly Leu Gly Leu Pro Val Asn Glu Gln Gln Leu
    50                  55                  60 agg acc cat gtc aac ctc agc caa gat atc agc atc cct agc gac ttt     240
Arg Thr His Val Asn Leu Ser Gln Asp Ile Ser Ile Pro Ser Asp Phe
65                  70                  75                  80 tct cag ctc tac gac gtc tat tgc agc gat aaa act tcc gca gaa tgg     288
Ser Gln Leu Tyr Asp Val Tyr Cys Ser Asp Lys Thr Ser Ala Glu Trp
                85                  90                  95 tgg aat aaa aac ctg tac ccc ctc atc att aaa tct gcc aac gat att     336
Trp Asn Lys Asn Leu Tyr Pro Leu Ile Ile Lys Ser Ala Asn Asp Ile
            100                 105                 110 gcc agc tac ggc ttc aag gtc gcg ggt gat cct tct att aag aag gac     384
Ala Ser Tyr Gly Phe Lys Val Ala Gly Asp Pro Ser Ile Lys Lys Asp
        115                 120                 125 ggc tac ttc aag aag ctg caa gat gag ctg gac aac att gtt gac aat     432
Gly Tyr Phe Lys Lys Leu Gln Asp Glu Leu Asp Asn Ile Val Asp Asn
    130                 135                 140 aat tcc gat gat gat gca ata gcg aaa gcc att aaa gac ttc aag gcg     480
Asn Ser Asp Asp Asp Ala Ile Ala Lys Ala Ile Lys Asp Phe Lys Ala
145                 150                 155                 160 cga tgc ggc atc cta att aaa gaa gca aag cag tat gaa gag gca gcg     528
```

-continued

```
                Arg Cys Gly Ile Leu Ile Lys Glu Ala Lys Gln Tyr Glu Glu Ala Ala
                              165                 170                 175 aaa aat atc gta aca tcc ctc gac caa ttt ctg cat ggc gat cag aag        576
Lys Asn Ile Val Thr Ser Leu Asp Gln Phe Leu His Gly Asp Gln Lys
            180                 185                 190 aaa ttg gag ggt gtg atc aac atc caa aaa cgt ctg aag gag gtg cag        624
Lys Leu Glu Gly Val Ile Asn Ile Gln Lys Arg Leu Lys Glu Val Gln
        195                 200                 205 acg gct ctt aat caa gcc cac ggg gaa agt tca cca gct cat aaa gag        672
Thr Ala Leu Asn Gln Ala His Gly Glu Ser Ser Pro Ala His Lys Glu
    210                 215                 220 ctg tta gag aaa gtc aag aat ctc aag acc aca ctt gag agg acc att        720
Leu Leu Glu Lys Val Lys Asn Leu Lys Thr Thr Leu Glu Arg Thr Ile
225                 230                 235                 240 aaa gct gag caa gac ctg gag aag aaa gtg gag tac agt ttc ctt ctc        768
Lys Ala Glu Gln Asp Leu Glu Lys Lys Val Glu Tyr Ser Phe Leu Leu
                245                 250                 255 ggc ccc ttg ctg ggc ttc gtc gtt tat gaa atc ctt gaa aat act gcc        816
Gly Pro Leu Leu Gly Phe Val Val Tyr Glu Ile Leu Glu Asn Thr Ala
            260                 265                 270 gtc cag cat ata aaa aac caa att gac gag ata aag aag caa ctg gac        864
Val Gln His Ile Lys Asn Gln Ile Asp Glu Ile Lys Lys Gln Leu Asp
        275                 280                 285 tct gcc cag cac gac ttg gac aga gac gtt aag atc ata ggg atg ctg        912
Ser Ala Gln His Asp Leu Asp Arg Asp Val Lys Ile Ile Gly Met Leu
    290                 295                 300 aac agt att aat aca gac att gat aac ttg tat agc caa gga caa gag        960
Asn Ser Ile Asn Thr Asp Ile Asp Asn Leu Tyr Ser Gln Gly Gln Glu
305                 310                 315                 320 gca att aaa gtg ttc caa aag ctc caa ggc atc tgg gca act atc gga       1008
Ala Ile Lys Val Phe Gln Lys Leu Gln Gly Ile Trp Ala Thr Ile Gly
                325                 330                 335 gcg cag ata gag aac ctt agg aca acg tcg ctc caa gaa gtg caa gac       1056
Ala Gln Ile Glu Asn Leu Arg Thr Thr Ser Leu Gln Glu Val Gln Asp
            340                 345                 350 tct gac gac gcc gat gag atc caa att gaa ctt gag gac gcg tct gat       1104
Ser Asp Asp Ala Asp Glu Ile Gln Ile Glu Leu Glu Asp Ala Ser Asp
        355                 360                 365 gct tgg tta gtg gtg gcc caa gaa gct cgc gac ttc aca cta aat gcc       1152
Ala Trp Leu Val Val Ala Gln Glu Ala Arg Asp Phe Thr Leu Asn Ala
    370                 375                 380 tac tca act aac tcg cgt cag aat cta ccg att aat gtt atc tcc gat       1200
Tyr Ser Thr Asn Ser Arg Gln Asn Leu Pro Ile Asn Val Ile Ser Asp
385                 390                 395                 400 tcc tgc aac tgt tcc aca acg aac atg acc tca aat caa tac agt aat       1248
Ser Cys Asn Cys Ser Thr Thr Asn Met Thr Ser Asn Gln Tyr Ser Asn
                405                 410                 415 cca acc aca aat atg acc tca aat caa tac atg atc tca cac gag tat       1296
Pro Thr Thr Asn Met Thr Ser Asn Gln Tyr Met Ile Ser His Glu Tyr
            420                 425                 430 acc tcg ttg ccg aat aat ttc atg ctc tca aga aat agc aat ctg gaa       1344
Thr Ser Leu Pro Asn Asn Phe Met Leu Ser Arg Asn Ser Asn Leu Glu
        435                 440                 445 tat aag tgt cct gaa aat aat ttc atg ata tac tgg tac aat aat tcg       1392
Tyr Lys Cys Pro Glu Asn Asn Phe Met Ile Tyr Trp Tyr Asn Asn Ser
    450                 455                 460 gac tgg tac aat aat tcg gat tgg tac aat aat tga                       1428
Asp Trp Tyr Asn Asn Ser Asp Trp Tyr Asn Asn
465                 470                 475
```

```
<210> SEQ ID NO 36
<211> LENGTH: 475
<212> TYPE: PRT
<213> ORGANISM: Artificial Sequence
<220> FEATURE:
<223> OTHER INFORMATION: Synthetic Construct

<400> SEQUENCE: 36

Met Ile Ile Asp Ser Lys Thr Thr Leu Pro Arg His Ser Leu Ile His
1               5                   10                  15

Thr Ile Lys Leu Asn Ser Asn Lys Lys Tyr Gly Pro Gly Asp Met Thr
            20                  25                  30

Asn Gly Asn Gln Phe Ile Ile Ser Lys Gln Glu Trp Ala Thr Ile Gly
        35                  40                  45

Ala Tyr Ile Gln Thr Gly Leu Gly Leu Pro Val Asn Glu Gln Gln Leu
    50                  55                  60

Arg Thr His Val Asn Leu Ser Gln Asp Ile Ser Ile Pro Ser Asp Phe
65                  70                  75                  80

Ser Gln Leu Tyr Asp Val Tyr Cys Ser Asp Lys Thr Ser Ala Glu Trp
                85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
        115                 120                 125

Gly Tyr Phe Lys Lys Leu Gln Asp Glu Leu Asp Asn Ile Val Asp Asn
    130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365
```

```
Ala Trp Leu Val Val Ala Gln Glu Ala Arg Asp Phe Thr Leu Asn Ala
    370                 375                 380
Tyr Ser Thr Asn Ser Arg Gln Asn Leu Pro Ile Asn Val Ile Ser Asp
385                 390                 395                 400
Ser Cys Asn Cys Ser Thr Thr Asn Met Thr Ser Asn Gln Tyr Ser Asn
                    405                 410                 415
Pro Thr Thr Asn Met Thr Ser Asn Gln Tyr Met Ile Ser His Glu Tyr
                420                 425                 430
Thr Ser Leu Pro Asn Asn Phe Met Leu Ser Arg Asn Ser Asn Leu Glu
            435                 440                 445
Tyr Lys Cys Pro Glu Asn Asn Phe Met Ile Tyr Trp Tyr Asn Asn Ser
        450                 455                 460
Asp Trp Tyr Asn Asn Ser Asp Trp Tyr Asn Asn
465                 470                 475

<210> SEQ ID NO 37
<211> LENGTH: 888
<212> TYPE: DNA
<213> ORGANISM: Sphingobiurn herbicidovorans
<220> FEATURE:
<221> NAME/KEY: CDS
<222> LOCATION: (1)..(888)
<223> OTHER INFORMATION: Native DNA sequence encoding Sphingobiurn
      herbicidovorans AAD1 protein

<400> SEQUENCE: 37 atg cat gct gca ctg tcc ccc ctc tcc cag cgc ttt gag cgc atc gcg      48
Met His Ala Ala Leu Ser Pro Leu Ser Gln Arg Phe Glu Arg Ile Ala
1               5                  10                  15 gtc cag ccg ctg acc ggc gtc ctg ggc gcc gag atc acc ggc gtc gac      96
Val Gln Pro Leu Thr Gly Val Leu Gly Ala Glu Ile Thr Gly Val Asp
            20                  25                  30 ctg cgc gag ccg ctc gac gac agc acc tgg aac gaa atc ctc gac gcg     144
Leu Arg Glu Pro Leu Asp Asp Ser Thr Trp Asn Glu Ile Leu Asp Ala
        35                  40                  45 ttc cac act tac cag gtc atc tat ttt ccc ggc cag gcg atc acc aac     192
Phe His Thr Tyr Gln Val Ile Tyr Phe Pro Gly Gln Ala Ile Thr Asn
    50                  55                  60 gaa cag cac atc gcc ttc agc cgg cgc ttc ggc ccc gtc gat ccc gtg     240
Glu Gln His Ile Ala Phe Ser Arg Arg Phe Gly Pro Val Asp Pro Val
65                  70                  75                  80 ccc ctg ctc aag agc atc gaa ggg tat cca gag gtg cag atg atc cgc     288
Pro Leu Leu Lys Ser Ile Glu Gly Tyr Pro Glu Val Gln Met Ile Arg
                85                  90                  95 cgc gaa gcc aac gaa agc ggg cgt gtg atc ggt gat gac tgg cac acc     336
Arg Glu Ala Asn Glu Ser Gly Arg Val Ile Gly Asp Asp Trp His Thr
            100                 105                 110 gac agc acc ttc ctg gac gca ccg ccg gcc gtg gtg atg cgc gcg          384
Asp Ser Thr Phe Leu Asp Ala Pro Pro Ala Ala Val Val Met Arg Ala
        115                 120                 125 atc gac gtg ccc gag cat ggc ggc gac acc ggt ttt ctg agc atg tac     432
Ile Asp Val Pro Glu His Gly Gly Asp Thr Gly Phe Leu Ser Met Tyr
    130                 135                 140 acc gcg tgg gag acg ctg tcg ccc acc atg cag gcc acc atc gaa ggg     480
Thr Ala Trp Glu Thr Leu Ser Pro Thr Met Gln Ala Thr Ile Glu Gly
145                 150                 155                 160 ttg aac gta gtg cac agc gcc acg cgt gtg ttc ggc tcg ctc tac cag     528
Leu Asn Val Val His Ser Ala Thr Arg Val Phe Gly Ser Leu Tyr Gln
                165                 170                 175 gcc cag aac cgg cgc ttc agc aac acc agc gtc aag gtg atg gac gtc     576
```

-continued

```
Ala Gln Asn Arg Arg Phe Ser Asn Thr Ser Val Lys Val Met Asp Val
                180                 185                 190 gac gcg ggc gac cgt gaa acc gtg cac ccc ctg gtg gtg acc cat ccg       624
Asp Ala Gly Asp Arg Glu Thr Val His Pro Leu Val Val Thr His Pro
            195                 200                 205 ggc agc ggc cgc aag ggc ctg tac gtg aac cag gtc tat tgc cag cgc       672
Gly Ser Gly Arg Lys Gly Leu Tyr Val Asn Gln Val Tyr Cys Gln Arg
        210                 215                 220 atc gag ggc atg acc gat gcc gaa agc aaa ccg ctg ctg cag ttc ctg       720
Ile Glu Gly Met Thr Asp Ala Glu Ser Lys Pro Leu Leu Gln Phe Leu
225                 230                 235                 240 tac gag cat gcg aca cgg ttc gat ttc acc tgc cgc gtg cgc tgg aag       768
Tyr Glu His Ala Thr Arg Phe Asp Phe Thr Cys Arg Val Arg Trp Lys
                245                 250                 255 aag gac cag gtc ctg gtc tgg gac aac ctg tgc acg atg cac cgg gcc       816
Lys Asp Gln Val Leu Val Trp Asp Asn Leu Cys Thr Met His Arg Ala
            260                 265                 270 gta ccc gac tac gcg ggc aag ttc cgc tac ctg acg cgc acc acg gtc       864
Val Pro Asp Tyr Ala Gly Lys Phe Arg Tyr Leu Thr Arg Thr Thr Val
        275                 280                 285 ggt ggc gtg cgc ccg gcg cgc tag                                       888
Gly Gly Val Arg Pro Ala Arg
    290                 295

<210> SEQ ID NO 38
<211> LENGTH: 295
<212> TYPE: PRT
<213> ORGANISM: Sphingobiurn herbicidovorans

<400> SEQUENCE: 38

Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
                20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
        50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Pro Ala Ala Val Val Met Arg Ala
        115                 120                 125

Ile Asp Val Pro Glu His Gly Gly Asp Thr Gly Phe Leu Ser Met Tyr
130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205

Gly Ser Gly Arg Lys Gly Leu Tyr Val Asn Gln Val Tyr Cys Gln Arg
```

```
                210                 215                 220
Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
            245                 250                 255

Lys Asp Gln Val Leu Val Trp Asp Asn Leu Cys Thr Met His Arg Ala
        260                 265                 270

Val Pro Asp Tyr Ala Gly Lys Phe Arg Tyr Leu Thr Arg Thr Thr Val
    275                 280                 285

Gly Gly Val Arg Pro Ala Arg
    290                 295

<210> SEQ ID NO 39
<211> LENGTH: 888
<212> TYPE: DNA
<213> ORGANISM: Artificial Sequence
<220> FEATURE:
<223> OTHER INFORMATION: Synthetic DNA sequence encoding the AAD1
      protein using codons optimized for maize and Table 1 and
      Table 2 sequences are maintained
<220> FEATURE:
<221> NAME/KEY: CDS
<222> LOCATION: (1)..(888)

<400> SEQUENCE: 39 atg cac gct gca ctg tca cca ctc tca cag cgc ttt gag aga att gcg    48
Met His Ala Ala Leu Ser Pro Leu Ser Gln Arg Phe Glu Arg Ile Ala
1               5                   10                  15 gtc cag ccg ctg act ggc gtc ttg ggc gct gag atc acc ggc gtc gat    96
Val Gln Pro Leu Thr Gly Val Leu Gly Ala Glu Ile Thr Gly Val Asp
            20                  25                  30 ctg agg gag cct ctc gac gat tca acg tgg aac gaa att ctc gac gcg   144
Leu Arg Glu Pro Leu Asp Asp Ser Thr Trp Asn Glu Ile Leu Asp Ala
        35                  40                  45 ttc cat act tac caa gtc atc tat ttt ccc ggg caa gct att acc aac   192
Phe His Thr Tyr Gln Val Ile Tyr Phe Pro Gly Gln Ala Ile Thr Asn
    50                  55                  60 gaa caa cac atc gct ttc tct cgg cga ttc ggc ccc gtc gat cca gtg   240
Glu Gln His Ile Ala Phe Ser Arg Arg Phe Gly Pro Val Asp Pro Val
65                  70                  75                  80 ccc tta ctc aag tct atc gaa ggc tac cca gag gtg cag atg ata aga   288
Pro Leu Leu Lys Ser Ile Glu Gly Tyr Pro Glu Val Gln Met Ile Arg
                85                  90                  95 agg gag gcc aac gaa agc ggg cgt gtg ata ggt gat gac tgg cac act   336
Arg Glu Ala Asn Glu Ser Gly Arg Val Ile Gly Asp Asp Trp His Thr
            100                 105                 110 gac agc aca ttc ctg gat gca ccg ccg gcc gct gtg gtg atg agg gca   384
Asp Ser Thr Phe Leu Asp Ala Pro Pro Ala Ala Val Val Met Arg Ala
        115                 120                 125 atc gac gtg ccc gag cac gga ggt gac act ggt ttc ttg agt atg tac   432
Ile Asp Val Pro Glu His Gly Gly Asp Thr Gly Phe Leu Ser Met Tyr
    130                 135                 140 act gct tgg gag acg ctt tcg cct act atg caa gcc aca atc gag ggg   480
Thr Ala Trp Glu Thr Leu Ser Pro Thr Met Gln Ala Thr Ile Glu Gly
145                 150                 155                 160 ttg aat gta gtt cac agc gcc acg cgt gtg ttc gga tct ctc tat caa   528
Leu Asn Val Val His Ser Ala Thr Arg Val Phe Gly Ser Leu Tyr Gln
                165                 170                 175 gcc caa aac cgg cgc ttt tca aat acc tcc gtc aag gtg atg gac gtt   576
Ala Gln Asn Arg Arg Phe Ser Asn Thr Ser Val Lys Val Met Asp Val
            180                 185                 190
```

```
gac gcg ggc gac cgt gaa acc gtg cac cct ctt gta acc cat ccg      624
Asp Ala Gly Asp Arg Glu Thr Val His Pro Leu Val Val Thr His Pro
            195                 200                 205 ggc agt ggt cgc aag ggc cta tac gtt aac caa gtc tat tgc cag cgc  672
Gly Ser Gly Arg Lys Gly Leu Tyr Val Asn Gln Val Tyr Cys Gln Arg
        210                 215                 220 atc gag gga atg aca gac gca gag agt aag ccg ctc ctg caa ttc ctg  720
Ile Glu Gly Met Thr Asp Ala Glu Ser Lys Pro Leu Leu Gln Phe Leu
225                 230                 235                 240 tac gag cac gcg aca cgg ttc gat ttc acc tgc cgc gtg cgc tgg aaa  768
Tyr Glu His Ala Thr Arg Phe Asp Phe Thr Cys Arg Val Arg Trp Lys
                245                 250                 255 aag gat caa gtc ctt gta tgg gac aac ctt tgt acg atg cac cgg gcc  816
Lys Asp Gln Val Leu Val Trp Asp Asn Leu Cys Thr Met His Arg Ala
            260                 265                 270 gtt cct gac tac gcg ggc aag ttc aga tac ctg acg agg acc acg gtc  864
Val Pro Asp Tyr Ala Gly Lys Phe Arg Tyr Leu Thr Arg Thr Thr Val
        275                 280                 285 ggt gga gtt agg cca gcg aga tga                                  888
Gly Gly Val Arg Pro Ala Arg
290                 295

<210> SEQ ID NO 40
<211> LENGTH: 295
<212> TYPE: PRT
<213> ORGANISM: Artificial Sequence
<220> FEATURE:
<223> OTHER INFORMATION: Synthetic Construct

<400> SEQUENCE: 40

Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
                20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
        50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
            100                 105                 110

Asp Ser Thr Phe Leu Asp Ala Pro Pro Ala Ala Val Val Met Arg Ala
        115                 120                 125

Ile Asp Val Pro Glu His Gly Gly Asp Thr Gly Phe Leu Ser Met Tyr
130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205

Gly Ser Gly Arg Lys Gly Leu Tyr Val Asn Gln Val Tyr Cys Gln Arg
```

```
                    210                 215                 220
Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
            260                 265                 270

Val Pro Asp Tyr Ala Gly Lys Phe Arg Tyr Leu Thr Arg Thr Thr Val
        275                 280                 285

Gly Gly Val Arg Pro Ala Arg
    290                 295

<210> SEQ ID NO 41
<211> LENGTH: 888
<212> TYPE: DNA
<213> ORGANISM: Artificial Sequence
<220> FEATURE:
<223> OTHER INFORMATION: Synthetic DNA sequence encoding the AAD1
      protein using codons optimized for maize and with sequences
      identified in Table 2 removed and Table 1 sequences are maintained
<220> FEATURE:
<221> NAME/KEY: CDS
<222> LOCATION: (1)..(888)

<400> SEQUENCE: 41 atg cac gct gca ctg tca cca ctc tca cag cgc ttt gag aga att gcg    48
Met His Ala Ala Leu Ser Pro Leu Ser Gln Arg Phe Glu Arg Ile Ala
1               5                   10                  15 gtc cag ccg ctg act ggc gtc ttg ggc gct gag atc acc ggc gtc gat    96
Val Gln Pro Leu Thr Gly Val Leu Gly Ala Glu Ile Thr Gly Val Asp
            20                  25                  30 ctg agg gag cct ctc gac gat tca acg tgg aac gaa att ctc gac gcg   144
Leu Arg Glu Pro Leu Asp Asp Ser Thr Trp Asn Glu Ile Leu Asp Ala
        35                  40                  45 ttc cat act tac caa gtc atc tac ttt ccc ggg caa gct att acc aac   192
Phe His Thr Tyr Gln Val Ile Tyr Phe Pro Gly Gln Ala Ile Thr Asn
    50                  55                  60 gaa caa cac atc gct ttc tct cgg cga ttc ggc ccc gtc gat cca gtg   240
Glu Gln His Ile Ala Phe Ser Arg Arg Phe Gly Pro Val Asp Pro Val
65                  70                  75                  80 ccc tta ctc aag tct atc gaa ggc tac cca gag gtg cag atg ata aga   288
Pro Leu Leu Lys Ser Ile Glu Gly Tyr Pro Glu Val Gln Met Ile Arg
                85                  90                  95 agg gag gcc aac gaa agc ggg cgt gtg ata ggt gat gac tgg cac act   336
Arg Glu Ala Asn Glu Ser Gly Arg Val Ile Gly Asp Asp Trp His Thr
            100                 105                 110 gac agc aca ttc ctg gat gca ccg ccg gcc gct gtg gtg atg agg gca   384
Asp Ser Thr Phe Leu Asp Ala Pro Pro Ala Ala Val Val Met Arg Ala
        115                 120                 125 atc gac gtg ccc gag cac gga ggt gac act ggt ttc ttg agt atg tac   432
Ile Asp Val Pro Glu His Gly Gly Asp Thr Gly Phe Leu Ser Met Tyr
    130                 135                 140 act gct tgg gag acg ctt tcg cct act atg caa gcc aca atc gag ggg   480
Thr Ala Trp Glu Thr Leu Ser Pro Thr Met Gln Ala Thr Ile Glu Gly
145                 150                 155                 160 ttg aat gta gtt cac agc gcc acg cgt gtg ttc gga tct ctc tat caa   528
Leu Asn Val Val His Ser Ala Thr Arg Val Phe Gly Ser Leu Tyr Gln
                165                 170                 175 gcc caa aac cgg cgc ttt tca aat acc tcc gtc aag gtg atg gac gtt   576
Ala Gln Asn Arg Arg Phe Ser Asn Thr Ser Val Lys Val Met Asp Val
            180                 185                 190
```

```
gac gcg ggc gac cgt gaa acc gtg cac cct ctt gta acc cat ccg      624
Asp Ala Gly Asp Arg Glu Thr Val His Pro Leu Val Val Thr His Pro
        195                 200                 205 ggc agt ggt cgc aag ggc cta tac gtt aac caa gtc tat tgc cag cgc  672
Gly Ser Gly Arg Lys Gly Leu Tyr Val Asn Gln Val Tyr Cys Gln Arg
    210                 215                 220 atc gag gga atg aca gac gca gag agt aag ccg ctc ctg caa ttc ctg  720
Ile Glu Gly Met Thr Asp Ala Glu Ser Lys Pro Leu Leu Gln Phe Leu
225                 230                 235                 240 tac gag cac gcg aca cgg ttc gat ttc acc tgc cgc gtg cgc tgg aaa  768
Tyr Glu His Ala Thr Arg Phe Asp Phe Thr Cys Arg Val Arg Trp Lys
                245                 250                 255 aag gat caa gtc ctt gta tgg gac aac ctt tgt acg atg cac cgg gcc  816
Lys Asp Gln Val Leu Val Trp Asp Asn Leu Cys Thr Met His Arg Ala
            260                 265                 270 gtt cct gac tac gcg ggc aag ttc aga tac ctg acg agg acc acg gtc  864
Val Pro Asp Tyr Ala Gly Lys Phe Arg Tyr Leu Thr Arg Thr Thr Val
        275                 280                 285 ggt gga gtt agg cca gcg aga tga                                  888
Gly Gly Val Arg Pro Ala Arg
290                 295

<210> SEQ ID NO 42
<211> LENGTH: 295
<212> TYPE: PRT
<213> ORGANISM: Artificial Sequence
<220> FEATURE:
<223> OTHER INFORMATION: Synthetic Construct

<400> SEQUENCE: 42

Met His Ala Ala Leu Ser Pro Leu Ser Gln Arg Phe Glu Arg Ile Ala
1               5                   10                  15

Val Gln Pro Leu Thr Gly Val Leu Gly Ala Glu Ile Thr Gly Val Asp
                20                  25                  30

Leu Arg Glu Pro Leu Asp Asp Ser Thr Trp Asn Glu Ile Leu Asp Ala
            35                  40                  45

Phe His Thr Tyr Gln Val Ile Tyr Phe Pro Gly Gln Ala Ile Thr Asn
        50                  55                  60

Glu Gln His Ile Ala Phe Ser Arg Arg Phe Gly Pro Val Asp Pro Val
65                  70                  75                  80

Pro Leu Leu Lys Ser Ile Glu Gly Tyr Pro Glu Val Gln Met Ile Arg
                85                  90                  95

Arg Glu Ala Asn Glu Ser Gly Arg Val Ile Gly Asp Asp Trp His Thr
                100                 105                 110

Asp Ser Thr Phe Leu Asp Ala Pro Pro Ala Ala Val Val Met Arg Ala
            115                 120                 125

Ile Asp Val Pro Glu His Gly Gly Asp Thr Gly Phe Leu Ser Met Tyr
        130                 135                 140

Thr Ala Trp Glu Thr Leu Ser Pro Thr Met Gln Ala Thr Ile Glu Gly
145                 150                 155                 160

Leu Asn Val Val His Ser Ala Thr Arg Val Phe Gly Ser Leu Tyr Gln
                165                 170                 175

Ala Gln Asn Arg Arg Phe Ser Asn Thr Ser Val Lys Val Met Asp Val
            180                 185                 190

Asp Ala Gly Asp Arg Glu Thr Val His Pro Leu Val Val Thr His Pro
        195                 200                 205

Gly Ser Gly Arg Lys Gly Leu Tyr Val Asn Gln Val Tyr Cys Gln Arg
```

```
                   210                 215                 220
Ile Glu Gly Met Thr Asp Ala Glu Ser Lys Pro Leu Leu Gln Phe Leu
225                 230                 235                 240

Tyr Glu His Ala Thr Arg Phe Asp Phe Thr Cys Arg Val Arg Trp Lys
                245                 250                 255

Lys Asp Gln Val Leu Val Trp Asp Asn Leu Cys Thr Met His Arg Ala
            260                 265                 270

Val Pro Asp Tyr Ala Gly Lys Phe Arg Tyr Leu Thr Arg Thr Thr Val
        275                 280                 285

Gly Gly Val Arg Pro Ala Arg
    290                 295

<210> SEQ ID NO 43
<211> LENGTH: 1368
<212> TYPE: DNA
<213> ORGANISM: Aspergillus nidulans
<220> FEATURE:
<221> NAME/KEY: CDS
<222> LOCATION: (1)..(1368)
<223> OTHER INFORMATION: Native DNA sequence encoding Aspergillus
      nidulans delta-9 fatty acid desaturase protein

<400> SEQUENCE: 43 atg tct gca cca acg gcg gac atc agg gct cgc gcc ccg gag gcc aaa      48
Met Ser Ala Pro Thr Ala Asp Ile Arg Ala Arg Ala Pro Glu Ala Lys
1               5                  10                  15 aag gtt cac atc gct gac act gct atc aac cgc cat aac tgg tac aag      96
Lys Val His Ile Ala Asp Thr Ala Ile Asn Arg His Asn Trp Tyr Lys
            20                  25                  30 cat gtg aac tgg ctg aac gtt ttc ctg atc atc ggt atc ccg ctt tat     144
His Val Asn Trp Leu Asn Val Phe Leu Ile Ile Gly Ile Pro Leu Tyr
        35                  40                  45 ggg tgc att cag gcg ttc tgg gtg cca ctg cag ctg aag act gcc atc     192
Gly Cys Ile Gln Ala Phe Trp Val Pro Leu Gln Leu Lys Thr Ala Ile
    50                  55                  60 tgg gcc gtc atc tac tac ttt ttc acc ggt ctc ggt atc aca gca ggt     240
Trp Ala Val Ile Tyr Tyr Phe Phe Thr Gly Leu Gly Ile Thr Ala Gly
65                  70                  75                  80 tac cat cgt cta tgg gct cac tgc tcg tac tcc gcc acc ctt cct ttg     288
Tyr His Arg Leu Trp Ala His Cys Ser Tyr Ser Ala Thr Leu Pro Leu
                85                  90                  95 cgt atc tgg ctc gct gcc gtt ggt ggt ggt gcc gtc gaa ggt tct atc     336
Arg Ile Trp Leu Ala Ala Val Gly Gly Gly Ala Val Glu Gly Ser Ile
            100                 105                 110 cgc tgg tgg gct cgt gac cac cgc gct cac cac cgc tac acc gat acc     384
Arg Trp Trp Ala Arg Asp His Arg Ala His His Arg Tyr Thr Asp Thr
        115                 120                 125 gac aaa gac ccg tac tcc gtt cgc aag ggt ctg ctc tac tct cac ctt     432
Asp Lys Asp Pro Tyr Ser Val Arg Lys Gly Leu Leu Tyr Ser His Leu
    130                 135                 140 ggc tgg atg gtg atg aag cag aac cct aag cgt att ggc cgt acc gat     480
Gly Trp Met Val Met Lys Gln Asn Pro Lys Arg Ile Gly Arg Thr Asp
145                 150                 155                 160 att tcc gac ctg aac gag gac ccc gtc gtt gtc tgg cag cac cgc aac     528
Ile Ser Asp Leu Asn Glu Asp Pro Val Val Val Trp Gln His Arg Asn
                165                 170                 175 tac ctc aag gtc gtt ttc acg atg gga ttg gct gtg cct atg ctt gtt     576
Tyr Leu Lys Val Val Phe Thr Met Gly Leu Ala Val Pro Met Leu Val
            180                 185                 190 gct ggt ctt gga tgg ggt gac tgg ttg ggc ggc ttc gtg tat gcc ggc     624
```

```
                                                                            -continued Ala Gly Leu Gly Trp Gly Asp Trp Leu Gly Gly Phe Val Tyr Ala Gly
        195                 200                 205 att ctg cgt atc ttc ttc gtc cag cag gcg act ttc tgc gtc aac tct       672
Ile Leu Arg Ile Phe Phe Val Gln Gln Ala Thr Phe Cys Val Asn Ser
210                 215                 220 ttg gcc cac tgg ctc ggt gac cag ccc ttc gat gac cgc aac tca cct       720
Leu Ala His Trp Leu Gly Asp Gln Pro Phe Asp Asp Arg Asn Ser Pro
225                 230                 235                 240 cgt gac cac gtt atc acc gct ctc gtc acc ctt gga gag ggc tac cac       768
Arg Asp His Val Ile Thr Ala Leu Val Thr Leu Gly Glu Gly Tyr His
            245                 250                 255 aac ttc cac cac gag ttc ccc tcg gac tac cgt aac gcc atc gaa tgg       816
Asn Phe His His Glu Phe Pro Ser Asp Tyr Arg Asn Ala Ile Glu Trp
        260                 265                 270 cac cag tat gat ccc acc aag tgg tcc atc tgg gcc tgg aag cag ctt       864
His Gln Tyr Asp Pro Thr Lys Trp Ser Ile Trp Ala Trp Lys Gln Leu
    275                 280                 285 ggt ctt gcc tac gac ctg aag aag ttc cgt gcc aac gag att gag aag       912
Gly Leu Ala Tyr Asp Leu Lys Lys Phe Arg Ala Asn Glu Ile Glu Lys
290                 295                 300 ggt cgt gtc cag cag ctc cag aag aag ctt gac cgt aag cgt gcc act       960
Gly Arg Val Gln Gln Leu Gln Lys Lys Leu Asp Arg Lys Arg Ala Thr
305                 310                 315                 320 ctc gat tgg ggt act cct ctt gac cag ctc ccc gtc atg gag tgg gac      1008
Leu Asp Trp Gly Thr Pro Leu Asp Gln Leu Pro Val Met Glu Trp Asp
            325                 330                 335 gac tac gtc gag cag gct aag aac ggc cgc ggt ctc gtg gct att gcc      1056
Asp Tyr Val Glu Gln Ala Lys Asn Gly Arg Gly Leu Val Ala Ile Ala
        340                 345                 350 ggt gtt gtc cac gat gtc acg gac ttc atc aaa gac cac ccc ggt ggc      1104
Gly Val Val His Asp Val Thr Asp Phe Ile Lys Asp His Pro Gly Gly
    355                 360                 365 aag gcc atg atc agc tcc ggt att ggg aag gac gcc acc gcc atg ttc      1152
Lys Ala Met Ile Ser Ser Gly Ile Gly Lys Asp Ala Thr Ala Met Phe
370                 375                 380 aac ggt ggt gtc tac tac cac tcc aac gcc gca cac aac ctc ctc tct      1200
Asn Gly Gly Val Tyr Tyr His Ser Asn Ala Ala His Asn Leu Leu Ser
385                 390                 395                 400 acc atg cgt gtt ggt gtt atc cgc ggc ggc tgt gaa gtc gaa atc tgg      1248
Thr Met Arg Val Gly Val Ile Arg Gly Gly Cys Glu Val Glu Ile Trp
            405                 410                 415 aag cgt gcc cag aag gag aac gtg gag tac gtg cgt gat ggc tct ggc      1296
Lys Arg Ala Gln Lys Glu Asn Val Glu Tyr Val Arg Asp Gly Ser Gly
        420                 425                 430 cag cgc gtc atc cgt gcc ggc gag cag cca acc aag atc cca gaa ccc      1344
Gln Arg Val Ile Arg Ala Gly Glu Gln Pro Thr Lys Ile Pro Glu Pro
    435                 440                 445 att ccc aca gcg gat gcg gcg tga                                      1368
Ile Pro Thr Ala Asp Ala Ala
    450                 455

<210> SEQ ID NO 44
<211> LENGTH: 455
<212> TYPE: PRT
<213> ORGANISM: Aspergillus nidulans

<400> SEQUENCE: 44

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
```

```
                20                  25                  30
His Val Asn Trp Leu Asn Val Phe Leu Ile Ile Gly Ile Pro Leu Tyr
            35                  40                  45

Gly Cys Ile Gln Ala Phe Trp Val Pro Leu Gln Leu Lys Thr Ala Ile
        50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Ala Val Glu Gly Ser Ile
            100                 105                 110

Arg Trp Trp Ala Arg Asp His Arg Ala His His Arg Tyr Thr Asp Thr
        115                 120                 125

Asp Lys Asp Pro Tyr Ser Val Arg Lys Gly Leu Leu Tyr Ser His Leu
    130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
            180                 185                 190

Ala Gly Leu Gly Trp Gly Asp Trp Leu Gly Gly Phe Val Tyr Ala Gly
        195                 200                 205

Ile Leu Arg Ile Phe Phe Val Gln Gln Ala Thr Phe Cys Val Asn Ser
    210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
            260                 265                 270

His Gln Tyr Asp Pro Thr Lys Trp Ser Ile Trp Ala Trp Lys Gln Leu
        275                 280                 285

Gly Leu Ala Tyr Asp Leu Lys Lys Phe Arg Ala Asn Glu Ile Glu Lys
    290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
            340                 345                 350

Gly Val Val His Asp Val Thr Asp Phe Ile Lys Asp His Pro Gly Gly
        355                 360                 365

Lys Ala Met Ile Ser Ser Gly Ile Gly Lys Asp Ala Thr Ala Met Phe
    370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
        435                 440                 445
```

```
Ile Pro Thr Ala Asp Ala Ala
    450             455

<210> SEQ ID NO 45
<211> LENGTH: 1368
<212> TYPE: DNA
<213> ORGANISM: Artificial Sequence
<220> FEATURE:
<223> OTHER INFORMATION: Synthetic DNA sequence encoding Aspergillus
      nidulans delta-9 fatty acid desaturase protein using codons
      optimized for maize and Table 1 & Table 2 sequences are maintained
<220> FEATURE:
<221> NAME/KEY: CDS
<222> LOCATION: (1)..(1368)

<400> SEQUENCE: 45 atg agt gca cca acg gcg gac ata agg gcg cgc gcc ccg gag gca aaa      48
Met Ser Ala Pro Thr Ala Asp Ile Arg Ala Arg Ala Pro Glu Ala Lys
1               5                   10                  15 aag gtt cac att gct gac act gct atc aat cgc cat aac tgg tat aag      96
Lys Val His Ile Ala Asp Thr Ala Ile Asn Arg His Asn Trp Tyr Lys
            20                  25                  30 cat gtg aat tgg ctg aac gtt ttt ctg atc atc ggc atc ccg ctt tat     144
His Val Asn Trp Leu Asn Val Phe Leu Ile Ile Gly Ile Pro Leu Tyr
        35                  40                  45 ggg tgt att caa gcg ttc tgg gtg cca ctc cag ctc aag act gcc atc     192
Gly Cys Ile Gln Ala Phe Trp Val Pro Leu Gln Leu Lys Thr Ala Ile
50                  55                  60 tgg gcc gta atc tac tac ttc ttt acc ggt ttg gga atc aca gcg ggt     240
Trp Ala Val Ile Tyr Tyr Phe Phe Thr Gly Leu Gly Ile Thr Ala Gly
65                  70                  75                  80 tat cac aga ttg tgg gca cac tgc tcg tac tcc gcc acc ctt cct tta     288
Tyr His Arg Leu Trp Ala His Cys Ser Tyr Ser Ala Thr Leu Pro Leu
                85                  90                  95 cgt ata tgg ctc gct gcc gta gga gga ggc gcc gtc gaa ggt tca atc     336
Arg Ile Trp Leu Ala Ala Val Gly Gly Gly Ala Val Glu Gly Ser Ile
            100                 105                 110 cgt tgg tgg gct aga gac cat cgt gct cat cat aga tat acc gat aca     384
Arg Trp Trp Ala Arg Asp His Arg Ala His His Arg Tyr Thr Asp Thr
        115                 120                 125 gac aaa gac ccg tac tcc gtt cgc aag ggg ctg cta tac tct cac ctt     432
Asp Lys Asp Pro Tyr Ser Val Arg Lys Gly Leu Leu Tyr Ser His Leu
    130                 135                 140 ggc tgg atg gtg atg aag cag aac cct aag cgt att ggc aga acc gat     480
Gly Trp Met Val Met Lys Gln Asn Pro Lys Arg Ile Gly Arg Thr Asp
145                 150                 155                 160 att tcc gac ctg aac gag gac ccc gtc gtt gtc tgg cag cac cgg aac     528
Ile Ser Asp Leu Asn Glu Asp Pro Val Val Val Trp Gln His Arg Asn
                165                 170                 175 tac ctc aag gtc gtt ttc acg atg gga ttg gct gtg cct atg ctt gtt     576
Tyr Leu Lys Val Val Phe Thr Met Gly Leu Ala Val Pro Met Leu Val
            180                 185                 190 gct ggg ctt ggc tgg gga gac tgg ttg ggc ggc ttc gtg tat gcc ggc     624
Ala Gly Leu Gly Trp Gly Asp Trp Leu Gly Gly Phe Val Tyr Ala Gly
        195                 200                 205 ata ctg aga atc ttt ttc gtc cag caa gcg act ttt tgc gtc aac tct     672
Ile Leu Arg Ile Phe Phe Val Gln Gln Ala Thr Phe Cys Val Asn Ser
    210                 215                 220 ttg gcc cac tgg ctc gga gat cag ccg ttc gat gac cgg aac agt cct     720
Leu Ala His Trp Leu Gly Asp Gln Pro Phe Asp Asp Arg Asn Ser Pro
225                 230                 235                 240
```

| | | |
|---|---|---|
| agg gac cac gtt atc act gct ctc gtc acc cta gga gag ggc tac cac<br>Arg Asp His Val Ile Thr Ala Leu Val Thr Leu Gly Glu Gly Tyr His<br>245 250 255 | | 768 |
| aac ttc cat cac gag ttc ccc tcg gac tac cgg aac gcc atc gaa tgg<br>Asn Phe His His Glu Phe Pro Ser Asp Tyr Arg Asn Ala Ile Glu Trp<br>260 265 270 | | 816 |
| cac cag tat gat cca acg aag tgg agc atc tgg gcc tgg aag cag ctt<br>His Gln Tyr Asp Pro Thr Lys Trp Ser Ile Trp Ala Trp Lys Gln Leu<br>275 280 285 | | 864 |
| ggt tta gcc tac gac ctg aag aaa ttc aga gcc aac gag att gag aaa<br>Gly Leu Ala Tyr Asp Leu Lys Lys Phe Arg Ala Asn Glu Ile Glu Lys<br>290 295 300 | | 912 |
| ggg cgt gtc caa cag ctg caa aag aaa ctg gac cgt aag cgg gcg act<br>Gly Arg Val Gln Gln Leu Gln Lys Lys Leu Asp Arg Lys Arg Ala Thr<br>305 310 315 320 | | 960 |
| ctc gat tgg gga aca cct ctg gat cag ctc ccc gtc atg gag tgg gac<br>Leu Asp Trp Gly Thr Pro Leu Asp Gln Leu Pro Val Met Glu Trp Asp<br>325 330 335 | | 1008 |
| gac tac gtg gag caa gca aag aac ggt cgc ggt ctc gtg gca ata gcg<br>Asp Tyr Val Glu Gln Ala Lys Asn Gly Arg Gly Leu Val Ala Ile Ala<br>340 345 350 | | 1056 |
| ggc gtg gtg cac gat gtc acg gat ttc atc aaa gat cac ccg ggg ggc<br>Gly Val Val His Asp Val Thr Asp Phe Ile Lys Asp His Pro Gly Gly<br>355 360 365 | | 1104 |
| aag gcc atg atc agc tcc ggg att ggc aag gac gca acc gcc atg ttc<br>Lys Ala Met Ile Ser Ser Gly Ile Gly Lys Asp Ala Thr Ala Met Phe<br>370 375 380 | | 1152 |
| aat ggg gga gtc tac tac cac agc aac gca gca cac aat ctc ttg tca<br>Asn Gly Gly Val Tyr Tyr His Ser Asn Ala Ala His Asn Leu Leu Ser<br>385 390 395 400 | | 1200 |
| aca atg agg gtg ggt gtt att agg ggc ggc tgt gaa gtc gaa atc tgg<br>Thr Met Arg Val Gly Val Ile Arg Gly Gly Cys Glu Val Glu Ile Trp<br>405 410 415 | | 1248 |
| aag agg gcg caa aag gag aat gtg gag tac gtg cga gat ggc tct ggt<br>Lys Arg Ala Gln Lys Glu Asn Val Glu Tyr Val Arg Asp Gly Ser Gly<br>420 425 430 | | 1296 |
| caa cgc gtg atc aga gcg ggc gag cag cca acc aag ata cca gaa ccg<br>Gln Arg Val Ile Arg Ala Gly Glu Gln Pro Thr Lys Ile Pro Glu Pro<br>435 440 445 | | 1344 |
| att ccc aca gcg gat gcg gcg tag<br>Ile Pro Thr Ala Asp Ala Ala<br>450 455 | | 1368 |

<210> SEQ ID NO 46
<211> LENGTH: 455
<212> TYPE: PRT
<213> ORGANISM: Artificial Sequence
<220> FEATURE:
<223> OTHER INFORMATION: Synthetic Construct

<400> SEQUENCE: 46

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
            20                  25                  30

His Val Asn Trp Leu Asn Val Phe Leu Ile Gly Ile Pro Leu Tyr
        35                  40                  45

Gly Cys Ile Gln Ala Phe Trp Val Pro Leu Gln Leu Lys Thr Ala Ile
    50                  55                  60

Trp Ala Val Ile Tyr Tyr Phe Phe Thr Gly Leu Gly Ile Thr Ala Gly

```
                65                  70                  75                  80
Tyr His Arg Leu Trp Ala His Cys Ser Tyr Ser Ala Thr Leu Pro Leu
                        85                  90                  95

Arg Ile Trp Leu Ala Ala Val Gly Gly Ala Val Glu Gly Ser Ile
            100                 105                 110

Arg Trp Trp Ala Arg Asp His Arg Ala His Arg Tyr Thr Asp Thr
            115                 120                 125

Asp Lys Asp Pro Tyr Ser Val Arg Lys Gly Leu Leu Tyr Ser His Leu
130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
                180                 185                 190

Ala Gly Leu Gly Trp Gly Asp Trp Leu Gly Gly Phe Val Tyr Ala Gly
            195                 200                 205

Ile Leu Arg Ile Phe Phe Val Gln Ala Thr Phe Cys Val Asn Ser
    210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
                260                 265                 270

His Gln Tyr Asp Pro Thr Lys Trp Ser Ile Trp Ala Trp Lys Gln Leu
            275                 280                 285

Gly Leu Ala Tyr Asp Leu Lys Lys Phe Arg Ala Asn Glu Ile Glu Lys
        290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
            340                 345                 350

Gly Val Val His Asp Val Thr Asp Phe Ile Lys Asp His Pro Gly Gly
        355                 360                 365

Lys Ala Met Ile Ser Ser Gly Ile Gly Lys Asp Ala Thr Ala Met Phe
370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
        435                 440                 445

Ile Pro Thr Ala Asp Ala Ala
    450                 455

<210> SEQ ID NO 47
<211> LENGTH: 1368
<212> TYPE: DNA
<213> ORGANISM: Artificial Sequence
```

<220> FEATURE:
<223> OTHER INFORMATION: Synthetic DNA sequence in accordance with the invention encoding Aspergillus nidulans delta-9 fatty acid desaturase protein using codons optimized for maize and with sequences identified in Table 2 removed and Table 1 sequences are maintained
<220> FEATURE:
<221> NAME/KEY: CDS
<222> LOCATION: (1)..(1368)

<400> SEQUENCE: 47

```
atg agt gca cca acg gcg gac ata agg gcg cgc gcc ccg gag gca aaa      48
Met Ser Ala Pro Thr Ala Asp Ile Arg Ala Arg Ala Pro Glu Ala Lys
1               5                  10                  15 aag gtt cac att gct gac act gct atc aat cgc cat aac tgg tat aag      96
Lys Val His Ile Ala Asp Thr Ala Ile Asn Arg His Asn Trp Tyr Lys
            20                  25                  30 cat gtg aat tgg ctg aac gtt ttt ctg atc atc ggc atc ccg ctt tat     144
His Val Asn Trp Leu Asn Val Phe Leu Ile Ile Gly Ile Pro Leu Tyr
        35                  40                  45 ggg tgt att caa gcg ttc tgg gtg cca ctc cag ctc aag act gcc atc     192
Gly Cys Ile Gln Ala Phe Trp Val Pro Leu Gln Leu Lys Thr Ala Ile
50                  55                  60 tgg gcc gta atc tac tac ttc ttt acc ggt ttg gga atc aca gcg ggt     240
Trp Ala Val Ile Tyr Tyr Phe Phe Thr Gly Leu Gly Ile Thr Ala Gly
65                  70                  75                  80 tat cac aga ttg tgg gca cac tgc tcg tac tcc gcc acc ctt cct tta     288
Tyr His Arg Leu Trp Ala His Cys Ser Tyr Ser Ala Thr Leu Pro Leu
                85                  90                  95 cgt ata tgg ctc gct gcc gta gga gga ggc gcc gtc gaa ggt tca atc     336
Arg Ile Trp Leu Ala Ala Val Gly Gly Gly Ala Val Glu Gly Ser Ile
            100                 105                 110 cgt tgg tgg gct aga gac cat cgt gct cat cat aga tat acc gat aca     384
Arg Trp Trp Ala Arg Asp His Arg Ala His His Arg Tyr Thr Asp Thr
        115                 120                 125 gac aaa gac ccg tac tcc gtt cgc aag ggg ctg cta tac tct cac ctt     432
Asp Lys Asp Pro Tyr Ser Val Arg Lys Gly Leu Leu Tyr Ser His Leu
130                 135                 140 ggc tgg atg gtg atg aag cag aac cct aag cgt att ggc aga acc gat     480
Gly Trp Met Val Met Lys Gln Asn Pro Lys Arg Ile Gly Arg Thr Asp
145                 150                 155                 160 att agc gac ctg aac gag gac ccc gtc gtt gtc tgg cag cac cgg aac     528
Ile Ser Asp Leu Asn Glu Asp Pro Val Val Val Trp Gln His Arg Asn
                165                 170                 175 tac ctc aag gtc gtt ttc acg atg gga ttg gct gtg cct atg ctt gtt     576
Tyr Leu Lys Val Val Phe Thr Met Gly Leu Ala Val Pro Met Leu Val
            180                 185                 190 gct ggg ctt ggc tgg gga gac tgg ttg ggc ggc ttc gtg tat gcc ggc     624
Ala Gly Leu Gly Trp Gly Asp Trp Leu Gly Gly Phe Val Tyr Ala Gly
        195                 200                 205 ata ctg aga atc ttt ttc gtc cag caa gcg act ttt tgc gtc aac tct     672
Ile Leu Arg Ile Phe Phe Val Gln Gln Ala Thr Phe Cys Val Asn Ser
210                 215                 220 ttg gcc cac tgg ctc gga gat cag ccg ttc gat gac cgg aac agt cct     720
Leu Ala His Trp Leu Gly Asp Gln Pro Phe Asp Asp Arg Asn Ser Pro
225                 230                 235                 240 agg gac cac gtt atc act gct ctc gtc acc cta gga gag ggc tac cac     768
Arg Asp His Val Ile Thr Ala Leu Val Thr Leu Gly Glu Gly Tyr His
                245                 250                 255 aac ttc cat cac gag ttc ccc tcg gac tac cgg aac gcc atc gaa tgg     816
Asn Phe His His Glu Phe Pro Ser Asp Tyr Arg Asn Ala Ile Glu Trp
            260                 265                 270
```

```
cac cag tat gat cca acg aag tgg agc atc tgg gcc tgg aag cag ctt        864
His Gln Tyr Asp Pro Thr Lys Trp Ser Ile Trp Ala Trp Lys Gln Leu
            275                 280                 285 ggt tta gcc tac gac ctg aag aaa ttc aga gcc aac gag att gag aaa        912
Gly Leu Ala Tyr Asp Leu Lys Lys Phe Arg Ala Asn Glu Ile Glu Lys
        290                 295                 300 ggg cgt gtc caa cag ctg caa aag aaa ctg gac cgt aag cgg gcg act        960
Gly Arg Val Gln Gln Leu Gln Lys Lys Leu Asp Arg Lys Arg Ala Thr
305                 310                 315                 320 ctc gat tgg gga aca cct ctg gat cag ctc ccc gtc atg gag tgg gac       1008
Leu Asp Trp Gly Thr Pro Leu Asp Gln Leu Pro Val Met Glu Trp Asp
                325                 330                 335 gac tac gtg gag caa gca aag aac ggt cgc ggt ctc gtg gca ata gcg       1056
Asp Tyr Val Glu Gln Ala Lys Asn Gly Arg Gly Leu Val Ala Ile Ala
            340                 345                 350 ggc gtg gtg cac gat gtc acg gat ttc atc aaa gat cac ccg ggg ggc       1104
Gly Val Val His Asp Val Thr Asp Phe Ile Lys Asp His Pro Gly Gly
        355                 360                 365 aag gcc atg atc agc tcc ggg att ggc aag gac gca acc gcc atg ttc       1152
Lys Ala Met Ile Ser Ser Gly Ile Gly Lys Asp Ala Thr Ala Met Phe
370                 375                 380 aat ggg gga gtc tac tac cac agc aac gca gca cac aat ctc ttg tca       1200
Asn Gly Gly Val Tyr Tyr His Ser Asn Ala Ala His Asn Leu Leu Ser
385                 390                 395                 400 aca atg agg gtg ggt gtt att agg ggc ggc tgt gaa gtc gaa atc tgg       1248
Thr Met Arg Val Gly Val Ile Arg Gly Gly Cys Glu Val Glu Ile Trp
                405                 410                 415 aag agg gcg caa aag gag aat gtg gag tac gtg cga gat ggc tct ggt       1296
Lys Arg Ala Gln Lys Glu Asn Val Glu Tyr Val Arg Asp Gly Ser Gly
            420                 425                 430 caa cgc gtg atc aga gcg ggc gag cag cca acc aag ata cca gaa ccg       1344
Gln Arg Val Ile Arg Ala Gly Glu Gln Pro Thr Lys Ile Pro Glu Pro
        435                 440                 445 att ccc aca gcg gat gcg gcg tag                                       1368
Ile Pro Thr Ala Asp Ala Ala
    450                 455

<210> SEQ ID NO 48
<211> LENGTH: 455
<212> TYPE: PRT
<213> ORGANISM: Artificial Sequence
<220> FEATURE:
<223> OTHER INFORMATION: Synthetic Construct

<400> SEQUENCE: 48

Met Ser Ala Pro Thr Ala Asp Ile Arg Ala Arg Ala Pro Glu Ala Lys
1               5                   10                  15

Lys Val His Ile Ala Asp Thr Ala Ile Asn Arg His Asn Trp Tyr Lys
                20                  25                  30

His Val Asn Trp Leu Asn Val Phe Leu Ile Ile Gly Ile Pro Leu Tyr
            35                  40                  45

Gly Cys Ile Gln Ala Phe Trp Val Pro Leu Gln Leu Lys Thr Ala Ile
        50                  55                  60

Trp Ala Val Ile Tyr Tyr Phe Phe Thr Gly Leu Gly Ile Thr Ala Gly
65                  70                  75                  80

Tyr His Arg Leu Trp Ala His Cys Ser Tyr Ser Ala Thr Leu Pro Leu
                85                  90                  95

Arg Ile Trp Leu Ala Ala Val Gly Gly Gly Ala Val Glu Gly Ser Ile
            100                 105                 110
```

Arg Trp Trp Ala Arg Asp His Arg Ala His Arg Tyr Thr Asp Thr
            115                 120                 125

Asp Lys Asp Pro Tyr Ser Val Arg Lys Gly Leu Leu Tyr Ser His Leu
    130                 135                 140

Gly Trp Met Val Met Lys Gln Asn Pro Lys Arg Ile Gly Arg Thr Asp
145                 150                 155                 160

Ile Ser Asp Leu Asn Glu Asp Pro Val Val Trp Gln His Arg Asn
                165                 170                 175

Tyr Leu Lys Val Val Phe Thr Met Gly Leu Ala Val Pro Met Leu Val
                180                 185                 190

Ala Gly Leu Gly Trp Gly Asp Trp Leu Gly Gly Phe Val Tyr Ala Gly
            195                 200                 205

Ile Leu Arg Ile Phe Phe Val Gln Gln Ala Thr Phe Cys Val Asn Ser
        210                 215                 220

Leu Ala His Trp Leu Gly Asp Gln Pro Phe Asp Asp Arg Asn Ser Pro
225                 230                 235                 240

Arg Asp His Val Ile Thr Ala Leu Val Thr Leu Gly Glu Gly Tyr His
                245                 250                 255

Asn Phe His His Glu Phe Pro Ser Asp Tyr Arg Asn Ala Ile Glu Trp
                260                 265                 270

His Gln Tyr Asp Pro Thr Lys Trp Ser Ile Trp Ala Trp Lys Gln Leu
            275                 280                 285

Gly Leu Ala Tyr Asp Leu Lys Lys Phe Arg Ala Asn Glu Ile Glu Lys
        290                 295                 300

Gly Arg Val Gln Gln Leu Gln Lys Lys Leu Asp Arg Lys Arg Ala Thr
305                 310                 315                 320

Leu Asp Trp Gly Thr Pro Leu Asp Gln Leu Pro Val Met Glu Trp Asp
                325                 330                 335

Asp Tyr Val Glu Gln Ala Lys Asn Gly Arg Gly Leu Val Ala Ile Ala
                340                 345                 350

Gly Val Val His Asp Val Thr Asp Phe Ile Lys Asp His Pro Gly Gly
            355                 360                 365

Lys Ala Met Ile Ser Ser Gly Ile Gly Lys Asp Ala Thr Ala Met Phe
        370                 375                 380

Asn Gly Gly Val Tyr Tyr His Ser Asn Ala Ala His Asn Leu Leu Ser
385                 390                 395                 400

Thr Met Arg Val Gly Val Ile Arg Gly Gly Cys Glu Val Glu Ile Trp
                405                 410                 415

Lys Arg Ala Gln Lys Glu Asn Val Glu Tyr Val Arg Asp Gly Ser Gly
            420                 425                 430

Gln Arg Val Ile Arg Ala Gly Glu Gln Pro Thr Lys Ile Pro Glu Pro
        435                 440                 445

Ile Pro Thr Ala Asp Ala Ala
    450                 455

<210> SEQ ID NO 49
<211> LENGTH: 798
<212> TYPE: DNA
<213> ORGANISM: Xerophyta viscosa
<220> FEATURE:
<221> NAME/KEY: CDS
<222> LOCATION: (1)..(798)
<223> OTHER INFORMATION: Native DNA sequence encoding Xerophyta viscosa
      SAP1 protein

<400> SEQUENCE: 49

```
atg agg aac gag ggt ttt ctg aaa atg aag acc gac gtt gga gtc gcc        48
Met Arg Asn Glu Gly Phe Leu Lys Met Lys Thr Asp Val Gly Val Ala
1               5                   10                  15 gac gag gtg atc tcc gga gat ctc aag cag ctt ggt gac gct gca aag        96
Asp Glu Val Ile Ser Gly Asp Leu Lys Gln Leu Gly Asp Ala Ala Lys
            20                  25                  30 cgg cta gct aaa cat gcg atc aag ctc ggc gcc agc ttc ggg gtt ggc       144
Arg Leu Ala Lys His Ala Ile Lys Leu Gly Ala Ser Phe Gly Val Gly
        35                  40                  45 tct acc ata gtc cag gct att gct tcg atc gct gct atc tat ttg ttg       192
Ser Thr Ile Val Gln Ala Ile Ala Ser Ile Ala Ala Ile Tyr Leu Leu
    50                  55                  60 ata ttg gac cgg aca aac tgg cgt aca aat atc ttg aca tca ctt cta       240
Ile Leu Asp Arg Thr Asn Trp Arg Thr Asn Ile Leu Thr Ser Leu Leu
65                  70                  75                  80 att cca tat gtt tac ttg agt ctt cct tca gtg ata ttc aac cta ttc       288
Ile Pro Tyr Val Tyr Leu Ser Leu Pro Ser Val Ile Phe Asn Leu Phe
                85                  90                  95 agg ggc gac ctg ggc aga tgg ctt tca ttc att ggc gta gta atg aag       336
Arg Gly Asp Leu Gly Arg Trp Leu Ser Phe Ile Gly Val Val Met Lys
            100                 105                 110 ctc ttc ttc cac cga cac ttc cca gtt acc ttg gaa ctg ctt gtg tct       384
Leu Phe Phe His Arg His Phe Pro Val Thr Leu Glu Leu Leu Val Ser
        115                 120                 125 ctc att ctc ctg att gtg gtt tcc ccc act ttc att gcc cac aca atc       432
Leu Ile Leu Leu Ile Val Val Ser Pro Thr Phe Ile Ala His Thr Ile
    130                 135                 140 aga ggc agt ctc att gga gtc ttc atc ttc ctt gtc atc gcc tgc tac       480
Arg Gly Ser Leu Ile Gly Val Phe Ile Phe Leu Val Ile Ala Cys Tyr
145                 150                 155                 160 ctc ctc caa gag cac att aga tca gct ggt ggc ttc aaa aac gcg ttc       528
Leu Leu Gln Glu His Ile Arg Ser Ala Gly Gly Phe Lys Asn Ala Phe
                165                 170                 175 aca aag agc aat ggg att tca aac agc gtc ggg atc atc att cta ctg       576
Thr Lys Ser Asn Gly Ile Ser Asn Ser Val Gly Ile Ile Ile Leu Leu
            180                 185                 190 atc cac ccg atc tgg agc ttg gtg gtg tat ttc ctc tac acg tct ttg       624
Ile His Pro Ile Trp Ser Leu Val Val Tyr Phe Leu Tyr Thr Ser Leu
        195                 200                 205 ctg caa ctt ctt gca tac tct cct tcc cct tgt tgt tgc ata tta tac       672
Leu Gln Leu Leu Ala Tyr Ser Pro Ser Pro Cys Cys Cys Ile Leu Tyr
    210                 215                 220 aat aag tgg ttt aat ttc atg cat gtt tgt aaa tgt gta agc ctt cat       720
Asn Lys Trp Phe Asn Phe Met His Val Cys Lys Cys Val Ser Leu His
225                 230                 235                 240 atg tat tct cag tca att ggg tca tgc gtg tcc ata ttt ttc gtg cag       768
Met Tyr Ser Gln Ser Ile Gly Ser Cys Val Ser Ile Phe Phe Val Gln
                245                 250                 255 ttt gta ttc atc tat gaa gct gaa ttt taa                               798
Phe Val Phe Ile Tyr Glu Ala Glu Phe
            260                 265

<210> SEQ ID NO 50
<211> LENGTH: 265
<212> TYPE: PRT
<213> ORGANISM: Xerophyta viscosa

<400> SEQUENCE: 50

Met Arg Asn Glu Gly Phe Leu Lys Met Lys Thr Asp Val Gly Val Ala
1               5                   10                  15
```

```
Asp Glu Val Ile Ser Gly Asp Leu Lys Gln Leu Gly Asp Ala Ala Lys
         20                  25                  30

Arg Leu Ala Lys His Ala Ile Lys Leu Gly Ala Ser Phe Gly Val Gly
         35                  40                  45

Ser Thr Ile Val Gln Ala Ile Ala Ser Ile Ala Ala Ile Tyr Leu Leu
         50                  55                  60

Ile Leu Asp Arg Thr Asn Trp Arg Thr Asn Ile Leu Thr Ser Leu Leu
 65                  70                  75                  80

Ile Pro Tyr Val Tyr Leu Ser Leu Pro Ser Val Ile Phe Asn Leu Phe
                     85                  90                  95

Arg Gly Asp Leu Gly Arg Trp Leu Ser Phe Ile Gly Val Val Met Lys
                100                 105                 110

Leu Phe Phe His Arg His Phe Pro Val Thr Leu Glu Leu Leu Val Ser
                115                 120                 125

Leu Ile Leu Leu Ile Val Val Ser Pro Thr Phe Ile Ala His Thr Ile
                130                 135                 140

Arg Gly Ser Leu Ile Gly Val Phe Ile Phe Leu Val Ile Ala Cys Tyr
145                 150                 155                 160

Leu Leu Gln Glu His Ile Arg Ser Ala Gly Gly Phe Lys Asn Ala Phe
                165                 170                 175

Thr Lys Ser Asn Gly Ile Ser Asn Ser Val Gly Ile Ile Leu Leu
                180                 185                 190

Ile His Pro Ile Trp Ser Leu Val Val Tyr Phe Leu Tyr Thr Ser Leu
                195                 200                 205

Leu Gln Leu Leu Ala Tyr Ser Pro Ser Pro Cys Cys Cys Ile Leu Tyr
                210                 215                 220

Asn Lys Trp Phe Asn Phe Met His Val Cys Lys Cys Val Ser Leu His
225                 230                 235                 240

Met Tyr Ser Gln Ser Ile Gly Ser Cys Val Ser Ile Phe Phe Val Gln
                245                 250                 255

Phe Val Phe Ile Tyr Glu Ala Glu Phe
                260                 265

<210> SEQ ID NO 51
<211> LENGTH: 798
<212> TYPE: DNA
<213> ORGANISM: Artificial Sequence
<220> FEATURE:
<223> OTHER INFORMATION: Synthetic DNA sequence encoding Xerophyta
      viscosa SAP1 protein using codons optimized for maize and
      Table 1 & Table 2 sequences are maintained
<220> FEATURE:
<221> NAME/KEY: CDS
<222> LOCATION: (1)..(798)

<400> SEQUENCE: 51 atg aga aac gaa ggt ttt ctg aag atg aaa acg gac gtt ggg gtt gct    48
Met Arg Asn Glu Gly Phe Leu Lys Met Lys Thr Asp Val Gly Val Ala
 1               5                  10                  15 gac gaa gtc atc agc ggt gat ttg aag cag ttg ggt gat gct gcc aaa    96
Asp Glu Val Ile Ser Gly Asp Leu Lys Gln Leu Gly Asp Ala Ala Lys
                 20                  25                  30 cgc ctt gct aag cac gct atc aaa ctg gga gcc agc ttt ggt gtt ggt   144
Arg Leu Ala Lys His Ala Ile Lys Leu Gly Ala Ser Phe Gly Val Gly
         35                  40                  45 tca act atc gtt caa gcc atc gca tca ata gca gcc atc tat ctt ctg   192
Ser Thr Ile Val Gln Ala Ile Ala Ser Ile Ala Ala Ile Tyr Leu Leu
         50                  55                  60
```

```
att ctc gat agg acc aac tgg agg acc aac atc ttg acg tcc ctc ctc      240
Ile Leu Asp Arg Thr Asn Trp Arg Thr Asn Ile Leu Thr Ser Leu Leu
 65                  70                  75                  80 att ccc tac gtg tat ctg tcc ctc ccg agc gtc atc ttc aat ctc ttt      288
Ile Pro Tyr Val Tyr Leu Ser Leu Pro Ser Val Ile Phe Asn Leu Phe
                 85                  90                  95 cgt ggg gac ctc ggg aga tgg ctg tca ttc ata ggc gtt gtg atg aag      336
Arg Gly Asp Leu Gly Arg Trp Leu Ser Phe Ile Gly Val Val Met Lys
            100                 105                 110 ctg ttc ttt cat agg cac ttt cct gtt act ttg gag ctg ctt gtg agc      384
Leu Phe Phe His Arg His Phe Pro Val Thr Leu Glu Leu Leu Val Ser
        115                 120                 125 ctc att ctt ttg att gtc gtg tca cct acc ttc ata gct cat aca att      432
Leu Ile Leu Leu Ile Val Val Ser Pro Thr Phe Ile Ala His Thr Ile
130                 135                 140 cgt gga tct ttg att ggg gtg ttc atc ttc ttg gtg ata gca tgt tat      480
Arg Gly Ser Leu Ile Gly Val Phe Ile Phe Leu Val Ile Ala Cys Tyr
145                 150                 155                 160 ctg ctt caa gag cac att aga tca gct ggt ggc ttc aag aac gcc ttt      528
Leu Leu Gln Glu His Ile Arg Ser Ala Gly Gly Phe Lys Asn Ala Phe
                165                 170                 175 aca aag tct aat gga atc tcc aac agc gtg ggc atc atc atc ctt ctg      576
Thr Lys Ser Asn Gly Ile Ser Asn Ser Val Gly Ile Ile Ile Leu Leu
            180                 185                 190 atc cac ccg att tgg tct ctc gtc gtc tac ttc ctc tac act tca ctt      624
Ile His Pro Ile Trp Ser Leu Val Val Tyr Phe Leu Tyr Thr Ser Leu
        195                 200                 205 ctc cag ctt ttg gcc tac tca cca tcc ccg tgc tgc tgc ata tta tac      672
Leu Gln Leu Leu Ala Tyr Ser Pro Ser Pro Cys Cys Cys Ile Leu Tyr
210                 215                 220 aac aag tgg ttc aac ttc atg cat gtt tgc aag tgc gtc tct ttg cac      720
Asn Lys Trp Phe Asn Phe Met His Val Cys Lys Cys Val Ser Leu His
225                 230                 235                 240 atg tac tct cag tcc ata ggc tca tgt gtt tca ata ttt ttc gtc cag      768
Met Tyr Ser Gln Ser Ile Gly Ser Cys Val Ser Ile Phe Phe Val Gln
                245                 250                 255 ttc gtg ttc atc tat gag gct gag ttt taa                              798
Phe Val Phe Ile Tyr Glu Ala Glu Phe
            260                 265
```

<210> SEQ ID NO 52
<211> LENGTH: 265
<212> TYPE: PRT
<213> ORGANISM: Artificial Sequence
<220> FEATURE:
<223> OTHER INFORMATION: Synthetic Construct

<400> SEQUENCE: 52

```
Met Arg Asn Glu Gly Phe Leu Lys Met Lys Thr Asp Val Gly Val Ala
1               5                   10                  15

Asp Glu Val Ile Ser Gly Asp Leu Lys Gln Leu Gly Asp Ala Ala Lys
            20                  25                  30

Arg Leu Ala Lys His Ala Ile Lys Leu Gly Ala Ser Phe Gly Val Gly
        35                  40                  45

Ser Thr Ile Val Gln Ala Ile Ala Ser Ile Ala Ala Ile Tyr Leu Leu
    50                  55                  60

Ile Leu Asp Arg Thr Asn Trp Arg Thr Asn Ile Leu Thr Ser Leu Leu
65                  70                  75                  80

Ile Pro Tyr Val Tyr Leu Ser Leu Pro Ser Val Ile Phe Asn Leu Phe
```

```
                      85                  90                  95
Arg Gly Asp Leu Gly Arg Trp Leu Ser Phe Ile Gly Val Val Met Lys
                100                 105                 110

Leu Phe Phe His Arg His Phe Pro Val Thr Leu Glu Leu Leu Val Ser
            115                 120                 125

Leu Ile Leu Leu Ile Val Val Ser Pro Thr Phe Ile Ala His Thr Ile
        130                 135                 140

Arg Gly Ser Leu Ile Gly Val Phe Ile Phe Leu Val Ile Ala Cys Tyr
145                 150                 155                 160

Leu Leu Gln Glu His Ile Arg Ser Ala Gly Gly Phe Lys Asn Ala Phe
                165                 170                 175

Thr Lys Ser Asn Gly Ile Ser Asn Ser Val Gly Ile Ile Leu Leu
            180                 185                 190

Ile His Pro Ile Trp Ser Leu Val Val Tyr Phe Leu Tyr Thr Ser Leu
        195                 200                 205

Leu Gln Leu Leu Ala Tyr Ser Pro Ser Pro Cys Cys Cys Ile Leu Tyr
    210                 215                 220

Asn Lys Trp Phe Asn Phe Met His Val Cys Lys Cys Val Ser Leu His
225                 230                 235                 240

Met Tyr Ser Gln Ser Ile Gly Ser Cys Val Ser Ile Phe Phe Val Gln
                245                 250                 255

Phe Val Phe Ile Tyr Glu Ala Glu Phe
            260                 265

<210> SEQ ID NO 53
<211> LENGTH: 798
<212> TYPE: DNA
<213> ORGANISM: Artificial Sequence
<220> FEATURE:
<223> OTHER INFORMATION: Synthetic DNA sequence in accordance with the
      invention encoding Xerophyta viscosa SAP1 protein using codons
      optimized for maize and with sequences identified in Table 2
      removed and Table 1 sequences are maintained
<220> FEATURE:
<221> NAME/KEY: CDS
<222> LOCATION: (1)..(798)

<400> SEQUENCE: 53 atg aga aac gaa ggt ttt ctg aag atg aaa acg gac gtt ggg gtt gct        48
Met Arg Asn Glu Gly Phe Leu Lys Met Lys Thr Asp Val Gly Val Ala
1               5                   10                  15 gac gaa gtc atc agc ggt gat ttg aag cag ttg ggt gat gct gcc aaa        96
Asp Glu Val Ile Ser Gly Asp Leu Lys Gln Leu Gly Asp Ala Ala Lys
                20                  25                  30 cgc ctt gct aag cac gct atc aaa ctg gga gcc agc ttt ggt gtt ggt       144
Arg Leu Ala Lys His Ala Ile Lys Leu Gly Ala Ser Phe Gly Val Gly
            35                  40                  45 tca act atc gtt caa gcc atc gca tca ata gca gcc atc tat ctt ctg       192
Ser Thr Ile Val Gln Ala Ile Ala Ser Ile Ala Ala Ile Tyr Leu Leu
        50                  55                  60 att ctc gat agg acc aac tgg agg acc aac atc ttg acg tcc ctc ctc       240
Ile Leu Asp Arg Thr Asn Trp Arg Thr Asn Ile Leu Thr Ser Leu Leu
65                  70                  75                  80 att ccc tac gtg tat ctg tcc ctc ccg agc gtc atc ttc aat ctc ttt       288
Ile Pro Tyr Val Tyr Leu Ser Leu Pro Ser Val Ile Phe Asn Leu Phe
                85                  90                  95 cgt ggg gac ctc ggg aga tgg ctg tca ttc ata ggc gtt gtg atg aag       336
Arg Gly Asp Leu Gly Arg Trp Leu Ser Phe Ile Gly Val Val Met Lys
                100                 105                 110
```

```
ctg ttc ttt cat agg cac ttt cct gtt act ttg gag ctg ctt gtg agc      384
Leu Phe Phe His Arg His Phe Pro Val Thr Leu Glu Leu Leu Val Ser
        115                 120                 125 ctc att ctt ttg att gtc gtg tct cct acc ttc ata gct cat aca att      432
Leu Ile Leu Leu Ile Val Val Ser Pro Thr Phe Ile Ala His Thr Ile
130                 135                 140 cgt gga tct ttg att ggg gtg ttc atc ttc ttg gtg ata gca tgt tat      480
Arg Gly Ser Leu Ile Gly Val Phe Ile Phe Leu Val Ile Ala Cys Tyr
145                 150                 155                 160 ctg ctt caa gag cac att aga tca gct ggt ggc ttc aag aac gcc ttt      528
Leu Leu Gln Glu His Ile Arg Ser Ala Gly Gly Phe Lys Asn Ala Phe
                165                 170                 175 aca aag tct aat gga atc tcc aac agc gtg ggc atc atc atc ctt ctg      576
Thr Lys Ser Asn Gly Ile Ser Asn Ser Val Gly Ile Ile Ile Leu Leu
            180                 185                 190 atc cac ccg att tgg tct ctc gtc gtc tac ttc ctc tac act tca ctt      624
Ile His Pro Ile Trp Ser Leu Val Val Tyr Phe Leu Tyr Thr Ser Leu
        195                 200                 205 ctc cag ctt ttg gcc tac tca cca tcc cca tgc tgc tgt att ctt tac      672
Leu Gln Leu Leu Ala Tyr Ser Pro Ser Pro Cys Cys Cys Ile Leu Tyr
210                 215                 220 aac aaa tgg ttc aac ttc atg cac gtg tgc aag tgc gtc tct ttg cac      720
Asn Lys Trp Phe Asn Phe Met His Val Cys Lys Cys Val Ser Leu His
225                 230                 235                 240 atg tac tct cag tcc att ggc tca tgt gtt tca atc ttc ttt gtc cag      768
Met Tyr Ser Gln Ser Ile Gly Ser Cys Val Ser Ile Phe Phe Val Gln
                245                 250                 255 ttc gtg ttc atc tat gag gct gag ttt taa                              798
Phe Val Phe Ile Tyr Glu Ala Glu Phe
                260                 265

<210> SEQ ID NO 54
<211> LENGTH: 265
<212> TYPE: PRT
<213> ORGANISM: Artificial Sequence
<220> FEATURE:
<223> OTHER INFORMATION: Synthetic Construct

<400> SEQUENCE: 54

Met Arg Asn Glu Gly Phe Leu Lys Met Lys Thr Asp Val Gly Val Ala
1               5                   10                  15

Asp Glu Val Ile Ser Gly Asp Leu Lys Gln Leu Gly Asp Ala Ala Lys
            20                  25                  30

Arg Leu Ala Lys His Ala Ile Lys Leu Gly Ala Ser Phe Gly Val Gly
        35                  40                  45

Ser Thr Ile Val Gln Ala Ile Ala Ser Ile Ala Ala Ile Tyr Leu Leu
50                  55                  60

Ile Leu Asp Arg Thr Asn Trp Arg Thr Asn Ile Leu Thr Ser Leu Leu
65                  70                  75                  80

Ile Pro Tyr Val Tyr Leu Ser Leu Pro Ser Val Ile Phe Asn Leu Phe
                85                  90                  95

Arg Gly Asp Leu Gly Arg Trp Leu Ser Phe Ile Gly Val Val Met Lys
            100                 105                 110

Leu Phe Phe His Arg His Phe Pro Val Thr Leu Glu Leu Leu Val Ser
        115                 120                 125

Leu Ile Leu Leu Ile Val Val Ser Pro Thr Phe Ile Ala His Thr Ile
130                 135                 140

Arg Gly Ser Leu Ile Gly Val Phe Ile Phe Leu Val Ile Ala Cys Tyr
145                 150                 155                 160
```

```
Leu Leu Gln Glu His Ile Arg Ser Ala Gly Gly Phe Lys Asn Ala Phe
            165                 170                 175

Thr Lys Ser Asn Gly Ile Ser Asn Ser Val Gly Ile Ile Ile Leu Leu
            180                 185                 190

Ile His Pro Ile Trp Ser Leu Val Val Tyr Phe Leu Tyr Thr Ser Leu
            195                 200                 205

Leu Gln Leu Leu Ala Tyr Ser Pro Ser Pro Cys Cys Cys Ile Leu Tyr
            210                 215                 220

Asn Lys Trp Phe Asn Phe Met His Val Cys Lys Cys Val Ser Leu His
225                 230                 235                 240

Met Tyr Ser Gln Ser Ile Gly Ser Cys Val Ser Ile Phe Phe Val Gln
            245                 250                 255

Phe Val Phe Ile Tyr Glu Ala Glu Phe
            260                 265

<210> SEQ ID NO 55
<211> LENGTH: 717
<212> TYPE: DNA
<213> ORGANISM: Aequorea victoria
<220> FEATURE:
<221> NAME/KEY: CDS
<222> LOCATION: (1)..(717)
<223> OTHER INFORMATION: Native DNA sequence encoding Aequorea
      victoria GFP1 protein

<400> SEQUENCE: 55
```

| | | | | | | | | | | | | | | | | |
|---|---|---|---|---|---|---|---|---|---|---|---|---|---|---|---|---|
| atg | agt | aaa | gga | gaa | gaa | ctt | ttc | act | gga | gtg | gtc | cca | gtt | ctt | gtt | 48 |
| Met | Ser | Lys | Gly | Glu | Glu | Leu | Phe | Thr | Gly | Val | Val | Pro | Val | Leu | Val | |
| 1 | | | | 5 | | | | | 10 | | | | | 15 | | |
| gaa | tta | gat | ggc | gat | gtt | aat | ggg | caa | aaa | ttc | tct | gtc | agt | gga | gag | 96 |
| Glu | Leu | Asp | Gly | Asp | Val | Asn | Gly | Gln | Lys | Phe | Ser | Val | Ser | Gly | Glu | |
| | | | 20 | | | | | 25 | | | | | 30 | | | |
| ggt | gaa | ggt | gat | gca | aca | tac | gga | aaa | ctt | acc | ctt | aat | ttt | att | tgc | 144 |
| Gly | Glu | Gly | Asp | Ala | Thr | Tyr | Gly | Lys | Leu | Thr | Leu | Asn | Phe | Ile | Cys | |
| | | 35 | | | | | 40 | | | | | 45 | | | | |
| act | act | ggg | aag | cta | cct | gtt | cca | tgg | cca | aca | ctt | gtc | act | act | ttc | 192 |
| Thr | Thr | Gly | Lys | Leu | Pro | Val | Pro | Trp | Pro | Thr | Leu | Val | Thr | Thr | Phe | |
| 50 | | | | | 55 | | | | | 60 | | | | | | |
| tct | tat | ggt | gtt | caa | tgc | ttc | tca | aga | tac | cca | gat | cat | atg | aaa | cag | 240 |
| Ser | Tyr | Gly | Val | Gln | Cys | Phe | Ser | Arg | Tyr | Pro | Asp | His | Met | Lys | Gln | |
| 65 | | | | 70 | | | | | 75 | | | | | 80 | | |
| cat | gac | ttt | ttc | aag | agt | gcc | atg | ccc | gaa | ggt | tat | gta | cag | gaa | aga | 288 |
| His | Asp | Phe | Phe | Lys | Ser | Ala | Met | Pro | Glu | Gly | Tyr | Val | Gln | Glu | Arg | |
| | | | 85 | | | | | 90 | | | | | 95 | | | |
| act | ata | ttt | tac | aaa | gat | gac | ggg | aac | tac | aag | aca | cgt | gct | gaa | gtc | 336 |
| Thr | Ile | Phe | Tyr | Lys | Asp | Asp | Gly | Asn | Tyr | Lys | Thr | Arg | Ala | Glu | Val | |
| | | | 100 | | | | | 105 | | | | | 110 | | | |
| aag | ttt | gaa | ggt | gat | acc | ctt | gtt | aat | aga | atc | gag | tta | aaa | ggt | att | 384 |
| Lys | Phe | Glu | Gly | Asp | Thr | Leu | Val | Asn | Arg | Ile | Glu | Leu | Lys | Gly | Ile | |
| | | 115 | | | | | 120 | | | | | 125 | | | | |
| gat | ttt | aaa | gaa | gat | gga | aac | att | ctt | gga | cac | aaa | atg | gaa | tac | aac | 432 |
| Asp | Phe | Lys | Glu | Asp | Gly | Asn | Ile | Leu | Gly | His | Lys | Met | Glu | Tyr | Asn | |
| | 130 | | | | | 135 | | | | | 140 | | | | | |
| tat | aac | tca | cat | aat | gta | tac | atc | atg | gga | gac | aaa | cca | aag | aat | ggc | 480 |
| Tyr | Asn | Ser | His | Asn | Val | Tyr | Ile | Met | Gly | Asp | Lys | Pro | Lys | Asn | Gly | |
| 145 | | | | | 150 | | | | | 155 | | | | | 160 | |
| atc | aaa | gtt | aac | ttc | aaa | att | aga | cac | aac | att | aaa | gat | gga | agc | gtt | 528 |
| Ile | Lys | Val | Asn | Phe | Lys | Ile | Arg | His | Asn | Ile | Lys | Asp | Gly | Ser | Val | |
| | | | | 165 | | | | | 170 | | | | | 175 | | |

```
caa tta gca gac cat tat caa caa aat act cca att ggc gat ggc cct    576
Gln Leu Ala Asp His Tyr Gln Gln Asn Thr Pro Ile Gly Asp Gly Pro
        180                 185                 190 gtc ctt tta cca gac aac cat tac ctg tcc aca caa tct gcc ctt tcc    624
Val Leu Leu Pro Asp Asn His Tyr Leu Ser Thr Gln Ser Ala Leu Ser
            195                 200                 205 aaa gat ccc aac gaa aag aga gat cac atg atc ctt ctt gag ttt gta    672
Lys Asp Pro Asn Glu Lys Arg Asp His Met Ile Leu Leu Glu Phe Val
    210                 215                 220 aca gct gct agg att aca cat ggc atg gat gaa cta tac aaa taa        717
Thr Ala Ala Arg Ile Thr His Gly Met Asp Glu Leu Tyr Lys
225                 230                 235

<210> SEQ ID NO 56
<211> LENGTH: 238
<212> TYPE: PRT
<213> ORGANISM: Aequorea victoria

<400> SEQUENCE: 56

Met Ser Lys Gly Glu Glu Leu Phe Thr Gly Val Val Pro Val Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Asn Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Arg Ile Thr His Gly Met Asp Glu Leu Tyr Lys
225                 230                 235

<210> SEQ ID NO 57
<211> LENGTH: 717
<212> TYPE: DNA
<213> ORGANISM: Artificial Sequence
<220> FEATURE:
<223> OTHER INFORMATION: Synthetic DNA sequence encoding Aequorea
      victoria GFP1 protein using codons optimized for maize and
      Table 1 & Table 2 sequences are maintained
<220> FEATURE:
```

<221> NAME/KEY: CDS
<222> LOCATION: (1)..(717)

<400> SEQUENCE: 57

```
atg agt aaa ggg gaa gaa ctt ttc acc ggc gtg gtc cca gtc ctc gtt      48
Met Ser Lys Gly Glu Glu Leu Phe Thr Gly Val Val Pro Val Leu Val
1               5                   10                  15 gag ttg gat ggc gat gtg aat ggg caa aaa ttc tct gtc tcc ggg gag      96
Glu Leu Asp Gly Asp Val Asn Gly Gln Lys Phe Ser Val Ser Gly Glu
            20                  25                  30 ggt gag ggt gat gca acc tac gga aag ctg acc cta aat ttt att tgc     144
Gly Glu Gly Asp Ala Thr Tyr Gly Lys Leu Thr Leu Asn Phe Ile Cys
        35                  40                  45 acg act ggg aag ttg cct gtg cct tgg ccg aca ctg gtg acg acg ttc     192
Thr Thr Gly Lys Leu Pro Val Pro Trp Pro Thr Leu Val Thr Thr Phe
    50                  55                  60 tct tat ggt gtg cag tgt ttc tca cgc tac ccg gat cat atg aaa cag     240
Ser Tyr Gly Val Gln Cys Phe Ser Arg Tyr Pro Asp His Met Lys Gln
65                  70                  75                  80 cat gac ttt ttc aag tcg gcc atg cca gaa ggc tat gta caa gag aga     288
His Asp Phe Phe Lys Ser Ala Met Pro Glu Gly Tyr Val Gln Glu Arg
                85                  90                  95 act ata ttt tac aag gac gac ggg aac tac aag aca cgt gct gag gtg     336
Thr Ile Phe Tyr Lys Asp Asp Gly Asn Tyr Lys Thr Arg Ala Glu Val
            100                 105                 110 aag ttc gag ggt gat acc ctt gtt aat cgg atc gag cta aag ggc att     384
Lys Phe Glu Gly Asp Thr Leu Val Asn Arg Ile Glu Leu Lys Gly Ile
        115                 120                 125 gac ttt aag gag gac gga aac att ctg gga cac aaa atg gaa tac aac     432
Asp Phe Lys Glu Asp Gly Asn Ile Leu Gly His Lys Met Glu Tyr Asn
    130                 135                 140 tat aac tcg cac aac gta tac atc atg gga gac aaa cca aag aat ggc     480
Tyr Asn Ser His Asn Val Tyr Ile Met Gly Asp Lys Pro Lys Asn Gly
145                 150                 155                 160 ata aag gtt aac ttc aag att cga cac aac att aaa gac ggc agc gtt     528
Ile Lys Val Asn Phe Lys Ile Arg His Asn Ile Lys Asp Gly Ser Val
                165                 170                 175 cag ttg gcc gac cac tat caa caa aat act cca att ggc gat ggc cct     576
Gln Leu Ala Asp His Tyr Gln Gln Asn Thr Pro Ile Gly Asp Gly Pro
            180                 185                 190 gtc ctc tta ccc gac aac cat tac ctg tcc acg caa tca gcg ctc agc     624
Val Leu Leu Pro Asp Asn His Tyr Leu Ser Thr Gln Ser Ala Leu Ser
        195                 200                 205 aag gac ccc aac gag aag agg gat cac atg atc ctc ctt gag ttt gtc     672
Lys Asp Pro Asn Glu Lys Arg Asp His Met Ile Leu Leu Glu Phe Val
    210                 215                 220 acc gca gct agg ata acc cac ggc atg gat gaa ctg tac aag taa         717
Thr Ala Ala Arg Ile Thr His Gly Met Asp Glu Leu Tyr Lys
225                 230                 235
```

<210> SEQ ID NO 58
<211> LENGTH: 238
<212> TYPE: PRT
<213> ORGANISM: Artificial Sequence
<220> FEATURE:
<223> OTHER INFORMATION: Synthetic Construct

<400> SEQUENCE: 58

```
Met Ser Lys Gly Glu Glu Leu Phe Thr Gly Val Val Pro Val Leu Val
1               5                   10                  15

Glu Leu Asp Gly Asp Val Asn Gly Gln Lys Phe Ser Val Ser Gly Glu
```

```
                  20                  25                  30
Gly Glu Gly Asp Ala Thr Tyr Gly Lys Leu Thr Leu Asn Phe Ile Cys
            35                  40                  45

Thr Thr Gly Lys Leu Pro Val Pro Trp Pro Thr Leu Val Thr Thr Phe
50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
        130                 135                 140

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Arg Ile Thr His Gly Met Asp Glu Leu Tyr Lys
225                 230                 235

<210> SEQ ID NO 59
<211> LENGTH: 717
<212> TYPE: DNA
<213> ORGANISM: Artificial Sequence
<220> FEATURE:
<223> OTHER INFORMATION: Synthetic DNA sequence in accordance with the
      invention encoding Aequorea victoria GFP1 protein using codons
      optimized for maize and with sequences identified in Table 2
      removed and Table 1 sequences are maintained
<220> FEATURE:
<221> NAME/KEY: CDS
<222> LOCATION: (1)..(717)

<400> SEQUENCE: 59 atg agt aaa ggg gaa gaa ctt ttc acc ggc gtg gtc cca gtc ctc gtt      48
Met Ser Lys Gly Glu Glu Leu Phe Thr Gly Val Val Pro Val Leu Val
1               5                  10                  15 gag ttg gat ggc gat gtg aat ggg caa aaa ttc tct gtc tcc ggg gag      96
Glu Leu Asp Gly Asp Val Asn Gly Gln Lys Phe Ser Val Ser Gly Glu
            20                  25                  30 ggt gag ggt gat gca acc tac gga aag ctg acc cta aat ttc atc tgc     144
Gly Glu Gly Asp Ala Thr Tyr Gly Lys Leu Thr Leu Asn Phe Ile Cys
        35                  40                  45 acg act ggg aag ttg cct gtg cct tgg ccg aca ctg gtg acg acg ttc     192
Thr Thr Gly Lys Leu Pro Val Pro Trp Pro Thr Leu Val Thr Thr Phe
    50                  55                  60 tct tat ggt gtg cag tgt ttc tca cgc tac ccg gat cat atg aaa cag     240
Ser Tyr Gly Val Gln Cys Phe Ser Arg Tyr Pro Asp His Met Lys Gln
65                  70                  75                  80 cat gac ttt ttc aag tcg gcc atg cca gaa ggc tat gta caa gag aga     288
His Asp Phe Phe Lys Ser Ala Met Pro Glu Gly Tyr Val Gln Glu Arg
```

```
                 85                  90                  95
act atc ttt tac aag gac gac ggg aac tac aag aca cgt gct gag gtg       336
Thr Ile Phe Tyr Lys Asp Asp Gly Asn Tyr Lys Thr Arg Ala Glu Val
            100                 105                 110 aag ttc gag ggt gat acc ctt gtt aat cgg atc gag cta aag ggc att       384
Lys Phe Glu Gly Asp Thr Leu Val Asn Arg Ile Glu Leu Lys Gly Ile
        115                 120                 125 gac ttt aag gag gac gga aac att ctg gga cac aaa atg gaa tac aac       432
Asp Phe Lys Glu Asp Gly Asn Ile Leu Gly His Lys Met Glu Tyr Asn
130                 135                 140 tat aac tcg cac aac gta tac atc atg gga gac aaa cca aag aat ggc       480
Tyr Asn Ser His Asn Val Tyr Ile Met Gly Asp Lys Pro Lys Asn Gly
145                 150                 155                 160 ata aag gtt aac ttc aag att cga cac aac att aaa gac ggc agc gtt       528
Ile Lys Val Asn Phe Lys Ile Arg His Asn Ile Lys Asp Gly Ser Val
                165                 170                 175 cag ttg gcc gac cac tat caa caa aat act cca att ggc gat ggc cct       576
Gln Leu Ala Asp His Tyr Gln Gln Asn Thr Pro Ile Gly Asp Gly Pro
            180                 185                 190 gtc ctc tta ccc gac aac cat tac ctg tcc acg caa tca gcg ctc agc       624
Val Leu Leu Pro Asp Asn His Tyr Leu Ser Thr Gln Ser Ala Leu Ser
        195                 200                 205 aag gac ccc aac gag aag agg gat cac atg atc ctc ctt gag ttt gtc       672
Lys Asp Pro Asn Glu Lys Arg Asp His Met Ile Leu Leu Glu Phe Val
210                 215                 220 acc gca gct agg ata acc cac ggc atg gat gaa ctg tac aag taa           717
Thr Ala Ala Arg Ile Thr His Gly Met Asp Glu Leu Tyr Lys
225                 230                 235

<210> SEQ ID NO 60
<211> LENGTH: 238
<212> TYPE: PRT
<213> ORGANISM: Artificial Sequence
<220> FEATURE:
<223> OTHER INFORMATION: Synthetic Construct

<400> SEQUENCE: 60

Met Ser Lys Gly Glu Glu Leu Phe Thr Gly Val Val Pro Val Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Asn Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Ser Val
```

```
                        165                 170                 175
Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Ile Leu Leu Glu Phe Val
        210                 215                 220

Thr Ala Ala Arg Ile Thr His Gly Met Asp Glu Leu Tyr Lys
225                 230                 235

<210> SEQ ID NO 61
<211> LENGTH: 1350
<212> TYPE: DNA
<213> ORGANISM: Leptosphaeria nodorum
<220> FEATURE:
<221> NAME/KEY: CDS
<222> LOCATION: (1)..(1350)
<223> OTHER INFORMATION: Native DNA sequence encoding Leptosphaeria
      nodorum delta-9 fatty acid desaturase protein

<400> SEQUENCE: 61 atg gcg gcc tt

|  |  |
|---|---|
| atc att cga gcg tgt ttc gtc cag cag gcg aca ttt tgc gtg aac tct<br>Ile Ile Arg Ala Cys Phe Val Gln Gln Ala Thr Phe Cys Val Asn Ser<br>210                             215                      220 | 672 |
| ctc gcg cat tgg atc ggc gag cag ccg ttc gac gac aga cgc acg cct<br>Leu Ala His Trp Ile Gly Glu Gln Pro Phe Asp Asp Arg Arg Thr Pro<br>225                             230                      235                  240 | 720 |
| cga gac cac gtt ttg aca gcg ttg gta acg atg gga gaa gga tat cat<br>Arg Asp His Val Leu Thr Ala Leu Val Thr Met Gly Glu Gly Tyr His<br>245                           250                      255 | 768 |
| aac ttc cac cac gaa ttc cca agc gat tat cgc aac gcg atc atc tgg<br>Asn Phe His His Glu Phe Pro Ser Asp Tyr Arg Asn Ala Ile Ile Trp<br>260                         265                      270 | 816 |
| tac caa tac gac cct acc aaa tgg ctc att tac ctc ttc tcc ctc ggc<br>Tyr Gln Tyr Asp Pro Thr Lys Trp Leu Ile Tyr Leu Phe Ser Leu Gly<br>275                         280                      285 | 864 |
| ccc ttc ccc ctc gca tac tcg ctc aaa acc ttc cgg tcc aat gag att<br>Pro Phe Pro Leu Ala Tyr Ser Leu Lys Thr Phe Arg Ser Asn Glu Ile<br>290                         295                      300 | 912 |
| gaa aaa ggg cgg ttg caa caa caa caa aaa gcc ctg gac aag aag cgc<br>Glu Lys Gly Arg Leu Gln Gln Gln Gln Lys Ala Leu Asp Lys Lys Arg<br>305                           310                      315                  320 | 960 |
| tca gga ctt gat tgg ggc cta ccc ctc ttc caa ctc cct gtc ata tcg<br>Ser Gly Leu Asp Trp Gly Leu Pro Leu Phe Gln Leu Pro Val Ile Ser<br>                         325                      330                      335 | 1008 |
| tgg gac gac ttc caa gcg cgt tgc aaa gag tcc ggc gag atg ctg gtt<br>Trp Asp Asp Phe Gln Ala Arg Cys Lys Glu Ser Gly Glu Met Leu Val<br>                      340                      345                  350 | 1056 |
| gct gtc gca ggt gtg att cac gac gtc agc cag ttt att gaa gat cac<br>Ala Val Ala Gly Val Ile His Asp Val Ser Gln Phe Ile Glu Asp His<br>                      355                      360                  365 | 1104 |
| cct gga ggc agg agt ttg att cgg agt gcg gtg ggc aaa gat ggg aca<br>Pro Gly Gly Arg Ser Leu Ile Arg Ser Ala Val Gly Lys Asp Gly Thr<br>370                           375                      380 | 1152 |
| ggg atg ttt aat gga ggc gta tat gag cac agt aat gcg gcg cat aat<br>Gly Met Phe Asn Gly Gly Val Tyr Glu His Ser Asn Ala Ala His Asn<br>385                           390                      395                  400 | 1200 |
| ctg ttg tcg aca atg agg gtg gga gtg ctt aga ggt ggg cag gag gtg<br>Leu Leu Ser Thr Met Arg Val Gly Val Leu Arg Gly Gly Gln Glu Val<br>                      405                      410                  415 | 1248 |
| gag gtg tgg aag aag cag aga gtg gat gtt tta ggg aag agc gac att<br>Glu Val Trp Lys Lys Gln Arg Val Asp Val Leu Gly Lys Ser Asp Ile<br>                      420                      425                  430 | 1296 |
| ttg aga cag gtt acg cgg gtg gag agg ttg gtt gag ggg gct gtg gct<br>Leu Arg Gln Val Thr Arg Val Glu Arg Leu Val Glu Gly Ala Val Ala<br>                  435                      440                  445 | 1344 |
| gcg tag<br>Ala | 1350 |

<210> SEQ ID NO 62
<211> LENGTH: 449
<212> TYPE: PRT
<213> ORGANISM: Leptosphaeria nodorum

<400> SEQUENCE: 62

Met Ala Ala Leu Asp Ser Ile Pro Glu Asp Lys Ala Thr Ser Ser Lys
1                 5                    10                   15

Ser Thr His Ile Gln Tyr Gln Glu Val Thr Phe Arg Asn Trp Tyr Lys
                20                    25                    30

Lys Ile Asn Trp Leu Asn Thr Thr Leu Val Val Leu Ile Pro Ala Leu
                35                    40                    45

```
Gly Leu Tyr Leu Thr Arg Thr Thr Pro Leu Thr Arg Pro Thr Leu Ile
     50                  55                  60

Trp Ser Val Leu Tyr Tyr Phe Cys Thr Ala Phe Gly Ile Thr Gly Gly
 65                  70                  75                  80

Tyr His Arg Leu Trp Ser His Arg Ser Tyr Ser Ala Arg Leu Pro Leu
                     85                  90                  95

Arg Leu Phe Leu Ala Phe Thr Gly Ala Gly Ala Ile Gln Gly Ser Ala
                100                 105                 110

Arg Trp Trp Ser Ala Asn His Arg Ala His His Arg Trp Thr Asp Thr
            115                 120                 125

Met Lys Asp Pro Tyr Ser Val Met Arg Gly Leu Leu Phe Ser His Ile
130                 135                 140

Gly Trp Met Val Leu Asn Ser Asp Pro Lys Val Lys Gly Arg Thr Asp
145                 150                 155                 160

Val Ser Asp Leu Asp Ser Asp Pro Val Val Trp Gln His Lys His
                165                 170                 175

Tyr Gly Lys Cys Leu Leu Phe Ala Ala Trp Ile Phe Pro Met Ile Val
                180                 185                 190

Ala Gly Leu Gly Trp Gly Asp Trp Trp Gly Gly Leu Val Tyr Ala Gly
                195                 200                 205

Ile Ile Arg Ala Cys Phe Val Gln Gln Ala Thr Phe Cys Val Asn Ser
210                 215                 220

Leu Ala His Trp Ile Gly Glu Gln Pro Phe Asp Asp Arg Arg Thr Pro
225                 230                 235                 240

Arg Asp His Val Leu Thr Ala Leu Val Thr Met Gly Glu Gly Tyr His
                245                 250                 255

Asn Phe His His Glu Phe Pro Ser Asp Tyr Arg Asn Ala Ile Ile Trp
                260                 265                 270

Tyr Gln Tyr Asp Pro Thr Lys Trp Leu Ile Tyr Leu Phe Ser Leu Gly
            275                 280                 285

Pro Phe Pro Leu Ala Tyr Ser Leu Lys Thr Phe Arg Ser Asn Glu Ile
290                 295                 300

Glu Lys Gly Arg Leu Gln Gln Gln Lys Ala Leu Asp Lys Lys Arg
305                 310                 315                 320

Ser Gly Leu Asp Trp Gly Leu Pro Leu Phe Gln Leu Pro Val Ile Ser
                325                 330                 335

Trp Asp Asp Phe Gln Ala Arg Cys Lys Glu Ser Gly Glu Met Leu Val
                340                 345                 350

Ala Val Ala Gly Val Ile His Asp Val Ser Gln Phe Ile Glu Asp His
            355                 360                 365

Pro Gly Gly Arg Ser Leu Ile Arg Ser Ala Val Gly Lys Asp Gly Thr
    370                 375                 380

Gly Met Phe Asn Gly Gly Val Tyr Glu His Ser Asn Ala Ala His Asn
385                 390                 395                 400

Leu Leu Ser Thr Met Arg Val Gly Val Leu Arg Gly Gln Glu Val
                405                 410                 415

Glu Val Trp Lys Lys Gln Arg Val Asp Val Leu Gly Lys Ser Asp Ile
                420                 425                 430

Leu Arg Gln Val Thr Arg Val Glu Arg Leu Val Glu Gly Ala Val Ala
        435                 440                 445

Ala
```

-continued

```
<210> SEQ ID NO 63
<211> LENGTH: 1350
<212> TYPE: DNA
<213> ORGANISM: Artificial Sequence
<220> FEATURE:
<223> OTHER INFORMATION: Synthetic DNA sequence encoding Leptosphaeria
      nodorum delta-9 fatty acid desaturase protein using codons
      optimized for maize and Table 1 & Table 2 sequences are maintained
<220> FEATURE:
<221> NAME/KEY: CDS
<222> LOCATION: (1)..(1350)

<400> SEQUENCE: 63 atg gca gcc ctt gac agc atc cca gag gat aag gct acc tcg tct aaa       48
Met Ala Ala Leu Asp Ser Ile Pro Glu Asp Lys Ala Thr Ser Ser Lys
1               5                   10                  15 tcg act cat att cag tac caa gaa gtg act ttt cgg aac tgg tac aaa       96
Ser Thr His Ile Gln Tyr Gln Glu Val Thr Phe Arg Asn Trp Tyr Lys
            20                  25                  30 aag ata aac tgg ctc aac acg acg ctg gtg gtg ctc ata cca gct ctt      144
Lys Ile Asn Trp Leu Asn Thr Thr Leu Val Val Leu Ile Pro Ala Leu
        35                  40                  45 ggt ctt tac cta aca agg acc acg cca ctt act agg cca acg ctc atc      192
Gly Leu Tyr Leu Thr Arg Thr Thr Pro Leu Thr Arg Pro Thr Leu Ile
50                  55                  60 tgg tcc gtc ctg tac tac ttt tgc acc gct ttc ggc att acc ggc gga      240
Trp Ser Val Leu Tyr Tyr Phe Cys Thr Ala Phe Gly Ile Thr Gly Gly
65                  70                  75                  80 tat cat aga cta tgg agt cat cgc agc tac tcc gct cgt cta ccg ctt      288
Tyr His Arg Leu Trp Ser His Arg Ser Tyr Ser Ala Arg Leu Pro Leu
                85                  90                  95 cgc ttg ttc ctg gcc ttc act ggc gcc ggg gcc atc caa ggt tca gct      336
Arg Leu Phe Leu Ala Phe Thr Gly Ala Gly Ala Ile Gln Gly Ser Ala
            100                 105                 110 agg tgg tgg agc gca aat cac cgc gcc cat cat agg tgg acc gac aca      384
Arg Trp Trp Ser Ala Asn His Arg Ala His His Arg Trp Thr Asp Thr
        115                 120                 125 atg aag gac ccc tac tcc gtt atg cgc ggt cta tta ttc tcg cac atc      432
Met Lys Asp Pro Tyr Ser Val Met Arg Gly Leu Leu Phe Ser His Ile
    130                 135                 140 ggt tgg atg gtt cta aac agc gac ccc aaa gtc aaa ggc cgc act gac      480
Gly Trp Met Val Leu Asn Ser Asp Pro Lys Val Lys Gly Arg Thr Asp
145                 150                 155                 160 gtc tca gac cta gat agc gac ccc gtc gtt gtc tgg cag cac aag cac      528
Val Ser Asp Leu Asp Ser Asp Pro Val Val Val Trp Gln His Lys His
                165                 170                 175 tac ggc aag tgc ctg cta ttt gcc gca tgg ata ttc ccg atg atc gta      576
Tyr Gly Lys Cys Leu Leu Phe Ala Ala Trp Ile Phe Pro Met Ile Val
            180                 185                 190 gcc ggc ctc gga tgg gga gat tgg tgg gga ggc ctt gtc tac gcc ggc      624
Ala Gly Leu Gly Trp Gly Asp Trp Trp Gly Gly Leu Val Tyr Ala Gly
        195                 200                 205 atc att agg gcg tgt ttc gtc cag caa gca acc ttt tgc gtg aac tct      672
Ile Ile Arg Ala Cys Phe Val Gln Gln Ala Thr Phe Cys Val Asn Ser
    210                 215                 220 ctc gcg cac tgg atc ggc gag cag ccg ttc gac gac aga cgc acc cct      720
Leu Ala His Trp Ile Gly Glu Gln Pro Phe Asp Asp Arg Arg Thr Pro
225                 230                 235                 240 aga gac cac gtt ttg acc gcg ttg gtc act atg gga gaa ggt tat cac      768
Arg Asp His Val Leu Thr Ala Leu Val Thr Met Gly Glu Gly Tyr His
                245                 250                 255 aac ttc cac cac gag ttc ccg tct gat tat agg aac gcg atc atc tgg      816
Asn Phe His His Glu Phe Pro Ser Asp Tyr Arg Asn Ala Ile Ile Trp
```

| | | | | | | | | | | | | |
|---|---|---|---|---|---|---|---|---|---|---|---|---|
| Asn | Phe | His | His | Glu | Phe | Pro | Ser | Asp | Tyr | Arg | Asn | Ala | Ile | Ile | Trp |
| | | | 260 | | | | | 265 | | | | 270 | | | |

```
tat cag tac gac cct acc aaa tgg ctc ata tac ctc ttc tcc ctc ggc      864
Tyr Gln Tyr Asp Pro Thr Lys Trp Leu Ile Tyr Leu Phe Ser Leu Gly
            275                 280                 285 ccg ttc cca ctg gca tac tcg ctc aaa acc ttc cgg tct aac gag atc      912
Pro Phe Pro Leu Ala Tyr Ser Leu Lys Thr Phe Arg Ser Asn Glu Ile
290                 295                 300 gaa aag ggg cgg ttg caa caa caa caa aag gcc ctg gat aag aag cgc      960
Glu Lys Gly Arg Leu Gln Gln Gln Gln Lys Ala Leu Asp Lys Lys Arg
305                 310                 315                 320 tct ggc ctt gat tgg ggc ctg ccc ctc ttc cag ctc cct gtg ata tct     1008
Ser Gly Leu Asp Trp Gly Leu Pro Leu Phe Gln Leu Pro Val Ile Ser
            325                 330                 335 tgg gac gac ttc caa gcg cgt tgt aag gag tcc ggc gag atg ctg gtt     1056
Trp Asp Asp Phe Gln Ala Arg Cys Lys Glu Ser Gly Glu Met Leu Val
            340                 345                 350 gct gtc gcc ggt gtg att cac gac gtc tca cag ttt att gaa gat cac     1104
Ala Val Ala Gly Val Ile His Asp Val Ser Gln Phe Ile Glu Asp His
            355                 360                 365 cct gga ggg agg agt ctg att cgg tct gcg gtg ggc aag gat ggg act     1152
Pro Gly Gly Arg Ser Leu Ile Arg Ser Ala Val Gly Lys Asp Gly Thr
370                 375                 380 ggg atg ttt aat gga ggc gtt tat gag cac agt aat gcg gcg cac aat     1200
Gly Met Phe Asn Gly Gly Val Tyr Glu His Ser Asn Ala Ala His Asn
385                 390                 395                 400 ctg ttg tca aca atg agg gtg ggt gtg ctt aga ggt ggg caa gag gtg     1248
Leu Leu Ser Thr Met Arg Val Gly Val Leu Arg Gly Gly Gln Glu Val
            405                 410                 415 gag gtg tgg aag aag cag cgt gtg gat gtt tta ggg aag agc gat atc     1296
Glu Val Trp Lys Lys Gln Arg Val Asp Val Leu Gly Lys Ser Asp Ile
            420                 425                 430 ttg cgt caa gtt acg cgg gtg gag agg ctg gtt gag ggg gct gtg gct     1344
Leu Arg Gln Val Thr Arg Val Glu Arg Leu Val Glu Gly Ala Val Ala
            435                 440                 445 gcc tag                                                              1350
Ala

<210> SEQ ID NO 64
<211> LENGTH: 449
<212> TYPE: PRT
<213> ORGANISM: Artificial Sequence
<220> FEATURE:
<223> OTHER INFORMATION: Synthetic Construct

<400> SEQUENCE: 64

Met Ala Ala Leu Asp Ser Ile Pro Glu Asp Lys Ala Thr Ser Ser Lys
1               5                   10                  15

Ser Thr His Ile Gln Tyr Gln Glu Val Thr Phe Arg Asn Trp Tyr Lys
            20                  25                  30

Lys Ile Asn Trp Leu Asn Thr Thr Leu Val Val Leu Ile Pro Ala Leu
        35                  40                  45

Gly Leu Tyr Leu Thr Arg Thr Thr Pro Leu Thr Arg Pro Thr Leu Ile
    50                  55                  60

Trp Ser Val Leu Tyr Tyr Phe Cys Thr Ala Phe Gly Ile Thr Gly Gly
65                  70                  75                  80

Tyr His Arg Leu Trp Ser His Arg Ser Tyr Ser Ala Arg Leu Pro Leu
                85                  90                  95

Arg Leu Phe Leu Ala Phe Thr Gly Ala Gly Ala Ile Gln Gly Ser Ala
```

-continued

|  | 100 |  |  | 105 |  |  | 110 |  |
| --- | --- | --- | --- | --- | --- | --- | --- | --- |

Arg Trp Trp Ser Ala Asn His Arg Ala His His Arg Trp Thr Asp Thr
            115                      120                      125

Met Lys Asp Pro Tyr Ser Val Met Arg Gly Leu Leu Phe Ser His Ile
    130                      135                      140

Gly Trp Met Val Leu Asn Ser Asp Pro Lys Val Lys Gly Arg Thr Asp
145                      150                      155                      160

Val Ser Asp Leu Asp Ser Asp Pro Val Val Trp Gln His Lys His
            165                      170                      175

Tyr Gly Lys Cys Leu Leu Phe Ala Ala Trp Ile Phe Pro Met Ile Val
            180                      185                      190

Ala Gly Leu Gly Trp Gly Asp Trp Trp Gly Gly Leu Val Tyr Ala Gly
            195                      200                      205

Ile Ile Arg Ala Cys Phe Val Gln Gln Ala Thr Phe Cys Val Asn Ser
        210                      215                      220

Leu Ala His Trp Ile Gly Glu Gln Pro Phe Asp Asp Arg Arg Thr Pro
225                      230                      235                      240

Arg Asp His Val Leu Thr Ala Leu Val Thr Met Gly Glu Gly Tyr His
                245                      250                      255

Asn Phe His His Glu Phe Pro Ser Asp Tyr Arg Asn Ala Ile Ile Trp
            260                      265                      270

Tyr Gln Tyr Asp Pro Thr Lys Trp Leu Ile Tyr Leu Phe Ser Leu Gly
        275                      280                      285

Pro Phe Pro Leu Ala Tyr Ser Leu Lys Thr Phe Arg Ser Asn Glu Ile
290                      295                      300

Glu Lys Gly Arg Leu Gln Gln Gln Lys Ala Leu Asp Lys Lys Arg
305                      310                      315                      320

Ser Gly Leu Asp Trp Gly Leu Pro Leu Phe Gln Leu Pro Val Ile Ser
                325                      330                      335

Trp Asp Asp Phe Gln Ala Arg Cys Lys Glu Ser Gly Glu Met Leu Val
                  340                      345                      350

Ala Val Ala Gly Val Ile His Asp Val Ser Gln Phe Ile Glu Asp His
            355                      360                      365

Pro Gly Gly Arg Ser Leu Ile Arg Ser Ala Val Gly Lys Asp Gly Thr
    370                      375                      380

Gly Met Phe Asn Gly Gly Val Tyr Glu His Ser Asn Ala Ala His Asn
385                      390                      395                      400

Leu Leu Ser Thr Met Arg Val Gly Val Leu Arg Gly Gly Gln Glu Val
                405                      410                      415

Glu Val Trp Lys Lys Gln Arg Val Asp Val Leu Gly Lys Ser Asp Ile
            420                      425                      430

Leu Arg Gln Val Thr Arg Val Glu Arg Leu Val Glu Gly Ala Val Ala
        435                      440                      445

Ala

<210> SEQ ID NO 65
<211> LENGTH: 1350
<212> TYPE: DNA
<213> ORGANISM: Artificial Sequence
<220> FEATURE:
<223> OTHER INFORMATION: Synthetic DNA sequence in accordance with the
    invention encoding Leptosphaeria nodorum delta-9 fatty acid
    desaturase protein using codons optimized for maize and with

<221> NAME/KEY: CDS
<222> LOCATION: (1)..(1350)

<400> SEQUENCE: 65

| | | | | | | | | | | | | | | | | |
|---|---|---|---|---|---|---|---|---|---|---|---|---|---|---|---|---|
| atg | gca | gcc | ctt | gac | agc | atc | cca | gag | gat | aag | gct | acc | tcg | tct | aaa | 48 |
| Met | Ala | Ala | Leu | Asp | Ser | Ile | Pro | Glu | Asp | Lys | Ala | Thr | Ser | Ser | Lys | |
| 1 | | | | 5 | | | | | 10 | | | | | 15 | | |

| tcg | act | cat | att | cag | tac | caa | gaa | gtg | act | ttt | cgg | aac | tgg | tac | aaa | 96 |
|---|---|---|---|---|---|---|---|---|---|---|---|---|---|---|---|---|
| Ser | Thr | His | Ile | Gln | Tyr | Gln | Glu | Val | Thr | Phe | Arg | Asn | Trp | Tyr | Lys | |
| | | | 20 | | | | | 25 | | | | | 30 | | | |

| aag | ata | aac | tgg | ctc | aac | acg | acg | ctg | gtg | gtg | ctc | ata | cca | gct | ctt | 144 |
|---|---|---|---|---|---|---|---|---|---|---|---|---|---|---|---|---|
| Lys | Ile | Asn | Trp | Leu | Asn | Thr | Thr | Leu | Val | Val | Leu | Ile | Pro | Ala | Leu | |
| | 35 | | | | | 40 | | | | | 45 | | | | | |

| ggt | ctt | tac | cta | aca | agg | acc | acg | cca | ctt | act | agg | cca | acg | ctc | atc | 192 |
|---|---|---|---|---|---|---|---|---|---|---|---|---|---|---|---|---|
| Gly | Leu | Tyr | Leu | Thr | Arg | Thr | Thr | Pro | Leu | Thr | Arg | Pro | Thr | Leu | Ile | |
| 50 | | | | | 55 | | | | | 60 | | | | | | |

| tgg | tcc | gtc | ctg | tac | tac | ttt | tgc | acc | gct | ttc | ggc | att | acc | ggc | gga | 240 |
|---|---|---|---|---|---|---|---|---|---|---|---|---|---|---|---|---|
| Trp | Ser | Val | Leu | Tyr | Tyr | Phe | Cys | Thr | Ala | Phe | Gly | Ile | Thr | Gly | Gly | |
| 65 | | | | 70 | | | | | 75 | | | | | 80 | | |

| tat | cat | aga | cta | tgg | agt | cat | cgc | agc | tac | tcc | gct | cgt | cta | ccg | ctt | 288 |
|---|---|---|---|---|---|---|---|---|---|---|---|---|---|---|---|---|
| Tyr | His | Arg | Leu | Trp | Ser | His | Arg | Ser | Tyr | Ser | Ala | Arg | Leu | Pro | Leu | |
| | | | | 85 | | | | | 90 | | | | | 95 | | |

| cgc | ttg | ttc | ctg | gcc | ttc | act | ggc | gcc | ggg | gcc | atc | caa | ggt | tca | gct | 336 |
|---|---|---|---|---|---|---|---|---|---|---|---|---|---|---|---|---|
| Arg | Leu | Phe | Leu | Ala | Phe | Thr | Gly | Ala | Gly | Ala | Ile | Gln | Gly | Ser | Ala | |
| | | | 100 | | | | | 105 | | | | | 110 | | | |

| agg | tgg | tgg | agc | gca | aat | cac | cgc | gcc | cat | cat | agg | tgg | acc | gac | aca | 384 |
|---|---|---|---|---|---|---|---|---|---|---|---|---|---|---|---|---|
| Arg | Trp | Trp | Ser | Ala | Asn | His | Arg | Ala | His | His | Arg | Trp | Thr | Asp | Thr | |
| | | 115 | | | | | 120 | | | | | 125 | | | | |

| atg | aag | gac | ccc | tac | tcc | gtt | atg | cgc | ggt | ctg | tta | ttc | tcg | cac | atc | 432 |
|---|---|---|---|---|---|---|---|---|---|---|---|---|---|---|---|---|
| Met | Lys | Asp | Pro | Tyr | Ser | Val | Met | Arg | Gly | Leu | Leu | Phe | Ser | His | Ile | |
| | 130 | | | | | 135 | | | | | 140 | | | | | |

| ggt | tgg | atg | gtt | cta | aac | agc | gac | ccc | aaa | gtc | aaa | ggc | cgc | act | gac | 480 |
|---|---|---|---|---|---|---|---|---|---|---|---|---|---|---|---|---|
| Gly | Trp | Met | Val | Leu | Asn | Ser | Asp | Pro | Lys | Val | Lys | Gly | Arg | Thr | Asp | |
| 145 | | | | 150 | | | | | 155 | | | | | 160 | | |

| gtc | tca | gac | cta | gat | agc | gac | ccc | gtc | gtt | gtc | tgg | cag | cac | aag | cac | 528 |
|---|---|---|---|---|---|---|---|---|---|---|---|---|---|---|---|---|
| Val | Ser | Asp | Leu | Asp | Ser | Asp | Pro | Val | Val | Val | Trp | Gln | His | Lys | His | |
| | | | | 165 | | | | | 170 | | | | | 175 | | |

| tac | ggc | aag | tgc | ctg | cta | ttt | gcc | gca | tgg | ata | ttc | ccg | atg | atc | gta | 576 |
|---|---|---|---|---|---|---|---|---|---|---|---|---|---|---|---|---|
| Tyr | Gly | Lys | Cys | Leu | Leu | Phe | Ala | Ala | Trp | Ile | Phe | Pro | Met | Ile | Val | |
| | | | 180 | | | | | 185 | | | | | 190 | | | |

| gcc | ggc | ctc | gga | tgg | gga | gat | tgg | tgg | gga | ggc | ctt | gtc | tac | gcc | ggc | 624 |
|---|---|---|---|---|---|---|---|---|---|---|---|---|---|---|---|---|
| Ala | Gly | Leu | Gly | Trp | Gly | Asp | Trp | Trp | Gly | Gly | Leu | Val | Tyr | Ala | Gly | |
| | | 195 | | | | | 200 | | | | | 205 | | | | |

| atc | att | agg | gcg | tgt | ttc | gtc | cag | caa | gca | acc | ttt | tgc | gtg | aac | tct | 672 |
|---|---|---|---|---|---|---|---|---|---|---|---|---|---|---|---|---|
| Ile | Ile | Arg | Ala | Cys | Phe | Val | Gln | Gln | Ala | Thr | Phe | Cys | Val | Asn | Ser | |
| | 210 | | | | | 215 | | | | | 220 | | | | | |

| ctc | gcg | cac | tgg | atc | ggc | gag | cag | ccg | ttc | gac | gac | aga | cgc | acc | cct | 720 |
|---|---|---|---|---|---|---|---|---|---|---|---|---|---|---|---|---|
| Leu | Ala | His | Trp | Ile | Gly | Glu | Gln | Pro | Phe | Asp | Asp | Arg | Arg | Thr | Pro | |
| 225 | | | | 230 | | | | | 235 | | | | | 240 | | |

| aga | gac | cac | gtt | ttg | acc | gcg | ttg | gtc | act | atg | gga | gaa | ggt | tat | cac | 768 |
|---|---|---|---|---|---|---|---|---|---|---|---|---|---|---|---|---|
| Arg | Asp | His | Val | Leu | Thr | Ala | Leu | Val | Thr | Met | Gly | Glu | Gly | Tyr | His | |
| | | | | 245 | | | | | 250 | | | | | 255 | | |

| aac | ttc | cac | cac | gag | ttc | ccg | tct | gat | tat | agg | aac | gcg | atc | atc | tgg | 816 |
|---|---|---|---|---|---|---|---|---|---|---|---|---|---|---|---|---|
| Asn | Phe | His | His | Glu | Phe | Pro | Ser | Asp | Tyr | Arg | Asn | Ala | Ile | Ile | Trp | |
| | | | 260 | | | | | 265 | | | | | 270 | | | |

| tat | cag | tac | gac | cct | acc | aaa | tgg | ctc | ata | tac | ctc | ttc | tcc | ctc | ggc | 864 |
|---|---|---|---|---|---|---|---|---|---|---|---|---|---|---|---|---|
| Tyr | Gln | Tyr | Asp | Pro | Thr | Lys | Trp | Leu | Ile | Tyr | Leu | Phe | Ser | Leu | Gly | |
| | 275 | | | | | 280 | | | | | 285 | | | | | |

| ccg | ttc | cca | ctg | gca | tac | tcg | ctc | aaa | acc | ttc | cgg | tct | aac | gag | atc | 912 |
|---|---|---|---|---|---|---|---|---|---|---|---|---|---|---|---|---|
| Pro | Phe | Pro | Leu | Ala | Tyr | Ser | Leu | Lys | Thr | Phe | Arg | Ser | Asn | Glu | Ile | |

```
                290                 295                 300
gaa aag ggg cgg ttg caa caa caa caa aag gcc ctg gat aag aag cgc      960
Glu Lys Gly Arg Leu Gln Gln Gln Gln Lys Ala Leu Asp Lys Lys Arg
305                 310                 315                 320 tct ggc ctt gat tgg ggc ctg ccc ctc ttc cag ctc cct gtg ata tct     1008
Ser Gly Leu Asp Trp Gly Leu Pro Leu Phe Gln Leu Pro Val Ile Ser
                325                 330                 335 tgg gac gac ttc caa gcg cgt tgt aag gag tcc ggc gag atg ctg gtt     1056
Trp Asp Asp Phe Gln Ala Arg Cys Lys Glu Ser Gly Glu Met Leu Val
                340                 345                 350 gct gtc gcc ggt gtg att cac gac gtc tca cag ttc att gaa gat cac     1104
Ala Val Ala Gly Val Ile His Asp Val Ser Gln Phe Ile Glu Asp His
            355                 360                 365 cct gga ggg agg agt ctg att cgg tct gcg gtg ggc aag gat ggg act     1152
Pro Gly Gly Arg Ser Leu Ile Arg Ser Ala Val Gly Lys Asp Gly Thr
        370                 375                 380 ggg atg ttt aat gga ggc gtt tat gag cac agt aat gcg gcg cac aat     1200
Gly Met Phe Asn Gly Gly Val Tyr Glu His Ser Asn Ala Ala His Asn
385                 390                 395                 400 ctg ttg tca aca atg agg gtg ggt gtg ctt aga ggt ggg caa gag gtg     1248
Leu Leu Ser Thr Met Arg Val Gly Val Leu Arg Gly Gly Gln Glu Val
                405                 410                 415 gag gtg tgg aag aag cag cgt gtg gat gta tta ggg aag agc gat atc     1296
Glu Val Trp Lys Lys Gln Arg Val Asp Val Leu Gly Lys Ser Asp Ile
                420                 425                 430 ttg cgt caa gtt acg cgg gtg gag agg ctg gtt gag ggg gct gtg gct     1344
Leu Arg Gln Val Thr Arg Val Glu Arg Leu Val Glu Gly Ala Val Ala
                435                 440                 445 gcc tag                                                             1350
Ala

<210> SEQ ID NO 66
<211> LENGTH: 449
<212> TYPE: PRT
<213> ORGANISM: Artificial Sequence
<220> FEATURE:
<223> OTHER INFORMATION: Synthetic Construct

<400> SEQUENCE: 66

Met Ala Ala Leu Asp Ser Ile Pro Glu Asp Lys Ala Thr Ser Ser Lys
1               5                   10                  15

Ser Thr His Ile Gln Tyr Gln Glu Val Thr Phe Arg Asn Trp Tyr Lys
                20                  25                  30

Lys Ile Asn Trp Leu Asn Thr Thr Leu Val Val Leu Ile Pro Ala Leu
            35                  40                  45

Gly Leu Tyr Leu Thr Arg Thr Thr Pro Leu Thr Arg Pro Thr Leu Ile
        50                  55                  60

Trp Ser Val Leu Tyr Tyr Phe Cys Thr Ala Phe Gly Ile Thr Gly Gly
65                  70                  75                  80

Tyr His Arg Leu Trp Ser His Arg Ser Tyr Ala Arg Leu Pro Leu
                85                  90                  95

Arg Leu Phe Leu Ala Phe Thr Gly Ala Gly Ala Ile Gln Gly Ser Ala
            100                 105                 110

Arg Trp Trp Ser Ala Asn His Arg Ala His His Arg Trp Thr Asp Thr
        115                 120                 125

Met Lys Asp Pro Tyr Ser Val Met Arg Gly Leu Leu Phe Ser His Ile
    130                 135                 140

Gly Trp Met Val Leu Asn Ser Asp Pro Lys Val Lys Gly Arg Thr Asp
```

| | | | | | | | | | | | | | | | |
|---|---|---|---|---|---|---|---|---|---|---|---|---|---|---|---|
| | 145 | | | | 150 | | | | 155 | | | | 160 | | |
| Val | Ser | Asp | Leu | Asp | Ser | Asp | Pro | Val | Val | Trp | Gln | His | Lys | His | |
| | | | | 165 | | | | | 170 | | | | | 175 | |
| Tyr | Gly | Lys | Cys | Leu | Leu | Phe | Ala | Ala | Trp | Ile | Phe | Pro | Met | Ile | Val |
| | | | 180 | | | | | 185 | | | | | 190 | | |
| Ala | Gly | Leu | Gly | Trp | Gly | Asp | Trp | Trp | Gly | Gly | Leu | Val | Tyr | Ala | Gly |
| | | 195 | | | | | 200 | | | | | 205 | | | |
| Ile | Ile | Arg | Ala | Cys | Phe | Val | Gln | Gln | Ala | Thr | Phe | Cys | Val | Asn | Ser |
| | 210 | | | | | 215 | | | | | 220 | | | | |
| Leu | Ala | His | Trp | Ile | Gly | Glu | Gln | Pro | Phe | Asp | Asp | Arg | Arg | Thr | Pro |
| 225 | | | | | 230 | | | | | 235 | | | | | 240 |
| Arg | Asp | His | Val | Leu | Thr | Ala | Leu | Val | Thr | Met | Gly | Glu | Gly | Tyr | His |
| | | | | 245 | | | | | 250 | | | | | 255 | |
| Asn | Phe | His | His | Glu | Phe | Pro | Ser | Asp | Tyr | Arg | Asn | Ala | Ile | Ile | Trp |
| | | | 260 | | | | | 265 | | | | | 270 | | |
| Tyr | Gln | Tyr | Asp | Pro | Thr | Lys | Trp | Leu | Ile | Tyr | Leu | Phe | Ser | Leu | Gly |
| | | 275 | | | | | 280 | | | | | 285 | | | |
| Pro | Phe | Pro | Leu | Ala | Tyr | Ser | Leu | Lys | Thr | Phe | Arg | Ser | Asn | Glu | Ile |
| | 290 | | | | | 295 | | | | | 300 | | | | |
| Glu | Lys | Gly | Arg | Leu | Gln | Gln | Gln | Lys | Ala | Leu | Asp | Lys | Lys | Arg | |
| 305 | | | | | 310 | | | | | 315 | | | | | 320 |
| Ser | Gly | Leu | Asp | Trp | Gly | Leu | Pro | Leu | Phe | Gln | Leu | Pro | Val | Ile | Ser |
| | | | | 325 | | | | | 330 | | | | | 335 | |
| Trp | Asp | Asp | Phe | Gln | Ala | Arg | Cys | Lys | Glu | Ser | Gly | Glu | Met | Leu | Val |
| | | | 340 | | | | | 345 | | | | | 350 | | |
| Ala | Val | Ala | Gly | Val | Ile | His | Asp | Val | Ser | Gln | Phe | Ile | Glu | Asp | His |
| | | 355 | | | | | 360 | | | | | 365 | | | |
| Pro | Gly | Gly | Arg | Ser | Leu | Ile | Arg | Ser | Ala | Val | Gly | Lys | Asp | Gly | Thr |
| | 370 | | | | | 375 | | | | | 380 | | | | |
| Gly | Met | Phe | Asn | Gly | Gly | Val | Tyr | Glu | His | Ser | Asn | Ala | Ala | His | Asn |
| 385 | | | | | 390 | | | | | 395 | | | | | 400 |
| Leu | Leu | Ser | Thr | Met | Arg | Val | Gly | Val | Leu | Arg | Gly | Gly | Gln | Glu | Val |
| | | | | 405 | | | | | 410 | | | | | 415 | |
| Glu | Val | Trp | Lys | Lys | Gln | Arg | Val | Asp | Val | Leu | Gly | Lys | Ser | Asp | Ile |
| | | | 420 | | | | | 425 | | | | | 430 | | |
| Leu | Arg | Gln | Val | Thr | Arg | Val | Glu | Arg | Leu | Val | Glu | Gly | Ala | Val | Ala |
| | | 435 | | | | | 440 | | | | | 445 | | | |
| Ala | | | | | | | | | | | | | | | |

<210> SEQ ID NO 67
<211> LENGTH: 660
<212> TYPE: DNA
<213> ORGANISM: Xerophyta viscosa
<220> FEATURE:
<221> NAME/KEY: CDS
<222> LOCATION: (1)..(660)
<223> OTHER INFORMATION: Native DNA sequence encoding Xerophyta
      viscosa PER1 protein

<400> SEQUENCE: 67

```
atg ccg ggg ctc acc att ggc gac acg atc ccc aac ctg gag ctt gac      48
Met Pro Gly Leu Thr Ile Gly Asp Thr Ile Pro Asn Leu Glu Leu Asp
1               5                   10                  15 acc acc cag ggt agg atc aaa atc cac gat tac gtc ggc aac ggc tac      96
Thr Thr Gln Gly Arg Ile Lys Ile His Asp Tyr Val Gly Asn Gly Tyr
            20                  25                  30
```

```
gtc atc ttg ttc tca cac cct gga gac ttc act cct gtc tgc acc acc      144
Val Ile Leu Phe Ser His Pro Gly Asp Phe Thr Pro Val Cys Thr Thr
         35                  40                  45 gaa ctt gga aag atg gct gct tac gcc gac gag ttc agc aag cgc ggg      192
Glu Leu Gly Lys Met Ala Ala Tyr Ala Asp Glu Phe Ser Lys Arg Gly
 50                  55                  60 gtt aag ctt ctt ggt ctt tcc tgc gac gat gta cag agc cac aag gag      240
Val Lys Leu Leu Gly Leu Ser Cys Asp Asp Val Gln Ser His Lys Glu
 65                  70                  75                  80 tgg atc aag gat atc gaa gcc tat acg ccg gga tgt cac gta aaa tat      288
Trp Ile Lys Asp Ile Glu Ala Tyr Thr Pro Gly Cys His Val Lys Tyr
                 85                  90                  95 cct atc gcg gcg gac cca acc cgc gag att atc cag cag cta aac atg      336
Pro Ile Ala Ala Asp Pro Thr Arg Glu Ile Ile Gln Gln Leu Asn Met
            100                 105                 110 gta gac cca gac gag aca gag tcc agc aaa tgc gcc gtg cct tcg cga      384
Val Asp Pro Asp Glu Thr Glu Ser Ser Lys Cys Ala Val Pro Ser Arg
        115                 120                 125 gct ctg cac atc att ggg ccc gac aag agg atc aag ctg agt ttc ctg      432
Ala Leu His Ile Ile Gly Pro Asp Lys Arg Ile Lys Leu Ser Phe Leu
    130                 135                 140 tac ccc gcg tcg acg ggg cga aac atg gat gag gtg ctg agg gca gtg      480
Tyr Pro Ala Ser Thr Gly Arg Asn Met Asp Glu Val Leu Arg Ala Val
145                 150                 155                 160 gag tcg ctc cag cag gcg gca aag cac aag gtg gca acg ccg gcg aac      528
Glu Ser Leu Gln Gln Ala Ala Lys His Lys Val Ala Thr Pro Ala Asn
                165                 170                 175 tgg aag cct ggt gaa cct gtt gtg atc aag cct gat gtg tcc agc gag      576
Trp Lys Pro Gly Glu Pro Val Val Ile Lys Pro Asp Val Ser Ser Glu
            180                 185                 190 gag gcc aag aag ctt ttc ccg cag ggt tat aaa agt gtt gat ctt cca      624
Glu Ala Lys Lys Leu Phe Pro Gln Gly Tyr Lys Ser Val Asp Leu Pro
        195                 200                 205 tcc aag aag gat tac ctt cgt ttt acg aac gtc tga                      660
Ser Lys Lys Asp Tyr Leu Arg Phe Thr Asn Val
    210                 215

<210> SEQ ID NO 68
<211> LENGTH: 219
<212> TYPE: PRT
<213> ORGANISM: Xerophyta viscosa

<400> SEQUENCE: 68

Met Pro Gly Leu Thr Ile Gly Asp Thr Ile Pro Asn Leu Glu Leu Asp
 1               5                  10                  15

Thr Thr Gln Gly Arg Ile Lys Ile His Asp Tyr Val Gly Asn Gly Tyr
            20                  25                  30

Val Ile Leu Phe Ser His Pro Gly Asp Phe Thr Pro Val Cys Thr Thr
         35                  40                  45

Glu Leu Gly Lys Met Ala Ala Tyr Ala Asp Glu Phe Ser Lys Arg Gly
 50                  55                  60

Val Lys Leu Leu Gly Leu Ser Cys Asp Asp Val Gln Ser His Lys Glu
 65                  70                  75                  80

Trp Ile Lys Asp Ile Glu Ala Tyr Thr Pro Gly Cys His Val Lys Tyr
                 85                  90                  95

Pro Ile Ala Ala Asp Pro Thr Arg Glu Ile Ile Gln Gln Leu Asn Met
            100                 105                 110

Val Asp Pro Asp Glu Thr Glu Ser Ser Lys Cys Ala Val Pro Ser Arg
        115                 120                 125
```

```
Ala Leu His Ile Ile Gly Pro Asp Lys Arg Ile Lys Leu Ser Phe Leu
        130                 135                 140

Tyr Pro Ala Ser Thr Gly Arg Asn Met Asp Glu Val Leu Arg Ala Val
145                 150                 155                 160

Glu Ser Leu Gln Gln Ala Ala Lys His Lys Val Ala Thr Pro Ala Asn
            165                 170                 175

Trp Lys Pro Gly Glu Pro Val Val Ile Lys Pro Asp Val Ser Ser Glu
                180                 185                 190

Glu Ala Lys Lys Leu Phe Pro Gln Gly Tyr Lys Ser Val Asp Leu Pro
            195                 200                 205

Ser Lys Lys Asp Tyr Leu Arg Phe Thr Asn Val
        210                 215

<210> SEQ ID NO 69
<211> LENGTH: 660
<212> TYPE: DNA
<213> ORGANISM: Artificial Sequence
<220> FEATURE:
<223> OTHER INFORMATION: Synthetic DNA sequence encoding Xerophyta
      viscosa PER1 protein using codons optimized for maize and
      Table 1 & Table 2 sequences are maintained
<220> FEATURE:
<221> NAME/KEY: CDS
<222> LOCATION: (1)..(660)

<400> SEQUENCE: 69 atg cct gga ttg act att ggt gac aca att ccc aac ttg gag ctg gat    48
Met Pro Gly Leu Thr Ile Gly Asp Thr Ile Pro Asn Leu Glu Leu Asp
1               5                   10                  15 acg aca caa ggt cgc atc aag atc cac gac tat gtc ggg aat gga tac    96
Thr Thr Gln Gly Arg Ile Lys Ile His Asp Tyr Val Gly Asn Gly Tyr
                20                  25                  30 gtg att ctc ttc tca cat cct ggt gat ttc act ccg gtg tgt acc acc   144
Val Ile Leu Phe Ser His Pro Gly Asp Phe Thr Pro Val Cys Thr Thr
            35                  40                  45 gaa ttg ggc aag atg gct gct tat gcc gac gag ttc tct aag cgt ggt   192
Glu Leu Gly Lys Met Ala Ala Tyr Ala Asp Glu Phe Ser Lys Arg Gly
 50                  55                  60 gtg aag ctg ctt ggg ttg tcc tgt gat gat gtc caa tca cat aag gag   240
Val Lys Leu Leu Gly Leu Ser Cys Asp Asp Val Gln Ser His Lys Glu
65                  70                  75                  80 tgg atc aaa gac ata gag gct tac aca cct ggc tgt cac gta aaa tat   288
Trp Ile Lys Asp Ile Glu Ala Tyr Thr Pro Gly Cys His Val Lys Tyr
                85                  90                  95 ccg att gct gct gat cca acc aga gaa atc ata cag cag ctg aac atg   336
Pro Ile Ala Ala Asp Pro Thr Arg Glu Ile Ile Gln Gln Leu Asn Met
            100                 105                 110 gtg gac cct gat gag acg gaa agc tct aag tgc gct gtg cct tct agg   384
Val Asp Pro Asp Glu Thr Glu Ser Ser Lys Cys Ala Val Pro Ser Arg
        115                 120                 125 gca ctt cac atc ata gga cca gat aag agg atc aag ctg tcc ttc ctc   432
Ala Leu His Ile Ile Gly Pro Asp Lys Arg Ile Lys Leu Ser Phe Leu
    130                 135                 140 tac cct gcc tct act ggt cgc aac atg gac gaa gtt ctt aga gcc gtt   480
Tyr Pro Ala Ser Thr Gly Arg Asn Met Asp Glu Val Leu Arg Ala Val
145                 150                 155                 160 gag tct ctt cag caa gca gct aaa cac aaa gtt gca act cct gct aac   528
Glu Ser Leu Gln Gln Ala Ala Lys His Lys Val Ala Thr Pro Ala Asn
                165                 170                 175 tgg aaa cct ggc gaa cca gtc gtc atc aaa cca gac gtc agc tcc gag   576
Trp Lys Pro Gly Glu Pro Val Val Ile Lys Pro Asp Val Ser Ser Glu
```

```
Trp Lys Pro Gly Glu Pro Val Val Ile Lys Pro Asp Val Ser Ser Glu
            180                 185                 190 gag gcc aag aag ctc ttt cct caa ggt tat aaa agc gtt gat ttg cct      624
Glu Ala Lys Lys Leu Phe Pro Gln Gly Tyr Lys Ser Val Asp Leu Pro
            195                 200                 205 tca aag aag gac tac ttg agg ttc acc aat gtt tga                      660
Ser Lys Lys Asp Tyr Leu Arg Phe Thr Asn Val
            210                 215
```

<210> SEQ ID NO 70
<211> LENGTH: 219
<212> TYPE: PRT
<213> ORGANISM: Artificial Sequence
<220> FEATURE:
<223> OTHER INFORMATION: Synthetic Construct

<400> SEQUENCE: 70

```
Met Pro Gly Leu Thr Ile Gly Asp Thr Ile Pro Asn Leu Glu Leu Asp
1               5                   10                  15

Thr Thr Gln Gly Arg Ile Lys Ile His Asp Tyr Val Gly Asn Gly Tyr
            20                  25                  30

Val Ile Leu Phe Ser His Pro Gly Asp Phe Thr Pro Val Cys Thr Thr
        35                  40                  45

Glu Leu Gly Lys Met Ala Ala Tyr Ala Asp Glu Phe Ser Lys Arg Gly
    50                  55                  60

Val Lys Leu Leu Gly Leu Ser Cys Asp Asp Val Gln Ser His Lys Glu
65                  70                  75                  80

Trp Ile Lys Asp Ile Glu Ala Tyr Thr Pro Gly Cys His Val Lys Tyr
                85                  90                  95

Pro Ile Ala Ala Asp Pro Thr Arg Glu Ile Ile Gln Gln Leu Asn Met
            100                 105                 110

Val Asp Pro Asp Glu Thr Glu Ser Ser Lys Cys Ala Val Pro Ser Arg
        115                 120                 125

Ala Leu His Ile Ile Gly Pro Asp Lys Arg Ile Lys Leu Ser Phe Leu
    130                 135                 140

Tyr Pro Ala Ser Thr Gly Arg Asn Met Asp Glu Val Leu Arg Ala Val
145                 150                 155                 160

Glu Ser Leu Gln Gln Ala Ala Lys His Lys Val Ala Thr Pro Ala Asn
                165                 170                 175

Trp Lys Pro Gly Glu Pro Val Val Ile Lys Pro Asp Val Ser Ser Glu
            180                 185                 190

Glu Ala Lys Lys Leu Phe Pro Gln Gly Tyr Lys Ser Val Asp Leu Pro
        195                 200                 205

Ser Lys Lys Asp Tyr Leu Arg Phe Thr Asn Val
    210                 215
```

<210> SEQ ID NO 71
<211> LENGTH: 660
<212> TYPE: DNA
<213> ORGANISM: Artificial Sequence
<220> FEATURE:
<223> OTHER INFORMATION: Synthetic DNA sequence in accordance with the
      invention encoding Xerophyta viscosa PER1 protein using codons
      optimized for maize and with sequences identified in Table 2
      removed and Table 1 sequences are maintained
<220> FEATURE:
<221> NAME/KEY: CDS
<222> LOCATION: (1)..(660)

<400> SEQUENCE: 71

```
atg cct gga ttg act att ggt gac aca att ccc aac ttg gag ctg gat    48
Met Pro Gly Leu Thr Ile Gly Asp Thr Ile Pro Asn Leu Glu Leu Asp
1               5                   10                  15 acg aca caa ggt cgc atc aag atc cac gac tat gtc ggg aat gga tac    96
Thr Thr Gln Gly Arg Ile Lys Ile His Asp Tyr Val Gly Asn Gly Tyr
            20                  25                  30 gtg att ctc ttc tca cat cct ggt gat ttc act ccg gtg tgt acc acc   144
Val Ile Leu Phe Ser His Pro Gly Asp Phe Thr Pro Val Cys Thr Thr
        35                  40                  45 gaa ttg ggc aag atg gct gct tat gcc gac gag ttc tct aag cgt ggt   192
Glu Leu Gly Lys Met Ala Ala Tyr Ala Asp Glu Phe Ser Lys Arg Gly
50                  55                  60 gtg aag ctg ctt ggg ttg tcc tgt gat gat gtc caa tca cat aag gag   240
Val Lys Leu Leu Gly Leu Ser Cys Asp Asp Val Gln Ser His Lys Glu
65                  70                  75                  80 tgg atc aaa gac ata gag gct tac aca cct ggc tgt cac gta aaa tat   288
Trp Ile Lys Asp Ile Glu Ala Tyr Thr Pro Gly Cys His Val Lys Tyr
                85                  90                  95 ccg att gct gct gat cca acc aga gaa atc ata cag cag ctg aac atg   336
Pro Ile Ala Ala Asp Pro Thr Arg Glu Ile Ile Gln Gln Leu Asn Met
            100                 105                 110 gtg gac cct gat gag acg gaa agc tct aag tgc gct gtg cct tct agg   384
Val Asp Pro Asp Glu Thr Glu Ser Ser Lys Cys Ala Val Pro Ser Arg
        115                 120                 125 gca ctt cac atc ata gga cca gat aag agg atc aag ctg tcc ttc ctc   432
Ala Leu His Ile Ile Gly Pro Asp Lys Arg Ile Lys Leu Ser Phe Leu
    130                 135                 140 tac cct gcc tct act ggt cgc aac atg gac gaa gtt ctt aga gcc gtt   480
Tyr Pro Ala Ser Thr Gly Arg Asn Met Asp Glu Val Leu Arg Ala Val
145                 150                 155                 160 gag tct ctt cag caa gca gct aaa cac aaa gtt gca act cct gct aac   528
Glu Ser Leu Gln Gln Ala Ala Lys His Lys Val Ala Thr Pro Ala Asn
                165                 170                 175 tgg aaa cct ggc gaa cca gtc gtc atc aaa cca gac gtc agc tcc gag   576
Trp Lys Pro Gly Glu Pro Val Val Ile Lys Pro Asp Val Ser Ser Glu
            180                 185                 190 gag gcc aag aag ctc ttt cct caa ggt tat aaa agc gtt gat ttg cct   624
Glu Ala Lys Lys Leu Phe Pro Gln Gly Tyr Lys Ser Val Asp Leu Pro
        195                 200                 205 tca aag aag gac tac ttg agg ttc acc aat gtt tga                    660
Ser Lys Lys Asp Tyr Leu Arg Phe Thr Asn Val
    210                 215

<210> SEQ ID NO 72
<211> LENGTH: 219
<212> TYPE: PRT
<213> ORGANISM: Artificial Sequence
<220> FEATURE:
<223> OTHER INFORMATION: Synthetic Construct

<400> SEQUENCE: 72

Met Pro Gly Leu Thr Ile Gly Asp Thr Ile Pro Asn Leu Glu Leu Asp
1               5                   10                  15

Thr Thr Gln Gly Arg Ile Lys Ile His Asp Tyr Val Gly Asn Gly Tyr
            20                  25                  30

Val Ile Leu Phe Ser His Pro Gly Asp Phe Thr Pro Val Cys Thr Thr
        35                  40                  45

Glu Leu Gly Lys Met Ala Ala Tyr Ala Asp Glu Phe Ser Lys Arg Gly
    50                  55                  60

Val Lys Leu Leu Gly Leu Ser Cys Asp Asp Val Gln Ser His Lys Glu
```

-continued

```
            65                  70                  75                  80
Trp Ile Lys Asp Ile Glu Ala Tyr Thr Pro Gly Cys His Val Lys Tyr
                85                  90                  95

Pro Ile Ala Ala Asp Pro Thr Arg Glu Ile Ile Gln Gln Leu Asn Met
               100                 105                 110

Val Asp Pro Asp Glu Thr Glu Ser Ser Lys Cys Ala Val Pro Ser Arg
           115                 120                 125

Ala Leu His Ile Ile Gly Pro Asp Lys Arg Ile Lys Leu Ser Phe Leu
           130                 135                 140

Tyr Pro Ala Ser Thr Gly Arg Asn Met Asp Glu Val Leu Arg Ala Val
145                 150                 155                 160

Glu Ser Leu Gln Gln Ala Ala Lys His Lys Val Ala Thr Pro Ala Asn
               165                 170                 175

Trp Lys Pro Gly Glu Pro Val Val Ile Lys Pro Asp Val Ser Ser Glu
           180                 185                 190

Glu Ala Lys Lys Leu Phe Pro Gln Gly Tyr Lys Ser Val Asp Leu Pro
           195                 200                 205

Ser Lys Lys Asp Tyr Leu Arg Phe Thr Asn Val
210                 215
```